US009567605B2

(12) United States Patent
Cohen et al.

(10) Patent No.: US 9,567,605 B2
(45) **Date of Patent: *Feb. 14, 2017**

(54) METHODS FOR USE OF A SPECIFIC ANTI-ANGIOGENIC ADENOVIRAL AGENT

(75) Inventors: Yael Cohen, Kiryat-Ono (IL); Naamit Sher, Rechovot (IL); Erez Feige, Hemed (IL); Livnat Bangio, Petach-Tikva (IL); Eyal Breitbart, Hashmonaim (IL)

(73) Assignee: Vascular Biogenics Ltd., Or Yehuda (IL)

( * ) Notice: Subject to any disclaimer, the term of this patent is extended or adjusted under 35 U.S.C. 154(b) by 143 days.

This patent is subject to a terminal disclaimer.

(21) Appl. No.: 13/520,457

(22) PCT Filed: Jan. 5, 2011

(86) PCT No.: PCT/IL2011/000007

§ 371 (c)(1), (2), (4) Date: Jul. 3, 2012

(87) PCT Pub. No.: WO2011/083464

PCT Pub. Date: Jul. 14, 2011

(65) Prior Publication Data

US 2014/0010785 A1 Jan. 9, 2014

Related U.S. Application Data

(60) Provisional application No. 61/282,228, filed on Jan. 5, 2010, provisional application No. 61/282,247, filed on Jan. 7, 2010.

(51) Int. Cl.

| | |
|---|---|
| ***A01N 63/00*** | (2006.01) |
| ***C12N 15/00*** | (2006.01) |
| ***C12N 7/01*** | (2006.01) |
| ***C12N 15/86*** | (2006.01) |
| ***A61K 48/00*** | (2006.01) |
| ***C07H 21/04*** | (2006.01) |
| ***C07K 14/705*** | (2006.01) |
| ***C07K 14/715*** | (2006.01) |
| ***A61K 38/17*** | (2006.01) |
| ***C12N 15/87*** | (2006.01) |

(52) U.S. Cl.

CPC ............. *C12N 15/86* (2013.01); *A61K 38/177* (2013.01); *A61K 48/005* (2013.01); *A61K 48/0058* (2013.01); *A61K 48/0083* (2013.01); *C07K 14/70578* (2013.01); *C07K 14/7151* (2013.01); *C12N 15/87* (2013.01); *C07K 2319/00* (2013.01); *C12N 2799/022* (2013.01); *C12N 2830/008* (2013.01); *C12N 2830/85* (2013.01)

(58) Field of Classification Search

None

See application file for complete search history.

(56) References Cited

U.S. PATENT DOCUMENTS

| | | | | |
|---|---|---|---|---|
| 6,194,191 | B1 | 2/2001 | Zhang et al. | |
| 6,867,022 | B1 * | 3/2005 | Imperiale | 435/91.4 |
| 7,067,649 | B2 | 6/2006 | Harats | |
| 7,579,327 | B2 | 8/2009 | Harats et al. | |
| 7,585,666 | B2 | 9/2009 | Harats et al. | |
| 7,989,427 | B2 | 8/2011 | Harats et al. | |
| 8,039,261 | B2 | 10/2011 | Harats et al. | |
| 8,071,740 | B2 | 12/2011 | Harats et al. | |
| 8,206,743 | B2 | 6/2012 | Harats et al. | |
| 8,415,318 | B2 | 4/2013 | Harats et al. | |
| 2003/0095957 | A1 | 5/2003 | Crystal et al. | |
| 2003/0124100 | A1 | 7/2003 | Harats | |
| 2004/0048280 | A1 | 3/2004 | Harats | |
| 2004/0170975 | A1 | 9/2004 | Savitzky et al. | |
| 2004/0197860 | A1 | 10/2004 | Harats et al. | |
| 2006/0223756 | A1 * | 10/2006 | Liau | C07K 7/06 514/200 |
| 2007/0082900 | A1 * | 4/2007 | Guzi et al. | 514/234.5 |
| 2007/0286845 | A1 | 12/2007 | Harats et al. | |
| 2008/0063656 | A1 | 3/2008 | Emini et al. | |
| 2008/0293652 | A1 | 11/2008 | Menander et al. | |
| 2009/0326052 | A1 | 12/2009 | Harats et al. | |
| 2010/0081193 | A1 | 4/2010 | Breitbart et al. | |
| 2010/0282634 | A1 | 11/2010 | Harats et al. | |
| 2011/0201677 | A1 | 8/2011 | Harats et al. | |
| 2011/0207985 | A1 | 8/2011 | Harats et al. | |
| 2011/0319479 | A1 | 12/2011 | Breitbart et al. | |
| 2012/0201790 | A1 | 8/2012 | Harats et al. | |

(Continued)

FOREIGN PATENT DOCUMENTS

| | | | |
|---|---|---|---|
| WO | WO 00/61150 | A1 | 10/2000 |
| WO | WO 02/40629 | A2 | 5/2002 |

(Continued)

OTHER PUBLICATIONS

Greenberger, S., et al., "Transcription-controlled gene therapy against tumor angiogenesis," *J. Clin. Invest.* 113(7):1017-1024, American Society for Clinical Investigation, United States (2004).

Peled, M., et al., "Antiangiogenic systemic gene therapy combine with doxorubicin administration induced caspase 8 and 9-mediated apoptosis in endothelial cells and an anti-metastasis effect," *Cancer Gene Ther.* 15:535-543, Nature Publishing Group, England (2008).

Roberts, D.M., et al., "Hexon-chimaeric adenovirus serotype 5 vectors circumvent pre-existing anti-vector immunity," *Nature* 441:239-243, Nature Publishing Group, England (2006).

Roskoski, R. Jr., "Sunitinib: A VEGF and PDGF receptor protein kinase and angiogenesis inhibitor," *Biochem. Biophys. Res. Commun.* 356:323-328, Elsevier, United States (2007).

(Continued)

*Primary Examiner* — Maria Leavitt
*Assistant Examiner* — Kimberly A Aron
(74) *Attorney, Agent, or Firm* — Sterne, Kessler, Goldstein & Fox P.L.L.C.

(57) ABSTRACT

Anti-angiogenic adenovirus vectors, and therapeutic use thereof are provided, and more particularly, but not exclusively, clinical protocols for treatment of solid tumors in patients with an Ad5-PPE-1-3X-fas-chimera adenovirus vector.

26 Claims, 14 Drawing Sheets

(56) References Cited

U.S. PATENT DOCUMENTS

| | | | |
|---|---|---|---|
| 2013/0011367 A1 | 1/2013 | Harats et al. |
| 2013/0052165 A1 | 2/2013 | Bangio et al. |
| 2013/0209450 A1 | 8/2013 | Cohen et al. |
| 2013/0272998 A1 | 10/2013 | Harats et al. |
| 2013/0280216 A1 | 10/2013 | Cohen et al. |
| 2013/0280217 A1 | 10/2013 | Cohen et al. |
| 2013/0295053 A1 | 11/2013 | Bangio et al. |
| 2013/0296404 A1 | 11/2013 | Harats et al. |
| 2013/0303595 A1 | 11/2013 | Cohen et al. |
| 2014/0155467 A1 | 6/2014 | Harats et al. |

FOREIGN PATENT DOCUMENTS

| | | |
|---|---|---|
| WO | WO 03/033514 A1 | 4/2003 |
| WO | WO 03/093409 A2 | 11/2003 |
| WO | WO 2006/051545 A2 | 5/2006 |
| WO | WO-2006079176 A1 | 8/2006 |
| WO | WO 2007/096882 A2 | 8/2007 |
| WO | WO-2008015675 A2 | 2/2008 |
| WO | WO 2008/132729 A2 | 11/2008 |
| WO | WO 2011/083464 A2 | 7/2011 |
| WO | WO 2011/083466 A1 | 7/2011 |
| WO | WO 2011/086509 A1 | 7/2011 |
| WO | WO-2014060848 A2 | 4/2014 |

OTHER PUBLICATIONS

U.S. Appl. No. 13/826,303 inventors Cohen, Y., et al., filed Mar. 14, 2013.

U.S. Appl. No. 13/826,396 inventors Bangio, L., et al., filed Mar. 14, 2013.

Brenner, A J., et al., "Antivascular acitivity of VB111 in glioblastoma xenografts," Journal of Clinical Oncology 28(15):1, American Society of Clinical Oncology, United States (May 2010).

Brenner, A J., et al., "Phase I/II dose escalation study of VB-111, an antiangiogenic gene therapy, in patients with recurrent glioblastoma multiforme," Journal of Clinical Oncology 31(Suppl 15S, Part I): 1-2, ASCO Annual Meeting, Chicago (Jun. 2013) (Abstract TPS2102).

Brenner, J., et al., "Phase I Dose-Escalation Study of VB-111, an Antiangiogenic Virotherapy, in Patients with Advanced Solid Tumors," Clinical Cancer Research 19:3996-4007, American Association for Cancer Research, United States (Apr. 2013).

Co-pending U.S. Appl. No. 13/520,452, filed Dec. 19, 2012.

Co-pending U.S. Appl. No. 13/521,691, filed Jul. 11, 2012.

Co-pending U.S. Appl. No. 13/785,863, filed Mar. 5, 2013.

Co-pending U.S. Appl. No. 13/796,991, filed Mar. 12, 2013.

Co-pending U.S. Appl. No. 13/797,160, filed Mar. 12, 2013.

Co-pending U.S. Appl. No. 13/800,478, filed Mar. 13, 2013.

Co-pending U.S. Appl. No. 14/059,426, filed Oct. 21, 2013.

Peled, M., et al., "Systemic Administration of a Conditionally Replicating Adenovirus, Targeted to Angiogenesis, Reduced Lung Metastases Burdne in Cotton Rats," Clinical Research 15(5):1664-1673, The American Association for Cancer Research, United States (Mar. 2009).

Tal, R., et al., "Activation of C-transactivation domain is essential for optimal HIF-1α-mediated transcriptional and angiogenic effects," Microvascular Research 76(1):1-6, Elsevier, Inc., United States (2008).

Tal, R., et al., "Endothelial-targeted Gene Transfer of Hypoxia-Inducible Factor-1α Augments Ischemic Neovascularization Following Systemic Administration," Molecular Therapy 16(12):1927-1936, Academic Press, United States (2008).

Tal, R., et al., "Systemic Gene Transfer of Stabilized Constitutively Activated Hypoxia-Inducible Factor-1 Targeted to Endothelium Augments Ischemic Neovascularization," Atherosclerosis Supplements 8(1):3, 76th Congress of the European Atherosclerosis Society, Finland (2007) (Abstract WO3-OR-3).

Varda-Bloom, N., et al., "Specific Induction of Tumor Neovasculature Death by Modified Murine PPE-1 Promoter Armed with HSV-TK," Pathobiology 75(6):346-355, S. Karger AG, Basel, Switzerland (2008).

Faivre, S., et al., "Molecular basis for sunitinib efficacy and future clinical development," *Nat Rev Drug Discov* 6(9):734-745, Nature Publishing Group, England (2007).

Ozao-Choy, J., et al.,"The novel role of tyrosine kinase inhibitor in the reversal of immune suppression and modulation of tumor microenvironment for immune-based cancer therapies," *Cancer Res* 69(6):2514-2522, American Association for Cancer Research, United States (2009).

Office Action mailed Dec. 8, 2014 in U.S. Appl. No. 13/796,991, inventors Cohen, Y., et al., filed Mar. 12, 2013.

Office Action mailed Jul. 1, 2015 in U.S. Appl. No. 13/796,991, inventors Cohen, Y., et al., filed Mar. 12, 2013.

Office Action mailed Mar. 29, 2016 in U.S. Appl. No. 13/796,991, inventors Cohen, Y., et al., filed Mar. 12, 2013.

Office Action mailed on Jul. 28, 2015 in U.S. Appl. No. 13/520,452, inventors Cohen, Y., et al., filed Dec. 19, 2012.

Office Action mailed on Feb. 23, 2016 in U.S. Appl. No. 13/520,452, inventors Cohen, Y., et al., filed Dec. 19, 2012.

Office Action mailed Feb. 25, 2016 in U.S. Appl. No. 13/826,303, inventors Cohen, Y, et al., filed Mar. 14, 2013.

Office Action mailed Jul. 31, 2015 in U.S. Appl. No. 13/826,303, inventors Cohen, Y, et al., filed Mar. 14, 2013.

Office Action mailed Jun. 2, 2016 in U.S. Appl. No. 13/521,691, inventors Bangio, L, et al., filed Jul. 11, 2012.

Office Action mailed Nov. 13, 2015 in U.S. Appl. No. 13/521,691, inventors Bangio, L, et al., filed Jul. 11, 2012.

Office Action mailed Oct. 20, 2014 in U.S. Appl. No. 13/521,691, inventors Bangio, L, et al., filed Jul. 11, 2012.

Office Action mailed Nov. 5, 2013 in U.S. Appl. No. 13/521,691, inventors Bangio, L, et al., filed Jul. 11, 2012.

Office Action mailed Feb. 26, 2016 in U.S. Appl. No. 13/826,396, inventors Bangio, L, et al., filed Mar. 14, 2013.

Office Action mailed Nov. 4, 2015 in U.S. Appl. No. 13/826,396, inventors Bangio, L, et al., filed Mar. 14, 2013.

Office Action mailed Jul. 7, 2015 in U.S. Appl. No. 13/826,396, inventors Bangio, L, et al., filed Mar. 14, 2013.

* cited by examiner

| | Average | SD | median | N |
|---|---|---|---|---|
| Vehicle | 0.930 | 0.16 | 0.90 | 17 |
| VB-111 1.00E+09 | 0.21 | 0.15 | 0.20 | 15 |
| VB-111 1.00E+11 | 0.04 | 0.04 | 0.02 | 16 |
| Sutent 40mg/kg | 0.14 | 0.11 | 0.10 | 15 |
| Sutent 80mg/kg | 0.09 | 0.11 | 0.06 | 16 |
| VB-111 1E9+Sutent 40mg/kg | 0.20 | 0.17 | 0.16 | 14 |
| VB-111 1E9+Sutent 80mg/kg | 0.03 | 0.06 | 0.02 | 16 |
| VB-111 1E11+ Sutent 40mg/kg | 0.24 | 0.17 | 0.19 | 18 |
| VB-111 1E11+Sute nt80mg/kg | 0 06 | 010 | 0.02 | 16 |

METHODS FOR USE OF A SPECIFIC ANTI-ANGIOGENIC ADENOVIRAL AGENT

REFERENCE TO SEQUENCE LISTING SUBMITTED ELECTRONICALLY VIA EFS-WEB

The content of the electronically submitted sequence listing (Name: SequenceListing_ascii.txt, Size: 391,736 bytes; and Date of Creation: Sep. 18, 2013) submitted in this application is incorporated herein by reference in its entirety.

FIELD AND BACKGROUND OF THE INVENTION

The present invention, in some embodiments thereof, relates to anti-angiogenic adenovirus vectors, and therapeutic use thereof, and more particularly, but not exclusively, to clinical protocols for treatment of solid tumors in patients with an Ad5-PPE-1-3X-fas-chimera adenovirus vector.

Angiogenesis is a process of new blood vessel formation by sprouting from pre-existing neighboring vessels. This process is common and major feature of several pathologies. Among these are diseases in which excessive angiogenesis is a part of the pathology and thus is a target of therapy, most significantly, cancer. Angiogenesis occurs in tumors and permits their growth, invasion and metastatic proliferation. In 1971, Folkman proposed that tumor growth and metastases are angiogenesis dependent, and suggested that inhibiting angiogenesis may be a strategy to arrest tumor growth.

There are several molecules involved in angiogenesis, from cell surface molecules to transcription factors to growth factors. Hypoxia is an important environmental factor that leads to neovascularization, inducing release of several pro-angiogenic cytokines, including vascular endothelial growth factors (VEGF) and their receptors, members of the angiopoietin family, basic fibroblast growth factor, and endothelin-1 (ET-1). These factors mediate induction of angiogenesis through control of activation, proliferation and migration of endothelial cells.

Recombinant forms of endogenous inhibitors of angiogenesis have been tested for the treatment of cancer, however the potential pharmacokinetic, biotechnological and economic drawbacks of chronic delivery of these recombinant inhibitors have led scientists to develop other approaches. The development of the anti-VEGF monoclonal antibody bevacizumab has validated anti-angiogenic targeting as a complementary therapeutic modality to chemotherapy. Several small molecule inhibitors, including second-generation multi-targeted tyrosine kinase inhibitors, have also shown promise as antiangiogenic agents for cancer.

The drawbacks of chronic delivery of recombinant inhibitors, antibodies, and small molecules, as well as the limited activity manifested when these drugs are administered as monotherapy have led to the development of anti-angiogenic gene therapies. Gene therapy is an emerging modality for treating inherited and acquired human diseases. However, a number of obstacles have impeded development of successful gene therapy, including duration of expression, induction of the immune response, cytotoxicity of the vectors and tissue specificity.

Two general strategies for anti-cancer gene therapy have proposed: tumor directed or systemic gene therapy. The lack of success in targeting gene therapy products to cancerous cells or their environment by systemic treatments, and the danger of significant anti-drug or anti-vector immunity has caused most therapies to be administered to the tumor itself, despite the advantages of systemic administration. "Adenoviral vaccines", designed to induce immunity to a recombinant antigen or epitope expressed in the patient's body, have been tried but produce mostly disappointing results. Thus, elaborate, potentially dangerous and costly strategies for eluding pathological host immune responses to systemic and repeated administration of therapeutic recombinant adenoviral vectors have been proposed, including immunosuppression, oral tolerization to vector antigens and genetic modification of the vectors (see Bangari et al, Current Gene Therapy 2006; 6: 215-226).

U.S. Pat. No. 5,747,340 teaches use of a murine endothelial cell-specific promoter which shows selectivity towards angiogenic cells, and therapeutic applications thereof.

International Application WO/2008/132729 discloses a non-replicating adenovirus vector (Ad5, E1 deleted), containing a modified murine pre-proendothelin promoter (PPE-1-3X) and a fas-chimera transgene [Fas and human tumor necrosis factor (TNF) receptor] which has been developed, in which the modified murine promoter (PPE-1-3X), is able to restrict expression of the fas chimera transgene to angiogenic blood vessels, leading to targeted apoptosis of these vessels.

Endothelial-specific gene therapy with the PPE-1-3X promoter does not increase the specificity of viral interactions with the host (e.g. transfection) but restricts the expression of the transgene to those tissues that endogenously recognize the modified promoter—angiogenic endothelial cells. The chimeric receptor can trigger the Fas pathway by binding TNFα, which is less toxic in non-tumoral tissues than using the Fas/Fas ligand mechanism, which is highly expressed in non-tumoral normal tissues such as the liver. Further, TNFα was found to be abundant in the microenvironment of tumors adding to the specificity of the transgene activity in the tumor and its surroundings.

Preliminary studies have shown that a single systemic injection of a PPE-1-3X-fas chimera results in transgene expression restricted to the tumor-bearing organ, causing tumor growth retardation, necrosis of the blood vessels in the metastatic tumor mass and reduction in tumor burden in B16 melanoma and Lewis lung carcinoma mice models.

However, an effective procedure for administration of a therapeutic amount of a recombinant anti-angiogenic adenovirus vector in the clinical setting is still lacking. As such, there is a great need for defining the parameters of clinically viable protocols for anti-angiogenic-adenoviral treatment of conditions associated with neovascularization, such as cancer, without the disadvantages of the current methods as described herein.

SUMMARY OF THE INVENTION

According to an aspect of some embodiments of the present invention there is provided a method of treating a solid tumor in a subject in need thereof, the method comprising administering to the subject a therapeutically effective amount of a non-replicating adenovirus vector, the vector comprises a polynucleotide which comprises a fas-chimera transgene transcriptionally linked to a murine pre-proendothelin promoter, wherein the therapeutically effective amount is at least $1\times10^8$ virus particles.

According to an aspect of some embodiments of the present invention there is provided a method of treating a solid tumor in a subject in need thereof, the method comprising administering to the subject a therapeutically effective amount of a non-replicating adenovirus vector which comprises a polynucleotide comprising a fas-chimera transgene transcriptionally linked to a murine pre-proendothelin promoter, the adenovirus vector comprising a nucleic acid sequence as set forth in SEQ ID NOs: 9 or 10.

According to an aspect of some embodiments of the present invention there is provided a method of treating a solid tumor in a subject in need thereof, the method comprising administering to the subject, in at least two separate doses, a therapeutically effective amount of a non-replicating adenovirus vector which comprises a polynucleotide comprising a fas-chimera transgene transcriptionally linked to a murine pre-proendothelin promoter, wherein the time between administration of the first dose and the at least a second dose is sufficient for anti-Ad5 antibody formation in the subject.

According to an aspect of some embodiments of the present invention there is provided a method of treating a solid tumor in a subject in need thereof, the method comprising administering to the subject a single intravenous dose of $3\times10^{12}$ or $1\times10^{13}$ virus particles of a non-replicating adenovirus vector comprising a polynucleotide having a nucleotide sequence as set forth in SEQ ID NOs: 9 or 10.

According to an aspect of some embodiments of the present invention there is provided a method of treating a thyroid cancer in a subject in need thereof, the method comprising administering to the subject a single intravenous dose of $3\times10^{12}$ or $1\times10^{13}$ virus particles of a non-replicating adenovirus vector comprising a polynucleotide having a nucleotide sequence as set forth in SEQ ID NOs: 9 or 10.

According to an aspect of some embodiments of the present invention there is provided a method of treating a neuroendocrine cancer in a subject in need thereof, the method comprising administering to the subject a single intravenous dose of $3\times10^{12}$ or $1\times10^{12}$ virus particles of a non-replicating adenovirus vector comprising a polynucleotide having a nucleotide sequence as set forth in SEQ ID NO: 9 or 10.

According to some embodiments of the present invention administering the dose of adenovirus vector inhibits angiogenesis of the tumor.

According to some embodiments of the present invention administering the dose of adenovirus inhibits growth of the tumor.

According to an aspect of some embodiments of the present invention there is provided a method for administering a therapeutically effective amount of a therapeutic composition comprising an adenoviral vector to a subject in need thereof comprising administering the composition to the subject at least twice, wherein the administration does not induce a dose-dependent increase in antibodies against the adenoviral vector in the subject.

According to an aspect of some embodiments of the present invention there is provided a kit for treating a solid tumor in a subject in need thereof, comprising a unit dosage of virus particles of a non-replicating adenovirus vector comprising a polynucleotide having a nucleotide sequence as set forth in SEQ ID NOs: 9 or 10, wherein the non-replicating adenovirus vector is formulated for intravenous administration, and instructions for administration of the adenovirus.

According to some embodiments of the present invention the unit dosage comprises about $3\times10^{12}$ virus particles, at least about $1\times10^{8}$ to about $1\times10^{16}$ virus particles, at least about $1\times10^{11}$ to about $1\times10^{13}$ virus particles, optionally at least about $3\times10^{12}$ virus particles.

According to some embodiments of the present invention the fas-chimera transgene comprises a polynucleotide having a nucleotide sequence as set forth in SEQ ID NO: 3.

According to yet other embodiments of the present invention the fas-chimera transgene comprises a polynucleotide having a nucleotide sequence as set forth in SEQ ID NO: 2.

According to still other embodiments of the present invention the fas-chimera transgene comprises a polynucleotide having a nucleotide sequence as set forth in SEQ ID NO: 4.

According to some embodiments of the present invention the murine pre-pro endothelin promoter comprises a polynucleotide having a nucleotide sequence as set forth in SEQ ID NO: 6.

According to some embodiments of the present invention the murine pre-pro endothelin promoter comprises a polynucleotide having a nucleotide sequence as set forth in SEQ ID NO: 7.

According to yet other embodiments of the present invention the murine pre-pro endothelin promoter comprises a polynucleotide having a nucleotide sequence as set forth in SEQ ID NO: 8.

According to yet other embodiments of the present invention the murine pre-pro endothelin promoter comprises a polynucleotide having a nucleotide sequence as set forth in SEQ ID NO: 5.

According to still other embodiments of the present invention the murine preproendothelin promoter comprises a polynucleotide having a nucleotide sequence as set forth in SEQ ID NO: 12.

According to some embodiments of the present invention the murine pre-pro endothelin promoter comprises a polynucleotide having a nucleotide sequence as set forth in SEQ ID NO: 13.

According to some embodiments of the present invention the non-replicating adenovirus vector is an adenovirus 5 vector.

According to yet other embodiments of the present invention the adenovirus 5 vector comprises a nucleic acid sequence as set forth in SEQ ID NOs: 9 or 10.

According to some embodiments of the present invention the solid tumor is a cancerous tumor.

According to still other embodiments of the present invention the solid tumor is a primary tumor.

According to yet other embodiments of the present invention the solid tumor is a metastatic tumor.

According to some embodiments the solid tumor is a thyroid tumor.

According to some embodiments the solid tumor is a neuroendocrine tumor.

According to some embodiments administering the dose of adenovirus vector inhibits angiogenesis of the tumor.

According to some embodiments administering the dose of the adenovirus vector inhibits growth of the tumor.

According to some embodiments the adenovirus is detected in the blood of the subject at least about 4 days post administration.

According to some embodiments an amount of serum anti-adenovirus antibodies is increased following the administering, and the adenovirus is detected in the blood of the subject at least about 21 days post administration.

According to some embodiments of the present invention the adenovirus vector is administered systemically.

According to still other embodiments of the present invention the vector is administered systemically by a route selected from the group consisting of intra-articular administration, intravenous administration, intraperitoneal administration, subcutaneous administration, infusion, oral administration, rectal administration, nasal administration and inhalation.

According to still other embodiments of the present invention administering the adenovirus vector is in at least two separate systemic doses.

According to some embodiments of the present invention the administering of the adenovirus vector is in a first dose and at least a second additional dose, wherein the first dose is sufficient to induce anti-Ad5 antibodies in the subject, and wherein the time between administration of the first dose and the at least a second dose is sufficient for anti-Ad5 antibody formation in the subject According to some embodiments of the present invention the subject is further receiving a chemotherapeutic agent as well as treatment with the virus particles of said non-replicating adenovirus vector.

According to some embodiments of the present invention the chemotherapeutic agent is administered prior to, concomitantly with, or following treatment with said virus particles.

According to some embodiments of the present invention the chemotherapeutic agent is sunitinib.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-1C are photos of exemplary lungs from control (saline) and Ad5-PPE-1-3X fas-chimera adenovirus vector treated mice. Note the strong, dose dependent inhibition of metastatic development by the Ad5-PPE-1-3X fas-chimera adenovirus vector, as reflected in both the gross morphology and weight of the excised lungs (FIG. 1C);

FIG. 3A represents values for cohort 6. FIG. 3B represents the values for cohorts 6 and 7. Note the lack of correlation between progressive disease (blue), stable disease (red) and the baseline titer of neutralizing antibodies;

FIG. 6A is an abdominal CT scan showing the metastatic lesion (circled) in the liver at 21 days post-administration. FIG. 6B is an abdominal CT scan showing significant regression of the lesion (circled) in the liver at 50 days post-administration. FIG. 6C is an abdominal CT scan showing even greater regression of the lesion (circled) in the liver at 112 days pok-administration;

FIGS. 7A-7C are CT scans from the same series, same subject as in FIGS. 6A-6C, showing the same lesion from a different orientation (CT slice at a different level);

FIG. 10A depicts the survival of a patient with refractory metastatic papillary thyroid cancer, receiving two doses the Ad5-PPE-1-3X fas-chimera adenovirus vector nearly two years apart, and has remained progression-free for most of that time. FIG. 10B shows the progression free survival of a patient with medullary thyroid cancer, who remained stable and progression free when monitored at 120 days after receiving a single dose of the Ad5-PPE-1-3X fas-chimera adenovirus vector. SD=stable disease. PD=progressive disease. PR=partial response;

FIG. 12A is a graph depicting the pharmacokinetics of the Ad5-PPE-1-3X fas-chimera adenovirus vector in blood, from administration to day 56, post-infusion. Whole blood samples of patients receiving $10^{10}$ (♦, solid black line), $3\times10^{10}$ (■, dotted black line), $10^{11}$ (▲, dashed black line), $3\times10^{11}$ (X, solid grey line), $10^{12}$ (■, dotted grey line) and $3\times10^{12}$ (●, dashed grey line) Ad5-PPE-1-3X fas-chimera adenovirus particles were analyzed by RT-PCR at indicated timepoints for adenovirus 5 DNA. Adenovirus levels were reduced by at least two orders of magnitude, or undetectable by day 56. FIG. 12B represents the average levels of adenovirus particles, analyzed by RT-PCR, in whole blood sampled at the end of the infusion with the virus vector;

FIG. 13 A is a histogram of the values in FIG. 13B. Note the enhanced effect of the combination therapy at 80 mg/kg sunitinib, and $10^9$ Ad5-PPE-1-3X fas-chimera virus particles.

Figures 1A, 1B, 1C, 1D:
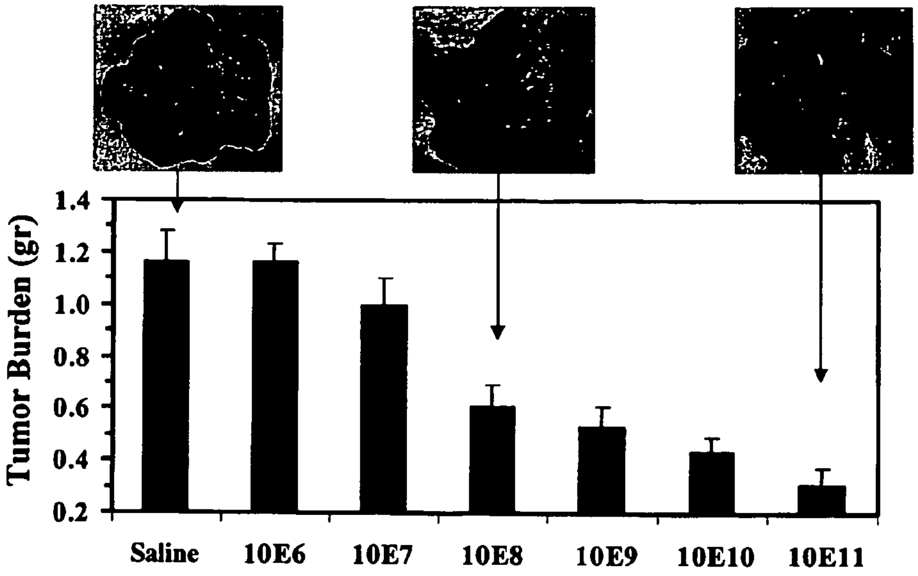
FIG. 1A-1D is a graph with photos illustrating inhibition of metastatic disease by systemic administration of Ad5-PPE-1-3X fas-chimera adenovirus vector in the Lewis Lung Cancer model.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

DESCRIPTION OF SPECIFIC EMBODIMENTS OF THE INVENTION

The present invention, in some embodiments thereof, relates to anti-angiogenic adenovirus vectors, and therapeutic use thereof, and more particularly, but not exclusively, to clinical protocols for treatment of solid tumors in patients with an Ad5-PPE-1-3X-fas-chimera adenovirus vector.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Angiogenesis is required for the development of neoplastic and hyperproliferative growths. Gene therapy for anti-angiogenic therapy in conditions associated with neovascularization, such as cancer, has been investigated, however, despite promising results in in-vitro experiments and in animal models, there has been little success with anti-angiogenic gene therapy in the clinical setting, likely due to obstacles including duration of expression of the transferred gene, induction of host immune response, cytotoxicity of the vectors and tissue specificity of expression.

The present inventors have developed a clinically safe and effective procedure for administration of a therapeutic recombinant adenovirus vector comprising a cytotoxic fas-chimera effector sequence under transcriptional control of an angiogenic endothelial-specific modified murine pre-pro endothelin promoter, which can be used for treatment of a variety of cancers and other hyperproliferative, neovascular-dependent diseases, for example, for solid tumors.

Thus, according to one aspect of the present invention, there is provided a method of treating a solid tumor in a subject in need thereof, the method comprising administering to the subject a therapeutically effective amount of a non-replicating adenovirus vector, said vector comprises a polynucleotide which comprises a fas-chimera transgene transcriptionally linked to a murine pre-proendothelin promoter, wherein said therapeutically effective amount is at least $1\times10^8$ virus particles, thereby treating the solid tumor.

As used herein, the phrases “cancer”, “malignancy”, “solid tumor” or “hyperproliferative disorder” are used as synonymous terms and refer to any of a number of diseases that are characterized by uncontrolled, abnormal proliferation of cells, the ability of affected cells to spread locally or through the bloodstream and lymphatic system to other parts of the body (i.e., metastasize) as well as any of a number of characteristic structural and/or molecular features. A “cancerous” or “malignant cell” or “solid tumor cell” is understood as a cell having specific structural properties, lacking differentiation and being capable of invasion and metastasis. “Cancer” refers to all types of cancer or neoplasm or malignant tumors found in mammals, including carcinomas and sarcomas. Examples are cancers of the breast, lung, non-small cell lung, stomach, brain, head and neck, medulloblastoma, bone, liver, colon, genitourinary, bladder, urinary, kidney, testes, uterus, ovary, cervix, prostate, melanoma, mesothelioma, sarcoma, (see DeVita, et al., (eds.), 2001, Cancer Principles and Practice of Oncology, 6th. Ed., Lippincott Williams & Wilkins, Philadelphia, Pa.; this reference is herein incorporated by reference in its entirety for all purposes).

“Cancer-associated” refers to the relationship of a nucleic acid and its expression, or lack thereof, or a protein and its level or activity, or lack thereof, to the onset of malignancy in a subject cell. For example, cancer can be associated with expression of a particular gene that is not expressed, or is expressed at a lower level, in a normal healthy cell. Conversely, a cancer-associated gene can be one that is not expressed in a malignant cell (or in a cell undergoing transformation), or is expressed at a lower level in the malignant cell than it is expressed in a normal healthy cell.

“Hyperproliferative disease” refers to any disease or disorder in which the cells proliferate more rapidly than normal tissue growth. Thus, a hyperproliferating cell is a cell that is proliferating more rapidly than normal cells.

“Neovascularization” and “angiogenesis” refer to the growth of new blood vessels. Pathological angiogenesis or neovascularization refers to unbalanced new blood vessel growth, including non-self-limiting endothelial and periendothelial cell-proliferation. “Angiogenic diseases” are conditions of unregulated angiogenesis, for example, cancer, ocular neovascularization, arthritis, diabetes, skin diseases, chronic inflammatory diseases such as rheumatoid arthritis, psoriasis and synovitis.

"Advanced cancer" means cancer that is no longer localized to the primary tumor site, or a cancer that is Stage III or IV according to the American Joint Committee on Cancer (AJCC).

"Well tolerated" refers to the absence of adverse changes in health status that occur as a result of the treatment and would affect treatment decisions.

"Metastatic" refers to tumor cells, e.g., human solid tumor or thyroid malignancy, that are able to establish secondary tumor lesions in the lungs, liver, bone or brain of immune deficient mice upon injection into the mammary fat pad and/or the circulation of the immune deficient mouse.

A "solid tumor" includes, but is not limited to, sarcoma, melanoma, carcinoma, or other solid tumor cancer. "Sarcoma" refers to a tumor which is made up of a substance like the embryonic connective tissue and is generally composed of closely packed cells embedded in a fibrillar or homogeneous substance. Sarcomas include, but are not limited to, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

"Melanoma" refers to a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, metastatic melanoma, nodular melanoma, subungal melanoma, and superficial spreading melanoma.

"Carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidernoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma viflosum.

Additional cancers include, for example, Leukemia, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, papillary thyroid cancer, neuroblastoma, neuroendocrine cancer, esophageal cancer, genitourinary tract cancer, malignant hypercalcemia, cervical cancer, endometrial cancer, adrenal cortical cancer, and prostate cancer.

Figure 4:
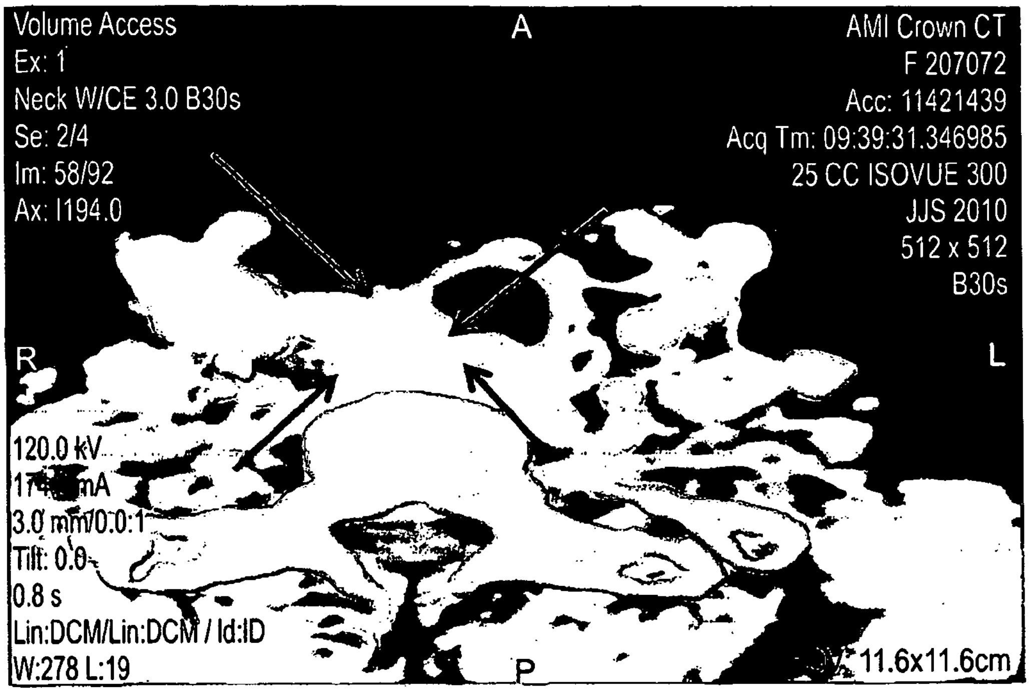
FIG. 4 is a baseline (pre-dose) cervical CT scan of a subject with advanced papillary thyroid cancer who received a single dose ($3\times10^{12}$ virus particles) of Ad5-PPE-1-3X fas-chimera adenovirus vector, demonstrating a paratracheal metastasis causing partial obstruction of the trachea (red arrows)
Figure 5:
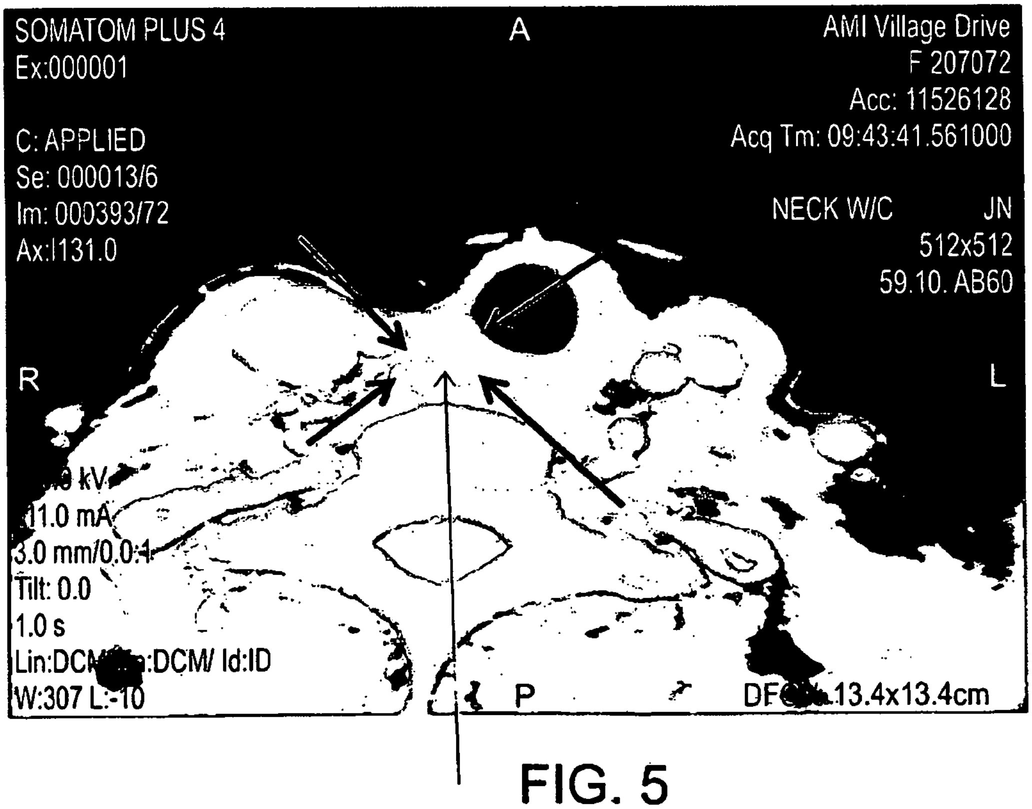
FIG. 5 is a follow-up cervical CT of the same subject as described in FIG. 4, 6 months post-administration of Ad5-PPE-1-3X fas-chimera adenovirus vector, demonstrating regression of the metastatic lesion (red arrows) with central liquefaction (blue arrow)

The present inventors have shown that systemic administration of the Ad5-PPE-1-3X-fas-c adenoviral vector was correlated with a reduction in tumor mass and prolonged stable disease in a patient suffering from metastatic papillary thyroid cancer (see Example II and FIGS. 4 and 5 that follow). Thus, according to one aspect of some embodiments of the present invention there is provided a method for treating a thyroid cancer in a patient in need thereof, the method comprising administering to the subject a single or multiple intravenous dose(s) of $3\times10^{12}$ or $10^{13}$ virus particles of a non-replicating adenovirus vector comprising a polynucleotide having a nucleotide sequence as set forth in SEQ ID NOs: 9 or 10. Disease progression in thyroid cancer can be assessed or monitored by methods including, but not limited to, radiographic analysis of tumor mass and density (e.g. RECIST criteria), measurement of thyroid and thyroid-associated hormone levels, thyroglobulin levels, and the like.

The present inventors have shown that systemic administration of the Ad5-PPE-1-3X-fas-c adenoviral vector was correlated with a reduction in a metastatic hepatic lesion and prolonged stable disease in a patient suffering from metastatic neuroendocrine cancer (see Example II and FIGS. 6A-6C, 7A-7C that follow). Thus, according to one aspect of some embodiments of the present invention there is provided a method for treating a neuroendocrine cancer in a patient in need thereof, the method comprising administering to the subject a single or multiple intravenous dose(s) of $3\times10^{12}$ or $10^{13}$ virus particles of a non-replicating adenovirus vector comprising a polynucleotide having a nucleotide sequence as set forth in SEQ ID NOs: 9 or 10. Methods for assessing or monitoring disease progression in neuroendocrine cancer include radiographic analysis of tumor mass and density (e.g. RECIST criteria), measurement of liver enzyme levels (where the tumor is a liver metastasis), and the like.

The method of the present invention as claimed has been indicated effective in treating other cancers. Thus, according to further aspects of some embodiments of the present invention there is provided a method for treating an ovarian cancer, a non small cell lung cancer and/or a renal cell carcinoma in a patient in need thereof, the method comprising administering to the subject a single or multiple intravenous dose(s) of $3\times10^{12}$ or $10^{13}$ virus particles of a non-replicating adenovirus vector comprising a polynucleotide having a nucleotide sequence as set forth in SEQ ID NOs: 9 or 10. Methods for assessing or monitoring disease progression in these cancers include radiographic analysis of tumor mass and density (e.g. RECIST criteria), measurement of organ function (e.g. kidney function in renal cell carcinoma), measurement of specific biomarkers, endocrine function, and the like.

Contemplated subjects to be treated include mammals—e.g. humans. According to one embodiment the subject has received a prior treatment for the solid tumor (e.g. radiotherapy and/or chemotherapy) and the malignant tumor has relapsed. According to another embodiment, the subject has not received a prior treatment for the malignant tumor.

The phrase “viral vector” refers to a replication-competent or replication-deficient viral particle which is capable of transferring nucleic acid molecules into a host.

The present inventors contemplate use of Replication Defective Vectors and Replication Defective Vector-Producing Packaging Cells. Examples of such vectors are adenoviral vectors, AAV vectors and retroviral vectors and others described in Shir et al, Cellular and Molecular Neurobiology, Vol. 21, No. 6, December 2001, the contents of which are incorporated herein by reference.

The term “virus” refers to any of the obligate intracellular parasites having no protein-synthesizing or energy-generating mechanism. The viral genome may be RNA or DNA contained with a coated structure of protein of a lipid membrane. Examples of viruses useful in the practice of the present invention include baculoviridiae, parvoviridiae, picornoviridiae, herepesviridiae, poxyiridiae, adenoviridiae, picotrnaviridiae. The term recombinant virus includes chimeric (or even multimeric) viruses, i.e. vectors constructed using complementary coding sequences from more than one viral subtype. (See, e.g. Feng, et al. Nature Biotechnology 15:866-870) The term “adenovirus” is synonymous with the term “adenoviral vector” and refers to viruses of the genus adenoviridiae. The term adenoviridiae refers collectively to animal adenoviruses of the genus mastadenovirus including but no limited to human, bovine, ovine, equine, canine, porcine, murine and simian adenovirus subgenera. In particular, human adenoviruses includes the A-F subgenera as well as the individual serotypes thereof the individual serotypes and A-F subgenera including but not limited to human adenovirus types 1, 2, 3, 4, 4a, 5, 6, 7, 8, 9, 10, 11 (Ad11A and Ad 11P), 12, 13, 14, 15, 16, 17, 18, 19, 19a, 20, 21, 22, 23, 24, 25, 26, 27, 28, 29, 30, 31, 32, 33, 34, 34a, 35, 35p, 36, 37, 38, 39, 40, 41, 42, 43, 44, 45, 46, 47, 48, and 91. The term bovine adenoviruses includes but is not limited to bovine adenovirus types 1, 2, 3, 4, 7, and 10. The term canine adenoviruses includes but is not limited to canine types 1 (strains CLL, Glaxo, R1261, Utrect, Toronto 26-61) and 2. The term equine adenoviruses includes but is not limited to equine types 1 and 2. The term porcine adenoviruses includes but is not limited to porcine types 3 and 4. In one embodiment of the invention, the adenovirus is derived from the human adenovirus serotypes 2 or 5. For purposes of this invention, adenovirus vectors can be replication-competent or replication deficient in a target cell. In some embodiments, the adenovirus vectors are conditionally or selectively replicating adenoviruses, wherein a gene[s] required for viral replication is [are] operatively linked to a cell and/or context-specific promoter. Examples of selectively replicating or conditionally replicating viral vectors are known in the art (see, for example, U.S. Pat. No. 7,691,370). In one embodiment, the adenovirus vector is a conditionally replicating adenovirus wherein the E1 gene is under transcriptional control of the pre-proendothelin promoter PPE-1 (PPE-1, SEQ ID NO: 13). In another embodiment, the adenovirus vector is a conditionally replicating or selectively replicating adenovirus wherein the E1 gene is under transcriptional control of the modified pre-proendothelin promoter PPE-1-3X (PPE-1-3X, SEQ ID NO: 12). In some embodiments, adenovirus vectors suitable for use with the present invention include all adenovirus serotypes having hexon protein structure. Viral vectors suitable for therapeutic use include adenoviral vectors, retrovirusal vectors, AAV, herpesvirus vectors and the like. Engineering and production of viral vectors is well known in the art, as described in detail in, for example, U.S. Pat. No. 7,732,129 or 6,649,158, which are incorporated herein by reference, in their entirety. In specific embodiments, the adenovirus is a C-type adenovirus (Ad5, Ad2), a B-type adenovirus (Ad3, Ad16, Ad21, Ad35, Ad50), an E-type adenovirus (Ad4) or an F-type adenovirus (Ad41).

As used herein, the phrase adenoviral vector refers to a vector in which, among the nucleic acid molecules in the viral particle, sequences necessary to function as a viral vector are based on the adenoviral genome.

According to one embodiment the adenoviral vector is a non-replicating serotype 5 (Ad5) adenoviral vector.

According to another embodiment, the adenoviral vector comprises a sequence as set forth in SEQ ID NO: 1 or SEQ ID NO: 11.

It will be appreciated that the present invention also contemplates use of oncolytic viruses which reproduce themselves in cancer cells and subsequently kill the initially infected cells by lysis. Such viruses proceed to infect adjacent cells thus repeating the cycle. Contemplated examples of oncolytic viruses include, but are not limited to Herpes Simplex Virus, conditionally replicative Ads (CRAds) and reoviruses.

Two major strategies for development of CRAd vectors have been developed, mainly focusing on the genetic engineering of the early 1 (E1) genes to restrict virus replication to target cells and to spare normal tissue. Genetic complementation-type (type 1) CRAds, such as Ad524, have a mutation in the immediately early (E1A) or early (E1B) adenoviral region, which is complemented in tumor cells but not in normal cells. In trans complementation-type (type 2) CRAds, virus replication is controlled via a tumor/tissue-specific promoter.

Reovirus is a naturally occurring oncolytic virus that requires activated Ras signaling pathways of tumor cells for its replication. Ras pathways are activated in most malignant tumors via upstream signaling by receptor tyrosine kinases.

As mentioned the viral vectors of this aspect of the present invention comprise a cytotoxic fas-chimera effector sequence under transcriptional control of an angiogenic endothelial-specific modified murine pre-pro endothelin promoter.

Typically, such viral vectors are constructed using genetic recombination technology i.e. recombinant viral vectors.

The Fas-chimera (Fas-c) polypeptide, is a previously described fusion of two "death receptors", constructed from the extracellular region of TNFR1 (SEQ ID NO: 2) and the trans-membrane and intracellular regions of Fas (SEQ ID NO: 3) [Boldin M P et al. J Biol Chem (1995) 270(14): 7795-8; the contents of which are incorporated herein by reference].

According to one embodiment the Fas-c is encoded by a polynucleotide as set forth in SEQ ID NO: 4.

It will be appreciated that the present invention also contemplates use of a viral construct (e.g. an adenoviral construct) comprising an endothelial/periendothelial cell-specific promoter operatively linked to other cytotoxic polypeptides for the treatment of solid tumors.

Such polypeptides, include but are not limited to suicide polypeptides such as p53 and egr-1-TNF-alpha, cytotoxic pro-drug/enzymes for drug susceptibility therapy such as ganciclovir/thymidine kinase and 5-fluorocytosine/cytosine deaminase, and antimetastatic polypeptides such as 5 E1A.

The term "promoter" as used herein refers to a DNA sequence which directs transcription of a polynucleotide sequence operatively linked thereto in the cell in a constitutive or inducible manner. The promoter may also comprise enhancer elements which stimulate transcription from the linked promoter.

The pre-pro endothelial promoter as used herein refers to the preproendothelin-1 (PPE-1) promoter, of mammalian origin. In one embodiment, the pre-proendothelin 1 promoter is a murine pre-pro endothelin 1 promoter (PPE-1, SEQ ID NO: 13) and modifications thereof. It will be appreciated that other endothelial specific promoters can be used with the present invention, for example, the TIE-1 promoter, the TIE-2 promoter, the Endoglin promoter, the von Willerband promoter, the ICDR/flk-1 promoter, The FLT-1 promoter, the Egr-1 promoter, the ICAM-1 promoter, the VCAM-1 promoter, the PECAM-1 promoter and the aortic carboxypeptidase-like protein (ACLP) promoter.

According to one embodiment the promoter comprises at least one copy of an enhancer element that confers endothelial cell specific transcriptional activity. According to one embodiment the enhancer element is naturally found positioned between the −364 bp and −320 bp of the murine PPE-1 promoter (as set forth in SEQ ID NO: 6). In one embodiment, the promoter comprises at least two and more preferably three of the above described enhancer elements. According to a specific embodiment, the promoter comprises two of the above described enhancer elements on one strand of the promoter DNA and one of the above described enhancer element on the complementary strand of the promoter DNA.

In yet another embodiment, the promoter comprises a modified enhancer element as set forth in SEQ ID NO: 8, optionally in combination with other enhancer elements. Thus, according to this embodiment, the promoter comprises a sequence as set forth in SEQ ID NO: 7.

According to another embodiment, the promoter further comprises at least one hypoxia response element—e.g. comprising a sequence as set forth in SEQ ID NO: 5.

An exemplary promoter which can be used in the context of the present invention comprises a sequence as set forth in SEQ ID NO: 12. This sequence comprises SEQ ID NO: 5 and SEQ ID NO: 7 (which itself comprises two copies of SEQ ID NO: 6 either side of one copy of SEQ ID NO: 8).

According to a particular embodiment of this aspect of the present invention, the viral vector consists of a sequence as set forth in SEQ ID NOs: 9 or 10.

The Ad5-PPE-1-3X-fas-c sequence, as set forth in SEQ ID NO: 9 or 10 comprises a sequence which is an anti-sense copy of SEQ ID NO: 7, located at nucleic acid coordinates 894-1036, a sequence which is a single antisense copy of SEQ ID NO: 8 located at nucleotide coordinates 951-997; a sequence which is a first antisense copy of SEQ ID NO: 6 located at nucleotide coordinates 907-950; a sequence which is a second antisense copy of SEQ ID NO: 6 located at nucleotide coordinates 993-1036; and a third copy of SEQ ID NO: 6 in the sense orientation at position 823-866.

In some embodiments of the invention, the viral vector comprises additional polynucleotide sequences capable of enhancing or inhibiting transcriptional activity of an endothelial specific promoter. According to an aspect of some embodiments of the invention, the additional polynucleotide sequence includes an isolated polynucleotide comprising at least 6 nucleotides of element X of a preproendothelin (PPE-1) promoter, the element X having a wild type sequence as set forth by SEQ ID NO:6, wherein the at least 6 nucleotides comprise at least 2 consecutive sequences derived from SEQ ID NO:6, each of the at least 2 consecutive sequences comprises at least 3 nucleotides, at least one of the at least 3 nucleotide being positioned next to at least one nucleotide position in SEQ ID NO:6, the at least one nucleotide position in SEQ ID NO:6 is selected from the group consisting of:

(i) at least one nucleotide of wild type M4 sequence set forth by SEQ ID NO: 15 (CATTC);

(ii) at least one nucleotide of wild type M5 sequence set forth by SEQ ID NO: 16 (CAATG);

(iii) at least one nucleotide of wild type M8 sequence set forth by SEQ ID NO: 19 (GCTTC);

(iv) at least one nucleotide of wild type M6 sequence set forth by SEQ ID NO: 17 (GGGTG);

(v) at least one nucleotide of wild type M7 sequence set forth by SEQ ID NO: 18 (ACTTT);

(vi) at least one nucleotide of wild type M1 sequence set forth by SEQ ID NO: 20 (GTACT); and (v) at least one nucleotide of wild type M3 sequence set forth by SEQ ID NO: 21 (CTTTT);

wherein the at least one nucleotide position is mutated as compared to SEQ ID NO:6 by at least one nucleotide substitution, at least one nucleotide deletion and/or at least one nucleotide insertion, with the proviso that a mutation of the at least one nucleotide position does not result in nucleotides GGTA at position 21-24 of SEQ ID NO:6 and/or in nucleotides CATG at position 29-32 of SEQ ID NO:6, such that when the isolated polynucleotide is integrated into the PPE-1 promoter and placed upstream of a reporter gene (e.g., luciferase coding sequence) the expression level of the reporter gene is upregulated or downregulated as compared to when SEQ ID NO:6 is similarly integrated into the PPE-1 promoter and placed upstream of the reporter gene coding sequence.

According to some embodiments of the invention, the isolated polynucleotide is not naturally occurring in a genome or a whole chromosome sequence of an organism.

As used herein the phrase "naturally occurring" refers to as found in nature, without any man-made modifications.

As described above, the at least 6 nucleotides of element X comprise at least 2 consecutive sequences derived from SEQ ID NO:6.

As used herein the phrase "consecutive sequence derived from SEQ ID NO:6" refers to a nucleic acid sequence (a polynucleotide) in which the nucleotides appear in the same order as in the nucleic acid sequence of SEQ ID NO:6 from which they are derived. It should be noted that the order of nucleotides is determined by the chemical bond (phosphodiester bond) formed between a 3'-OH of a preceding nucleotide and the 5'-phosphate of the following nucleotide.

According to some embodiments of the invention, each of the at least 2 consecutive sequences comprises at least 3 nucleotides, e.g., 3 nucleotides, 4 nucleotides, 5 nucleotides, 6 nucleotides, 7 nucleotides, 8 nucleotides, 9 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, 30 nucleotide, 31 nucleotides, 32 nucleotides, 33 nucleotides, 34 nucleotides, 35 nucleotides, 36 nucleotides, 37 nucleotides, 38 nucleotides, 39 nucleotides, 40 nucleotides, 41 nucleotides of SEQ ID NO:6.

As described, the isolated polynucleotide comprises at least 2 consecutive sequences derived from SEQ ID NO:6. According to some embodiments of the invention, the isolated polynucleotide comprises 2, 3, 4, 5, 6, 7, 8, 9, 10, 11, 12, 13 or 14 consecutive sequences derived from SEQ ID NO:6.

As used herein the phrase "wild type" with respect to a nucleotide sequence refers to the nucleic acid sequence as appears in SEQ ID NO:6. Examples include, but are not limited to wild type M4 sequence (SEQ ID NO: 15), wild type M5 sequence (SEQ ID NO: 16), wild type M8 (SEQ ID NO:19), wild type M6 sequence (SEQ ID NO:17), wild type M7 sequence (SEQ ID NO:18), wild type M1 (SEQ ID NO:20) and wild type M3 sequence (SEQ ID NO:21).

According to some embodiments of the invention, the mutation is an insertion of at least one nucleotide in a nucleotide position with respect to SEQ ID NO:6. According to some embodiments of the invention, the insertion includes at least 1, 2, 3, 4, 5, 6, 7, 8, 9, 10 nucleotides, e.g., at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 200, at least about 300, or more nucleotides.

It should be noted that the sequence which is inserted by the mutation can be derived from any source (e.g., species, tissue or cell type), and is not limited to the source of the sequence of element X.

According to some embodiments of the invention, the mutation is a combination of any of the mutation types described above, i.e., substitution, insertion and deletion. For example, while one nucleotide position in SEQ ID NO:6 can be subject to a substitution mutation, another nucleotide position in SEQ ID NO:6 can be subject to a deletion or insertion. Additionally or alternatively, while one nucleotide position in SEQ ID NO:6 can be subject to a deletion mutation, another nucleotide position in SEQ ID NO:6 can be subject to a substitution or insertion. Additionally or alternatively, while one nucleotide position in SEQ ID NO:6 can be subject to an insertion mutation, another nucleotide position in SEQ ID NO:6 can be subject to a substitution or deletion. It should be noted that various other combinations are possible.

According to specific embodiments of the invention, the mutation in the isolated polynucleotide of the invention does not result in nucleotides GGTA at position 21-24 of SEQ ID NO:6 and/or in nucleotides CATG at position 29-32 of SEQ ID NO:6.

As used herein the phrase "integrated into the PPE-1 promoter" refers to a nucleotide sequence (the isolated polynucleotide) which is covalently conjugated within the PPE-1 promoter sequence.

According to some embodiments of the invention, the isolated polynucleotide further comprises at least one copy of a nucleic acid sequence selected from the group consisting of:

(i) wild type M4 sequence set forth by SEQ ID NO: 15 (CATTC), (ii) wild type M5 sequence set forth by SEQ ID NO: 16 (CAATG), (iii) wild type M8 sequence set forth by SEQ ID NO: 19 (GCTTC), (iv) wild type M6 sequence set forth by SEQ ID NO: 17 (GGGTG), (v) wild type M7 sequence set forth by SEQ ID NO: 18 (ACTTT);

(vi) wild type M1 sequence set forth by SEQ ID NO: 20 (GTACT), and (vii) wild type M3 sequence set forth by SEQ ID NO: 21 (CTTTT).

According to some embodiments of the invention, the isolated polynucleotide is integrated into (within), downstream of, or upstream of any known (or unknown) promoter sequence to thereby regulate (e.g., increase, decrease, modulate tissue-specificity, modulate inductive or constitutive expression) the transcriptional promoting activity of the promoter.

According to some embodiments of the invention, the isolated polynucleotide is for increasing expression of a heterologous polynucleotide operably linked thereto in endothelial cells. Such a polynucleotide can include wild type sequences of M4 and/or M5 in the presence or absence of additional sequences from element X, and/or in the presence of other mutated sequences from element X.

According to some embodiments of the invention, the isolated polynucleotide comprises at least one copy of the wild type M4 sequence set forth by SEQ ID NO: 15 (CATTC).

According to some embodiments of the invention, the isolated polynucleotide comprises at least one copy of the wild type M5 sequence set forth by SEQ ID NO: 16 (CAATG).

According to some embodiments of the invention, the isolated polynucleotide comprises at least one copy of the wild type M4 sequence set forth by SEQ ID NO: 15 (CATTC) and at least one copy of the wild type M5 sequence set forth by SEQ ID NO: 16 (CAATG).

According to some embodiments of the invention, the at least one nucleotide position which is mutated as compared to SEQ ID NO:6 is at least one nucleotide of the wild type M8 sequence set forth by SEQ ID NO: 19 (GCTTC). It should be noted that such an isolated polynucleotide may further include a wild type M6 sequence (SEQ ID NO:17) and/or a wild type M7 sequence (SEQ ID NO:18)

Non-limiting examples of isolated polynucleotides which include at least one copy of the wild type M4 sequence set forth by SEQ ID NO: 15 (CATTC) and a mutation in at least one nucleotide of the wild type M8 sequence set forth by SEQ ID NO: 19 (GCTTC) are provided in SEQ ID NOs: 55-62.

Non-limiting examples of isolated polynucleotides which include at least one copy of the wild type M5 sequence set forth by SEQ ID NO: 16 (CAATG) and a mutation in at least one nucleotide of the wild type M8 sequence set forth by SEQ ID NO: 19 (GCTTC) are provided in SEQ ID NOs: 63-66.

Non-limiting examples of isolated polynucleotides which include at least one copy of the wild type M4 sequence set forth by SEQ ID NO: 15 (CATTC), at least one copy of the wild type M5 sequence set forth by SEQ ID NO: 16 (CAATG) and a mutation in at least one nucleotide of the wild type M8 sequence set forth by SEQ ID NO: 19 (GCTTC) are provided in SEQ ID NOs: 67-70.

According to some embodiments of the invention, the isolated polynucleotide further comprising at least one copy of wild type M1 sequence set forth by SEQ ID NO: (GTACT).

Non-limiting examples of isolated polynucleotides which include at least one copy of the wild type M4 sequence set forth by SEQ ID NO: 15 (CATTC), at least one copy of the wild type M1 sequence set forth by SEQ ID NO: 20 (GTACT), and a mutation in at least one nucleotide of the wild type M8 sequence set forth by SEQ ID NO: 19 (GCTTC) are provided in SEQ ID NOs: 71-105.

Non-limiting examples of isolated polynucleotides which include at least one copy of the wild type M5 sequence set forth by SEQ ID NO: 16 (CAATG), at least one copy of the wild type M1 sequence set forth by SEQ ID NO: 20 (GTACT) and a mutation in at least one nucleotide of the wild type M8 sequence set forth by SEQ ID NO: 19 (GCTTC) are provided in SEQ ID NOs: 106-136.

Non-limiting examples of isolated polynucleotides which include at least one copy of the wild type M4 sequence set forth by SEQ ID NO: 15 (CATTC), at least one copy of the wild type M5 sequence set forth by SEQ ID NO: 16 (CAATG), at least one copy of the wild type M1 sequence set forth by SEQ ID NO: 20 (GTACT) and a mutation in at least one nucleotide of the wild type M8 sequence set forth by SEQ ID NO: 19 (GCTTC) are provided in SEQ ID NOs:137-152.

According to some embodiments of the invention, the isolated polynucleotide reduces expression of a heterologous polynucleotide operably linked thereto in endothelial cells. Such a polynucleotide can include mutations in M4 and/or M5 in the presence or absence of additional sequences from element X, and/or in the presence of other mutated sequences from element X.

According to some embodiments of the invention, the at least one nucleotide position which is mutated as compared to SEQ ID NO:6 is at least one nucleotide of the wild type M4 sequence set forth by SEQ ID NO: 15 (CATTC).

Non-limiting examples of isolated polynucleotides which includes a mutation in at least one nucleotide of the wild type M4 sequence set forth by SEQ ID NO:46 (CATTC) are provided in SEQ ID NOs:153-162.

According to some embodiments of the invention, the at least one nucleotide position which is mutated as compared to SEQ ID NO:6 is at least one nucleotide of the wild type M5 sequence set forth by SEQ ID NO: 16 (CAATG).

Non-limiting examples of isolated polynucleotides which include a mutation in at least one nucleotide of the wild type M5 sequence set forth by SEQ ID NO: 16 (CAATG) are provided in SEQ ID NOs:163-171.

According to some embodiments of the invention, the at least one nucleotide position which is mutated as compared to SEQ ID NO:6 is at least one nucleotide of the wild type M4 sequence set forth by SEQ ID NO: 15 (CATTC) and at least one nucleotide of the wild type M5 sequence set forth by SEQ ID NO: 16 (CAATG).

Non-limiting examples of isolated polynucleotides which include a mutation in at least one nucleotide of the wild type M4 sequence set forth by SEQ ID NO: 15 (CATTC) and a mutation in at least one nucleotide of the wild type M5 sequence set forth by SEQ ID NO: 16 (CAATG) are provided in SEQ ID NOs:172-180.

According to some embodiments of the invention, the isolated polynucleotide is for increasing expression of a heterologous polynucleotide operably linked thereto in cells other than endothelial cells. Such a polynucleotide can include mutations in M4 and/or M5 and wild type sequences of M6 and/or M7, in the presence or absence of additional sequences from element X, and/or in the presence of other mutated sequences from element X.

According to some embodiments of the invention, the isolated polynucleotide comprises a mutation in M4 (SEQ ID NO: 15) and/or in M5 (SEQ ID NO: 16) and at least one copy of the wild type M6 set forth by SEQ ID NO: 17 (GGGTG) and/or at least one copy of wild type M7 set forth by SEQ ID NO:18.

Non-limiting examples of isolated polynucleotides which include a mutation in at least one nucleotide of the wild type M4 sequence set forth by SEQ ID NO: 15 (CATTC) and at least one copy of the wild type M6 set forth by SEQ ID NO: 17 (GGGTG) are provided in SEQ ID NOs:181-182.

Non-limiting examples of isolated polynucleotides which include a mutation in at least one nucleotide of the wild type M5 sequence set forth by SEQ ID NO: 16 (CAATG) and at least one copy of the wild type M6 set forth by SEQ ID NO: 17 (GGGTG) are provided in SEQ ID NOs:183-189.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG) and at least one copy of the wild type M6 set forth by SEQ ID NO: 17 (GGGTG) are provided in SEQ ID NOs:190-191.

According to some embodiments of the invention, the isolated polynucleotide further comprises at least one copy of the wild type M7 sequence set forth by SEQ ID NO: 18 (AC111).

Non-limiting examples of isolated polynucleotides which include a mutation in at least one nucleotide of the wild type M4 sequence set forth by SEQ ID NO: 15 (CATTC) and at least one copy of the wild type M7 sequence set forth by SEQ ID NO: 18 (ACTTT) are provided in SEQ ID NOs: 192-195.

Non-limiting examples of isolated polynucleotides which include a mutation in at least one nucleotide of the wild type M5 sequence set forth by SEQ ID NO: 16 (CAATG) and at least one copy of the wild type M7 sequence set forth by SEQ ID NO: 18 (ACTTT) are provided in SEQ ID NOs: 196-198.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG) and at least one copy of the wild type M7 sequence set forth by SEQ ID NO: 18 (ACTTT) are provided in SEQ ID NOs:199-202.

According to some embodiments of the invention, the isolated polynucleotide further comprises at least one copy of the wild type M6 set forth by SEQ ID NO: 17 (GGGTG) and at least one copy of the wild type M7 sequence set forth by SEQ ID NO: 18 (AC111).

Non-limiting examples of isolated polynucleotides which include a mutation in at least one nucleotide of the wild type M4 sequence set forth by SEQ ID NO: 15 (CATTC), at least one copy of the wild type M6 set forth by SEQ ID NO: 17 (GGGTG) and at least one copy of the wild type M7 sequence set forth by SEQ ID NO: 18 (ACITT) are provided in SEQ ID NOs:203-205.

Non-limiting examples of isolated polynucleotides which include a mutation in at least one nucleotide of the wild type M5 sequence set forth by SEQ ID NO: 16 (CAATG), at least one copy of the wild type M6 set forth by SEQ ID NO: 17 (GGGTG) and at least one copy of the wild type M7 sequence set forth by SEQ ID NO: 18 (ACM) are provided in SEQ ID NOs:206-207.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), at least one copy of the wild type M6 set forth by SEQ ID NO: 17 (GGGTG) and at least one copy of the wild type M7 sequence set forth by SEQ ID NO: 18 (ACTTT) are provided in SEQ ID NOs:208-209.

According to some embodiments of the invention, the isolated polynucleotide reduces expression in cells of a heterologous polynucleotide operably linked thereto. Such a polynucleotide can include mutations in M4, M5, M6 and/or M7, in the presence or absence of additional sequences from element X, and/or in the presence of other mutated sequences from element X.

According to some embodiments of the invention, the isolated polynucleotide comprises at least one mutation in wild type M4 (SEQ ID NO: 15) and/or in wild type M5 (SEQ ID NO:47) and in wild type M6 set forth by SEQ ID NO: 17 (GGGTG).

Non-limiting examples of isolated polynucleotides which include a mutation in at least one nucleotide of the wild type M4 sequence set forth by SEQ ID NO: 15 (CATTC) and a mutation in at least one nucleotide position of the wild type M6 set forth by SEQ ID NO: 17 (GGGTG) are provided in SEQ ID NOs:210-213.

Non-limiting examples of isolated polynucleotides which include a mutation in at least one nucleotide of the wild type M5 sequence set forth by SEQ ID NO: 16 (CAATG) and a mutation in at least one nucleotide position of the wild type M6 set forth by SEQ ID NO: 17 (GGGTG) are provided in SEQ ID NOs:214-222.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), and a mutation in at least one nucleotide position of the wild type M6 set forth by SEQ ID NO: 17 (GGGTG) are provided in SEQ ID NOs:223-231.

According to some embodiments of the invention, the isolated polynucleotide further comprises at least one mutation in wild type M7 set forth by SEQ ID NO: 18 (ACTTT).

Non-limiting examples of isolated polynucleotides which include a mutation in at least one nucleotide of the wild type M4 sequence set forth by SEQ ID NO: 15 (CATTC) and a mutation in at least one nucleotide position of the wild type M7 set forth by SEQ ID NO: 18 (ACTTT) are provided in SEQ ID NOs:232-236.

Non-limiting examples of isolated polynucleotides which include a mutation in at least one nucleotide of the wild type M5 sequence set forth by SEQ ID NO: 16 (CAATG) and a mutation in at least one nucleotide position of the wild type M7 set forth by SEQ ID NO: 18 (ACTTT) are provided in SEQ ID NOs:237-240.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), and a mutation in at least one nucleotide position of the wild type M7 set forth by SEQ ID NO: 18 (ACTTT) are provided in SEQ ID NOs:241-248.

According to some embodiments of the invention, the isolated polynucleotide further comprises at least one mutation in wild type M6 set forth by SEQ ID NO: 17 (GGGTG) and at least one mutation in wild type M7 set forth by SEQ ID NO: 18 (ACTTT).

Non-limiting examples of isolated polynucleotides which include a mutation in at least one nucleotide of the wild type M4 sequence set forth by SEQ ID NO: 15 (CATTC), a mutation in at least one nucleotide position of the wild type M6 set forth by SEQ ID NO: 17 (GGGTG) and a mutation in at least one nucleotide position of the wild type M7 set forth by SEQ ID NO: 18 (ACTTT) are provided in SEQ ID NOs:249-258.

Non-limiting examples of isolated polynucleotides which include a mutation in at least one nucleotide of the wild type M5 sequence set forth by SEQ ID NO: 16 (CAATG), a mutation in at least one nucleotide position of the wild type M6 set forth by SEQ ID NO: 17 (GGGTG) and a mutation in at least one nucleotide position of the wild type M7 set forth by SEQ ID NO: 18 (ACTTT) are provided in SEQ ID NOs:259-264.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), a mutation in at least one nucleotide position of the wild type M6 set forth by SEQ ID NO: 17 (GGGTG) and a mutation in at least one nucleotide position of the wild type M7 set forth by SEQ ID NO: 18 (ACTTT) are provided in SEQ ID NOs:265-270.

According to some embodiments of the invention, the isolated polynucleotide comprises at least one copy of the wild type M8 sequence set forth by SEQ ID NO: 19 (GCTTC) with additional wild type or mutated sequences derived from element X (SEQ ID NO:6).

Non-limiting examples of isolated polynucleotides which includes a mutation in at least one nucleotide of the wild type M4 sequence set forth by SEQ ID NO: 15 (CATTC) and at least one copy of the wild type M8 sequence set forth by SEQ ID NO: 19 (GCTTC) are provided in SEQ ID NOs: 271-279.

Non-limiting examples of isolated polynucleotides which include a mutation in at least one nucleotide of the wild type M5 sequence set forth by SEQ ID NO: 16 (CAATG) and at least one copy of the wild type M8 sequence set forth by SEQ ID NO: 19 (GCTTC) are provided in SEQ ID NOs: 280-287.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG) and at least one copy of the wild type M8 sequence set forth by SEQ ID NO: 19 (GCTTC) are provided in SEQ ID NOs:288-291.

Non-limiting examples of isolated polynucleotides which include a mutation in at least one nucleotide of the wild type M4 sequence set forth by SEQ ID NO: 15 (CATTC), at least one copy of the wild type M6 set forth by SEQ ID NO: 17 (GGGTG) and at least one copy of the wild type M8 sequence set forth by SEQ ID NO: 19 (GCrTC) are provided in SEQ ID NOs:294-298.

Non-limiting examples of isolated polynucleotides which include a mutation in at least one nucleotide of the wild type M5 sequence set forth by SEQ ID NO: 16 (CAATG), at least one copy of the wild type M6 set forth by SEQ ID NO: 17 (GGGTG) and at least one copy of the wild type M8 sequence set forth by SEQ ID NO: 19 (GCTTC) are provided in SEQ ID NOs:299-301.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), at least one copy of the wild type M6 set forth by SEQ ID NO: 17 (GGGTG) and at least one copy of the wild type M8 sequence set forth by SEQ ID NO: 19 (GCTTC) are provided in SEQ ID NOs:302-303.

Non-limiting examples of isolated polynucleotides which include a mutation in at least one nucleotide of the wild type M4 sequence set forth by SEQ ID NO: 15 (CATTC), at least one copy of the wild type M7 sequence set forth by SEQ ID NO: 18 (ACITI) and at least one copy of the wild type M8 sequence set forth by SEQ ID NO: 19 (GCTTC) are provided in SEQ ID NOs:304-308.

Non-limiting examples of isolated polynucleotides which include a mutation in at least one nucleotide of the wild type M5 sequence set forth by SEQ ID NO: 16 (CAATG), at least one copy of the wild type M7 sequence set forth by SEQ ID NO: 18 (ACTTT) and at least one copy of the wild type M8 sequence set forth by SEQ ID NO: 19 (GCTTC) are provided in SEQ ID NOs:309-311.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), at least one copy of the wild type M7 sequence set forth by SEQ ID NO: 18 (ACTTT) and at least one copy of the wild type M8 sequence set forth by SEQ ID NO: 19 (GCTTC) are provided in SEQ ID NOs:312-315.

Non-limiting examples of isolated polynucleotides which include a mutation in at least one nucleotide of the wild type M4 sequence set forth by SEQ ID NO: 15 (CATTC), at least one copy of the wild type M6 set forth by SEQ ID NO: 17 (GGGTG), at least one copy of the wild type M7 sequence set forth by SEQ ID NO: 18 (ACM) and at least one copy of the wild type M8 sequence set forth by SEQ ID NO: 19 (GCTTC) are provided in SEQ ID NO:316.

Non-limiting examples of isolated polynucleotides which include a mutation in at least one nucleotide of the wild type M5 sequence set forth by SEQ ID NO: 16 (CAATG), at least one copy of the wild type M6 set forth by SEQ ID NO: 17 (GGGTG), at least one copy of the wild type M7 sequence set forth by SEQ ID NO: 18 (ACM) and at least one copy of the wild type M8 sequence set forth by SEQ 113 NO: 19 (GCTTC) are provided in SEQ ID NO:317.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), at least one copy of the wild type M6 set forth by SEQ ID NO: 17 (GGGTG), at least one copy of the wild type M7 sequence set forth by SEQ ID NO: 18 (Aerro and at least one copy of the wild type M8 sequence set forth by SEQ ID NO: 19 (GCTTC) are provided in SEQ ID NO:318.

Non-limiting examples of isolated polynucleotides which include a mutation in at least one nucleotide of the wild type M4 sequence set forth by SEQ ID NO: 15 (CATTC), a mutation in at least one nucleotide position of the wild type M6 set forth by SEQ ID NO: 17 (GGGTG) and at least one copy of the wild type M8 sequence set forth by SEQ ID NO: 19 (GCTTC) are provided in SEQ ID NOs:319-327.

Non-limiting examples of isolated polynucleotides which include a mutation in at least one nucleotide of the wild type M5 sequence set forth by SEQ ID NO: 16 (CAATG), a mutation in at least one nucleotide position of the wild type M6 set forth by SEQ ID NO: 17 (GGGTG) and at least one copy of the wild type M8 sequence set forth by SEQ ID NO: 19 (GCTTC) are provided in SEQ ID NOs:328-333.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), a mutation in at least one nucleotide position of the wild type M6 set forth by SEQ ID NO: 17 (GGGTG) and at least one copy of the wild type M8 sequence set forth by SEQ ID NO: 19 (GCTTC) are provided in SEQ ID NOs:334-337.

Non-limiting examples of isolated polynucleotides which include a mutation in at least one nucleotide of the wild type M4 sequence set forth by SEQ ID NO: 15 (CATTC), a mutation in at least one nucleotide position of the wild type M7 set forth by SEQ ID NO: 18 (ACTTT) and at least one copy of the wild type M8 sequence set forth by SEQ ID NO: 19 (GCTTC) are provided in SEQ ID NOs:338-344.

Non-limiting examples of isolated polynucleotides which include a mutation in at least one nucleotide of the wild type M5 sequence set forth by SEQ ID NO: 16 (CAATG), a mutation in at least one nucleotide position of the wild type M7 set forth by SEQ ID NO: 18 (ACTTT) and at least one copy of the wild type M8 sequence set forth by SEQ ID NO: 19 (GCTTC) are provided in SEQ ID NOs:345-348.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), a mutation in at least one nucleotide position of the wild type M7 set forth by SEQ ID NO: 18 (ACTTT) and at least one copy of the wild type M8 sequence set forth by SEQ ID NO: 19 (GCTTC) are provided in SEQ ID NOs:349-354.

Non-limiting examples of isolated polynucleotides which include a mutation in at least one nucleotide of the wild type M4 sequence set forth by SEQ ID NO: 15 (CATTC), a mutation in at least one nucleotide position of the wild type M6 set forth by SEQ ID NO: 17 (GGGTG), a mutation in at least one nucleotide position of the wild type M7 set forth by SEQ ID NO: 18 (ACTTT) and at least one copy of the wild type M8 sequence set forth by SEQ ID NO: 19 (GCTTC) are provided in SEQ ID NOs:355-361.

Non-limiting examples of isolated polynucleotides which include a mutation in at least one nucleotide of the wild type M5 sequence set forth by SEQ ID NO: 16 (CAATG), a mutation in at least one nucleotide position of the wild type M6 set forth by SEQ ID NO: 17 (GGGTG), a mutation in at least one nucleotide position of the wild type M7 set forth by SEQ ID NO: 18 (ACM) and at least one copy of the wild type M8 sequence set forth by SEQ ID NO: 19 (GCTTC) are provided in SEQ ID NOs:362-365.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), a mutation in at least one nucleotide position of the wild type M6 set forth by SEQ ID NO: 17 (GGGTG), a mutation in at least one nucleotide position of the wild type M7 set forth by SEQ ID NO: 18 (ACITT) and at least one copy of the wild type M8 sequence set forth by SEQ ID NO: 19 (GCTTC) are provided in SEQ ID NOs:366-369.

According to some embodiments of the invention, the isolated polynucleotide comprises at least one copy of the wild type M3 sequence set forth by SEQ ID NO: 21 (CTTIT) with additional wild type or mutated sequences derived from element X (SEQ ID NO:6).

Non-limiting examples of isolated polynucleotides which includes a mutation in at least one nucleotide of the wild type M4 sequence set forth by SEQ ID NO: 15 (CATTC) and at least one copy of the wild type M3 sequence set forth by SEQ ID NO: 21 (CMT) are provided in SEQ ID NOs:378-384.

Non-limiting examples of isolated polynucleotides which include a mutation in at least one nucleotide of the wild type M5 sequence set forth by SEQ ID NO: 16 (CAATG) and at least one copy of the wild type M3 sequence set forth by SEQ ID NO: 21 (CTTTT) are provided in SEQ ID NOs: 628-634.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG) and at least one copy of the wild type M3 sequence set forth by SEQ ID NO: 21 (CTTTT) are provided in SEQ ID NOs:370-377.

Non-limiting examples of isolated polynucleotides which include a mutation in at least one nucleotide of the wild type M4 sequence set forth by SEQ ID NO: 15 (CATTC), at least one copy of the wild type M6 set forth by SEQ ID NO: 17 (GGGTG) and at least one copy of the wild type M3 sequence set forth by SEQ ID NO: 21 (CTTTT) are provided in SEQ ID NOs:385-390.

Non-limiting examples of isolated polynucleotides which include a mutation in at least one nucleotide of the wild type M5 sequence set forth by SEQ ID NO: 16 (CAATG), at least one copy of the wild type M6 set forth by SEQ ID NO: 17 (GGGTG) and at least one copy of the wild type M3 sequence set forth by SEQ ID NO: 21 (CTTTT) are provided in SEQ ID NOs:391-396.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), at least one copy of the wild type M6 set forth by SEQ ID NO: 17 (GGGTG) and at least one copy of the wild type M3 sequence set forth by SEQ ID NO: 21 (CTTTT) are provided in SEQ ID NOs:397-401.

Non-limiting examples of isolated polynucleotides which include a mutation in at least one nucleotide of the wild type M4 sequence set forth by SEQ ID NO: 15 (CATTC), at least one copy of the wild type M7 sequence set forth by SEQ ID NO: 18 (ACTTT) and at least one copy of the wild type M3 sequence set forth by SEQ ID NO: 21 (CTTTT) are provided in SEQ ID NOs:402-409.

Non-limiting examples of isolated polynucleotides which include a mutation in at least one nucleotide of the wild type M5 sequence set forth by SEQ ID NO: 16 (CAATG), at least one copy of the wild type M7 sequence set forth by SEQ ID NO: 18 (ACTTT) and at least one copy of the wild type M3 sequence set forth by SEQ ID NO: 21 (CTTTT) are provided in SEQ ID NOs:410-417.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), at least one copy of the wild type M7 sequence set forth by SEQ ID NO: 18 (ACTTT) and at least one copy of the wild type M3 sequence set forth by SEQ ID NO: 21 (cirro are provided in SEQ ID NOs:418-423.

Non-limiting examples of isolated polynucleotides which include a mutation in at least one nucleotide of the wild type M4 sequence set forth by SEQ ID NO: 15 (CATTC), at least one copy of the wild type M6 set forth by SEQ ID NO: 17 (GGGTG), at least one copy of the wild type M7 sequence set forth by SEQ ID NO: 18 (ACTTT) and at least one copy of the wild type M3 sequence set forth by SEQ ID NO: 21 (CTTTT) are provided in SEQ ID NOs:424-425.

Non-limiting examples of isolated polynucleotides which include a mutation in at least one nucleotide of the wild type M5 sequence set forth by SEQ ID NO: 16 (CAATG), at least one copy of the wild type M6 set forth by SEQ ID NO: 17 (GGGTG), at least one copy of the wild type M7 sequence set forth by SEQ ID NO: 18 (ACTTT) and at least one copy of the wild type M3 sequence set forth by SEQ ID NO: 21 (CTTTT) are provided in SEQ ID NOs:538-540.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), at least one copy of the wild type M6 set forth by SEQ ID NO: 17 (GGGTG), at least one copy of the wild type M7 sequence set forth by SEQ ID NO: 18 (ACTTT) and at least one copy of the wild type M3 sequence set forth by SEQ ID NO: 21 (CTTTT) are provided in SEQ ID NO:426.

Non-limiting examples of isolated polynucleotides which include a mutation in at least one nucleotide of the wild type M4 sequence set forth by SEQ ID NO: 15 (CATTC), a mutation in at least one nucleotide position of the wild type M6 set forth by SEQ ID NO: 17 (GGGTG) and at least one copy of the wild type M3 sequence set forth by SEQ ID NO: 21 (CITTT) are provided in SEQ ID NOs:427-435.

Non-limiting examples of isolated polynucleotides which include a mutation in at least one nucleotide of the wild type M5 sequence set forth by SEQ ID NO: 16 (CAATG), a mutation in at least one nucleotide position of the wild type M6 set forth by SEQ ID NO: 17 (GGGTG) and at least one copy of the wild type M3 sequence set forth by SEQ ID NO: 21 (CTTTT) are provided in SEQ ID NOs:436-444.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), a mutation in at least one nucleotide position of the wild type M6 set forth by SEQ ID NO: 17 (GGGTG) and at least one copy of the wild type M3 sequence set forth by SEQ ID NO: 21 (CTTTT) are provided in SEQ ID NOs:445-451.

Non-limiting examples of isolated polynucleotides which include a mutation in at least one nucleotide of the wild type M4 sequence set forth by SEQ ID NO: 15 (CATTC), a mutation in at least one nucleotide position of the wild type M7 set forth by SEQ ID NO: 18 (ACTTT) and at least one copy of the wild type M3 sequence set forth by SEQ ID NO: 21 (CTTTT) are provided in SEQ ID NOs:452-458.

Non-limiting examples of isolated polynucleotides which include a mutation in at least one nucleotide of the wild type M5 sequence set forth by SEQ ID NO: 16 (CAATG), a mutation in at least one nucleotide position of the wild type M7 set forth by SEQ ID NO: 18 (ACTTT) and at least one copy of the wild type M3 sequence set forth by SEQ ID NO: 21 (CTTTT) are provided in SEQ ID NOs:459-465.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), a mutation in at least one nucleotide position of the wild type M7 set forth by SEQ ID NO: 18 (ACTTT) and at least one copy of the wild type M3 sequence set forth by SEQ ID NO: 21 (CTTTT) are provided in SEQ ID NO:466.

Non-limiting examples of isolated polynucleotides which include a mutation in at least one nucleotide of the wild type M4 sequence set forth by SEQ ID NO: 15 (CATTC), a mutation in at least one nucleotide position of the wild type M6 set forth by SEQ ID NO: 17 (GGGTG), a mutation in at least one nucleotide position of the wild type M7 set forth by SEQ ID NO: 18 (ACTTT) and at least one copy of the wild type M3 sequence set forth by SEQ ID NO: 21 (CTTTT) are provided in SEQ ID NOs:467-471.

Non-limiting examples of isolated polynucleotides which include a mutation in at least one nucleotide of the wild type M5 sequence set forth by SEQ ID NO: 16 (CAATG), a mutation in at least one nucleotide position of the wild type M6 set forth by SEQ ID NO: 17 (GGGTG), a mutation in at least one nucleotide position of the wild type M7 set forth by SEQ ID NO: 18 (ACTTT) and at least one copy of the wild type M3 sequence set forth by SEQ ID NO: 21 (CTTTT) are provided in SEQ ID NOs:472-477.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), a mutation in at least one nucleotide position of the wild type M6 set forth by SEQ ID NO: 17 (GGGTG), a mutation in at least one nucleotide position of the wild type M7 set forth by SEQ ID NO: 18 (ACTTT) and at least one copy of the wild type M3 sequence set forth by SEQ ID NO: 21 (CTTTT) are provided in SEQ ID NOs:478-483.

According to some embodiments of the invention, the isolated polynucleotide further comprises at least one copy of the wild type M8 sequence set forth by SEQ ID NO: 19 (GCTTC) and at least one copy of the wild type M3 sequence set forth by SEQ ID NO: 21 (CTTTT) with additional wild type or mutated sequences derived from element X (SEQ ID NO:6).

Non-limiting examples of isolated polynucleotides which includes a mutation in at least one nucleotide of the wild type M4 sequence set forth by SEQ ID NO: 15 (CATTC), at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NOs:484-495.

Non-limiting examples of isolated polynucleotides which include a mutation in at least one nucleotide of the wild type M5 sequence set forth by SEQ ID NO: 16 (CAATG), at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NOs:496-507.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NOs:508-515.

Non-limiting examples of isolated polynucleotides which include a mutation in at least one nucleotide of the wild type M4 sequence set forth by SEQ ID NO: 15 (CATTC), at least one copy of the wild type M6 set forth by SEQ ID NO: 17 (GGGTG), at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NOs:516-519.

Non-limiting examples of isolated polynucleotides which include a mutation in at least one nucleotide of the wild type M5 sequence set forth by SEQ ID NO: 16 (CAATG), at least one copy of the wild type M6 set forth by SEQ ID NO: 17 (GGGTG), at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NOs:520-523.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), at least one copy of the wild type M6 set forth by SEQ ID NO: 17 (GGGTG), at least one copy of the wild type M8 sequence set forth by SEQ ID NO: 19 (GCTTC), and at least one copy of the wild type M3 sequence set forth by SEQ ID NO: 21 (CTTTT) are proyided in SEQ ID NOs:524-525.

Non-limiting examples of isolated polynucleotides which include a mutation in at least one nucleotide of the wild type M4 sequence set forth by SEQ ID NO: 15 (CATTC), at least one copy of the wild type M7 sequence set forth by SEQ ID NO: 18 (ACTTT), at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NOs:526-529.

Non-limiting examples of isolated polynucleotides which include a mutation in at least one nucleotide of the wild type M5 sequence set forth by SEQ ID NO: 16 (CAATG), at least one copy of the wild type M7 sequence set forth by SEQ ID NO: 18 (ACTTT), at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NOs:530-533.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), at least one copy of the wild type M7 sequence set forth by SEQ ID NO: 18 (ACTTT), at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NOs:534-535.

Non-limiting examples of isolated polynucleotides which include a mutation in at least one nucleotide of the wild type M4 sequence set forth by SEQ ID NO: 15 (CATTC), at least one copy of the wild type M6 set forth by SEQ ID NO: 17 (GGGTG), at least one copy of the wild type M7 sequence set forth by SEQ ID NO: 18 (ACTTT), at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NOs:536-537.

Non-limiting examples of isolated polynucleotides which include a mutation in at least one nucleotide of the wild type M5 sequence set forth by SEQ ID NO: 16 (CAATG), at least one copy of the wild type M6 set forth by SEQ ID NO: 17 (GGGTG), at least one copy of the wild type M7 sequence set forth by SEQ ID NO: 18 (ACTTT) at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NOs:538-539.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), at least one copy of the wild type M6 set forth by SEQ ID NO: 17 (GGGTG), at least one copy of the wild type M7 sequence set forth by SEQ ID NO: 18 (ACTTT), at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NO:540.

Non-limiting examples of isolated polynucleotides which include a mutation in at least one nucleotide of the wild type M4 sequence set forth by SEQ ID NO: 15 (CATTC), a mutation in at least one nucleotide position of the wild type M6 set forth by SEQ ID NO: 17 (GGGTG), at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NOs:541-547.

Non-limiting examples of isolated polynucleotides which include a mutation in at least one nucleotide of the wild type M5 sequence set forth by SEQ ID NO: 16 (CAATG), a mutation in at least one nucleotide position of the wild type M6 set forth by SEQ ID NO: 17 (GGGTG), at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NOs:548-554.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), a mutation in at least one nucleotide position of the wild type M6 set forth by SEQ ID NO: 17 (GGGTG), at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NOs:555-559.

Non-limiting examples of isolated polynucleotides which include a mutation in at least one nucleotide of the wild type M4 sequence set forth by SEQ ID NO: 15 (CATTC), a mutation in at least one nucleotide position of the wild type M7 set forth by SEQ ID NO: 18 (ACTTT), at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NOs:560-566.

Non-limiting examples of isolated polynucleotides which include a mutation in at least one nucleotide of the wild type M5 sequence set forth by SEQ ID NO: 16 (CAATG), a mutation in at least one nucleotide position of the wild type M7 set forth by SEQ ID NO: 18 (ACTTT), at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NOs:567-573.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), a mutation in at least one nucleotide position of the wild type M7 set forth by SEQ ID NO: 18 (ACTTT), at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NOs:574-578.

Non-limiting examples of isolated polynucleotides whith include a mutation in at least one nucleotide of the wild type M4 sequence set forth by SEQ ID NO: 15 (CATTC), a mutation in at least one nucleotide position of the wild type M6 set forth by SEQ ID NO: 17 (GGGTG), a mutation in at least one nucleotide position of the wild type M7 set forth by SEQ ID NO: 18 (ACTTT), at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NOs: 579-583.

Non-limiting examples of isolated polynucleotides which include a mutation in at least one nucleotide of the wild type M5 sequence set forth by SEQ ID NO: 16 (CAATG), a mutation in at least one nucleotide position of the wild type M6 set forth by SEQ ID NO: 17 (GGGTG), a mutation in at least one nucleotide position of the wild type M7 set forth by SEQ ID NO: 18 (ACTTT), at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NOs: 584-588.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), a mutation in at least one nucleotide position of the wild type M6 set forth by SEQ ID NO: 17 (GGGTG), a mutation in at least one nucleotide position of the wild type M7 set forth by SEQ ID NO: 18 (ACTTT), at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NOs:589-592.

According to some embodiments of the invention, the isolated polynucleotide comprises at least one-copy of wild type M3 sequence (SEQ ID NO: 21) and at least one copy of wild type M8 sequence (SEQ ID NO: 19), with at least one mutation in wild type M6 (SEQ ID NO: 17) and/or in wild type M7 (SEQ ID NO:50).

Non-limiting examples of isolated polynucleotides which include at least one copy of the wild type M8 sequence set forth by SEQ ID NO: 19 (GCTTC) and at least one copy of the wild type M3 sequence set forth by SEQ ID NO: 21 (CTTTT), with a mutation in at least one nucleotide of the wild type M6 sequence (SEQ ID NO: 17), and/or a mutation in at least one nucleotide of the wild type M7 (SEQ ID NO: 18) are provided in SEQ ID NOs:593-600.

The present inventors have envisaged that an isolated polynucleotide which includes the wild type M8 sequence (SEQ ID NO: 19) and/or the wild type M3 (SEQ ID NO: 21) sequence in addition to tissue specific enhancers (e.g., wild type M4 and/or wild type M5), and/or induced enhancers (e.g., developmentally related- or stress related-enhancers) is expected to exert a more specific regulatory effect by suppressing expression in non-target cells or under non-induced conditions.

According to some embodiments of the invention, the isolated polynucleotide comprises at least one copy of the wild type M8 sequence set forth by SEQ ID NO: 19 (GCTTC) and an endothelial specific enhancer sequence.

According to some embodiments of the invention, the isolated polynucleotide comprises at least one copy of the wild type M8 sequence set forth by SEQ ID NO: 19 (GCTTC) and at least one copy of wild type M4 sequence set forth by SEQ ID NO: 15.

According to some embodiments of the invention, the isolated polynucleotide comprises at least one copy of the wild type M8 sequence set forth by SEQ ID NO: 19 (GCTTC) and at least one copy of wild type M5 sequence set forth by SEQ ID NO:16.

According to some embodiments of the invention, the isolated polynucleotide comprises at least one copy of the wild type M8 sequence set forth by SEQ ID NO: 19 (GCTTC), at least one copy of wild type M4 sequence set forth by SEQ ID NO: 15 and at least one copy of wild type M5 sequence set forth by SEQ ID NO:16.

According to some embodiments of the invention, the isolated polynucleotide comprises at least one copy of the wild type M3 sequence set forth by SEQ ID NO: 21 (CTTTT) and an endothelial specific enhancer sequence.

According to some embodiments of the invention, the isolated polynucleotide comprises at least one copy of the wild type M3 sequence set forth by SEQ ID NO: 21 (CTTTT) and at least one copy of wild type M4 sequence set forth by SEQ ID NO: 15.

According to some embodiments of the invention, the isolated polynucleotide comprises at least one copy of the wild type M3 sequence set forth by SEQ ID NO: 21 (CTTTT) and at least one copy of wild type M5 sequence set forth by SEQ ID NO:16.

According to some embodiments of the invention, the isolated polynucleotide comprises at least one copy of the wild type M3 sequence set forth by SEQ ID NO: 21 (CTTTT), at least one copy of wild type M4 sequence set forth by SEQ ID NO: 15 and at least one copy of wild type M5 sequence set forth by SEQ ID NO:16.

According to some embodiments of the invention, the isolated polynucleotide comprises at least one copy of the wild type M3 sequence set forth by SEQ ID NO: 21 (CTTTT), at least one copy of wild type M8 sequence set forth by SEQ ID NO: 19 (GCTTC) and an endothelial specific enhancer sequence.

According to some embodiments of the invention, the isolated polynucleotide comprises at least one copy of the wild type M3 sequence set forth by SEQ ID NO: 21 (CTTTT), at least one copy of wild type M8 sequence set forth by SEQ ID NO: 19 (GCTTC) and at least one copy of wild type M4 sequence set forth by SEQ ID NO: 15.

According to some embodiments of the invention, the isolated polynucleotide comprises at least one copy of the wild type M3 sequence set forth by SEQ ID NO: 21 (CTTTT), at least one copy of wild type M8 sequence set forth by SEQ ID NO: 19 (GCTTC) and at least one copy of wild type M5 sequence set forth by SEQ ID NO: 16.

According to some embodiments of the invention, the isolated polynucleotide comprises at least one copy of the wild type M3 sequence set forth by SEQ ID NO: 21 (CTTTT), at least one copy of wild type M8 sequence set forth by SEQ ID NO: 19 (GCTTC), at least one copy of wild type M4 sequence set forth by SEQ ID NO: 15 and at least one copy of wild type M5 sequence set forth by SEQ ID NO: 16.

According to some embodiments of the invention, the isolated polynucleotide comprises at least one copy of the wild type M3 sequence set forth by SEQ ID NO: 21 (CTTTT), at least one copy of wild type M8 sequence set forth by SEQ ID NO: 19 (GCTTC) and at least one enhancer element such as wild type M6 (SEQ ID NO: 17) and/or wild type M7 sequence (SEQ ID NO:18).

According to some embodiments of the invention, the isolated polynucleotide includes at least one copy of wild type M8 with additional flanking sequences such as at least one copy of a wild type M8 sequence (SEQ ID NO:19), at least one copy of wild type M7 (SEQ ID NO: 18) and/or wild type M9 sequence (SEQ ID NO: 14, CTGGA); and/or the isolated polynucleotide includes at least one copy of wild type M8 and at least one mutation in M7, with or without M9 (SEQ ID NO: 22). Such polynucleotides can be used as a non-specific repressor.

According to some embodiments of the invention, the isolated polynucleotide is for increasing expression of a heterologous polynucleotide operably linked thereto in cells/tissues.

According to some embodiments of the invention, the isolated polynucleotide comprises at least one copy of wild type M6 sequence set forth by SEQ ID NO: 17 (GGGTG) and/or at least one copy of wild type M7 sequence set forth by SEQ ID NO: 18 (ACTTT).

According to some embodiments of the invention, the isolated polynucleotide includes at least one copy of wild type M6 (SEQ ID NO: 17) and a mutation in at least one nucleotide of wild type M8 (SEQ ID NO: 19).

Non-limiting examples of isolated polynucleotide which include at least one copy of wild type M6 (SEQ ID NO: 17) and a mutation in at least one nucleotide of the wild type M8 (SEQ ID NO: 19) are provided in SEQ ID NOs:23-26.

According to some embodiments of the invention, the isolated polynucleotide includes at least one copy of wild type M7 (SEQ ID NO: 18) and a mutation in at least one nucleotide of wild type M8 (SEQ ID NO: 19).

Non-limiting examples of isolated polynucleotide which include at least one copy of wild type M7 (SEQ ID NO: 18) and a mutation in at least one nucleotide of the wild type M8 (SEQ ID NO: 19) are provided in SEQ ID NOs:27-28.

According to some embodiments of the invention, the isolated polynucleotide includes at least one copy of wild type M6 (SEQ ID NO: 17), at least one copy of wild type M7 (SEQ ID NO: 18) and a mutation in at least one nucleotide of wild type M8 (SEQ ID NO: 19).

According to some embodiments of the invention, the isolated polynucleotide includes at least one copy of wild type M1 (SEQ ID NO: 20) and a mutation in at least one nucleotide of wild type M8 (SEQ ID NO: 19).

Non-limiting examples of isolated polynucleotide which include at least one copy of wild type M1 (SEQ ID NO: 20) and a mutation in at least one nucleotide of the wild type M8 (SEQ ID NO: 19) are provided in SEQ ID NOs:43-54 and 601-632.

According to some embodiments of the invention, the isolated polynucleotide includes at least one copy of wild type M1 (SEQ ID NO: 20), at least one copy of wild type M6 (SEQ ID NO: 17) and/or at least one copy of wild type M7 (SEQ ID NO: 18) and a mutation in at least one nucleotide of wild type M8 (SEQ ID NO: 19).

Non-limiting examples of isolated polynucleotides which include a mutation in at least one nucleotide of wild type M8 (SEQ ID NO: 19) and at least one copy of wild type M1 (SEQ ID NO: 20), wild type M6 (SEQ ID NO: 17) and/or wild type M7 (SEQ ID NO: 18) are provided in SEQ ID NOs:29-42.

Additional examples of regulatory isolated polynucleotides which can be used according to some embodiments of the invention are provided (; SEQ ID NOs: 633-644) in the Examples section which follows.

According to an aspect of some embodiments of the invention, there is provided an isolated polynucleotide comprising a nucleic acid sequence which comprises a first polynucleotide comprising the pre-proendothelin (PPE-1) promoter set forth by SEQ ID NO:13 and a second polynucleotide comprising at least one copy of a nucleic acid sequence selected from the group consisting of:

(i) wild type M4 sequence set forth by SEQ ID NO: 15 (CATTC), (ii) wild type M5 sequence set forth by SEQ ID NO: 16 (CAATG), (iii) wild type M8 sequence set forth by SEQ ID NO: 19 (GCTTC), (iv) wild type M6 sequence set forth by SEQ ID NO: 17 (GGGTG), (v) wild type M7 sequence set forth by SEQ ID NO: 18 (ACTTT);

(vi) wild type M1 sequence set forth by SEQ ID NO: 20 (GTACT), and (vii) wild type M3 sequence set forth by SEQ ID NO: 21 (CTTTT);

with the proviso that the second polynucleotide is not SEQ ID NO:6 (element X), and wherein the isolated polynucleotide is not SEQ ID NO:12 (PPE-1-3X).

According to some embodiments of the invention, each of the wild type M4, M5, M8, M6, M7 and/or M1 sequences is placed in a head to tail (5'→3) orientation with respect to the PPE-1 promoter set forth by SEQ ID NO:13.

According to some embodiments of the invention, each of the wild type M4, M5, M8, M6, M7 and/or M1 sequences is placed in a tail to head (3'→5) orientation with respect to the PPE-1 promoter set forth by SEQ ID NO:13.

According to some embodiments of the invention, the wild type M4, M5, M8, M6, M7 and/or M1 sequences are placed in various orientations (head to tail or tail to head) and/or sequential order with respect the other wild type M4, M5, M8, M6, M7 and/or M1 sequences, and/or with respect to the orientation of SEQ ID NO:13.

Construction of such viral vectors may be effected using known molecular biology techniques such as those described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986].

Construction of the viral vector of SEQ ID NO: 9 is described in International Application WO/2008/132729, the contents of which are incorporated herein by reference.

As used herein, the term "administration" refers to providing or giving a subject an agent, such as an anti-angiogenic viral composition, by any effective route.

The viral vector of this aspect of the present invention may be administered per se or as part of a pharmaceutical composition which also includes a physiologically acceptable carrier. The purpose of a pharmaceutical composition is to facilitate administration of the active ingredient to an organism.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the viral vector of the present invention accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, intradermal, intraperitoneal, subcutaneous and intramedullary injections as well as intrathecal, direct intraventricular, intracardiac, e.g., into the right or left ventricular cavity, into the common coronary artery, intravenous, inrtaperitoneal, intranasal, or intraocular injections, sublingual, rectal, transdermal, intranasal, vaginal and inhalation routes. Injection of the viral vectors into a spinal fluid can also be used as a mode of administration.

The viral vectors or compositions thereof can be administered in an in-patient or out-patient setting. In one particular embodiment, the viral vectors or compositions thereof are administered in an injection or in an intravenous drip.

The present invention also contemplates engineering of the viral vectors in order to avoid, suppress or manipulate the immune response, ideally resulting in sustained expression and immune tolerance to the transgene product such methods are described for example in Nayak et al., *Gene Therapy* (12 Nov. 2009), incorporated herein by reference.

Alternately, one may administer the pharmaceutical composition in a local rather than systemic manner, for example, via injection of the pharmaceutical composition directly into the tissue or tumor mass of a patient and even more directly into the tumor cells themselves.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (i.e. viral particles) effective to prevent, alleviate or ameliorate symptoms of a disorder (e.g., thyroid cancer, neuroendocrine cancer) or prolong the survival of the subject being treated.

Determination of a therapeutically effective amount is well within the capability of those skilled in the art, especially in light of the detailed disclosure provided herein. Therapeutic efficacy Of administration of the adenoviral vector of the present invention can be assessed according to a variety of criteria, including clinical presentation, biochemical parameters, radiological evaluation and the like. In some embodiments, efficacy is evaluated according to one or more of the following exemplary parameters:

Biodistribution: for example, levels of virus DNA in blood and urine samples, expression of the fas-c transgene (mRNA) in blood;

Antibodies: for example, levels of total anti-Ad-5 Ig, IgG and neutralizing anti-Ad5 antibodies in serum;

Angiogenic biomarkers: for example, von Willebrand Factor, TNF$\alpha$, VEGFR1 and VEGFR2 levels in the blood;

Cytokine levels: for example, peripheral blood cytokine levels (e.g. IL-6, IL-8—see Table 6);

Tumor response: Tumor dimensions can be measured on CT (or MRI) scans, or other radiographic means. Tumor response can then be evaluated according to accepted criteria, such as Response Evaluation Criteria in Solid Tumors (RECIST).

The criteria can be evaluated at any time following administration, and can also be compared to pre-dosing values. In one embodiment, the evaluation criteria are assessed prior to administration of the adenovirus vector, and then on days 4±1, 7±1, 14±1, 28±2, day 56±3, day 112±4, about 3 months, about 4 months, about 5 months, about 6 months, about 1 year or more post dosing. In some embodiments, the evaluation criteria are assessed at day 7±1, 14±1, 28±2, day 56±3, day 112±4, about 3 months, about 6 months, about 9 months, about 1 year and about every 3 months thereafter for up to 2, up to 3, up to 4 or more years post dosing.

Determination of safety of dosing or dosing regimen is well within the ability of one skilled in the art. Safety can be assessed according to a variety of criteria, including, but not limited to, clinical presentation, tissue and organ pathology, presence of abnormal vital signs (e.g. pyrexia, fatigue, chills, tachycardia, hypertension, constipation and the like), hematology values (e.g. hemoglobin, hematocrit, RCV and the like), chemistry or urinalysis abnormalities (elevated enzymes such as alkaline phosphatase ALT, AST, bilirubin and the like) and ECG, EEG, etc.

As used herein, the term "antibody" refers to a molecule including an antigen binding site which specifically binds (immunoreacts with) an antigen. The term "antibody" includes intact molecules as well as functional fragments thereof, such as Fab, $F(ab')_2$, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) $(Fab')_2$, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

As used herein, the term "antigen" refers to a substance that can stimulate the production of antibodies or a T-cell response in a mammal, including compositions that are injected or absorbed into a mammal. An antigen reacts with the products of specific humoral or cellular immunity, including those induced by heterologous immunogens. The term "antigen" includes all related antigenic epitopes. In one example, an antigen is a cancer antigen. A target antigen is an antigen against which an immune response is desired, for example to achieve a therapeutic effect, such as tumor regression.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

The therapeutically effective amount of the active ingredient can be formulated in a unit dose. As used herein "unit dose" refers to a physically discrete unit containing a predetermined quantity of an active material calculated to individually or collectively produce a desired effect such as an anti-cancer effect. A single unit dose or a plurality of unit doses can be used to, provide the desired effect, such as an anti-cancer therapeutic effect. In some embodiments, the unit dosage is $1\times10^{8}$ to about $1\times10^{16}$ virus particles, at least about $1\times10^{11}$ to about $1\times10^{13}$ virus particles, and optionally about $1\times10^{11}$, about $3\times10^{11}$, about $5\times10^{11}$, about $1\times10^{12}$, about $3\times10^{12}$, about $5\times10^{12}$, about $1\times10^{13}$, about $3\times10^{13}$ or more virus particles.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide levels of the active ingredient sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

According to one embodiment, about $10^{3}$ to about $10^{16}$ virus particles are administered to the subject.

According to another embodiment, about $10^{5}$ to about $10^{13}$ virus particles are administered to the subject.

According to one embodiment, about $10^{7}$ to about $10^{12}$ virus particles are administered to the subject.

According to one embodiment, about $1\times10^{12}$ to about $5\times10^{12}$ virus particles are administered to the subject.

According to yet another embodiment, about $1\times10^{9}$ to about $1\times10^{16}$ virus particles, at least about $1\times10^{11}$ to about $1\times10^{13}$ virus particles are administered to the subject.

According to yet another embodiment the subject is administered intravenously with $1\times10^{12}$-$1\times10^{13}$ viral particles of SEQ ID NO: 9. or SEQ ID NO: 10.

According to yet another embodiment the subject is administered intravenously with at least two doses of $1\times10^{12}$-$1\times10^{13}$ viral particles of SEQ ID NO: 9. or SEQ ID NO: 10. According to yet another embodiment the subject is administered intravenously with at least three or more doses of $1\times10^{12}$-$1\times10^{13}$ viral particles of SEQ ID NO: 9. or SEQ ID NO: 10. In a particular embodiment, the at least two doses are administered at least about 1 day, at least about 3 days, at least about 5 days, at least about 7 days, at least about 2 weeks, at least about 3 weeks, at least about 4 weeks, at least about 2 months, at least about 6 months, at least about 9 months, at least about 1 year, at least about 1.25 years, at least about 1.5 years, at least about 1.75 years, at least about 2 years, at least about 2.5 years, at least about 3 years or more apart.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

Thus, according to some aspects of some embodiments of the present invention there is provided a kit for treating a solid tumor in a subject in need thereof, comprising a unit dosage of virus particles of a non-replicating adenovirus vector comprising a polynucleotide having a nucleotide sequence as set forth in SEQ ID NOs: 9 or 10, wherein the non-replicating adenovirus vector is formulated for intravenous administration, and instructions for administration of the adenovirus.

The adenovirus vector can be used in combination with other treatments. For example, the uptake of adenoviral vectors into EC cells can be enhanced by treating the vectors with engineered antibodies or small peptides. Such "adenobody" treatment, was shown effective in directing adenovirus constructs to EGF receptors on cells (Watkins et al 1997, Gene Therapy 4:1004-1012). In addition, Nicklin et al have shown that a small peptide, isolated via phage display, increased specificity and efficiency of vectors in endothelial cells and decreased the expression in liver cells in culture (Nicklin et al 2000, Circulation 102:231-237). In a recent study, an FGF retargeted adenoviral vector reduced the toxicity of tk in mice (Printz et al 2000, Human Gene Therapy 11:191-204).

Low dose radiation has been shown to cause breaks in DNA strands primarily in the G2/M phase, cell membrane damage enhancing the bystander effect, and thus may potentiate other cytotoxic and anti-neoplastic therapies, when administered in combination. Vascular endothelial cells may be particularly suitable to such combination, or adjunct, therapies, since it has been demonstrated that low dose radiation specifically targets the apoptotic system of the microvascular endothelial cells (Kolesnick et al., Oncogene 2003; 22:5897-906). Angiostatin has been shown to potentiate the therapeutic effects of low dose radiation (Gorski et al. Can Res 1998; 58:5686-89). However, the effects of radiation are still poorly understood, since irradiation has also been shown to increase pro-angiogenic "tissue repair factors" (Itasaka et al., Am Assoc Canc Res, 2003; abstract 115). Similarly, certain chemotherapeutic agents have been shown to activate specific cytotoxic and apoptotic pathways [doxorubicin, cisplatin and mitomycin C induce accumulation of Fas receptor, FADD, and other proapoptotic signals in the FADD/MORT-1 pathway (Micheau et al., BBRC 1999 256:603-07)].

For example International Application WO/2008/132729 teaches combined doxorubicin and AdPPE-1 (3x)-Fas-c chimera construct administration in endothelial cells (BAEC). Thus, the viral vectors and the pharmaceutical compositions comprising same of the present invention can be used to treat solid tumors alone or in combination with one or more other established or experimental therapeutic regimen for such disorders. Therapeutic regimen for treatment of solid tumors suitable for combination with the viral vectors of the present invention include, but are not limited to chemotherapy, radiotherapy, phototherapy and photodynamic therapy, surgery, nutritional therapy, ablative therapy, combined radiotherapy and chemotherapy, brachiotherapy, proton beam therapy, immunotherapy, cellular therapy and photon beam radiosurgical therapy. The vectors of the present invention may be administered with additional ingredients which may improve the uptake of the nucleic acid construct by the cells, expression of the chimeric polypeptide by the nucleic acid construct in the cells, the activity of the expressed chimeric polypeptide or the efficacy of the treatment on any aspects of the disease. Protocols for use of recombinant anti-angiogenic adenovirus vectors for cancer treatment are known in the art. Many clinical trials of adenovirus-based anti-angiogenic gene therapy are currently being conducted, mostly involving a recombinant anti-angiogenic adenovirus in combination with other cancer therapies, and administered intra-tumorally, such as an adenovirus-p53 vaccine with chemotherapy for small cell lung cancer (NCT0049218), adenovirus-suicide gene with chemotherapy for small cell lung cancer (NCT00964756), an adenovirus-endostatin construct with chemotherapy for head and neck cancer (NCT00634595), an adenovirus-suicide gene with chemotherapy for malignant melanoma (NCT00005057) and an adenovirus-tk construct with chemotherapy for hepatocellular carcinoma (NCT00844623).

Anti-cancer drugs that can be co-administered with the compounds of the invention include, but are not limited to Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bevacizumab, Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Fluorocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; MitomyCin; Mitosper; Mitotane; Mitoxantrone Hydrochloride; Mycophenolic Acid; Nocodazole; Nogalamycin; Ormaplatin; Oxisuran; pazotinib; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sorafinib; Sparfosate Sodium; Sparsomycin; Spirogermanium Hydrochloride; Spiromustine; Spiroplatin; Streptonigrin; Streptozocin; Sulofenur; Sunitinib; Talisomycin; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofuirin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride. Additional antineoplastic agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division).

The present inventors have shown that administering a single dose of the viral vectors of the present invention (e.g. Ad5PPE-1-3X fas-chimera) in combination with the chemotherapeutic drug sunitinib (Sutent), can improve the efficacy of the chemotherapy treatment, or of the viral vector's effect on a metastatic cancer, in the Lewis Lung Carcinoma model (see Example VI below). Thus, in some embodiments the viral vectors of the present invention are administered in combination with one or more of the chemotherapeutic drugs, such as sunitinib (Sutent).

Chemotherapeutic agents can be administered along with the viral vectors of the invention, prior to treatment with the viral vectors of the present invention, or following treatment with the viral vectors of the present invention. In a particular embodiment, the chemotherapeutic agent is administered at least about 1 day, at least about 3 days, at least about 5 days, at least about 7 days, at least about 2 weeks, at least about 3 weeks, at least about 4 weeks, at least about 2 months, at least about 6 months, at least about 9 months, at least about 1 year prior to initiation of treatment with the viral vector of the present invention. In another particular embodiment, the chemotherapeutic agent is administered at least about 1 day, at least about 3 days, at least about 5 days, at least about 7 days, at least about 2 weeks, at least about 3 weeks, at least about 4 weeks, at least about 2 months, at least about 6 months, at least about 9 months, at least about 1 year following initiation of treatment with the viral vector of the present invention. In another particular embodiment, the chemotherapeutic agent is administered during, or alongside with initiation of treatment with the viral vector of the present invention.

The viral vectors of the present invention may also be administered with an agent that enhances expression of transgenes in adenoviral-mediated transient expression. For example International Application WO/2008/132729 teaches administration of a corticosteroid (e.g. dexamethasone and/or N-Acetyl Cysteine (NAC) prior to AdPPE-1 (3x)-Fas-c chimera construct administration, or concomitant treatment with an endothelin inhibitor such as bosentan.

In addition, the viral vectors of the present invention may also be administered with an agent that brings about transient immunosuppression, such as for example deoxyspergualin (DSG) or cyclophosphamide (see for example Smith et al., Gene Ther. 1996 June; 3(6):496-502) in order to allow for repetitive dosing.

Figure 2:
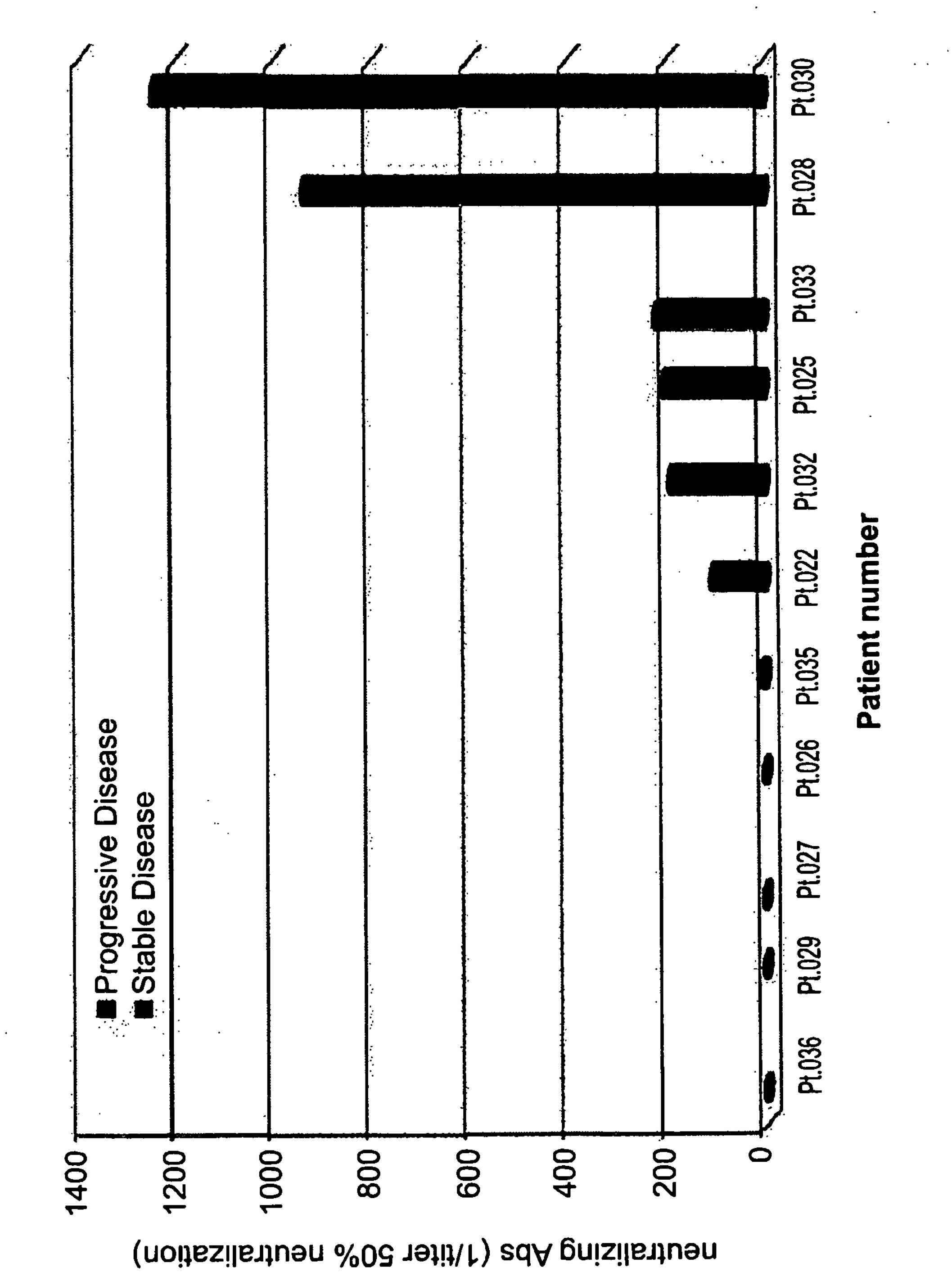
FIG. 2 is a histogram showing the pre-treatment titer of pre-treatment neutralizing anti-Ad5 antibodies in the serum of patients in cohort 6 ($3\times10^{12}$ vp), as a function of their disease progression at day 28 post administration of Ad5-PPE-1-3X fas-chimera adenovirus vector. Note the lack of correlation between progressive disease (blue), stable disease (red) and antibody titer (Y-axis)
Figure 3A:
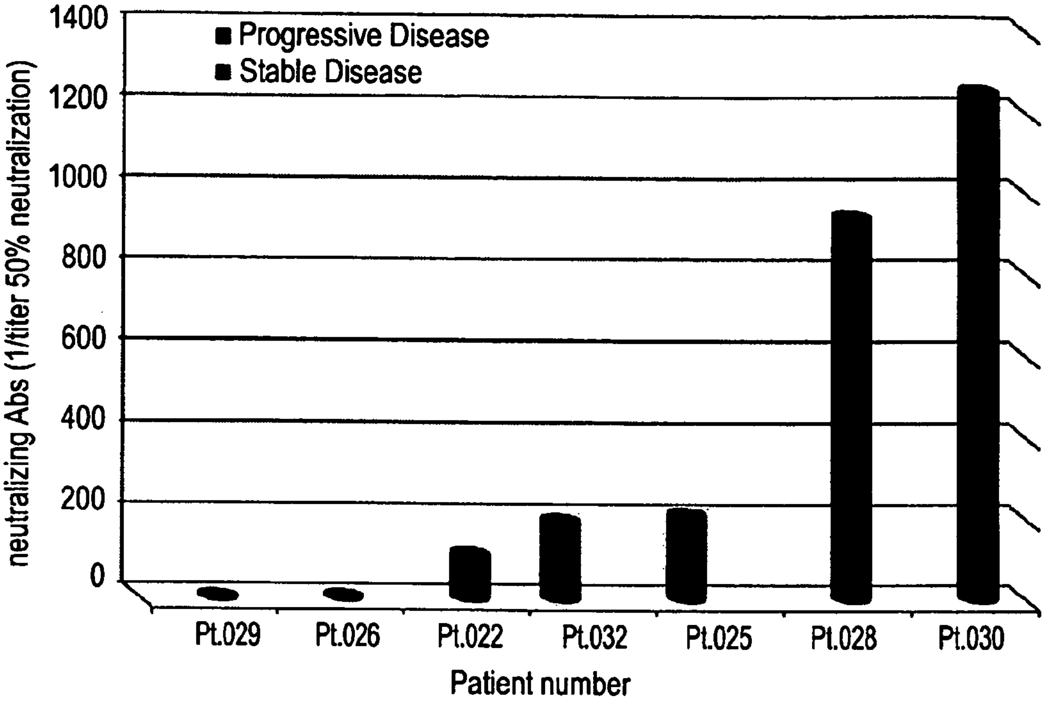
FIGS. 3A and 3B are histograms showing the pre-treatment titer of neutralizing anti-Ad5 antibodies in the serum of patients, as a function of their disease progression at day 56 post administration of Ad5-PPE-1-3X fas-chimera adenovirus vector.
Figure 3B:
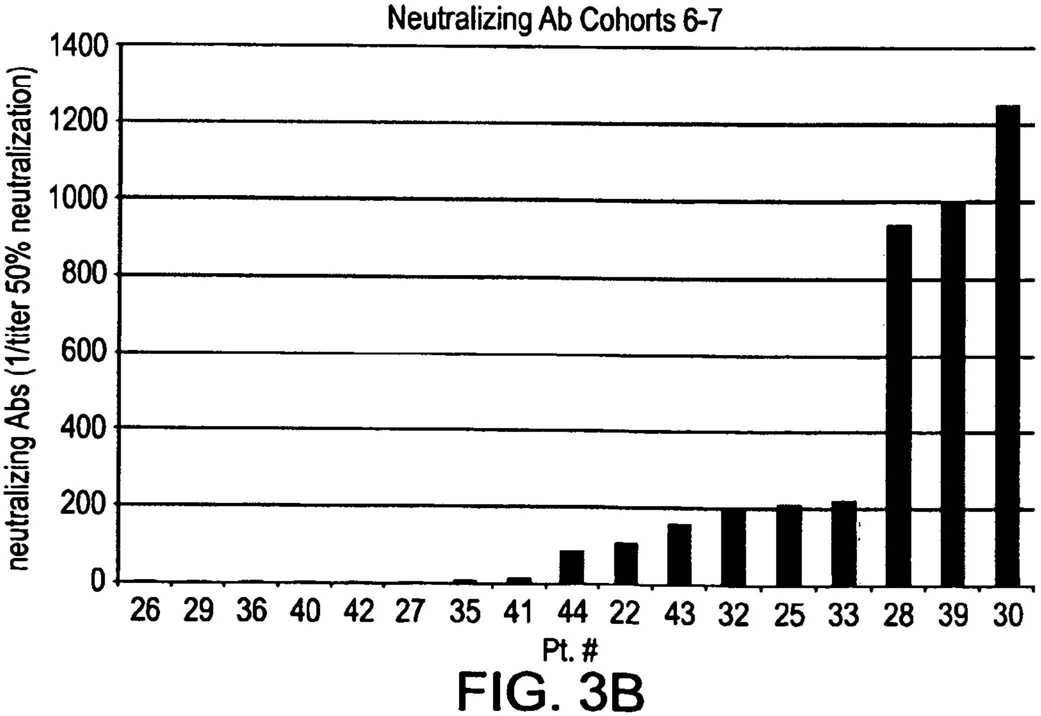

Adenovirus-based gene therapy protocols have commonly been limited to single doses, for reasons pertaining to safety and efficacy of the drug, particularly concerning patient anti-adenovirus immune response, as most populations are repeatedly exposed and sensitized to various adenoviral antigens. The present inventors have surprisingly found no correlation between levels of anti-adenovirus antibodies in serum of patients following administration of the adenovirus of the invention, and the dose of adenovirus administered. Evaluation of antibody titers, including anti-Ad5 neutralizing antibodies, IgG and total anti-Ad5 antibodies in the patients (see Example II, and FIGS. 2 and 3A-3B) revealed no effect of the baseline levels of neutralizing anti-adenovirus antibody on disease progression following dosing. Evaluation of total anti-adenovirus Ad5 antibody titers, and specific anti-Ad5 IgG in serum of patients prior to, and following administration of the Ad5-PPE-1-3X-fas-c adenoviral vectors revealed increased antibody titers following adenovirus vector administration, but indicated no correlation with the doses administered (see Table 4 in Example II that follows), suggesting that repeated doses of the adenovirus as described herein may not lead to an immune response limiting the clinical utility of the adenovirus in the host. Further, it was found that administration of AdSPPE-1-3X-fas chimera was effective in reducing disease progression even in subjects with high levels of neutralizing anti-Ad5 antibodies and total anti-Ad5 antibodies detected prior to first injection of the construct (see FIGS. 2 and 3). Yet further, assays of blood and urine Ad5-PPE-1-3X-fas-c levels (biodistribution) following administration revealed high levels of the adenovirus constructs of the invention 28 days post-administration, even in the presence of elevated total or IgG anti-Ad5 antibody levels (see Tables 4 and 7 of Example II that follows, specifically, see subjects 2, 9 and 10). In one subject [036], for example, significant levels of transgene expression were detected in an aspirate from a metastatic lesion as many as 28 days following adenovirus vector administration, despite a massive fold increase (X3125) in anti-Ad5 antibody titer (see Tables 4 and 9 in Example II that follows).

Thus, in some embodiments, administering the dose of the adenovirus vector of the present invention inhibits growth of a tumor. In other embodiments, administering the adenovirus vector inhibits angiogenesis of the tumor.

Thus, the adenovirus vectors of the present invention can be administered in one, at least two, three or more doses, with intervals therebetween sufficient for antibody formation, without causing a dose-dependent antiviral antibody response. Such intervals are typically 21-28 days, but may be as few as 1 or 2 days, or as many as 7 days, 10 days, 2 weeks, three weeks, four, six, eight ten or more weeks. Thus, according to another aspect of some embodiments of the present invention there is provided a method for administering a therapeutically effective amount of a therapeutic composition comprising an adenoviral vector to a subject in need thereof comprising administering the composition to the subject at least twice, wherein the administration does not induce a dose-dependent increase in antibodies against the adenoviral vector in the subject. According to another aspect of one embodiment of the present invention, the time between administration between a first dose and an at least second dose is sufficient for anti-Ad5 antibody formation.

In yet another embodiment, the adenovirus vectors of the present invention are effective when administered to subjects having elevated levels of serum anti Ad5 antibodies. In some particular embodiments the anti-Ad5 antibody levels are elevated compared to the subjects pre-dosing baseline anti-Ad5 levels. In yet other embodiments, the adenovirus vectors of the present invention are detected in the blood of the subjects having elevated anti-Ad5 antibody levels are compared to the subjects pre-dosing baseline anti-Ad5 levels, at day 4 post-administration, day 7 post-administration, day 15 post-administration, day 21 post-administration, day 28 post-administration, day 37 post-administration, day 56 post-administration or day 112 post-administration or more. Such anti-Ad5 antibodies can be neutralizing antibodies, total anti-Ad5 antibodies, or a specific anti-Ad5 antibody subtype, such as anti-Ad5 IgG.

Thus, in some embodiments, the adenovirus is detected in the blood of the subject at least about 4 days post administration. According to other embodiments an amount of serum anti-adenovirus antibodies is increased following the administering, and the adenovirus is detected in the blood of the subject at least about 21 days post administration.

It is expected that during the life of a patent maturing from this application many relevant chemotherapeutic agents will be developed and the scope of the term chemotherapeutic agent is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients; steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example I

Efficacy of Ad5PPE-1-3X-Fas Chimera in Lewis Lung Carcinoma Model

In order to evaluate effective dosage ranges Ad5PPE-1-3X-fas chimera adenovirus for treatment of solid tumors, metastatic tumors were induced in the mouse Lewis Lung Carcinoma model, and a range of doses of Ad5PPE-1-3X-fas chimera adenovirus (SEQ ID NO: 10) administered systemically.

Materials and Experimental Methods

Construction and Cloning of the Viral Vector:

The vector was constructed using a backbone containing most of the genome of adenovirus type 5, as well as partial homology to an adaptor plasmid, which enables recombination.

The E1 early transcriptional unit was deleted from the backbone plasmid, and further modified by deleting the pWE25 and the Amp resistance selection marker site.

The adaptor plasmid, containing sequences of the Ad5, CMV promoter, MCS, and SV40 polyA was modified to delete deleting the CMV promoter, and the PPE-1 promoter and Fas-c fragment were inserted by restriction digestion.

The modified PPE-1 promoter (PPE-1-3X, SEQ ID NO: 12) and the Fas-chimera transgene (Fas-c, SEQ ID NO: 4) were utilized for construction of the adenoviral vector. The PPE-1-(3X)-Fas-c element (2115 bp) was constructed from the PPE-1-(3X)-luc element. This element contains the 1.4 kb of the murine preproendothelin PPE-1-(3X) promoter, the Luciferase gene, the SV40 polyA site and the first intron of the murine ET-1 gene, originated from the pEL8 plasmid (8848 bp) used by Harats et at (Harats D. et al., JCI, 1995). The PPE-3-Luc cassette was extracted from the pEL8 plasmid using the BamHI restriction enzyme. The Luciferase gene was substituted by the Fas-c gene [composed of the extra cellular and intra membranal domains of the human TNF-R1 (Tumor Necrosis Factor Receptor 1, SEQ ID NO: 2) and of the Fas (p55) intracellular domain (SEQ ID NO: 3) (Boldin et al, JBC, 1995)] to obtain the PPE-1-3x-Fas-c cassette.

PPE-1(3x)-Fas-c Plasmid—The cassette was further introduced into the backbone plasmid by restriction digestion, resulting with the PPE-1-(3x)-Fas-c plasmid. Adaptor-PPE-1(3x)-Fas-c Plasmid—The PPE-1-3x-Fas-c element was extracted from the first generation construct PPE-1-3x-Fas-c plasmid, and was amplified with designated PCR primers introducing SnaB1 and EcoR1 restriction sites at the 5'-and-3'-end respectively. These sites were used to clone the PPE-Fas-c fragment into the adaptor plasmid digested with SnaB1 and EcoR1, resulting in the adaptor-PPE-1-3x-Fas-c used for transfection of the host cells (for example, PER.C6 cells).

Lewis Lung Carcinoma Model

Freshly harvested D122 Lewis Lung Carcinoma (LLC) cells ($5\times10^5$ per mouse) were administered to C57BL/6 mice (3 months old), by subcutaneous injection into the foot pad. Primary tumors developed in the feet in about 14 days. When tumors reached a diameter of at least 7 mm, the mice were anesthetized and the distal segment of the limb was amputated. Five days after limb amputation, mice were randomized to one of the following groups:

| | Treatment | Dose- virus particles (vp/mouse) |
|---|---|---|
| Group 1 | Ad5PPE-1-3X-fas chimera adenovirus | $10^{11}$ |
| Group 2 | Ad5PPE-1-3X-fas chimera adenovirus | $10^{10}$ |
| Group 3 | Ad5PPE-1-3X-fas chimera adenovirus | $10^{9}$ |
| Group 4 | Ad5PPE-1-3X-fas chimera adenovirus | $10^{8}$ |

-continued

| | Treatment | Dose- virus particles (vp/mouse) |
|---|---|---|
| Group 5 | Ad5PPE-1-3X-fas chimera adenovirus | $10^{7}$ |
| Group 6 | Ad5PPE-1-3X-fas chimera adenovirus | $10^{6}$ |
| Group 7 | Vehicle | 0 |

Vehicle=PBS, 10% glycerol

Viruses were intravenously injected to the mouse tail. Mice were sacrificed upon death of 5 control (vehicle injected) mice (approximately 24 days after virus/control administration). Mice in which the primary tumor re-emerged after treatment, were withdrawn from the study. Upon sacrifice, animal's lungs were removed, washed and weighed, and blood was collected for liver function testing.

Liver and tumor tissues were cut and frozen in 4% formaldehyde or in OCT compound for histological analysis by hematoxylin-eosin staining or anti PECAM1 (anti-CD31) staining, respectively. Tumor weight differences were evaluated using the Mann-Whitney U-test.

The purpose of this study was to evaluate the dose dependent efficacy of Ad5PPE-1-3X-fas chimera adenovirus and to assess the minimal effective dose.

Results

Clinically Significant Doses ($10^6$ to $10^{11}$ Vp/Mouse) of Ad5PPE-1-3X-Fas Chimera Adenovirus do not Cause Non-Specific Systemic Effects Mortality was observed in all groups prior to scheduled sacrifice with no dose response trend. Clinical signs of surviving mice did not reveal any abnormalities. No dose response trend was observed in mice weights.

No statistical significant differences were observed in the kidney function in all groups, except for an increase in uric acid observed at the lowest dose cohort on day 5 post dosing. No statistical significant differences were observed in the SGOP and SGPT levels of treated vs. non treated mice.

Macroscopic examination at necropsy (brain, liver heart, spleen, gonads, kidneys, small intestine, lungs), did not reveal any abnormalities except for metastases found in the lungs. No statistical differences were found in the weight of organs between groups (liver, spleen, small intestine, heart, kidney, lung, and brain), except for the heart and spleen where an increase (not dose dependent) in the weight was observed in mice treated with adenovirus compared to the untreated mice.

Microscopic observations (on the lung, liver and heart) showed mild to moderate inflammation and regenerative changes of the liver following treatment with $10^{8}$-$10^{11}$ vp/mouse.

Ad5PPE-1-3X-Fas Chimera Adenovirus ($10^8$ to $10^{11}$ Vp/Mouse) Suppresses Metastatic Tumor Growth FIGS. 1A-1C show exemplary lungs of treatment and control groups, at the completion of the study. In the lung, large metastases were found in mice treated with vehicle (FIG. 1A). These metastases were reduced in a dose dependent fashion in Ad5PPE-1-3X-fas chimera adenovirus-treated mice (FIGS. 1B-1C), with the strongest effect in the highest dose ($10^{11}$ vp/mouse) cohort (FIG. 1C), in which most of the lungs appeared to be normal or with only small metastases. This effect decreased to non observable levels at low titers of the virus ($10^7$ vp/mouse and $10^6$ vp/mouse). The protective, anti-tumor effect of the Ad5PPE-1-3X-fas chimera adenovirus was confirmed by the difference in weight of the lungs of the Ad5PPE-1-3X-fas chimera adenovirus-treated mice, which was significantly reduced when compared to control mice but diminished to non observable level at low virus titers (FIG. 1D).

Thus, a single, systemic injection of a clinically significant amount of Ad5PPE-1-3X-fas chimera adenovirus was highly effective in reducing the tumor burden in Lewis Lung Carcinoma model in a dose dependent fashion. $10^{11}$ vp/mouse resulted in a 70% decrease in tumor burden. No efficacy of treatment was observed at the lowest doses ($10^6$ vp/mouse-$10^7$ vp/mouse).

Example II

Administration of Ad5PPE-1-3X-Fas Chimera in the Clinical Setting

In order to determine the safety and efficacy of administration of AD5PPE-1-3X-fas-chimera in the clinical setting, outcomes such as toxicity, adverse effects, antibody titer, biodistribution, disease progression and disease recurrence and survival were monitored in subjects with solid primary and metastatic tumors receiving intravenous infusion of a range of doses of the Ad5PPE-1-3X-fas chimera adenovirus vector.

Materials and Experimental Methods

Subject Population:

Subjects with advanced and/or metastatic solid organ cancer 18 years of age and older, without remaining options for standard curative or palliative measures are enrolled.

Criteria for subject's inclusion in the treatment group are:

1. Subjects at least 18 years of age;
2. Histologically confirmed malignancy that is metastatic or unresectable and for which standard curative or palliative measures do not exist or are no longer effective;
3. Karnofsky performance status of ≥70%;
4. Adequate haematological profile: ANC>1500/μl, hemoglobin ≥10 g/dl, platelets >100,000/μl, and INR within normal limits;
5. Adequate renal function (CCT >60 mL/min/1.73 m2);
6. Adequate hepatic function: (ALT and AST<2.5×ULN) and total bilirubin within normal limits.

Criteria for subject's exclusion from the treatment group are:

1. Recent cardiac event (within 12 months) or active cardiac/vascular disease;
2. Recent surgery (within 4 weeks);
3. Proliferative retinopathy;
4. Liver disease;
5. CNS metastasis;
6. Recent anti-angiogenic therapy (within 6 weeks);
7. Current/recent (within 4 weeks) immunosuppressive therapy;
8. Recent chemo/radiotherapy or investigational agent (within 4 weeks);
9. Uncontrolled co-morbidity.

Composition: Ad5-PPE-1-3X-Fas-Chimera

Ad5-PPE-1-3X-fas-chimera (SEQ ID NO: 10) is a vascular disruptive gene therapeutic, consisting of a non-replicating adenovirus vector (Ad5, E1 deleted, SEQ ID NO: 1) which contains a modified murine pre-proendothelin promoter (PPE-1-3x, SEQ ID NO: 12) and a fas-chimera transgene [Fos and human tumor necrosis factor (TNF) receptor](SEQ ID NO: 4). It is formulated as a sterile vector solution and supplied frozen (below −65° C.), in single use vials. Each vial contains 0.5 mL of vector solution at a specific viral titer.

Dosage

Dose escalation is done by cohort as follows:

| | Dose (virus particles) | Subjects per Cohort |
|---|---|---|
| Cohort 1 | $1 \times 10^{10}$ | 3 |
| Cohort 2 | $3 \times 10^{10}$ | 3 |
| Cohort 3 | $1 \times 10^{11}$ | 3 |
| Cohort 4 | $3 \times 10^{11}$ | 3 |
| Cohort 5 | $1 \times 10^{12}$ | 3 |
| Cohort 6 | $3 \times 10^{12}$ | 12 |
| Cohort 7 | $1 \times 10^{13}$ | 6 |

Since no dose limiting toxicity was observed after dosing 3 subjects in each of the first 6 cohorts, 9 additional subjects were enrolled into cohort 6 according to the protocol and after approval of the Institutional Review Boards. 27 subjects (3 in each of cohorts 1-5 [total of 15 subjects] and 12 in Cohort 6) were treated. Since no dose limiting toxicity was observed, 6 more patients were enrolled to cohort 7. A total of 33 subjects were treated. One case of NCI Grade 3 fever, shortly following administration of the highest dose (cohort 7), was observed.

The Ad5-PPE-1-3X-fas-chimera is administered as an intravenous infusion. The same drug volume and saline volume were used for each subject within each cohort, and each subject was infused with the same volume of the drug. The infusion duration was between 3 and 5 minutes in cohorts 1-5 and 15 minutes in cohort 6 and 50 minutes for cohort 7. In general, these numbers reflect the instructions specified in the pharmacy manual provided with the study.

Subject Evaluation Criteria

Biodistribution:

Blood and urine samples were collected prior to dosing, at the end of the infusion (blood samples only), 3 hours, 6 hours, and on days 4(±1), 7(±1), 14(±1), 28(±2) and at day 56(±3) for evaluation of levels of virus DNA (in blood and urine) and the expression of the transgene (messenger RNA in blood). Only samples with detectable viral DNA are tested for transgene expression.

Antibodies:

Serum samples were collected prior to dosing for analysis of total anti-Ad-5 Ig, IgG and neutralizing anti-Ad5 antibody levels, and on day 28 and day 56 for analysis of total anti-Ad-5 Ig, IgG anti-Ad5 antibody levels.

Ad-5-IgG assay: Serum samples were diluted and analyzed for adenovirus-specific immunoglobulin G (IgG) by ELISA. For the ELISA, 96 well flat bottomed, high-binding Inunulon-IV plates were coated with 50 ul Ad5-antigen (Upenn Vector Core) at (5×10^8 particles/well) in pH 9.5 carbonate buffer (coating buffer) overnight at 4° C., washed two times in PBS/0.05% Tween, blocked in PBS/1% HSA for 1 hour at 24° C., and then washed two times in PBS/0.05 Tween. Appropriately diluted (3-fold) samples were added to antigen-coated plates and incubated for 4 hours at room temperature. Plates were washed three times with PBS/0.05% Tween and incubated with peroxidase conjugated goat anti-human Ig (1:5000 dilution, Jackson ImmunoResearch Laboratories, Inc.) for 1 hour at room temperature. Plates were washed three times as above and TMB substrate (Sigma Chemical Co., St Louis, Mo.) is added at 100 ul/well for 30 minutes. Reaction was stopped when 100 ul 2N $H_2SO_4$ was added, and optical densities were read at 450 nm on a VersaMAX tunable microplate reader (Molecular Devices). Titer is the dilution achieving 0.5 maximum OD.

Neutralizing anti-Ad5 antibodies assay: The ability of serum to block adenovirus infection of Hela cells (ATCC) in vitro was analyzed utilizing adenovirus expressing green fluorescent protein (GFP) as a reporter (Upenn Vector Core). Various dilutions of test sera and, as a control/standard, pooled AB sera (Sigma), pre-incubated with moi of 1000 of reporter viruses for 1 hour at 37° C. were added to 90% confluent cell cultures. Cells were incubated for 16 hours and expression of GFP quantified by fluoroimaging using the Victor$^2$ (Wallace/PerkinElmer) and visually. The neutralizing titer of the sera was calculated as the reciprocal dilution of serum with 50% of the maximum fluorescence at 1000 MOI.

Angiogenic Biomarkers:

Blood samples were collected prior to dosing, and at the following visits thereafter, for evaluation of von Willebrand Factor levels and TNFα levels, on days 4±1, 7±1, 14±1, 28±2 and at day 56±3 post dosing.

Cytokine Levels:

Peripheral blood cytokine (see Table 6 below) levels were measured in cohort 6 patients at baseline, and at the following times after dosing with Ad5-PPE-1-3X-fas-chimera, at 6 hours, 4 days, 7 days, 14 days, 28 days, and 56 days post dosing.

Tumor Response:

The possible effect of the drug treatment on tumor response was evaluated by measuring the tumor dimensions on CT (or MRI) scans according to Response Evaluation Criteria in Solid Tumors (RECIST) criteria at screening and at week 4 and 8 post dosing, or according to RECIST criteria at screening, baseline day −1/0 and at day 7±1, week 4 (day 28±2) and week 8 (day 56±3) post dosing.

RECIST Criteria:

Evaluation of Target Lesions

Complete Response (CR):

Disappearance of all target lesions.

Partial Response (PR):

At least a 30% decrease in the sum of the LD of target lesions, taking as reference the baseline sum LD.

Stable Disease (SD):

Neither sufficient shrinkage to qualify for PR nor sufficient increase to qualify for PD, taking as reference the smallest sum LD since the treatment started.

Progressive Disease (PD):

At least a 20% increase in the sum of the LD of target lesions, taking as reference the smallest sum LD recorded since the treatment started or the appearance of one or more new lesions Evaluation of Non-Target Lesions Complete Response (CR):

Disappearance of all non-target lesions and normalization of tumor marker level

Incomplete Response/Stable Disease (SD):

Persistence of one or more non-target lesion(s) or/and maintenance of tumor marker level above the normal limits Progressive Disease (PD):

Appearance of one or more new lesions and/or unequivocal progression of existing non-target lesions Evaluation of Best Overall Response The best overall response is the best response recorded from the start of the treatment until disease progression/recurrence (taking as reference for PD the smallest measurements recorded since the treatment started). In general, the patient's best response assignment will depend on the achievement of both measurement and confirmation criteria Patients with a global deterioration of health status requiring discontinuation of treatment without objective evidence of disease progression at that time should be classified as having "symptomatic deterioration". Every effort should be made to document the objective progression even after discontinuation of treatment.

In some circumstances it may be difficult to distinguish residual disease from normal tissue. When the evaluation of complete response depends on this determination, it is recommended that the residual lesion be investigated (fine needle aspirate/biopsy) to confirm the complete response status.

Results

Patient Disposition

Disposition of patients is summarized herein: 26 subjects in 6 cohorts were enrolled between November 2007 and August 2009, and a total of 33 subjects had enrolled by December 2010. Each of the 3 subjects in cohorts 1-4 discontinued the study prematurely: 2 subjects due to death, 8 due to voluntary subject drop out, and 2 to pursue other treatment protocols. Of the 2 deaths, patient no. 1 was reported as a serious adverse effect, whereas patient no. 9 died 88 days post dosing and therefore, as defined in the protocol, was not reported as an SAE. In cohort 5, one subject completed the study (up to day 56), one withdrew prior to day 56 and one designated as "Other" withdrew due to disease progression. Five cohort 6 patients completed the study, 5 withdrew due to disease progression (2 had brain metastases), and one died approximately 2 months after receiving study treatment. Four cohort 7 patients completed the study; two withdrew due to disease progression.

Among the initial 33 patients enrolled, 31 attended the day 28 visit, and 19 attended the day 56 visit. Subjects were contacted for follow-up every 2-3 months thereafter for a period of up to 3 years or more post dosing for monitoring.

Patient Population Profile

Demographics

Demographics and baseline characteristics are summarized in Table 1 that follows. Overall, 54% of the subjects were male and 46% female. All but five of the subjects (4-Hispanic and 1-Asian) enrolled were Caucasian. The mean age of the subjects enrolled was 58.5 years, with the youngest 35.1 years old and the oldest 74.1 years. The mean Karnofsky score at entry was 85.4; the lowest score at entry was 70 (the minimum permitted by the protocol inclusion criteria) and the highest 100.

TABLE 1

Demographics/Baseline Characteristics Summary

| Demographic/Baseline Characteristic | Number | % |
|---|---|---|
| Gender | | |
| Male | 14 | 53.8 |
| Female | 12 | 46.2 |
| Race | | |
| Caucasian | 21 | 80.8 |
| Asian | 1 | 3.8 |

TABLE 1-continued

| Demographics/Baseline Characteristics Summary | | |
|---|---|---|
| Demographic/Baseline Characteristic | Number | % |
| Hispanic | 4 | 15.4 |
| Age, mean (years) | 58.5 | — |
| Karnofsky score (mean) | 85.4 | — |

Medical History

Medical history is summarized herewith: As expected in a patient population with a mean age of 58.5 years, all subjects had other medical conditions at baseline. The most common medical conditions (defined as those present in at least three subjects) were: hypertension (13 subjects); fatigue (10 subjects); constipation (6 subjects); diarrhea and anemia (5 subjects each); nausea, GERD, hypercholesterolemia, hyperlipidemia, seasonal allergy, and cholecystectomy (4 subjects each); abdominal pain, cough, hypothyroidism, low back pain, and pneumonia (3 subjects each).

Primary Diagnosis

The frequency of tumor type at baseline is summarized in Table 2 that follows. The most frequent tumor types were colorectal adenocarcinoma, non-small cell lung cancer, melanoma, sarcoma, and carcinoid/neuroendocrine. One subject each had the following tumor types: transitional cell carcinoma of the bladder, cancer of the distal esophagus, Merkle cell carcinoma, lung small cell carcinoma, renal cell carcinoma, gastro-intestinal stromal tumor, testicular sex cord tumor, and papillary thyroid carcinoma.

TABLE 2

| Primary Tumor Diagnoses (cohorts 1-7) | | |
|---|---|---|
| Tumor Type | Total number | Number at cohort 6-7 |
| Colorectal Adenocarcinoma | 11 | 5 |
| Carcinoid/Neuroendocrine | 4 | 4 |
| Non-small cell lung cancer | 3 | 1 |
| Renal Cell Carcinoma | 3 | 3 |
| Melanoma | 2 | 1 |
| Sarcoma | 2 | 0 |
| Thyroid cancer | 2 | 2 |
| Esophageal Adenocarcinoma | 1 | 1 |
| Merkle cell carcinoma | 1 | 1 |
| Bladder/Transitional Cell | 1 | 0 |
| Lung small cell carcinoma | 1 | 0 |
| G-I stromal tumor | 1 | 0 |
| Testicular/sex cord tumor | 1 | 0 |

Prior Chemotherapy

Prior chemotherapy is summarized by the number and frequency of chemotherapy herewith: All subjects enrolled in the trial had previous chemotherapy with multiple agents, with 3.7 (range 1-8) mean previous chemotherapy lines. The most frequently utilized medications were: 5-FU (10.9%), Bevacizumab (10.9%), Capecitabine (8.6%), Leucovorin (8.0%), Irinotecan (8.0%), Cetuximab (5.2%), Oxaliplatin (4.6%), Temozolomide (3.4%), Cisplatin (3.4%), Folfox (3.4%), Sunitinib (2.9%), Dacarbazine (2.3%), and Docetaxel (2.3%). Most subjects (16/26, 61.5%), received at least one prior anti-angiogenic agent: Bevacizumab (12 patients), Sunitinib (4 patients), and Sorafenib (2 patients). The use of these chemotherapeutic agents reflects the types of tumors occurring in this patient population.

Other Anti-Tumor Interventions

Essentially all subjects had previous surgery for their tumor. The details of the surgery and of other anti-tumor interventions, excluding chemotherapy, are summarized herewith: The average number of previous surgical procedures related to the tumor was >2/subject, with a few subjects having had 4 surgical procedures. Also, 12 of the subjects had previous radiation therapy. All of the courses of radiation therapy occurred at least 8 months prior to study treatment except for subject no. 13, whose last course of radiotherapy ended about 4.5 months previously. The protocol required no radiotherapy for at least 4 weeks prior to enrolment.

Tumor Evaluation at Baseline

All subjects had CT evaluations of tumor target lesions with measurement of tumor size at baseline for subsequent comparison post-treatment. For these measurements, the longest diameter of each target lesion was utilized.

Summary of Patient Population

Most subjects enrolled in this study were Caucasian with an almost equal gender distribution and a mean age of 58.5 years. The mean entry Karnofsky score was 85.4, and all subjects had concurrent medical conditions. The most frequent tumor types were colorectal adenocarcinoma, non-small cell lung cancer, melanoma, sarcoma and carcinoid/neuroendocrine. All subjects enrolled in the trial had previous cancer-related surgery and chemotherapy with multiple agents, the most common of which were 5-FU, Bevacizumab, Capecitabine, Leucovorin, Irinotecan, Cetuximab, Oxaliplatin, Temozolomide, Cisplatin, Folofox, Sunitinib, Dacarbazine, and Docetaxel; the majority also had previous anti-angiogenic therapy and radiation therapy.

Safety Evaluations

Adverse Events

The incidence and frequency of adverse events are summarized in Table 3 that follows: Overall, events experienced by at least 4 (15.4%) subjects included: pyrexia (50%); fatigue (46.2%); prolonged aPTT (38.5%); chills, hyponatremia and decreased hemoglobin (26.9% each); constipation (23.1%); nausea, vomiting, anorexia, and dyspoena (19.2% each); lymphopenia, elevated aspartate aminotransferase, hyperglycemia, myalgia, and hyperhidrosis (15.4% each). Pyrexia and chills occurred at higher doses only (cohorts 4-6). In cohort 6, 9 of 11 subjects experienced pyrexia and 6 of 11 also had chills. In cohort 7, one subject experienced a grade 3 fever. In all patients, the pyrexia and chills occurred on the day of study treatment (post-infusion), were transient, and resolved within 24 hours.

TABLE 3

| Most Frequent Adverse Events (cohort 1-6) | | |
|---|---|---|
| Adverse Event | Number Patients | % |
| Pyrexia | 13 | 50.0 |
| Fatigue | 12 | 46.2 |
| aPTT Prolonged | 10 | 38.5 |
| Chills | 7 | 26.9 |
| Hyponatremia | 7 | 26.9 |
| Hemoglobin decreased | 7 | 26.9 |
| Constipation | 6 | 23.1 |
| Nausea | 5 | 19.2 |
| Vomiting | 5 | 19.2 |
| Anorexia | 5 | 19.2 |
| Dyspnea | 5 | 19.2 |
| Lymphopenia | 4 | 15.4 |
| AST Increased | 4 | 15.4 |

TABLE 3-continued

| Most Frequent Adverse Events (cohort 1-6) | | |
|---|---|---|
| Adverse Event | Number Patients | % |
| Hyperglycemia | 4 | 15.4 |
| Myalgia | 4 | 15.4 |
| Hyperhidrosis | 4 | 15.4 |

Most of the events of pyrexia (11 of 14) and chills (7 of 8) that occurred in the higher dose groups were considered possibly, probably or definitely related to study drug. The only other events considered definitely related to study drug included two events of nausea and one event each of anemia, vomiting, fatigue, hyperhidrosis, anorexia, and headache. None of these events were classified as NCI Grade 3 or higher. Thus, no dose limiting toxicities had occurred. Most of the other adverse events were considered unrelated or unlikely related to study drug.

Of the most common adverse events, fatigue was considered unrelated in 9/12 subjects and unlikely in one subject; prolonged aPTT unrelated in 7/10 subjects; decreased hemoglobin was considered unrelated in all 7 subjects; and constipation unrelated in all occurrences. Note: The local investigator commented that the aPTT local lab test is highly sensitive (as used for screening for lupus anti-coagulant); indeed, all aPTT elevation adverse events occurred in patients of that clinic.

The following Grade 3 or higher adverse events were reported; all were considered unrelated or unlikely related to the investigational drug: Subject no. 001 (cohort 1): Grade 3 disease progression; subject no. 007 (cohort 3): Grade 3 hyponatremia and hyperkalemia; subject no. 008 (cohort 3): Grade 3 hemoglobin decreased; subject no. 009 (cohort 3): Grade 3 fatigue; subject no. 013 (cohort 4): Grade 3 hypokalemia, hyponatremia, hypochloremia, and fatigue; subject no. 025 (cohort 6): Grade 4 suicidal ideation; subject no. 027 (cohort 6): Grade 3 weakness; subject no. 033 (cohort 6): Grade 4 abdominal pain and Grade 3 hyperglycemia; subject no. 035 (cohort 6): Grade 3 elevated total bilirubin, elevated AST, elevated ALT, and elevated alkaline phosphatase; and subject no. 036 (cohort 6): Grade 3 hyponatremia. Disease progression in subject no. 1 was a serious adverse event; all of the other events were not serious. All of the subjects with Grade 3 hyponatremia (no. 007, no. 013, and no. 036) with or without other Grade 3 metabolic events had gastrointestinal malignancies.

Serious Adverse Events

No serious adverse events (SAEs) related to treatment with the study drug were reported.

Laboratory Testing:

Hematology and Coagulation

No significant trends in mean changes occurred after treatment in any of the cohorts for the following tests: basophil count, eosinophil count, lymphocyte count, hematocrit, hemoglobin, neutrophil count, platelet count, RBC, and PT. A trend for increased aPTT after treatment was observed in each cohort, although most mean values remained within the normal range. Mean and median white blood cell counts (WBC) tended to decrease in cohorts 3-6 from the day of dosing to day 4, but individual values remained within normal limits in all subjects except for two subjects in cohort 6: (1) subject no. 26 had a low WBC (3700 K/μL) on the day of dosing that decreased to 2700 K/μL on Day 4 but then increased to at least 4000 K/μL for the remainder of the study and (2) subject no. 32 had a normal WBC of 6.3 K/μL on the day of dosing that decreased to 4.5 K/μL on Day 4 and then varied between 4.3 and 6.0 K/μL.

Values for hematology tests that were considered clinically significant findings include:

Subject no. 8 (in cohort 3) had a hematocrit of 32.3% and hemoglobin of 10.6 g/dL on the day of dosing that gradually decreased over time to 25.5% and 7.9 g/dL, respectively, on day 28. This subject's platelet count was 443,000 K/μL on the day of dosing and increased to 516,000 K/μL on day 28.

Subject no. 14 (in cohort 4) had a hematocrit of 34.2% and hemoglobin of 10.8 g/dL at screening; these values gradually decreased over time to 26.4% and 8.3 g/dL, respectively, on day 14. This subject's aPTT was 33.1 seconds at screening, 34.4 seconds at day 4, and then increased to 49.6 seconds at day 7 and 53.6 seconds at day 14.

Subject no. 33 (in cohort 6) had a hematocrit of 38.3% at screening and 33.1% on the day of dosing and hemoglobin of 12.3 g/dL at screening and 10.9 g/dL on the day of dosing; both stabilized for the duration of the study. This subject's platelet count was 116,000 K/μL on the day of dosing and decreased to 89,000 K/μL on day 4 but subsequently increased to 129,000 K/μL on Day 28. The PTT was normal at 31 seconds on the day of dosing but increased to 44.5 and 48.2 seconds on Days 14 and 28, respectively.

Summarizing the shift in hematology and coagulation lab values from the day of dosing to day 28 for the combined cohorts: The shift did not suggest any trend for values to shift to below or above the normal range at 28 days post-treatment. In particular, for both hematocrit and hemoglobin, no trend was observed for values to shift to below the normal range.

Chemistry

Summary of serum chemistry testing: No significant trends in median changes occurred after treatment in any of the cohorts for the following tests: ALT, AST, albumin, alkaline phosphatase, calcium, creatinine, glucose, potassium, sodium, bilirubin, total protein, and BUN. Mean levels of the following were increased, due to a high level observed in one subject: ALT and AST in cohort 6 at Day 28 due to levels of 406 U/L and 232 U/L, respectively, in subject no. 35; total bilirubin in cohort 6 at Day 28 due to a level of 7.4 in subject no. 35. Very high alkaline phosphatase levels in the following subjects accounted for elevated mean levels in their respective cohorts: subjects no. 4 (cohort 2), no. 24 (cohort 5), and no. 22, 26, 30, 35, and 36 (all in cohort 6).

Chemistry tests: Subjects no. 4 and no. 22 had elevated ALT and AST tests on the day of dosing that subsequently decreased/normalized. Subject no. 35 in cohort 6 had elevated levels of ALT and AST at day 28: 406 U/L and 232 U/L, respectively, but these levels normalized by day 56. This subject (no. 35) was hospitalized for bile duct obstruction due to tumor progression and also had markedly elevated levels of total bilirubin, 7.4 mg/dL, and alkaline phosphatase, 1176 U/L, at day 28. Otherwise, all ALT and AST elevations were <3× the upper limits of normal and tended to be sporadic. No subject other than no. 35 had an abnormal total bilirubin level during participation in the study. Elevated alkaline phosphatase on the day of dosing was common, presumably due to tumor and/or metastatic disease, but a significant progressive increase in this lab test only occurred in two subjects (no. 4 who had a level of 383 U/L at screening, 493 U/L on the day of dosing and 609 U/L at Day 28 and no. 36 who had a level of 163 U/L on the day of dosing and 377 U/L on Day 28). No subjects developed clinically significant post-treatment levels for any of the other chemistry tests.

Summarizing the shift in serum chemistry values from the day of dosing to day 28 for the combined cohorts: 5/15 subjects who had a normal level at the day of dosing had a low level of serum sodium on day 28. However, the sodium levels were abnormal only intermittently, usually only slightly below normal, and not clinically significant. The shift tables did not suggest any other trend for values to shift to below or above the normal range at 28 days post-treatment.

Urinalysis

The frequency of an abnormality on urinalysis on the day of dosing (89.5%) and at screening (76.0%) was high, but no trends were observed at the post-dosing visits. A review of the data indicated that no clinically significant abnormalities occurred on urinalysis, although a few subjects had small amounts of protein in their urine, and subject no. 30 in cohort 6 had 2+ proteinuria at day 28.

Antibodies to Adenovirus 5

Figure 11:
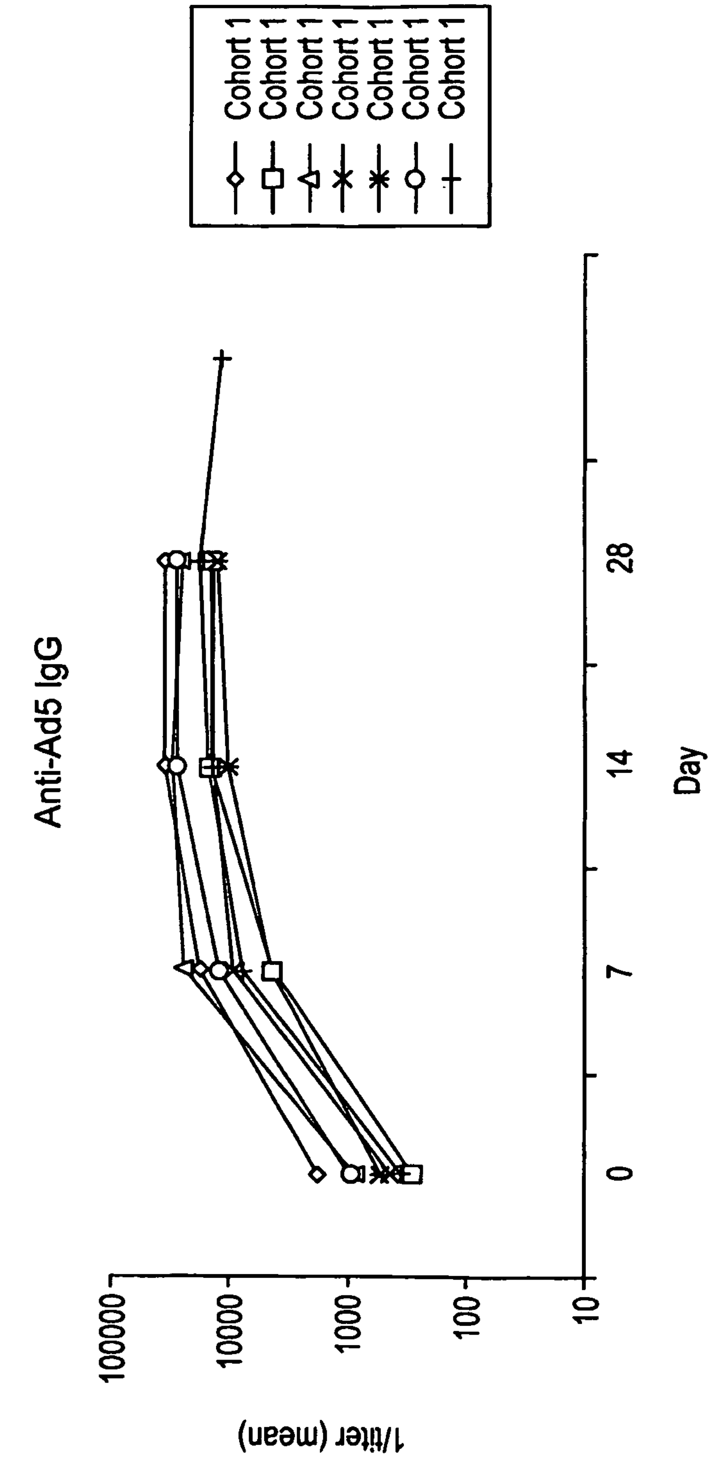
FIG. 11 is a graph illustrating the humoral immune response to a single administration of the Ad5-PPE-1-3X fas-chimera adenovirus, in cohorts 1 to 7 (cohort 1=diamond ♦; cohort 2=square ■; cohort 3=triangle ▲; cohort 4="X"; cohort 5=star; cohort 6=circle ●; cohort 7=vertical line |). Individual patients' anti-Adenovirus 5 IgG levels were assayed (as detailed in Example II) at day 0 (administration), and days 7, 14, 21 and 28 post infusion. Note the plateau of the immune response as early as day 7 in some cohorts (e.g. 1, 3, 4) and later in others (e.g. cohorts 2, 5, 6, 7)

Serum samples from subjects tested for antibodies to Adenovirus 5 (total and IgG); increase in titers between pre- and post-dose for IgG antibodies are summarized in Table 4 and FIG. 11. The post-dose samples were collected at day 28 or 56 in all but 3 subjects; these 3 had post-dose samples tested earlier due to the non-availability of samples at day 28. All post-dose IgG antibody titers increased at least 7-fold; 8 of 33 subjects had at least a 100-fold increase in IgG antibodies over the pre-dose titer. All post-dose total antibody titers to adenovirus 5 increased at least 5-fold; 10 of 26 subjects had at least a 625-fold increase in total antibodies over the pre-dose titer. There was no correlation between fold increase (total and IgG antibody titers) and dose level (P>0.05, Pearson and Spearman correlation tests). Data collected at day 56 for cohort 7 subjects indicated a trend of decreased IgG levels, compared to day 28 (see Table 4 that follows).

TABLE 4

Summary of Anti-Adenovirus 5 Increase in IgG Antibody Titers and Total Antibody Titers

| | | Anti-Ad5 Titer | | | Anti-Ad5 IgG Titer | | | |
|---|---|---|---|---|---|---|---|---|
| Cohort | Patient | Pre-dose | Post-dose (day 28) | Fold increase | Pre-dose | Post-dose (day 28) | Fold increase | Post-dose (day 56) |
| 1 | 1 | 62500 | 1562500 | 25 | 3500 | 43,740 | 12 | |
| | 2 | 2500 | 1562500 | 625 | 400 | 43,740 | 109 | |
| | 3 | 12500 | 1562500 | 125 | 1500 | 43,740 | 29 | |
| 2 | 4 | 2500 | 62500 | 25 | 300 | 5,500 | 18 | |
| | 5 | 500 | 12500 | 25 | 180 | 1500 | 8 | |
| | 6 | 2500 | 7812500 | 3125 | 350 | 35,000 | 100 | |
| 3 | 7 | 2500 | 12500 | 5 | 600 | 4100 | 7 | |
| | 8 | 2500 | 312500 | 125 | 950 | 43,740 | 46 | |
| | 9 | 2500 | 7812500 | 3125 | 1000 | 29,000 | 29 | |
| 4 | 10 | 12500 | 1562500 | 125 | 420 | 20,000 | 48 | |
| | 13 | 2500 | 1562500 | 625 | 200 | 9,000 | 45 | |
| | 14 | 2500 | 1562500 | 625 | 650 | 11,000 | 17 | |
| 5 | 20 | 12500 | 312500 | 25 | 90 | 13,000 | 144 | |
| | 21 | 2500 | 312500 | 125 | 300 | 14,000 | 47 | |
| | 24 | 12500 | 312500 | 25 | 1,200 | 12,000 | 10 | |
| 6 | 22 | 12500 | 1562500 | 125 | 850 | 11,500 | 14 | |
| | 25 | 2500 | 312500 | 125 | 850 | 11,000 | 13 | |
| | 26 | 2500 | 312500 | 125 | 70 | 11,000 | 157 | |
| | 27 | 12500 | 7812500 | 625 | 540 | 43,740 | 81 | |
| | 28 | ND | 312500 | ND | 700 | 43,740 | 62 | |
| | 29 | 12500 | 312500 | 25 | 120 | 18,000 | 150 | |
| | 30 | 62500 | 7812500 | 125 | 6000 | 43,740 | 7 | |
| | 32 | 2500 | 1562500 | 625 | 200 | 43,740 | 219 | |
| | 33 | 2500 | 7812500 | 3125 | 500 | 43,740 | 87 | |
| | 35 | 2500 | 62500 | 25 | ND | ND | ND | |
| | 36 | 2500 | 7812500 | 3125 | 400 | 30,000 | 75 | |
| | 38 | 12500 | 7812500 | 625 | 800 | 43,470 | 54 | |
| 7 | 39 | 62,500 | 1,562,500 | 25 | 800 | 30000 | 38 | 18000 |
| | 40 | 12,500 | 312,500 | 25 | 300 | 35000 | 117 | 22000 |
| | 41 | 62,500 | 7,812,500 | 125 | 200 | 7500 | 38 | 10000 |
| | 42 | 12,500 | 1,562,500 | 125 | 450 | 5500 | 12 | 4500 |
| | 43 | 62,500 | 1,562,500 | 25 | 140 | 7000 | 50 | 5000 |
| | 44 | 12,500 | 312,500 | 25 | 200 | 22000 | 110 | NA |

All subjects were also assessed as to their level of neutralizing Adenovirus 5 antibodies at baseline (Table 5). Results show that 35% had highly elevated baseline levels (>210) and 41% of the subjects had low levels (≤18) of neutralizing antibodies.

TABLE 5

Summary of Anti-Adenovirus 5 Neutralizing Antibody Titers at Baseline

| Subject ID | Cohort | Titer |
|---|---|---|
| 001 | 1 | 620 |
| 002 | 1 | 750 |
| 003 | 1 | 210 |
| 004 | 2 | 10.5 |
| 005 | 2 | 10.5 |
| 006 | 2 | 400 |
| 007 | 3 | 5 |
| 008 | 3 | 380 |
| 009 | 3 | 210 |
| 010 | 4 | 1050 |
| 013 | 4 | 860 |
| 014 | 4 | 5 |
| 020 | 5 | 18 |
| 021 | 5 | 5 |
| 024 | 5 | 520 |
| 022 | 6 | 110 |
| 025 | 6 | 210 |
| 026 | 6 | 5 |

TABLE 5-continued

| Summary of Anti-Adenovirus 5 Neutralizing Antibody Titers at Baseline | | |
|---|---|---|
| Subject ID | Cohort | Titer |
| 027 | 6 | 5 |
| 028 | 6 | 940 |
| 029 | 6 | 5 |
| 030 | 6 | 1250 |
| 032 | 6 | 195 |
| 033 | 6 | 220 |
| 035 | 6 | 10.5 |
| 036 | 6 | 5 |
| 038 | 6 | 620 |
| 039 | 7 | 1000 |
| 040 | 7 | 5 |
| 041 | 7 | 15 |
| 042 | 7 | 5 |
| 043 | 7 | 160 |
| 044 | 7 | 85 |

No correlation could be discerned between the presence of neutralizing anti-Ad5 antibodies at baseline and disease progression at days 28 (FIG. 2) or 56 (FIGS. 3A, 3B Table 5) (Pearson Product Moment Correlation; P>0.050; Spearman Rank Order Correlation; P>0.050).

Cytokine Levels in Peripheral Blood in Cohort 6

Peripheral blood cytokine levels were measured in cohort 6 patients at baseline, and at the following times after dosing with AD5-PPE-1-3x-FAS-CHIMERA-: 6 hours, 4 days, 7 days, 14 days, 28 days, and 56 days post infusion. Results are summarized in Table 6 that follows.

TABLE 6

| Summary of Mean Peripheral Blood Cytokine Levels in Cohort 6 | | | | | | | |
|---|---|---|---|---|---|---|---|
| Cytokine | Baseline (n = 10) | 6 h (n = 10) | D4 (n = 2) | D7 (n = 9) | D14 (n = 9) | D28 (n = 9) | D56 (n = 3) |
| IL-6 | 10.38 | 1018.28 | 2.92 | 7.2 | 47.99 | 12.13 | 0 |
| IL-8 | 21.85 | 181.68 | 42.6 | 33.93 | 43.68 | 31.59 | 21.62 |
| VEGF | 73.47 | 54.82 | 0 | 147.09 | 132.77 | 133.53 | 0 |
| FGF | 11.92 | 9.95 | 5.75 | 20.42 | 19.55 | 12.43 | 7.30 |
| TNF-a | 0 | 1.53 | 0 | 0 | 0 | 0 | 0 |
| sTNFRI | 1746.44 | 3143.89 | 1725.60 | 2383.03 | 2706.33 | 2222.37 | 1456.77 |
| sTNFRII | 5819.81 | 7509.75 | 10063.71 | 7921.62 | 10155.62 | 7717.02 | 5866.12 |

A significant increase in mean IL-6 levels occurred 6 hours post-infusion; this level returned to baseline by day 4. A smaller increase in TNFR11 levels was noted, peaking between days 4 and 14. No major elevations occurred with the other measured cytokines.

Vital Signs

No significant post-treatment trends were observed for systolic BP, diastolic BP, and respiratory rate, and no subject developed any clinically significant abnormalities.

Significant elevations in temperature (>38 degrees Centigrade) occurred in 5 subjects at 6 hours post-infusion: one subject in cohort 5: no. 20 (38.3 degrees Centigrade) and 4 subjects in cohort 6: no. 26 (39.1 degrees Centigrade), no. 27 (39.7 degrees Centigrade), no. 32 (39.8 degrees Centigrade), and no. 36 (39 degrees Centigrade). In each, the temperature had normalized prior to or by day 4 (which was the first recording of temperature following that of 6. hours post-infusion). The mean heart rate was increased to 101.2 beats/minute in cohort 6 at 6 hours post-dosing. This was due to amore rapid heart rate in the subjects that had experienced pyrexia in this cohort (heart rate of 107-140 beats/minute). Weight is summarized herein: no major change in weight occurred, except for a decrease in mean weight at follow-up (75.0 kg at screening, 75.0 kg at day 56, and 63.5 kg at follow-up).

Physical Exams

No treatment-related or clinically significant changes on exams are apparent from the data of by-subject physical exams at screening and day 56.

ECGs

ECG parameters at screening are summarized herein: At screening, 15 subjects had normal ECGs, and 11 had abnormalities that were considered not clinically significant. The original protocol specified that a follow-up ECG should be performed at the day 56 follow-up visit. As most subjects withdrew from the study prior to day 56, in cohorts 1-5 only subject no. 7 had a follow-up ECG and this showed ECG changes considered not clinically significant.

The protocol was later amended to obtain the follow-up ECG at the day 28 visit. In cohort 6, there were 4 follow-up ECGs obtained: two were normal and 2 had minor, non-clinically significant findings with no major changes from the screening ECG.

Biodistribution of Ad5-PPE-1-3X-fas-chimera

Due to an error, no whole blood samples were drawn for some of the patients in cohorts 5 and 6[3]). Urine samples were tested for 11 of the 12 cohort 6 patients and for the 12 additional patients from lower cohorts tested for levels in blood.

Analysis of the Urine Samples for Presence of Adenovirus:

Maximum levels of Adenovirus Vector DNA detected in urine are summarized in Table 7.

TABLE 7

| Maximum Levels of Adenovirus Vector in Urine (cohorts 1-6) | | |
|---|---|---|
| Cohort | Subject ID | Adenovirus Vector DNA copies/μg gDNA |
| 1 | 001 | 0 |
| 1 | 002 | $3.2 \times 10^3$ (Day 28) |
| 1 | 003 | 5.3 (Day 56) |
| 2 | 004 | $6.2 \times 10^2$ (3 hr) |
| 2 | 005 | 0 |
| 2 | 006 | 0 |
| 3 | 007 | 0 |
| 3 | 008 | 0 |
| 3 | 009 | $2.2 \times 10^3$ (Day 4) |
| 4 | 010 | 5.3 (Day 14) |
| 4 | 014 | $1.1 \times 10^3$ (6 hr) |
| 5 | 024 | 5.3 (6 hr) |

TABLE 7-continued

| Maximum Levels of Adenovirus Vector in Urine (cohorts 1-6) | | |
|---|---|---|
| Cohort | Subject ID | Adenovirus Vector DNA copies/μg gDNA |
| 6 | 022 | $1.1 \times 10^4$ (3 hr) |
| 6 | 025 | $1.5 \times 10^4$ (3 hr) |
| 6 | 026 | 5.3 (3 hr) |
| 6 | 028 | 5.3 (3 hr) |
| 6 | 029 | $1.6 \times 10^7$ (3 hr) |
| 6 | 030 | $4.7 \times 10^5$ (3 hr) |
| 6 | 032 | 5.3 (3 hr) |
| 6 | 033 | $2.3 \times 10^4$ (3 hr) |
| 6 | 035 | $1.8 \times 10^4$ (3 hr) |
| 6 | 036 | 0 |
| 6 | 038 | 0 |

VP—Viral particles; BLQ < 20 copies; BLD < 1.4 copies

Analysis of the Whole Blood Samples for the Presence of Adenovirus Vector

Figure 12A:
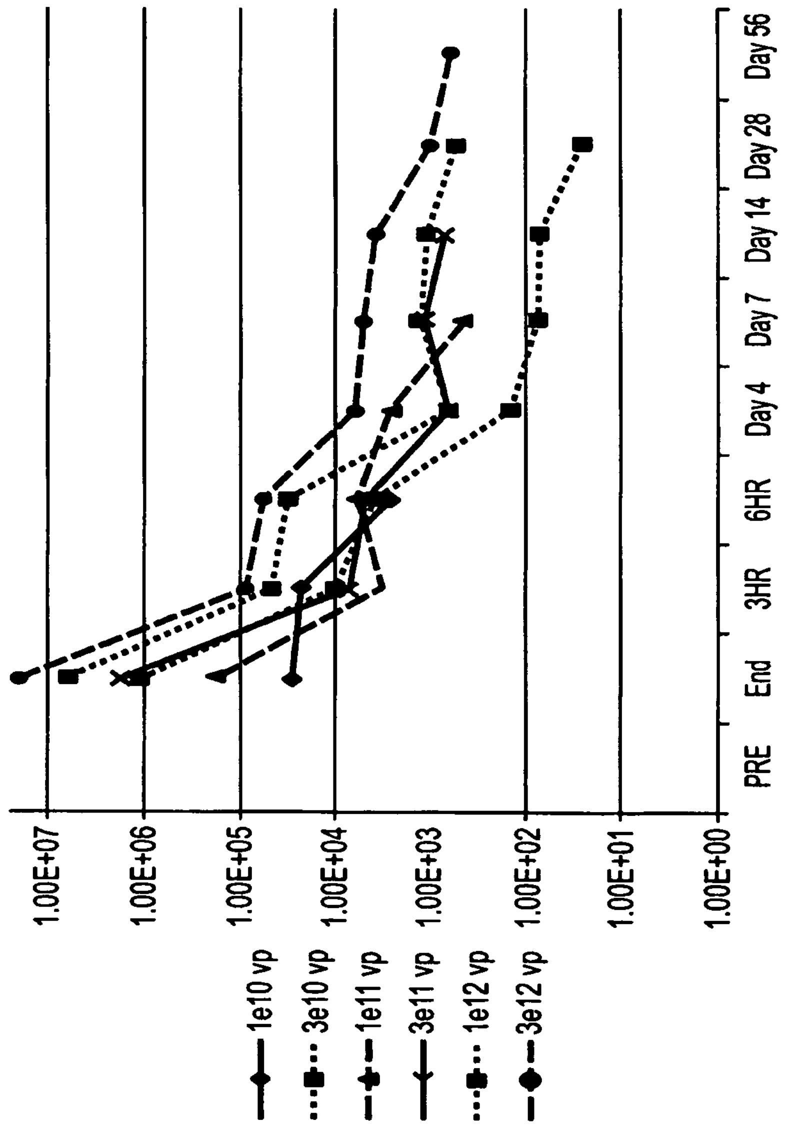
FIGS. 12A and 12B show the pharmacokinetics of the Ad5-PPE-1-3X fas-chimera adenovirus vector, following intravenous administration.

Average levels of Adenovirus Vector DNA, as detected by RT-PCR in whole blood for cohorts 1-6 are summarized over time in FIG. 12A. Table 8 that follows shows the median values for cohorts 1-6. Before infusion of the adenovirus vector, none of the patients tested showed amplification of adenoviral gene (below detectable levels). A dose-dependent increase in average maximum levels of adenovirus vector DNA found in whole blood is evident from the data. At the end of the infusion all patients had individual blood virus levels in the range of $1.9\times10^3$ and $5.5\times10^7$ copies/μg gDNA, correlating positively with dose received.

Figure 12B:
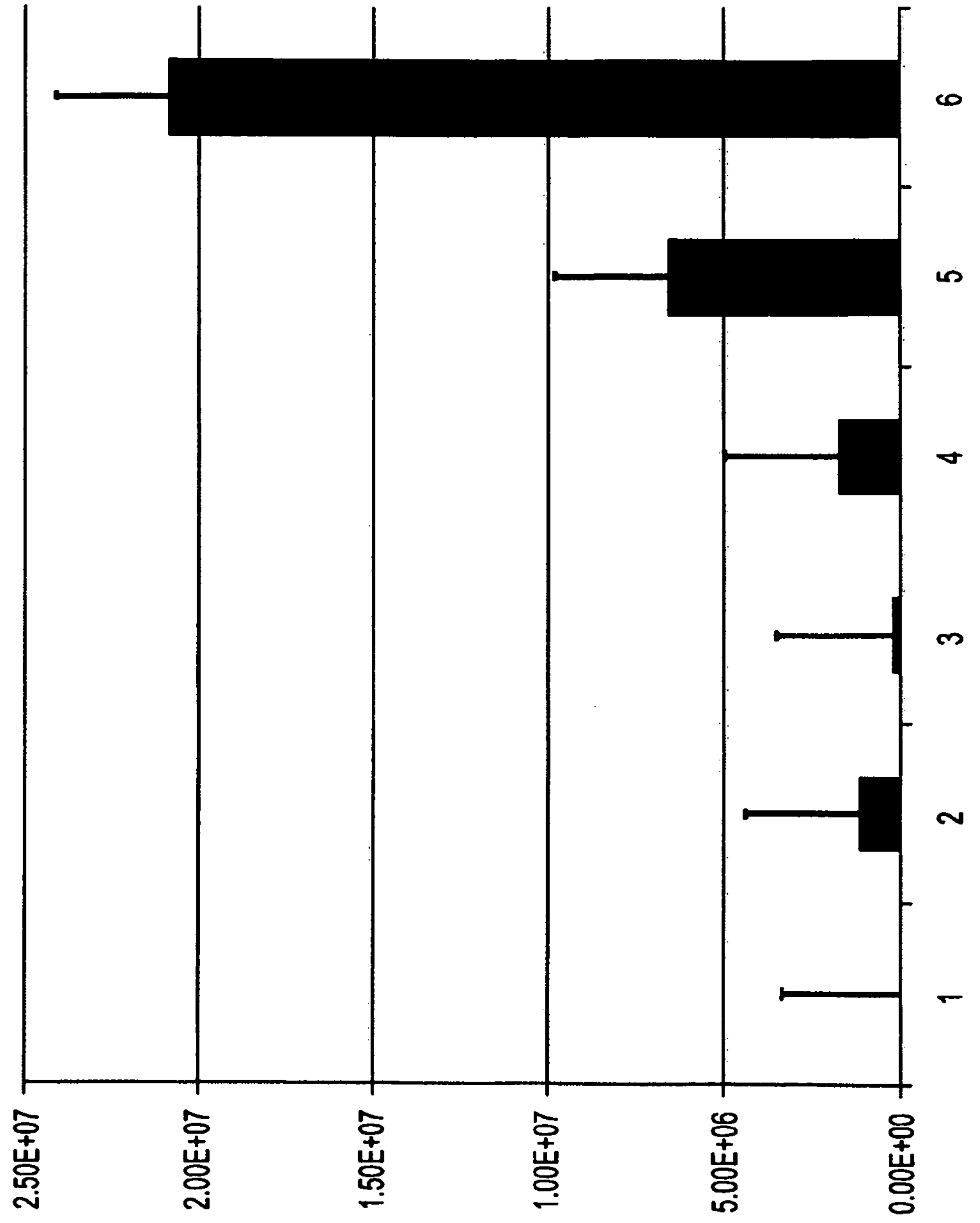

In cohort 6 patients (FIG. 12A, grey dashed line), average levels of adenovirus decreased from a range of $2.1\times10^5$-$5.5\times10^7$ (end of infusion) to a range of $1.1\times10^4$-$2.6\times10^5$ copies/μg gDNA (three hours post infusion, see FIG. 12B). Levels of adenovirus continued to decrease 6 hours post infusion and subsequently decreased throughout the final time points. By day 56, Adenovirus DNA levels were either all reduced by at least 2 log-fold, or were undetectable.

TABLE 8

| Presence of Adenovirus Vector in Whole Blood: Median Values | | |
|---|---|---|
| Cohort | Dose vp | Median Adenovirus Vector DNA copies/μg gDNA at end of infusion (Maximum) |
| 1 | $1 \times 10^{10}$ | $1.6 \times 10^4$ |
| 2 | $3 \times 10^{10}$ | $4.5 \times 10^5$ |
| 3 | $1 \times 10^{11}$ | $1.6 \times 10^5$ |
| 4 | $3 \times 10^{11}$ | $1.7 \times 10^6$ |
| 5 | $1 \times 10^{12}$ | $6.5 \times 10^6$ |
| 6 | $3 \times 10^{12}$ | $2.5 \times 10^7$ |

Analysis of the Expression Levels of Fas-Chimera Transgene in Whole Blood

None of the 21 subjects tested had detectable levels of transgene cDNA (as determined by RT-PCR, representing blood mRNA levels) in whole blood. However, in one patient 01-036 (esophageal cancer) a sample from a subcutaneous metastasis was tested and detectable levels of adenovirus transgene expression were found in the aspirate on days 4 ($1.4\times10^5$ copies/μg RNA) and 28 ($3.9\times10^5$ copies/μg RNA) after treatment (Table 9), providing direct evidence of the specificity of the transgene expression in the target tumor tissue.

TABLE 9

| Aspirate from tumor of patient 01-036 (copies/μg RNA) | | | | |
|---|---|---|---|---|
| time | Pt no. | cohort | sample | copies |
| Pre | 36 | 6 | Tumor | 0.00E+00 |
| Day 4 | 36 | 6 | Tumor | 1.40E+05 |
| Day 28 | 36 | 6 | Tumor | 3.90E+04 |

Summary of Safety Results

No signs of significant safety issues with Ad5-PPE-1-3X-fas-chimera were observed in this study. The maximal therapeutic dose (MTD) was determined to be $10^3$ virus particles per dose, in view of a dose limiting toxicity of a NCI grade 3 fever, shortly following dosing at the highest dose tested (cohort 7). Other than abnormal lab results, the most frequent adverse events were pyrexia, fatigue, chills, and constipation. Pyrexia and chills occurred mostly in the higher dose groups and were usually considered related to study medication. Although no trend for hematology values to shift outside the normal range was observed, several subjects had declines in hemoglobin and hematocrit values after study treatment. No clinically significant post-treatment chemistry or urinalysis abnormalities occurred during the study with the exception of a markedly elevated alkaline phosphatase and elevations of ALT, AST, and total bilirubin occurring in a subject with bile duct obstruction due to progression of cancer. No clinically significant post-treatment changes in vital signs were observed, except for the occurrence of fever 6 hours post-infusion in one cohort 5 and 4 cohort 6 subjects; the cohort 6 subjects with fever also had increased heart rates, resulting in a mean increase in heart rate for cohort 6 at 6 hours post-infusion. No treatment-related changes were observed on physical exams or ECGs.

All subjects had pre-dose anti-Adenovirus 5 antibodies (total and IgG) with total antibody titers increasing at least 5-fold post-treatment. FIG. 11 shows the anti-Adenovirus 5 antibodies in each of cohorts 1-6, measured at baseline, day 7, day 14 and day 28, and illustrates the tendency of the anti-Adenovirus 5 antibodies to plateau between 7 and 14 days post infusion, despite the variability observed between patients in the baseline antibody titer levels. Levels of anti-Adenovirus 5 antibodies (total and IgG) tended to increase post dosing, peaking on day 28 and tending to decrease by day 56 (FIG. 11). Overall, the fold increase was higher for the total anti-Adenovirus 5 titers than for the IgG titers, but no correlation was discerned between fold increase in anti-Adenovirus 5 antibodies and the dosage level. 34.6% of subjects had highly elevated levels of neutralizing antibodies to Adenovirus 5, measured at baseline, 23.1% had moderately elevated levels, and 42.3% had low levels. However, there was no correlation discernable between neutralizing anti-body titer at baseline and a clinical response (measured as stable disease). A significant increase in mean IL-6 blood levels occurred 6 hours post-dosing with Ad5-PPE-1-3X-fas-chimera; this level returned to baseline by day 4. No major elevations occurred with the other measured cytokines (Il-8, VEGF, FGF, and TNF-alpha).

In most subjects with detectable levels of Adenovirus 5 in the urine, the presence was transient, with levels detectable only within the initial 24 hours after the intravenous (IV) infusion of Ad5-PPE-1-3X-fas-chimera. The Ad5-PPE-1-3X-fas-chimera adenovirus vector was present in high copy numbers in whole blood directly after the IV infusion. The levels of adenovirus vector subsequently decreased with time in whole blood. Samples with vector present in the whole blood were tested for the expression of the Fas-chimera transgene (RT-PCR for the transgene mRNA). None of the 21 subjects tested had detectable levels of transgene cDNA (cDNA is the RT-PCR reaction product representing blood mRNA levels) in whole blood.

Preliminary Efficacy Assessment

Disease Progression or Recurrence

Disease progression was assessed according to clinical deterioration and radiographic growth, based on RECIST criteria. In cohorts 1-5, at day 56, 3/14 patients had stable disease. In cohort 6, on day 56 (n=12), 1 PR, 4 SD ("stable disease") and 7 had progressive disease. Thus at day 56, 5/12 (42%) had stable disease or better. In cohort 7, at day 56, 4 out of 6 subjects (67%) had stable disease; In cohorts 1-6, at day 28, 21/26 (80.8%) of the subjects were considered not to have deterioration, one had deteriorated (5.6%), and 4 had no observation for this endpoint. Only 8 subjects from cohorts 1-6 had observations at the Day 56 visit, and all of these were negative for deterioration.

Disease progression was also assessed by frequency of radiographic growth (measured according to % growth in the sum longest diameter of target lesions as defined in the RECIST scoring criteria). Where no new lesions were present and there was either no growth in the longest diameter sum of the target lesions or that growth was no more than 20%, the subject was considered to have stable radiographic disease at that visit.

Reduction in Refractory Metastatic Papillary Thyroid Cancer Following Multiple Infusions of $3\times10^{12}$ Virus Particles of Ad5-PPE-1-3X-Fas-Chimera Of these patients, Subject 026, a 69 year-old Hispanic female, was enrolled with metastatic papillary thyroid cancer that was resistant to radioiodine and was dosed in cohort 6 on Mar. 16, 2009. Baseline CT scan showed a mass lesion in the neck with pressure on the airway (FIG. 4, arrows). Day 28 scan showed stable disease, and a follow-up scan 6 months (FIG. 5, arrows) and 12 months after treatment showed a greater than 30% reduction in the long diameter of the mass and no pressure on the airway, with radiographic lucency suggestive of central necrosis (FIG. 5, blue arrow). Additionally, thyroglobulin levels have decreased in this patient: the level at baseline was 426 ng/mL and 10 months later had decreased to 326 ng/mL (normal levels <55 mg/mL).

Figure 10A:
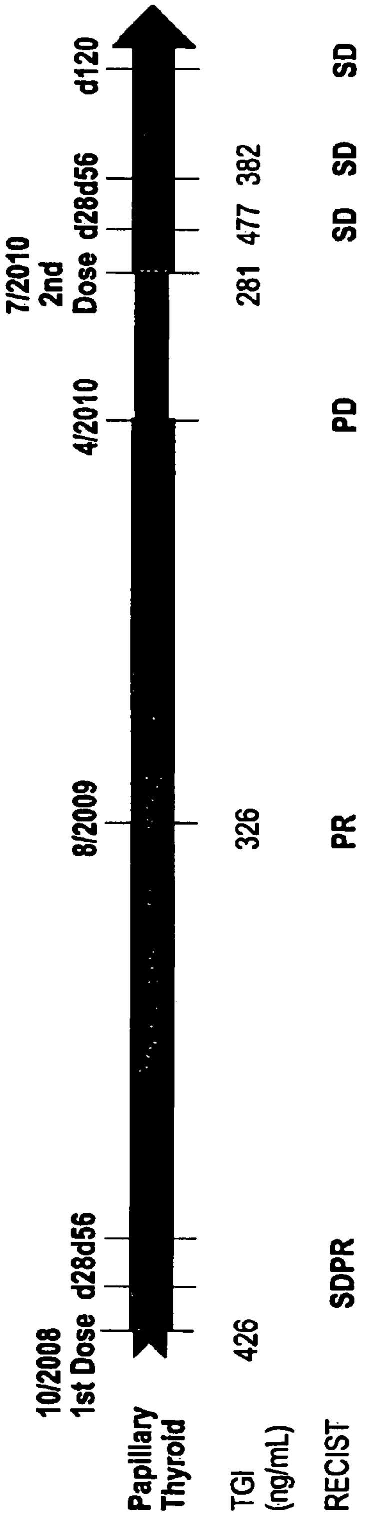
FIGS. 10A and 10B is a timeline showing the effects of administration of a single dose of Ad5-PPE-1-3X fas-chimera adenovirus vector ($3\times10^{12}$ virus particles) on disease progression in two thyroid cancer patients (see Example II herein).

A second dose was administered one and one half years after the first dosing, and the patient was progression free at day 120 post infusion. Thyroglobulin levels at the time of second doging were 281 ng/mL, rising to 477 ng/mL at day 28, and dropping to 382 ng/mL at day 56 post infusion. No dose limiting toxicities, severe side effects or cytokine storm were observed throughout the treatment period. (FIG. 10A)

Figure 10B:
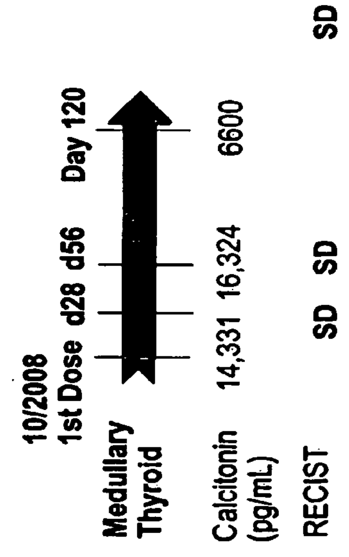

In another patient with a medullary thyroid cancer lesion, administration of $3\times10^{12}$ virus particles of Ad5-PPE-1-3X-fas-chimera resulted in dramatic reduction in levels of the thyroid cancer biomarker calcitonin: levels were greatly elevated before administration (14, 331 pg/ml, normal=<10 pg/ml), increased (16,324 pg/ml) at 56 days post infusion, but showed marked reduction (6600 pg/ml) at 120 days post infusion. At 120 days post-treatment the patient was still progression free. (FIG. 10B)

Reduction in metastatic lesion of advanced neuroendocrine cancer following a single infusion of $3\times10^{12}$ virus particles of Ad5-PPE-1-3X-fas-chimera.

Figure 6A:
FIGS. 6A-6C are abdominal CT scans illustrating regression of a metastatic lesion following administration of a single dose of Ad5-PPE-1-3X fas-chimera adenovirus vector ($3\times10^{12}$ virus particles) in a subject with advanced neuroendocrine cancer.
Figure 6B:
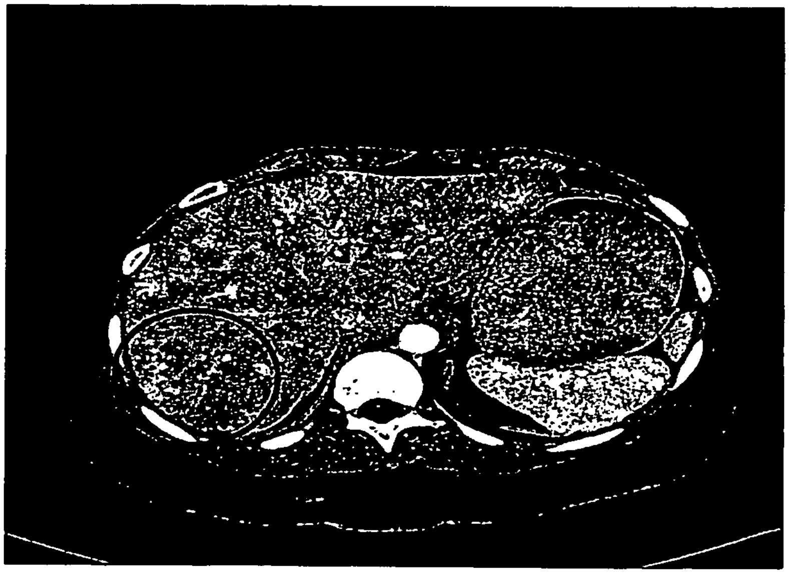
Figure 6C:
Figure 7A:
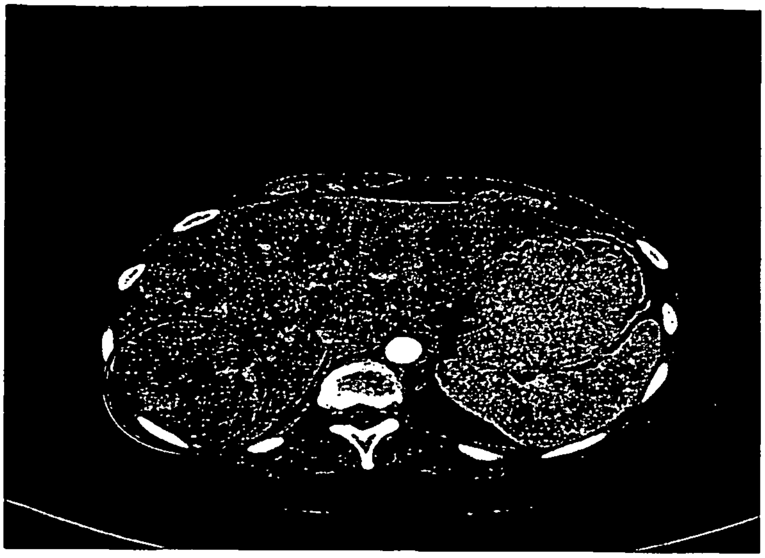
FIGS. 7A-7C are abdominal CT scans illustrating regression of a metastatic lesion following administration of a single dose of Ad5-PPE-1-3X fas-chimera adenovirus vector ($3\times10^{12}$ virus particles) as described in FIGS. 6A-6C.
Figure 7B:
Figure 7C:

Another patient in cohort 6, enrolled with advanced neuroendocrine cancer, was dosed in cohort 6 on Mar. 16, 2009. Day 21 CT scan showed several hepatic metastases (FIGS. 6A and 7A, red circle). Follow-up CT scans at 50 (FIGS. 6B and 7B, red circle) and 112 (FIGS. 6C and 7C, red circle) days post dosing showed continued regression of one of these metastatic lesions. According to RECIST criteria, this patient was scored as "stable disease", and has maintained "stable disease" classification for four months afterwards.

Summary of Efficacy

Although this single infusion study with patients having advanced or metastatic solid organ cancer is small, certain trends can be discerned from the efficacy data.

On day 56 evaluation, three of the 14 patients in Cohorts 1-5 had stable radiographic disease (SD); among the 12 Cohort-6 patients, five had stable disease on day 56, and one patient (with papillary thyroid carcinoma) had a near partial response on day 56 (out of 12 patients on cohort 6), which became a partial response (PR) later.

Figure 8:
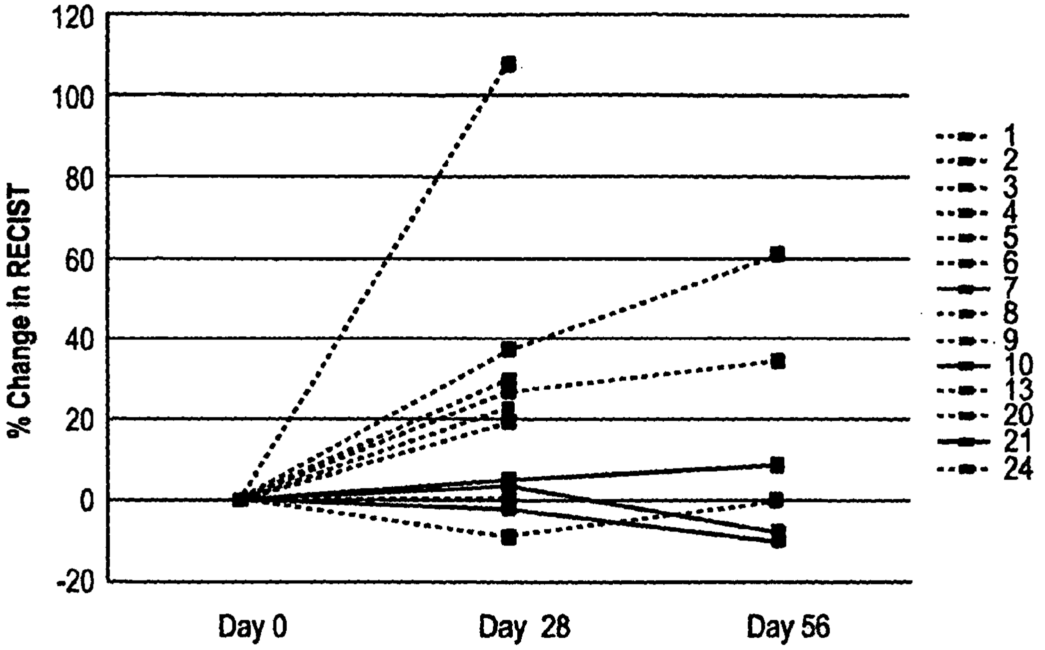
FIG. 8 is a graph illustrating the disease response of individual patients in cohorts 1-5, measured at days 0, 28 and 56, and expressed as percent change in RECIST scores, relative to those observed on day 0. Greater increase in RECIST scores is typically indicative of progressive disease (solid line=stable disease, dotted line=progressive disease)
Figure 9:
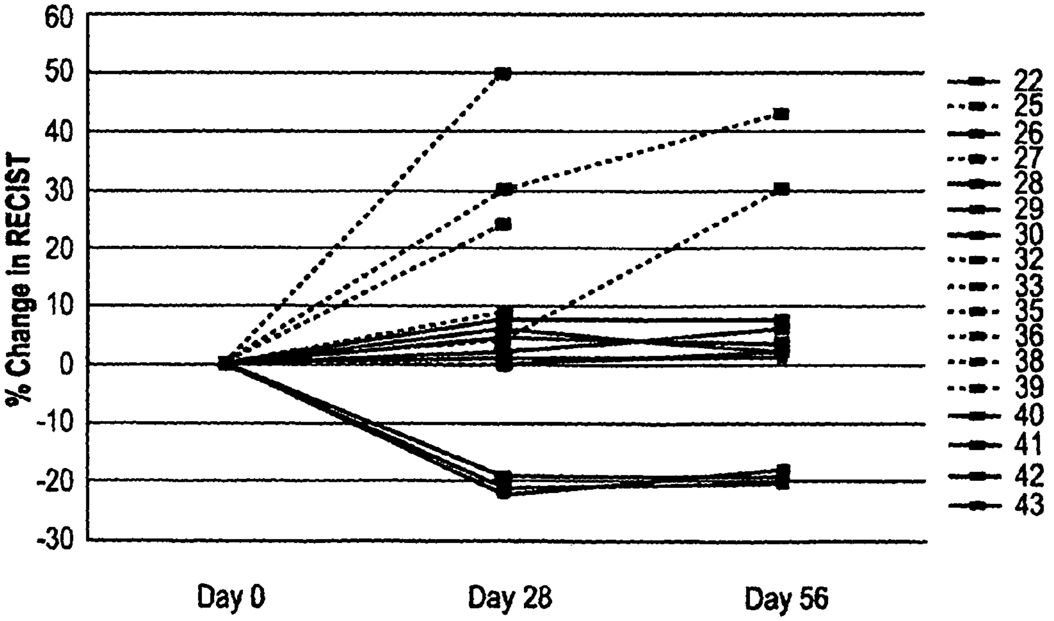
FIG. 9 is a graph illustrating the disease response of individual patients in cohorts 6 and 7, measured at days 0, 28 and 56, and expressed as percent change in RECIST scores, relative to those observed on day 0. Greater increase in RECIST scores is typically indicative of progressive disease (solid line=stable disease, dotted line=progressive disease). Note the trend to lesser change in RECIST scores among cohorts 6 and 7.

Among the 5 cohort 7 patients, 5 remained classified as having "stable disease" (SD). When the percent change in RECIST scores is plotted for days 0, 28 and 56, and correlated with the evaluations of stable and progressive disease, it can be seen that three out of 14 (21%) in cohorts 1-5 were stable at day 56 (FIG. 8). In cohorts 6 and 7 (FIG. 9), however, 9 out of 17 patients were stable at day 56.

In this open-label, dose-ranging study evaluating a single IV infusion of safety and efficacy of administration of Ad5PPE-1-3X-fas-chimera (SEQ ID NO: 9) in the clinical setting, 3 subjects with advanced or metastatic cancer have been enrolled in each of the first 5 ascending dose cohorts and 12 subjects have been enrolled in the 6" cohort. Taken together, the data indicates Ad5-PPE-1-3X-fas-chimera is safe for systemic administration, in all of the doses tested, as no safety or dose-limiting toxicities (DLT) have been observed at any of the utilized doses. Although two serious adverse events were reported, these were related to progression of the cancer and unrelated to study treatment. Several subjects who received Ad5-PPE-1-3X-fas-chimera at one of the 2 highest doses developed transient pyrexia and chills shortly after receiving study treatment, events commonly occurring after the administration of adenovirus vectors. Clinically significant abnormalities on laboratory testing were infrequent and considered unrelated to Ad5-PPE-1-3X-fas-chimera treatment.

Maximally tolerated dose (MTD) was determined as $10^{13}$ virus particles per dose, in view of the single incident of dose limiting toxicity (NCI Grade 3 fever) observed in the cohort receiving the highest dose tested (cohort 7). Although being a small single infusion study among patients with multiple types of advanced, refractory cancer, evidence for efficacy of Ad5-PPE-1-3X-fas-chimera infusion includes patients with stable radiographic disease and one prolonged partial response among patients receiving $3\times10^{12}$ virus particles of Ad5-PPE-1-3X-fas-chimera (cohort 6)(Table 10).

TABLE 10

Disease response to a single dose of Ad5PPE-1-3X-Fas-chimera: Percent stable disease at day 56, by indication (cohorts 6 and 7).

| Type of Cancer | Number of Patients | % SD at Day 56 |
|---|---|---|
| Colorectal Adenocarcinoma | 5 | 40% |
| Carcinoid/Neuroendocrine | 4 | 75% |
| Non-small cell lung cancer | 1 | 100% |
| Renal cell carcinoma | 3 | 33% |
| Melanoma | 1 | 0% |
| Thyroid cancer | 2 | 100% |

TABLE 10-continued

| Disease response to a single dose of Ad5PPE-1-3X-Fas-chimera: Percent stable disease at day 56, by indication (cohorts 6 and 7). | | |
|---|---|---|
| Type of Cancer | Number of Patients | % SD at Day 56 |
| Merkle cell carcinoma | 1 | 0% |
| Esophageal Adenocarcinoma | 1 | 0% |

In one patient suffering from esophageal cancer the subcutaneous metastasis was sampled and detectable levels of Ad5-PPE-1-3X-fas-chimera transgene expression were found in the aspirate on days 4 and 28 after treatment.

Example III

Effect of Ad5PPE-1-3X-Fas Chimera Administration on Thyroid Cancer in the Clinical Setting In order to determine the efficacy of administration of AD5PPE-1-3X-fas-chimera on Thyroid Cancer in the clinical setting, outcomes such as toxicity, adverse effects, antibody titer, biodistribution, disease progression and disease recurrence and survival were monitored in subjects with Thyroid Cancer tumors receiving intravenous infusion of the Ad5PPE-1-3X-fas chimera adenovirus vector.

Materials and Experimental Methods

Indications:

Advanced progressive and radioiodine-refractory differentiated thyroid cancer (DTC) (papillary, follicular, Hurthle cell) cancer patients.

Safety Objectives:

To evaluate the safety of a single systemic dose of the Ad5PPE-1-3X-fas chimera adenovirus vector in patients with advanced thyroid cancer.

Efficacy and Pharmacodynamics Objectives:

1. To evaluate the response to treatment for patients with advanced DTC with measurable disease using Response Evaluation Criteria in Solid Tumors (RECIST Criteria);

2. To assess the pharmacokinetic and pharmacodynamic profile of Ad5PPE-1-3X-fas chimera adenovirus vector;

3. Evaluation of changes in candidate biomarkers in response to Ad5PPE-1-3X-fas chimera adenovirus vector treatment.

4. To explore influences of pre-treatment tumor genetic alterations on response to Ad5PPE-1-3X-fas chimera adenovirus vector treatment using archival tumor materials.

Efficacy Endpoints:

1. The primary efficacy endpoint is the proportion of patients who have achieved an objective response to the study agent (according to RECIST criteria).

2. Secondary endpoints will include changes in thyroglobulin levels in response to treatment (in anti-thyroglobulin antibody-negative patients only).

Study Design:

Prospective, open-label, single dose study in 2 groups of patients (parallel enrolment):

Group A—Treatment of 12 evaluable patients with progressive thyroid cancer disease despite treatment with radioiodine, but naive to targeted anti-angiogenic therapies (e.g. tyrosine kinase inhibitors or anti-VEGF monoclonal antibodies). Subjects may also have had treatment with other cancer chemotherapy.

Group B—Treatment of 12 evaluable patients with progressive thyroid cancer despite prior treatment with radioiodine and with at least one anti-angiogenic therapy. Subjects may also have had treatment with other cancer chemotherapy.

Treatment Plan and Study Duration:

Ad5PPE-1-3X-fas chimera adenovirus vectors are administered as a single intravenous infusion of $3\times10^{12}$ vp (virus particles). The post-infusion efficacy follow up period will be until disease progression occurs. The post-treatment safety and efficacy evaluation visits will be every four weeks until week 12 or disease progression (whichever occurs later). Thereafter, restaging evaluations will occur every 2 months until at least one year after study enrolment or until progression (the earlier). Formal restaging of indicator lesions is performed every 8 weeks.

Population Size:

Groups A and B of this study will each enroll 12 evaluable subjects, for a total of 24 evaluable subjects. Evaluable subject are subjects for whom the chosen evaluation criteria can be applied through the duration of the study. The trial is designed according to the 2-stage Simon statistical method. If at least 1 response is observed in the initial 12 patients, further 24 patients will be enrolled from that group (up to a total of 37 patients per group or 74 total).

Inclusion Criteria:

1. Patients ≥18 years of age;

2. Histologically or cytologically confirmed advanced DTC (papillary, follicular, Hurthle cell);

3. Absence of sensitivity to therapeutic radioiodine;

4. No previous treatment with anti-angiogenic agents (Group A patients only);

5. Measurable disease, defined as at least one lesion that can be accurately measured in at least one dimension (longest diameter to be recorded) as ≥20 mm with conventional techniques or as ≥10 mm with spiral CT scan (Note: Disease that is measurable by physical examination only is not eligible, and CT and/or MRI are required in assessing indicator lesions);

6. Life expectancy >3 months;

7. ECOG performance status (PS) 0, 1, or 2; Karnofsky performance status of ≥60%;

8. Objective evidence of tumor progression in the 6 month period prior to the Screening Visit, as assessed by:

i. Progressively increasing suitable tumor markers, where appropriate; and ii. Unequivocal progression of objectively measured disease on successive appropriate imaging (e.g. CT scan). In cases of uncertainty of tumor progression, the Principal Investigator of the study will be available to assist in decisions.

9. Patients with a normal/acceptable hematological profile, as demonstrated by a peripheral leukocyte count >3000 cells/mcL, an absolute neutrophil count >1500 cells/μl, hemoglobin ≥10 g/dl, platelets >100,000/μl, and International Normalized Ratio (INR) <1.2× the Upper Limit of Normal (ULN);

10. Patients with adequate renal function, i.e. serum creatinine <1.5 times upper normal limits; and adequate hepatic function, as defined by ALT and AST<2.5× the upper limit of normal and total bilirubin below the upper limit of normal;

11. Males and females of childbearing potential must utilize, throughout the course of the trial a standard contraception method;

12. Ability to understand and the willingness to sign a written informed consent document;

13. Willingness to comply with study requirements.

Exclusion Criteria:

1. Pregnant or breastfeeding females;

2. Disease that is measurable by physical examination only;

3. Presence of any of the following:

Radiotherapy or chemotherapy <4 weeks prior to baseline visit;

Radiotherapy to ≥25% of bone marrow;

Major surgery <4 weeks prior to baseline visit;

Concurrent and/or prior therapy with octreotide will be allowed, provided tumor progression on this therapy has been demonstrated;

Concurrent and/or prior therapy with biphosphonates will be allowed;

4. Any other ongoing investigational agents within 4 weeks before enrolment;

5. Patients, who suffered from an acute cardiac event within the last 12 months, including myocardial infarction, cardiac arrythmia, admission for unstable angina, cardiac angioplasty, or stenting;

6. QTc prolongation (defined as QTc interval ≥500 msecs) or other significant ECG abnormalities (e.g. frequent ventricularectopy, evidence of ongoing myocardial ischemia);

7. Patients with active vascular disease, either myocardial or peripheral;

8. Patients with proliferative and/or vascular retinopathy;

9. Patients with known active liver disease (alcoholic, drug/toxin induced, genetic, or autoimmune) other than related to tumor metastases;

10. Patients with known CNS metastatic disease (Exception: patients with treated CNS metastases stable by radiographic examinations >6 moths after definitive therapy administered, are eligible);

11. Patients testing positive to one of the following viruses: HIV, HBV or HCV;

12. Any of the following conditions:

Serious or non-healing wound, ulcer, or bone fracture;

History of abdominal fistula, gastro-intestinal perforation, active diverticulitis, intra-abdominal abscess or gastro-intestinal tract bleeding within 28 days of enrolment;

Any history of cerebrovascular accident (CVA) within 6 months of enrolment;

Current use of therapeutic warfarin (Note: Low molecular weight heparin and prophylactic low-dose warfarin [International Normalized Ratio (INR) <1.2× Upper Limit of Normal (ULN)] are permitted);

History of bleeding disorder, including patients with hemophilia, disseminated intravascular coagulation (DIC), or any other abnormality of coagulation potentially predisposing patients to bleeding;

Poorly controlled depression or anxiety disorder, or recent (within the previous 6 months) suicidal ideation;

13. Patients with an ongoing requirement for an immunosuppressive treatment, including the use of glucocorticoids or cyclosporin, or with a history of chronic use of any such medication within the last 4 weeks before enrolment;

14. Uncontrolled intercurrent illness including, but not limited to ongoing or active infection, or psychiatric illness/social situations that would limit compliance with study requirements.

Formulation, Dosage and Administration:

Ad5PPE-1-3X-fas chimera adenovirus vector is formulated as a sterile vector solution. The solution is supplied frozen (below-65° C.), in single use vials. Each vial contains 0.5 ml of vector solution at a specific viral titer. The vector solution is thawed and maintained on ice during dilution and handling.

AdSPPE-1-3X-fas chimera adenovirus vector is administered as a single intravenous infusion, maximal dose being $1\times10^{12}$-$1\times10^{13}$ virus particles (vp). Prior to infusion, the solution for injection is brought to room temperature. The vials are opened in a biological safety cabinet and diluted (by injection) 1:4 with of normal saline for infusion. A single infusion of diluted Ad5PPE-1-3X-fas chimera adenovirus vector is administered at a rate of 1 ml/minute. Multiple doses may be administered at predetermined minimal intervals.

Safety Evaluation:

1. Adverse events are recorded on an ongoing basis during. The events are followed until resolved, or until the study end, whichever comes sooner.

2. Vital signs are recorded at screening, prior to dosing, 30, 60 minutes, 4 and 6 hours after dosing and at all patient visits.

3. A physical examination is conducted in conjunction with each study visit.

4. Safety laboratory assessment (vital signs, blood haematology and chemistry, urine analysis) are conducted at screening, prior to dosing, and at all patient visits, starting from day 4±1 until disease progression or Week 12, whichever occurs later.

5. After disease progression or Week 12 (whichever occurs later), each patient is contacted for safety follow-up by telephone every 2 months until 1 year after study enrolment.

Biodistribution:

Blood and urine samples for evaluation of levels of adenovirus vector DNA and the fas transgene are collected for adenovirus vector DNA: at several time points post-infusion.

Evaluation of Efficacy: Tumor Response

The effect of Ad5PPE-1-3X-fas chimera adenovirus vector treatment on tumor response is evaluated by measuring the tumor according to RECIST criteria (see above) at screening and at subsequent visits until disease progression. Changes in tumor volume are evaluated and analyzed based on radiological studies.

Biochemical and Laboratory Assays:

Antibodies: Serum samples are collected prior to dosing and at all patient visits, starting from Week 1, for analysis of levels of antibodies to the adenovirus (both total immunoglobulin, total IgG and Ad-5 neutralizing Abs) and to the fas-chimera transgene.

Tumor markers: TSH, anti-thyroglobulin antibody, and thyroglobulin are tested in conjunction with all follow-up evaluations.

Tumor measurement: Evaluation of biological effect on indicator lesion (CT, MRI).

Statistical Evaluation:

Patients are divided into two groups of subjects based upon previous treatment of their thyroid cancer: Group A, DTC radioiodine resistant and nave to anti-angiogenics; Group B; DTC radioiodine resistant with progression on anti-angiogenics. These two groups are evaluated independently for efficacy and toxicity end points.

Patient recruitment for each group is in 2 stages:

Stage 1: Enter 12 patients into the study. 12 subjects for each group. If no clinical responses are observed, the therapy is considered ineffective in this patient population and the study is terminated. If at least 1 response is observed, the study group proceeds to Stage 2.

Stage 2: Enter an additional 25 evaluable patients into the each group study. If three or fewer responses are observed after all 37 evaluable patients have been evaluated for response, the therapy is considered insufficiently effective in this patient population. If 4 or more responses are observed, this is considered adequate evidence of promising activity and this treatment may be recommended for further testing in subsequent studies in this patient population.

Unless toxicity is encountered or the study is stopped at the interim analysis, this study will accruing 37 eligible subjects for each group and evaluable patients. In order to account for ineligibility, cancellation, major treatment violation, or other reasons or early withdrawal or drop out, an additional 4 patients will be enrolled for each group. Thus 41 patients will be enrolled into this study for each group. Total of 82 subjects.

Assessments will be carried out according to the schedule in Table 10 that follows.

TABLE 10

SCHEDULE OF ASSESSMENTS

| | Screening (≤2 wks from $D_0$) | $D_0$ Prior to Dosing day of dosing | Follow up after Dosing ($D_{\le 1}$) | Day 4±1 | Week 1 ±1 Day | Week 2 ±1 Day | Weeks 4 & 8 ±3 Days | Week 12, ±3 Days | Weeks[10] 20, 28, 36, 44, 52 ±3 Days | F/U[11] |
|---|---|---|---|---|---|---|---|---|---|---|
| Inclusion Criteria | X | | | | | | | | | |
| Exclusion Criteria | X | | | | | | | | | |
| Medical History | X | | | | | | | | | |
| Informed Consent | X | | | | | | | | | |
| Pregnancy Test[1] | X | | | | | | | | | |
| Physical Exam ECG | X | | | | | | | X | | |
| Vital Signs[2] | X | X | X | | | | X | X | X | |
| Hematology[3] | X | X | | X | X | X | X | X | X | |
| Chemistry[4] | X | X | | X | X | X | X | X | X[12] | |
| HIV, HBV, HCV | X | | | | | | | | | |
| Urinalysis[5] | X | X | | | X | X | X | X | X | |
| ECG | X | | | | | | | X | | |
| Drug infusion | | X | | | | | | | | |
| Antibody[6] | | X | X | | X | X | X | X | X | |
| Distribution[7] | | X | X | X | X | X | X | | | |
| Concomitant Medications | X | X | | | | | X | X | X | X |
| Adverse Events | | X | X | X | X | X | X | X | X | X |
| Tumor Measure[8] | X | | | | | | X | X | XX | |
| Tumor Markers[9] | X | | | | | | X | X | XX | |

Legend

[1]Women of childbearing potential will be tested for pregnancy with the use of a serum pregnancy test at Screening and Week 12

[2]Vital signs (blood pressure, body temperature and heart rate) will be recorded at screening, prior to dosing at 30 and 60 minutes after dosing and at 6 hours post-dosing, and at all patient visits thereafter.

[3]Hematology will include: complete blood count with differential, PT and PTT Fibrinogen

[4]Chemistry will include: electrolytes (sodium, potassium, calcium), creatinine; bilirubin, alkaline phosphatase, ALT and AST; total protein and albumin

[5]Routine urine analysis

[6]Blood samples will be collected for levels of serum antibodies against the adenovirus and the transgene

[7]Blood and urine samples will be collected for biodistribution determination (levels of the viral DNA and transgene). See protocol for details.

[8]Evaluation of indicator lesion (CT, MRI, etc.) to be done at each visit until disease progression

[9]TSH, anti-thyroglobulin antibody, and thyroglobulin should be tested at each visit until disease progression

[10]Visits at Weeks 20, 28, 36, 44, and 52 to be conducted only if no disease progression has occurred prior to the visit

[11]Telephone contact will be performed every 2 months after Week 12 or disease progression (whichever occurs later) until one year after study enrolment.

Thyroglobulin is to be tested every 2 months until 13 months post dosing or until progression, whichever occurs first.

Example IV

Effect of Ad5PPE-1-3X-Fas Chimera Administration Combined with Chemotherapy

In order to evaluate the combined therapeutic oncolytic effect of Ad5PPE-1-3X-fas chimera and chemotherapy on tumor size in cancer, systemic administration of Ad5PPE-1-3X-fas chimera and concomitant chemotherapy in the rapidly metastasizing Lewis Lung Carcinoma model was chosen.

The Lewis Lung Cancer model provides a method for observing the effects of treatment on established, metastatic cancer.

Sunitinib (Sutent) targets tyrosine kinase, and inhibits the action of VEGF, producing an anti-angiogenic effect, and is used, among others, in stromal tumors and advanced renal cell cancer.

Antimetastatic Effects of a Single Systemic Dose of Ad5PPE-1-3X-Fas Chimera and Oral Sunitinib in Mice Bearing Lung Metastases:

C57BL/6 male mice (13 to 19 in each group) aged 8 weeks were inoculated with $5\times10^5$ LLC cells into the left footpad. The foot was amputated under general anesthesia as soon as the primary tumor developed to 7 mm. 2 days later (post foot amputation) a single intravenous injection of Ad5PPE-1-3X-fas chimera ($10^9$ or $10^{11}$ virus particles) was administered through the tail vein. After receiving the vector, a daily regimen of oral sunitinib was administered, 40 or 80 mg/kg once a day, on days 1-5, 8-13 and 16-17. Mouse sacrifice was scheduled for the 22$^{nd}$ day post primary tumor removal. Mouse well-being was monitored daily by observation and weighing. Results (Tumor burden) relate to the tumor mass, in grams (known as Tumor Burden).

Figures 13A, 13B:
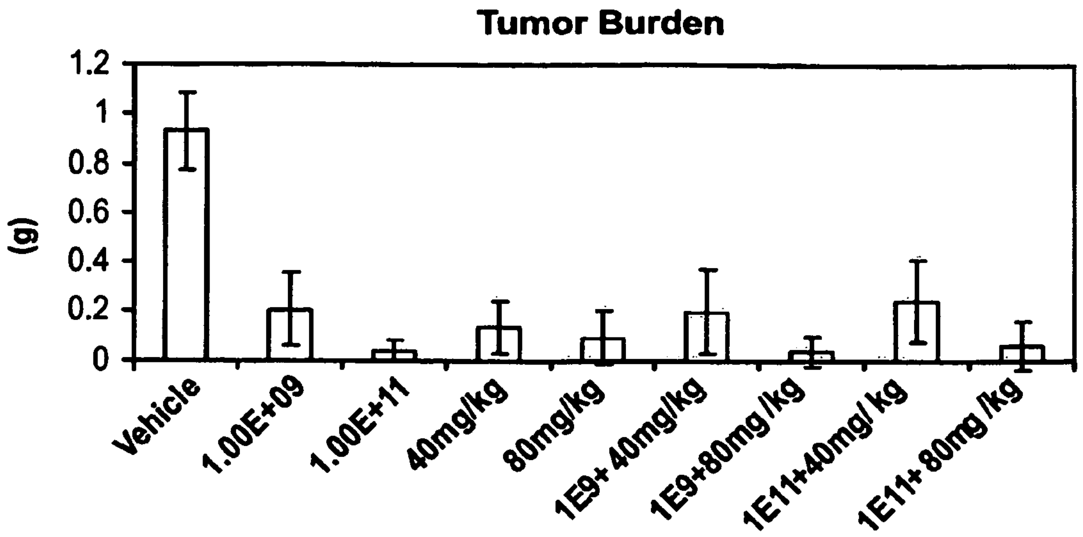
FIGS. 13A and 13B illustrate the effects of combined Ad5-PPE-1-3X fas-chimera adenovirus vector and sunitinib on the Lewis Lung metastatic cancer model. Mice with induced lung metastases received either the Ad5-PPE-1-3X fas-chimera adenovirus vector or oral sunitinib, in the indicated dosages, or a combination of the two therapies. Control mice received empty (sham) virus vehicles. Lung metastases were evaluated according to the tumor mass in grams (tumor burden) at 22 days post-primary tumor removal.

FIGS. 13A and 13B detail the results of two groups of the metastatic mice receiving the combination therapy, compared to each treatment mode alone. While a dose effect of the treatments could be discerned in the tumor burden of mice receiving 80 mg/kg sunitinib compared to those receiving 40 mg/kg sunitinib, and in the tumor burden of mice receiving $10^{11}$ Ad5PPE-1-3X fas-c compared to those receiving $10^9$ Ad5PPE-1-3X fas-c, the results of combining the two treatment modes reveals a statistically significant difference ($P<0.05$) between the control group and all the treatment groups, the mean tumor burden in the control group being significantly greater than in each of the other groups. The high viral dose ($10^{11}$ virus particles) and the low dose-combination treatment ($10^9$ virus particles and 80 mg/kg sunitinib), were found to be most effective in reducing the tumor burden, resulting in a statistically lower tumor burden than that of either the $10^9$ virus particles and 40 mg/kg sunitinib groups. These combination groups also showed reduced variability and generally lower scores, compared to the other experimental groups. The results show that combined treatment of systemically administered AdPPE-1-3X-fas-chimera+oral sunitinib is effective against metastatic disease.

Taken together, these results indicate that when administered in combination with currently employed clinical chemotherapy protocols, AdSPPE-1-3X fas-c can increase their therapeutic effectiveness and potentially allow reduced dosage and frequency of treatments.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating an angiogenic disease which is a solid tumor in a human subject in need thereof, the method comprising administering to the subject a therapeutically effective amount of adenovirus particles via intravenous administration, wherein the adenovirus particles comprises an adenoviral nucleic acid, wherein said nucleic acid comprises a fas-chimera transgene transcriptionally linked to a PPE-1-3X promoter, wherein said PPE-1-3X promoter restricts expression of the fas-chimera transgene to angiogenic blood vessels, and wherein said therapeutically effective amount is about $3\times10^{12}$ to about $1\times10^{13}$ adenovirus particles and inhibits growth of the solid tumor.

2. The method of claim 1, wherein said therapeutically effective amount is about $3\times10^{12}$ adenovirus particles.

3. The method of claim 1, wherein said fas-chimera transgene comprises the sequence as set forth in SEQ ID NO: 2.

4. The method of claim 1, wherein said fas-chimera transgene comprises the sequence as set forth in SEQ ID NO: 3.

5. The method of claim 1, wherein said fas-chimera transgene comprises the sequence as set forth in SEQ ID NO: 4.

6. The method of claim 1, wherein said PPE-1-3X promoter comprises the sequence as set forth in SEQ ID NO: 6 or the complementary sequence thereof.

7. The method of claim 1, wherein said PPE-1-3X promoter comprises the sequence as set forth in SEQ ID NO: 8 or the complementary sequence thereof.

8. The method of claim 1, wherein said PPE-1-3X promoter comprises the sequence as set forth in SEQ ID NO: 7 or the complementary sequence thereof.

9. The method of claim 1, wherein said PPE-1-3X promoter comprises the sequence as set forth in SEQ ID NO: 12.

10. The method of claim 1, wherein said adenoviral nucleic acid is an adenovirus 5 nucleic acid.

11. The method of claim 1, wherein said solid tumor is a cancer.

12. The method of claim 1, wherein said solid tumor is a primary tumor.

13. The method of claim 1, comprising administering said viral particles in at least two separate intravenous doses.

14. The method of claim 1, wherein said solid tumor is a thyroid cancer.

15. The method of claim 14, wherein said therapeutically effective amount is about $1\times10^{13}$ adenovirus particles.

16. The method of claim 1, wherein said solid tumor is a neuroendocrine cancer.

17. The method of claim 16, wherein said therapeutically effective amount is about $1\times10^{13}$ adenovirus particles.

18. The method of claim 1, wherein said subject is further receiving a chemotherapeutic agent.

19. The method of claim 18, wherein said chemotherapeutic agent is administered prior to treatment with said adenovirus particles.

20. The method of claim 18, wherein said chemotherapeutic agent is sunitinib.

21. The method of claim 1, wherein said therapeutically effective amount is about $1\times10^{13}$ adenovirus particles.

22. The method of claim 1, wherein said solid tumor is a metastatic tumor.

23. The method of claim 18, wherein said chemotherapeutic agent is administered concomitantly with treatment with said adenovirus particles or following treatment with said adenovirus particles.

24. The method of claim 1, wherein said adenoviral nucleic acid is a non-replicating adenoviral nucleic acid.

25. The method of claim 1, wherein said adenoviral nucleic acid comprises the sequence of SEQ ID NO:9.

26. The method of claim 1, wherein said fas-chimera transgene comprises the sequence as set forth in SEQ ID NO: 4, wherein said PPE-1-3X promoter comprises the sequence as set forth in SEQ ID NO: 8 or the complementary sequence thereof, wherein said adenoviral nucleic acid is a non-replicating adenovirus 5 nucleic acid, and wherein said therapeutically effective amount is about $1\times10^{13}$ adenovirus particles.

* * * * *

SEQUENCE LISTING

<160> NUMBER OF SEQ ID NOS: 644

<210> SEQ ID NO 1
<211> LENGTH: 34350
<212> TYPE: DNA
<213> ORGANISM: Artificial sequence
<220> FEATURE:
<223> OTHER INFORMATION: Empty Ad5 vector sequence without repeats

<400> SEQUENCE: 1
catcatcaat aatatacctt attttggatt gaagccaata tgataatgag ggggtggagt 60
ttgtgacgtg gcgcggggcg tgggaacggg gcgggtgacg tagtagtgtg gcggaagtgt 120
gatgttgcaa gtgtggcgga acacatgtaa gcgacggatg tggcaaaagt gacgtttttg 180
gtgtgcgccg gtgtacacag gaagtgacaa ttttcgcgcg gttttaggcg gatgttgtag 240
taaatttggg cgtaaccgag taagatttgg ccattttcgc gggaaaactg aataagagga 300
agtgaaatct gaataatttt gtgttactca tagcgcgtaa tatttgtcta gggccgcggg 360
gactttgacc gtttacgtgg agactcgccc aggtgttttt ctcaggtgtt ttccgcgttc 420
cgggtcaaag ttggcgtttt attattatag tcagtacgtc tcgagcatgc atctaggcgg 480
ccgcatggca gaaattcgcg aattcgctag cgttaacgga tcctctagac gagatccgaa 540
cttgtttatt gcagcttata atggttacaa ataaagcaat agcatcacaa atttcacaaa 600
taaagcattt ttttcactgc attctagttg tggtttgtcc aaactcatca atgtatctta 660
tcatgtctag atctgtactg aaatgtgtgg gcgtggctta agggtgggaa agaatatata 720
aggtgggggt cttatgtagt tttgtatctg ttttgcagca gccgccgccg ccatgagcac 780
caactcgttt gatggaagca ttgtgagctc atatttgaca acgcgcatgc ccccatgggc 840
cggggtgcgt cagaatgtga tgggctccag cattgatggt cgccccgtcc tgcccgcaaa 900
ctctactacc ttgacctacg agaccgtgtc tggaacgccg ttggagactg cagcctccgc 960
cgccgcttca gccgctgcag ccaccgcccg cgggattgtg actgactttg ctttcctgag 1020
cccgcttgca agcagtgcag cttcccgttc atccgcccgc gatgacaagt tgacggctct 1080
tttggcacaa ttggattctt tgacccggga acttaatgtc gtttctcagc agctgttgga 1140
tctgcgccag caggtttctg ccctgaaggc ttcctcccct cccaatgcgg tttaaaacat 1200

-continued aaataaaaaa ccagactctg tttggatttg gatcaagcaa gtgtcttgct gtctttattt 1260
aggggttttg cgcgcgcggt aggcccggga ccagcggtct cggtcgttga gggtcctgtg 1320 tatttttcc aggacgtggt aaaggtgact ctggatgttc agatacatgg gcataagccc 1380
gtctctgggg tggaggtagc accactgcag agcttcatgc tgcggggtgg tgttgtagat 1440
gatccagtcg tagcaggagc gctgggcgtg gtgcctaaaa atgtctttca gtagcaagct 1500
gattgccagg ggcaggccct tggtgtaagt gtttacaaag cggttaagct gggatgggtg 1560
catacgtggg gatatgagat gcatcttgga ctgtattttt aggttggcta tgttcccagc 1620
catatccctc cggggattca tgttgtgcag aaccaccagc acagtgtatc cggtgcactt 1680
gggaaatttg tcatgtagct tagaaggaaa tgcgtggaag aacttggaga cgcccttgtg 1740
acctccaaga ttttccatgc attcgtccat aatgatggca atgggcccac gggcggcggc 1800
ctgggcgaag atatttctgg gatcactaac gtcatagttg tgttccagga tgagatcgtc 1860
ataggccatt tttacaaagc gcgggcggag ggtgccagac tgcggtataa tggttccatc 1920
cggcccaggg gcgtagttac cctcacagat ttaagggtgg gaaagaatat ataaggtggg 1980
ggtcttatgt agttttgtat ctgttttgca gcagccgccg ccgccatgag caccaactcg 2040
tttgatggaa gcattgtgag ctcatatttg acaacgcgca tgcccccatg ggccggggtg 2100
cgtcagaatg tgatgggctc cagcattgat ggtcgccccg tcctgcccgc aaactctact 2160
accttgacct acgagaccgt gtctggaacg ccgttggaga ctgcagcctc cgccgccgct 2220
tcagccgctg cagccaccgc ccgcgggatt gtgactgact ttgctttcct gagcccgctt 2280
gcaagcagtg cagcttcccg ttcatccgcc cgcgatgaca agttgacggc tcttttggca 2340
caattggatt ctttgacccg ggaacttaat gtcgtttctc agcagctgtt ggatctgcgc 2400
cagcaggttt ctgccctgaa ggcttcctcc cctcccaatg cggtttaaaa cataaataaa 2460
aaaccagact ctgtttggat ttggatcaag caagtgtctt gctgtcttta tttaggggtt 2520
ttgcgcgcgc ggtaggcccg ggaccagcgg tctcggtcgt tgagggtcct gtgtattttt 2580
tccaggacgt ggtaaaggtg actctggatg ttcagataca tgggcataag cccgtctctg 2640
gggtggaggt agcaccactg cagagcttca tgctgcgggg tggtgttgta gatgatccag 2700
tcgtagcagg agcgctgggc gtggtgccta aaaatgtctt tcagtagcaa gctgattgcc 2760
aggggcaggc ccttggtgta agtgtttaca aagcggttaa gctgggatgg gtgcatacgt 2820
ggggatatga gatgcatctt ggactgtatt tttaggttgg ctatgttccc agccatatcc 2880
ctccggggat tcatgttgtg cagaaccacc agcacagtgt atccggtgca cttgggaaat 2940
ttgtcatgta gcttagaagg aaatgcgtgg aagaacttgg agacgccctt gtgacctcca 3000
agattttcca tgcattcgtc cataatgatg gcaatgggcc cacgggcggc ggcctgggcg 3060
aagatatttc tgggatcact aacgtcatag ttgtgttcca ggatgagatc gtcataggcc 3120
atttttacaa agcgcgggcg gagggtgcca gactgcggta taatggttcc atccggccca 3180
ggggcgtagt taccctcaca gatttgcatt tcccacgctt tgagttcaga tggggggatc 3240
atgtctacct gcggggcgat gaagaaaacg gtttccgggg taggggagat cagctgggaa 3300
gaaagcaggt tcctgagcag ctgcgactta ccgcagccgg tgggcccgta aatcacacct 3360
attaccggct gcaactggta gttaagagag ctgcagctgc cgtcatccct gagcaggggg 3420
gccacttcgt taagcatgtc cctgactcgc atgttttccc tgaccaaatc cgccagaagg 3480
cgctcgccgc ccagcgatag cagttcttgc aaggaagcaa agtttttcaa cggtttgaga 3540
ccgtccgccg taggcatgct tttgagcgtt tgaccaagca gttccaggcg gtcccacagc 3600

-continued

```
tcggtcacct gctctacggc atctcgatcc agcatatctc ctcgtttcgc gggttggggc   3660
ggctttcgct gtacggcagt agtcggtgct cgtccagacg ggccagggtc atgtctttcc   3720
acgggcgcag ggtcctcgtc agcgtagtct gggtcacggt gaaggggtgc gctccgggct   3780
gcgcgctggc cagggtgcgc ttgaggctgg tcctgctggt gctgaagcgc tgccggtctt   3840
cgccctgcgc gtcggccagg tagcatttga ccatggtgtc atagtccagc ccctccgcgg   3900
cgtggccctt ggcgcgcagc ttgcccttgg aggaggcgcc gcacgagggg cagtgcagac   3960
ttttgagggc gtagagcttg ggcgcgagaa ataccgattc cggggagtag gcatccgcgc   4020
cgcaggcccc gcagacggtc tcgcattcca cgagccaggt gagctctggc cgttcggggt   4080
caaaaaccag gtttccccca tgctttttga tgcgtttctt acctctggtt tccatgagcc   4140
ggtgtccacg ctcggtgacg aaaaggctgt ccgtgtcccc gtatacagac ttgagaggcc   4200
tgtcctcgag cggtgttccg cggtcctcct cgtatagaaa ctcggaccac tctgagacaa   4260
aggctcgcgt ccaggccagc acgaaggagg ctaagtggga ggggtagcgg tcgttgtcca   4320
ctagggggtc cactcgctcc agggtgtgaa gacacatgtc gccctcttcg gcatcaagga   4380
aggtgattgg tttgtaggtg taggccacgt gaccgggtgt tcctgaaggg gggctataaa   4440
agggggtggg ggcgcgttcg tcctcactct cttccgcatc gctgtctgcg agggccagct   4500
gttggggtga gtactccctc tgaaaagcgg gcatgacttc tgcgctaaga ttgtcagttt   4560
ccaaaaacga ggaggatttg atattcacct ggcccgcggt gatgcctttg agggtggccg   4620
catccatctg gtcagaaaag acaatctttt tgttgtcaag cttggtggca aacgacccgt   4680
agagggcgtt ggacagcaac ttggcgatgg agcgcagggt ttggtttttg tcgcgatcgg   4740
cgcgctcctt ggccgcgatg tttagctgca cgtattcgcg cgcaacgcac cgccattcgg   4800
gaaagacggt ggtgcgctcg tcgggcacca ggtgcacgcg ccaaccgcgg ttgtgcaggg   4860
tgacaaggtc aacgctggtg gctacctctc cgcgtaggcg ctcgttggtc cagcagaggc   4920
ggccgccctt gcgcgagcag aatggcggta gggggtctag ctgcgtctcg tccggggggt   4980
ctgcgtccac ggtaaagacc ccgggcagca ggcgcgcgtc gaagtagtct atcttgcatc   5040
cttgcaagtc tagcgcctgc tgccatgcgc gggcggcaag cgcgcgctcg tatgggttga   5100
gtgggggacc ccatggcatg gggtgggtga gcgcggaggc gtacatgccg caaatgtcgt   5160
aaacgtagag gggctctctg agtattccaa gatatgtagg gtagcatctt ccaccgcgga   5220
tgctggcgcg cacgtaatcg tatagttcgt gcgagggagc gaggaggtcg ggaccgaggt   5280
tgctacgggc gggctgctct gctcggaaga ctatctgcct gaagatggca tgtgagttgg   5340
atgatatggt tggacgctgg aagacgttga agctggcgtc tgtgagacct accgcgtcac   5400
gcacgaagga ggcgtaggag tcgcgcagct tgttgaccag ctcggcggtg acctgcacgt   5460
ctagggcgca gtagtccagg gtttccttga tgatgtcata cttatcctgt cccttttttt   5520
tccacagctc gcggttgagg acaaactctt cgcggtcttt ccagtactct tggatcggaa   5580
acccgtcggc ctccgaacgg taagagccta gcatgtagaa ctggttgacg gcctggtagg   5640
cgcagcatcc cttttctacg ggtagcgcgt atgcctgcgc ggccttccgg agcgaggtgt   5700
gggtgagcgc aaaggtgtcc ctgaccatga ctttgaggta ctggtatttg aagtcagtgt   5760
cgtcgcatcc gccctgctcc cagagcaaaa agtccgtgcg ctttttggaa cgcggatttg   5820
gcagggcgaa ggtgacatcg ttgaagagta tctttcccgc gcgaggcata aagttgcgtg   5880
tgatgcggaa gggtcccggc acctcggaac ggttgttaat tacctgggcg gcgagcacga   5940
```

```
tctcgtcaaa gccgttgatg ttgtggccca caatgtaaag ttccaagaag cgcgggatgc   6000
ccttgatgga aggcaatttt ttaagttcct cgtaggtgag ctcttcaggg gagctgagcc   6060
cgtgctctga aagggcccag tctgcaagat gagggttgga agcgacgaat gagctccaca   6120
ggtcacgggc cattagcatt tgcaggtggt cgcgaaaggt cctaaactgg cgacctatgg   6180
ccattttttc tggggtgatg cagtagaagg taagcgggtc ttgttcccag cggtcccatc   6240
caaggttcgc ggctaggtct cgcgcggcag tcactagagg ctcatctccg ccgaacttca   6300
tgaccagcat gaagggcacg agctgcttcc caaaggcccc catccaagta taggtctcta   6360
catcgtaggt gacaaagaga cgctcggtgc gaggatgcga gccgatcggg aagaactgga   6420
tctcccgcca ccaattggag gagtggctat tgatgtggtg aaagtagaag tccctgcgac   6480
gggccgaaca ctcgtgctgg cttttgtaaa aacgtgcgca gtactggcag cggtgcacgg   6540
gctgtacatc ctgcacgagg ttgacctgac gaccgcgcac aaggaagcag agtgggaatt   6600
tgagcccctc gcctggcggg tttggctggt ggtcttctac ttcggctgct tgtccttgac   6660
cgtctggctg ctcgagggga gttacggtgg atcggaccac cacgccgcgc gagcccaaag   6720
tccagatgtc cgcgcgcggc ggtcggagct tgatgacaac atcgcgcaga tgggagctgt   6780
ccatggtctg gagctcccgc ggcgtcaggt caggcgggag ctcctgcagg tttacctcgc   6840
atagacgggt cagggcgcgg gctagatcca ggtgatacct aatttccagg ggctggttgg   6900
tggcggcgtc gatggcttgc aagaggccgc atccccgcgg cgcgactacg gtaccgcgcg   6960
gcgggcggtg ggccgcgggg gtgtccttgg atgatgcatc taaaagcggt gacgcgggcg   7020
agcccccgga ggtagggggg gctccggacc cgccgggaga gggggcaggg gcacgtcggc   7080
gccgcgcgcg ggcaggagct ggtgctgcgc gcgtaggttg ctggcgaacg cgacgacgcg   7140
gcggttgatc tcctgaatct ggcgcctctg cgtgaagacg acgggcccgg tgagcttgaa   7200
cctgaaagag agttcgacag aatcaatttc ggtgtcgttg acggcggcct ggcgcaaaat   7260
ctcctgcacg tctcctgagt tgtcttgata ggcgatctcg gccatgaact gctcgatctc   7320
ttcctcctgg agatctccgc gtccggctcg ctccacggtg gcggcgaggt cgttggaaat   7380
gcgggccatg agctgcgaga aggcgttgag gcctccctcg ttccagacgc ggctgtagac   7440
cacgccccct tcggcatcgc gggcgcgcat gaccacctgc gcgagattga gctccacgtg   7500
ccgggcgaag acggcgtagt ttcgcaggcg ctgaaagagg tagttgaggg tggtggcggt   7560
gtgttctgcc acgaagaagt acataaccca gcgtcgcaac gtggattcgt tgatatcccc   7620
caaggcctca aggcgctcca tggcctcgta gaagtccacg gcgaagttga aaaactggga   7680
gttgcgcgcc gacacggtta actcctcctc cagaagacgg atgagctcgg cgacagtgtc   7740
gcgcacctcg cgctcaaagg ctacaggggc ctcttcttct tcttcaatct cctcttccat   7800
aagggcctcc ccttcttctt cttctggcgg cggtggggga gggggggacac ggcggcgacg   7860
acggcgcacc gggaggcggt cgacaaagcg ctcgatcatc tccccgcggc gacggcgcat   7920
ggtctcggtg acggcgcggc cgttctcgcg gggggcgcagt tggaagacgc cgcccgtcat   7980
gtcccggtta tgggttggcg gggggctgcc atgcggcagg gatacggcgc taacgatgca   8040
tctcaacaat tgttgtgtag gtactccgcc gccgagggac ctgagcgagt ccgcatcgac   8100
cggatcggaa aacctctcga gaaaggcgtc taaccagtca cagtcgcaag gtaggctgag   8160
caccgtggcg ggcggcagcg ggcggcggtc ggggttgttt ctggcggagg tgctgctgat   8220
gatgtaatta aagtaggcgg tcttgagacg gcggatggtc gacagaagca ccatgtcctt   8280
gggtccggcc tgctgaatgc gcaggcggtc ggccatgccc caggcttcgt tttgacatcg   8340
```

-continued

```
gcgcaggtct ttgtagtagt cttgcatgag cctttctacc ggcacttctt cttctccttc   8400
ctcttgtcct gcatctcttg catctatcgc tgcggcggcg gcggagtttg gccgtaggtg   8460
gcgccctctt cctcccatgc gtgtgacccc gaagcccctc atcggctgaa gcagggctag   8520
gtcggcgaca acgcgctcgg ctaatatggc ctgctgcacc tgcgtgaggg tagactggaa   8580
gtcatccatg tccacaaagc ggtggtatgc gcccgtgttg atggtgtaag tgcagttggc   8640
cataacggac cagttaacgg tctggtgacc cggctgcgag agctcggtgt acctgagacg   8700
cgagtaagcc ctcgagtcaa atacgtagtc gttgcaagtc cgcaccaggt actggtatcc   8760
caccaaaaag tgcggcggcg gctggcggta gaggggccag cgtagggtgg ccggggctcc   8820
gggggcgaga tcttccaaca taaggcgatg atatccgtag atgtacctgg acatccaggt   8880
gatgccggcg gcggtggtgg aggcgcgcgg aaagtcgcgg acgcggttcc agatgttgcg   8940
cagcggcaaa aagtgctcca tggtcgggac gctctggccg gtcaggcgcg cgcaatcgtt   9000
gacgctctag accgtgcaaa aggagagcct gtaagcgggc actcttccgt ggtctggtgg   9060
ataaattcgc aagggtatca tggcggacga ccggggttcg agccccgtat ccggccgtcc   9120
gccgtgatcc atgcggttac cgcccgcgtg tcgaacccag gtgtgcgacg tcagacaacg   9180
ggggagtgct ccttttggct tccttccagg cgcggcggct gctgcgctag ctttttggc   9240
cactggccgc gcgcagcgta agcggttagg ctggaaagcg aaagcattaa gtggctcgct   9300
ccctgtagcc ggagggttat ttccaaggg ttgagtcgcg ggacccccgg ttcgagtctc   9360
ggaccggccg gactgcggcg aacgggggtt tgcctccccg tcatgcaaga ccccgcttgc   9420
aaattcctcc ggaaacaggg acgagcccct tttttgcttt tcccagatgc atccggtgct   9480
gcggcagatg cgccccctc ctcagcagcg gcaagagcaa gagcagcggc agacatgcag   9540
ggcaccctcc cctcctccta ccgcgtcagg aggggcgaca tccgcggttg acgcggcagc   9600
agatggtgat tacgaacccc cgcggcgccg ggcccggcac tacctggact tggaggaggg   9660
cgagggcctg gcgcggctag gagcgccctc tcctgagcgg cacccaaggg tgcagctgaa   9720
gcgtgatacg cgtgaggcgt acgtgccgcg gcagaacctg tttcgcgacc gcgagggaga   9780
ggagcccgag gagatgcggg atcgaaagtt ccacgcaggg cgcgagctgc ggcatggcct   9840
gaatcgcgag cggttgctgc gcgaggagga ctttgagccc gacgcgcgaa ccgggattag   9900
tcccgcgcgc gcacacgtgg cggccgccga cctggtaacc gcatacgagc agacggtgaa   9960
ccaggagatt aactttcaaa aaagctttaa caaccacgtg cgtacgcttg tggcgcgcga  10020
ggaggtggct ataggactga tgcatctgtg ggactttgta agcgcgctgg agcaaaaccc  10080
aaatagcaag ccgctcatgg cgcagctgtt ccttatagtg cagcacagca gggacaacga  10140
ggcattcagg gatgcgctgc taaacatagt agagcccgag ggccgctggc tgctcgattt  10200
gataaacatc ctgcagagca tagtggtgca ggagcgcagc ttgagcctgg ctgacaaggt  10260
ggccgccatc aactattcca tgcttagcct gggcaagttt tacgcccgca agatatacca  10320
taccccttac gttcccatag acaaggaggt aaagatcgag gggttctaca tgcgcatggc  10380
gctgaaggtg cttaccttga gcgacgacct gggcgtttat cgcaacgagc gcatccacaa  10440
ggccgtgagc gtgagccggc ggcgcgagct cagcgaccgc gagctgatgc acagcctgca  10500
aagggccctg gctggcacgg gcagcggcga tagagaggcc gagtcctact ttgacgcggg  10560
cgctgacctg cgctgggccc caagccgacg cgccctggag gcagctgggg ccggacctgg  10620
gctggcggtg gcacccgcgc gcgctggcaa cgtcggcggc gtggaggaat atgacgagga  10680
```

cgatgagtac gagccagagg acggcgagta ctaagcggtg atgtttctga tcagatgatg 10740
caagacgcaa cggacccggc ggtgcgggcg gcgctgcaga gccagccgtc cggccttaac 10800
tccacggacg actggcgcca ggtcatggac cgcatcatgt cgctgactgc gcgcaatcct 10860
gacgcgttcc ggcagcagcc gcaggccaac cggctctccg caattctgga agcggtggtc 10920
ccggcgcgcg caaaccccac gcacgagaag gtgctggcga tcgtaaacgc gctggccgaa 10980
aacagggcca tccggcccga cgaggccggc ctggtctacg acgcgctgct tcagcgcgtg 11040
gctcgttaca acagcggcaa cgtgcagacc aacctggacc ggctggtggg ggatgtgcgc 11100
gaggccgtgg cgcagcgtga gcgcgcgcag cagcagggca acctgggctc catggttgca 11160
ctaaacgcct tcctgagtac acagcccgcc aacgtgccgc ggggacagga ggactacacc 11220
aactttgtga gcgcactgcg gctaatggtg actgagacac cgcaaagtga ggtgtaccag 11280
tctgggccag actatttttt ccagaccagt agacaaggcc tgcagaccgt aaacctgagc 11340
caggctttca aaaacttgca ggggctgtgg ggggtgcggg ctcccacagg cgaccgcgcg 11400
accgtgtcta gcttgctgac gcccaactcg cgcctgttgc tgctgctaat agcgcccttc 11460
acggacagtg gcagcgtgtc ccgggacaca tacctaggtc acttgctgac actgtaccgc 11520
gaggccatag gtcaggcgca tgtggacgag catactttcc aggagattac aagtgtcagc 11580
cgcgcgctgg ggcaggagga cacgggcagc ctggaggcaa ccctaaacta cctgctgacc 11640
aaccggcggc agaagatccc ctcgttgcac agtttaaaca gcgaggagga gcgcattttg 11700
cgctacgtgc agcagagcgt gagccttaac ctgatgcgcg acggggtaac gcccagcgtg 11760
gcgctggaca tgaccgcgcg caacatggaa ccgggcatgt atgcctcaaa ccggccgttt 11820
atcaaccgcc taatggacta cttgcatcgc gcggccgccg tgaaccccga gtatttcacc 11880
aatgccatct tgaacccgca ctggctaccg ccccctggtt tctacaccgg gggattcgag 11940
gtgcccgagg gtaacgatgg attcctctgg gacgacatag acgacagcgt gttttccccg 12000
caaccgcaga ccctgctaga gttgcaacag cgcgagcagg cagaggcggc gctgcgaaag 12060
gaaagcttcc gcaggccaag cagcttgtcc gatctaggcg ctgcggcccc gcggtcagat 12120
gctagtagcc catttccaag cttgataggg tctcttacca gcactcgcac cacccgcccg 12180
cgcctgctgg gcgaggagga gtacctaaac aactcgctgc tgcagccgca gcgcgaaaaa 12240
aacctgcctc cggcatttcc caacaacggg atagagagcc tagtggacaa gatgagtaga 12300
tggaagacgt acgcgcagga gcacagggac gtgccaggcc cgcgcccgcc cacccgtcgt 12360
caaaggcacg accgtcagcg gggtctggtg tgggaggacg atgactcggc agacgacagc 12420
agcgtcctgg atttgggagg gagtggcaac ccgtttgcgc accttcgccc caggctgggg 12480
agaatgtttt aaaaaaaaaa aaagcatgat gcaaaataaa aaactcacca aggccatggc 12540
accgagcgtt ggttttcttg tattcccctt agtatgcggc gcgcggcgat gtatgaggaa 12600
ggtcctcctc cctcctacga gagtgtggtg agcgcggcgc cagtggcggc ggcgctgggt 12660
tctcccttcg atgctcccct ggacccgccg tttgtgcctc cgcggtacct gcggcctacc 12720
ggggggagaa acagcatccg ttactctgag ttggcacccc tattcgacac cacccgtgtg 12780
tacctggtgg acaacaagtc aacggatgtg gcatccctga actaccagaa cgaccacagc 12840
aactttctga ccacggtcat tcaaaacaat gactacagcc cgggggaggc aagcacacag 12900
accatcaatc ttgacgaccg gtcgcactgg ggcggcgacc tgaaaaccat cctgcatacc 12960
aacatgccaa atgtgaacga gttcatgttt accaataagt ttaaggcgcg ggtgatggtg 13020
tcgcgcttgc ctactaagga caatcaggtg gagctgaaat acgagtgggt ggagttcacg 13080
ctgcccgagg gcaactactc cgagaccatg accatagacc ttatgaacaa cgcgatcgtg 13140
gagcactact tgaaagtggg cagacagaac ggggttctgg aaagcgacat cggggtaaag 13200
tttgacaccc gcaacttcag actggggttt gaccccgtca ctggtcttgt catgcctggg 13260
gtatatacaa acgaagcctt ccatccagac atcattttgc tgccaggatg cggggtggac 13320
ttcacccaca gccgcctgag caacttgttg ggcatccgca agcggcaacc cttccaggag 13380
ggctttagga tcacctacga tgatctggag ggtggtaaca ttcccgcact gttggatgtg 13440
gacgcctacc aggcgagctt gaaagatgac accgaacagg gcgggggtgg cgcaggcggc 13500
agcaacagca gtggcagcgg cgcggaagag aactccaacg cggcagccgc ggcaatgcag 13560
ccggtggagg acatgaacga tcatgccatt cgcggcgaca cctttgccac acgggctgag 13620
gagaagcgcg ctgaggccga agcagcggcc gaagctgccg cccccgctgc gcaacccgag 13680
gtcgagaagc ctcagaagaa accggtgatc aaacccctga cagaggacag caagaaacgc 13740
agttacaacc taataagcaa tgacagcacc ttcacccagt accgcagctg gtaccttgca 13800
tacaactacg gcgaccctca gaccggaatc cgctcatgga ccctgctttg cactcctgac 13860
gtaacctgcg gctcggagca ggtctactgg tcgttgccag acatgatgca agaccccgtg 13920
accttccgct ccacgcgcca gatcagcaac tttccggtgg tgggcgccga gctgttgccc 13980
gtgcactcca agagcttcta caacgaccag gccgtctact cccaactcat ccgccagttt 14040
acctctctga cccacgtgtt caatcgcttt cccgagaacc agattttggc gcgcccgcca 14100
gcccccacca tcaccaccgt cagtgaaaac gttcctgctc tcacagatca cgggacgcta 14160
ccgctgcgca acagcatcgg aggagtccag cgagtgacca ttactgacgc cagacgccgc 14220
acctgcccct acgtttacaa ggccctgggc atagtctcgc cgcgcgtcct atcgagccgc 14280
actttttgag caagcatgtc catccttata tcgcccagca ataacacagg ctggggcctg 14340
cgcttcccaa gcaagatgtt tggcggggcc aagaagcgct ccgaccaaca cccagtgcgc 14400
gtgcgcgggc actaccgcgc gccctggggc gcgcacaaac gcggccgcac tgggcgcacc 14460
accgtcgatg acgccatcga cgcggtggtg gaggaggcgc gcaactacac gcccacgccg 14520
ccaccagtgt ccacagtgga cgcggccatt cagaccgtgg tgcgcggagc ccggcgctat 14580
gctaaaatga agagacggcg gaggcgcgta gcacgtcgcc accgccgccg acccggcact 14640
gccgcccaac gcgcggcggc ggccctgctt aaccgcgcac gtcgcaccgg ccgacgggcg 14700
gccatgcggg ccgctcgaag gctggccgcg ggtattgtca ctgtgccccc caggtccagg 14760
cgacgagcgg ccgccgcagc agccgcggcc attagtgcta tgactcaggg tcgcaggggc 14820
aacgtgtatt gggtgcgcga ctcggttagc ggcctgcgcg tgcccgtgcg cacccgcccc 14880
ccgcgcaact agattgcaag aaaaaactac ttagactcgt actgttgtat gtatccagcg 14940
gcggcggcgc gcaacgaagc tatgtccaag cgcaaaatca aagaagagat gctccaggtc 15000
atcgcgccgg agatctatgg ccccccgaag aaggaagagc aggattacaa gccccgaaag 15060
ctaaagcggg tcaaaaagaa aaagaaagat gatgatgatg aacttgacga cgaggtggaa 15120
ctgctgcacg ctaccgcgcc caggcgacgg gtacagtgga aaggtcgacg cgtaaaacgt 15180
gttttgcgac ccggcaccac cgtagtcttt acgcccggtg agcgctccac ccgcacctac 15240
aagcgcgtgt atgatgaggt gtacggcgac gaggacctgc ttgagcaggc caacgagcgc 15300
ctcggggagt ttgcctacgg aaagcggcat aaggacatgc tggcgttgcc gctggacgag 15360
ggcaacccaa cacctagcct aaagcccgta acactgcagc aggtgctgcc cgcgcttgca 15420

-continued

```
ccgtccgaag aaaagcgcgg cctaaagcgc gagtctggtg acttggcacc caccgtgcag  15480
ctgatggtac ccaagcgcca gcgactggaa gatgtcttgg aaaaaatgac cgtggaacct  15540
gggctggagc ccgaggtccg cgtgcggcca atcaagcagg tggcgccggg actgggcgtg  15600
cagaccgtgg acgttcagat acccactacc agtagcacca gtattgccac cgccacagag  15660
ggcatggaga cacaaacgtc cccggttgcc tcagcggtgg cggatgccgc ggtgcaggcg  15720
gtcgctgcgg ccgcgtccaa gacctctacg gaggtgcaaa cggacccgtg gatgtttcgc  15780
gtttcagccc cccggcgccc gcgccgttcg aggaagtacg gcgccgccag cgcgctactg  15840
cccgaatatg ccctacatcc ttccattgcg cctacccccg gctatcgtgg ctacacctac  15900
cgccccagaa gacgagcaac tacccgacgc cgaaccacca ctggaacccg ccgccgccgt  15960
cgccgtcgcc agcccgtgct ggccccgatt tccgtgcgca gggtggctcg cgaaggaggc  16020
aggaccctgg tgctgccaac agcgcgctac caccccagca tcgtttaaaa gccggtcttt  16080
gtggttcttg cagatatggc cctcacctgc cgcctccgtt tcccggtgcc gggattccga  16140
ggaagaatgc accgtaggag gggcatggcc ggccacggcc tgacgggcgg catgcgtcgt  16200
gcgcaccacc ggcggcggcg cgcgtcgcac cgtcgcatgc gcggcggtat cctgcccctc  16260
cttattccac tgatcgccgc ggcgattggc gccgtgcccg gaattgcatc cgtggccttg  16320
caggcgcaga gacactgatt aaaaacaagt tgcatgtgga aaatcaaaa taaaaagtct  16380
ggactctcac gctcgcttgg tcctgtaact attttgtaga atggaagaca tcaactttgc  16440
gtctctggcc ccgcgacacg gctcgcgccc gttcatggga aactggcaag atatcggcac  16500
cagcaatatg agcggtggcg ccttcagctg gggctcgctg tggagcggca ttaaaaattt  16560
cggttccacc gttaagaact atggcagcaa ggcctggaac agcagcacag gccagatgct  16620
gagggataag ttgaaagagc aaaatttcca acaaaaggtg gtagatggcc tggcctctgg  16680
cattagcggg gtggtggacc tggccaacca ggcagtgcaa aataagatta acagtaagct  16740
tgatccccgc cctcccgtag aggagcctcc accggccgtg gagacagtgt ctccagaggg  16800
gcgtggcgaa aagcgtccgc gccccgacag ggaagaaact ctggtgacgc aaatagacga  16860
gcctccctcg tacgaggagg cactaaagca aggcctgccc accacccgtc ccatcgcgcc  16920
catggctacc ggagtgctgg gccagcacac acccgtaacg ctggacctgc ctccccccgc  16980
cgacacccag cagaaacctg tgctgccagg cccgaccgcc gttgttgtaa cccgtcctag  17040
ccgcgcgtcc ctgcgccgcg ccgccagcgg tccgcgatcg ttgcggcccg tagccagtgg  17100
caactggcaa agcacactga acagcatcgt gggtctgggg gtgcaatccc tgaagcgccg  17160
acgatgcttc tgatagctaa cgtgtcgtat gtgtgtcatg tatgcgtcca tgtcgccgcc  17220
agaggagctg ctgagccgcc gcgcgcccgc tttccaagat ggctacccct tcgatgatgc  17280
cgcagtggtc ttacatgcac atctcgggcc aggacgcctc ggagtacctg agccccgggc  17340
tggtgcagtt tgcccgcgcc accgagacgt acttcagcct gaataacaag tttagaaacc  17400
ccacggtggc gcctacgcac gacgtgacca cagaccggtc ccagcgtttg acgctgcggt  17460
tcatccctgt ggaccgtgag gatactgcgt actcgtacaa ggcgcggttc accctagctg  17520
tgggtgataa ccgtgtgctg gacatggctt ccacgtactt tgacatccgc ggcgtgctgg  17580
acaggggccc tacttttaag ccctactctg gcactgccta caacgccctg gctcccaagg  17640
gtgccccaaa tccttgcgaa tgggatgaag ctgctactgc tcttgaaata aacctagaag  17700
aagaggacga tgacaacgaa gacgaagtag acgagcaagc tgagcagcaa aaaactcacg  17760
tatttgggca ggcgccttat tctggtataa atattacaaa ggagggtatt caaataggtg  17820
```

tcgaaggtca aacacctaaa tatgccgata aaacatttca acctgaacct caaataggag 17880
aatctcagtg gtacgaaaca gaaattaatc atgcagctgg gagagtccta aaaaagacta 17940
ccccaatgaa accatgttac ggttcatatg caaaacccac aaatgaaaat ggagggcaag 18000
gcattcttgt aaagcaacaa aatggaaagc tagaaagtca agtggaaatg caatttttct 18060
caactactga ggcagccgca ggcaatggtg ataacttgac tcctaaagtg gtattgtaca 18120
gtgaagatgt agatatagaa accccagaca ctcatatttc ttacatgccc actattaagg 18180
aaggtaactc acgagaacta atgggccaac aatctatgcc caacaggcct aattacattg 18240
cttttaggga caattttatt ggtctaatgt attacaacag cacgggtaat atgggtgttc 18300
tggcgggcca agcatcgcag ttgaatgctg ttgtagattt gcaagacaga aacacagagc 18360
tttcatacca gcttttgctt gattccattg gtgatagaac caggtacttt tctatgtgga 18420
atcaggctgt tgacagctat gatccagatg ttagaattat tgaaaatcat ggaactgaag 18480
atgaacttcc aaattactgc tttccactgg gaggtgtgat taatacagag actcttacca 18540
aggtaaaacc taaaacaggt caggaaaatg gatgggaaaa agatgctaca gaattttcag 18600
ataaaaatga aataagagtt ggaaataatt ttgccatgga aatcaatcta aatgccaacc 18660
tgtggagaaa tttcctgtac tccaacatag cgctgtattt gcccgacaag ctaaagtaca 18720
gtccttccaa cgtaaaaatt tctgataacc caaacaccta cgactacatg aacaagcgag 18780
tggtggctcc cgggctagtg gactgctaca ttaaccttgg agcacgctgg tcccttgact 18840
atatggacaa cgtcaaccca tttaaccacc accgcaatgc tggcctgcgc taccgctcaa 18900
tgttgctggg caatggtcgc tatgtgccct tccacatcca ggtgcctcag aagttctttg 18960
ccattaaaaa cctccttctc ctgccgggct catacaccta cgagtggaac ttcaggaagg 19020
atgttaacat ggttctgcag agctccctag gaaatgacct aagggttgac ggagccagca 19080
ttaagtttga tagcatttgc ctttacgcca ccttcttccc catggcccac aacaccgcct 19140
ccacgcttga ggccatgctt agaaacgaca ccaacgacca gtcctttaac gactatctct 19200
ccgccgccaa catgctctac cctatacccg ccaacgctac caacgtgccc atatccatcc 19260
cctcccgcaa ctgggcggct ttccgcggct gggccttcac gcgccttaag actaaggaaa 19320
ccccatcact gggctcgggc tacgaccctt attacaccta ctctggctct ataccctacc 19380
tagatggaac cttttacctc aaccacacct ttaagaaggt ggccattacc tttgactctt 19440
ctgtcagctg gcctggcaat gaccgcctgc ttacccccaa cgagtttgaa attaagcgct 19500
cagttgacgg ggagggttac aacgttgccc agtgtaacat gaccaaagac tggttcctgg 19560
tacaaatgct agctaactat aacattggct accagggctt ctatatccca gagagctaca 19620
aggaccgcat gtactccttc tttagaaact tccagcccat gagccgtcag gtggtggatg 19680
atactaaata caaggactac caacaggtgg gcatcctaca ccaacacaac aactctggat 19740
ttgttggcta ccttgccccc accatgcgcg aaggacaggc ctaccctgct aacttcccct 19800
atccgcttat aggcaagacc gcagttgaca gcattaccca gaaaaagttt ctttgcgatc 19860
gcaccctttg gcgcatccca ttctccagta actttatgtc catgggcgca ctcacagacc 19920
tgggccaaaa ccttctctac gccaactccg cccacgcgct agacatgact tttgaggtgg 19980
atcccatgga cgagcccacc cttctttatg ttttgtttga agtctttgac gtggtccgtg 20040
tgcaccagcc gcaccgcggc gtcatcgaaa ccgtgtacct gcgcacgccc ttctcggccg 20100
gcaacgccac aacataaaga agcaagcaac atcaacaaca gctgccgcca tgggctccag 20160

```
tgagcaggaa ctgaaagcca ttgtcaaaga tcttggttgt gggccatatt ttttgggcac  20220
ctatgacaag cgctttccag gctttgtttc tccacacaag ctcgcctgcg ccatagtcaa  20280
tacggccggt cgcgagactg gggcgtaca ctggatggcc tttgcctgga acccgcactc  20340
aaaaacatgc tacctctttg agccctttgg cttttctgac cagcgactca agcaggttta  20400
ccagtttgag tacgagtcac tcctgcgccg tagcgccatt gcttcttccc ccgaccgctg  20460
tataacgctg gaaaagtcca cccaaagcgt acaggggccc aactcggccg cctgtggact  20520
attctgctgc atgtttctcc acgcctttgc caactggccc caaactccca tggatcacaa  20580
ccccaccatg aaccttatta ccggggtacc caactccatg ctcaacagtc cccaggtaca  20640
gcccaccctg cgtcgcaacc aggaacagct ctacagcttc ctggagcgcc actcgcccta  20700
cttccgcagc cacagtgcgc agattaggag cgccacttct ttttgtcact tgaaaaacat  20760
gtaaaaataa tgtactagag acactttcaa taaaggcaaa tgcttttatt tgtacactct  20820
cgggtgatta tttacccca cccttgccgt ctgcgccgtt taaaaatcaa aggggttctg  20880
ccgcgcatcg ctatgcgcca ctggcaggga cacgttgcga tactggtgtt tagtgctcca  20940
cttaaactca ggcacaacca tccgcggcag ctcggtgaag ttttcactcc acaggctgcg  21000
caccatcacc aacgcgttta gcaggtcggg cgccgatatc ttgaagtcgc agttggggcc  21060
tccgccctgc gcgcgcgagt tgcgatacac agggttgcag cactggaaca ctatcagcgc  21120
cgggtggtgc acgctggcca gcacgctctt gtcggagatc agatccgcgt ccaggtcctc  21180
cgcgttgctc agggcgaacg gagtcaactt tggtagctgc cttcccaaaa agggcgcgtg  21240
cccaggcttt gagttgcact cgcaccgtag tggcatcaaa aggtgaccgt gcccggtctg  21300
ggcgttagga tacagcgcct gcataaaagc cttgatctgc ttaaaagcca cctgagcctt  21360
tgcgccttca gagaagaaca tgccgcaaga cttgccggaa aactgattgg ccggacaggc  21420
cgcgtcgtgc acgcagcacc ttgcgtcggt gttggagatc tgcaccacat ttcggcccca  21480
ccggttcttc acgatcttgg ccttgctaga ctgctccttc agcgcgcgct gcccgttttc  21540
gctcgtcaca tccatttcaa tcacgtgctc cttatttatc ataatgcttc cgtgtagaca  21600
cttaagctcg ccttcgatct cagcgcagcg gtgcagccac aacgcgcagc ccgtgggctc  21660
gtgatgcttg taggtcacct ctgcaaacga ctgcaggtac gcctgcagga atcgccccat  21720
catcgtcaca aaggtcttgt tgctggtgaa ggtcagctgc aacccgcggt gctcctcgtt  21780
cagccaggtc ttgcatacgg ccgccagagc ttccacttgg tcaggcagta gtttgaagtt  21840
cgcctttaga tcgttatcca cgtggtactt gtccatcagc gcgcgcgcag cctccatgcc  21900
cttctcccac gcagacacga tcggcacact cagcgggttc atcaccgtaa tttcactttc  21960
cgcttcgctg ggctcttcct cttcctcttg cgtccgcata ccacgcgcca ctgggtcgtc  22020
ttcattcagc cgccgcactg tgcgcttacc tcctttgcca tgcttgatta gcaccggtgg  22080
gttgctgaaa cccaccattt gtagcgccac atcttctctt tcttcctcgc tgtccacgat  22140
tacctctggt gatggcgggc gctcgggctt gggagaaggg cgcttctttt tcttcttggg  22200
cgcaatggcc aaatccgccg ccgaggtcga tggccgcggg ctgggtgtgc gcggcaccag  22260
cgcgtcttgt gatgagtctt cctcgtcctc ggactcgata cgccgcctca tccgcttttt  22320
tgggggcgcc cggggaggcg gcggcgacgg ggacggggac gacacgtcct ccatggttgg  22380
gggacgtcgc gccgcaccgc gtccgcgctc gggggtggtt tcgcgctgct cctcttcccg  22440
actggccatt tccttctcct ataggcagaa aaagatcatg gagtcagtcg agaagaagga  22500
cagcctaacc gccccctctg agttcgccac caccgcctcc accgatgccg ccaacgcgcc  22560
```

```
taccaccttc cccgtcgagg cacccccgct tgaggaggag gaagtgatta tcgagcagga  22620
cccaggtttt gtaagcgaag acgacgagga ccgctcagta ccaacagagg ataaaaagca  22680
agaccaggac aacgcagagg caaacgagga acaagtcggg cggggggacg aaaggcatgg  22740
cgactaccta gatgtgggag acgacgtgct gttgaagcat ctgcagcgcc agtgcgccat  22800
tatctgcgac gcgttgcaag agcgcagcga tgtgcccctc gccatagcgg atgtcagcct  22860
tgcctacgaa cgccacctat tctcaccgcg cgtacccccc aaacgccaag aaaacggcac  22920
atgcgagccc aacccgcgcc tcaacttcta ccccgtattt gccgtgccag aggtgcttgc  22980
cacctatcac atctttttcc aaaactgcaa gatacccta tcctgccgtg ccaaccgcag  23040
ccgagcggac aagcagctgg ccttgcggca gggcgctgtc atacctgata tcgcctcgct  23100
caacgaagtg ccaaaaatct ttgagggtct tggacgcgac gagaagcgcg cggcaaacgc  23160
tctgcaacag gaaaacagcg aaaatgaaag tcactctgga gtgttggtgg aactcgaggg  23220
tgacaacgcg cgcctagccg tactaaaacg cagcatcgag gtcacccact ttgcctaccc  23280
ggcacttaac ctacccccca aggtcatgag cacagtcatg agtgagctga tcgtgcgccg  23340
tgcgcagccc ctggagaggg atgcaaattt gcaagaacaa acagaggagg gcctacccgc  23400
agttggcgac gagcagctag cgcgctggct tcaaacgcgc gagcctgccg acttggagga  23460
gcgacgcaaa ctaatgatgg ccgcagtgct cgttaccgtg gagcttgagt gcatgcagcg  23520
gttctttgct gacccggaga tgcagcgcaa gctagaggaa acattgcact acacctttcg  23580
acagggctac gtacgccagg cctgcaagat ctccaacgtg gagctctgca acctggtctc  23640
ctaccttgga attttgcacg aaaaccgcct tgggcaaaac gtgcttcatt ccacgctcaa  23700
gggcgaggcg cgccgcgact acgtccgcga ctgcgtttac ttatttctat gctacacctg  23760
gcagacggcc atgggcgttt ggcagcagtg cttggaggag tgcaacctca aggagctgca  23820
gaaactgcta aagcaaaact tgaaggacct atggacggcc ttcaacgagc gctccgtggc  23880
cgcgcacctg gcggacatca ttttccccga acgcctgctt aaaaccctgc aacagggtct  23940
gccagacttc accagtcaaa gcatgttgca gaactttagg aactttatcc tagagcgctc  24000
aggaatcttg cccgccacct gctgtgcact tcctagcgac tttgtgccca ttaagtaccg  24060
cgaatgccct ccgccgcttt ggggccactg ctaccttctg cagctagcca actaccttgc  24120
ctaccactct gacataatgg aagacgtgag cggtgacggt ctactggagt gtcactgtcg  24180
ctgcaaccta tgcaccccgc accgctccct ggtttgcaat tcgcagctgc ttaacgaaag  24240
tcaaattatc ggtacctttg agctgcaggg tccctcgcct gacgaaaagt ccgcggctcc  24300
ggggttgaaa ctcactccgg ggctgtggac gtcggcttac cttcgcaaat ttgtacctga  24360
ggactaccac gcccacgaga ttaggttcta cgaagaccaa tcccgcccgc ctaatgcgga  24420
gcttaccgcc tgcgtcatta cccagggcca cattcttggc caattgcaag ccatcaacaa  24480
agcccgccaa gagtttctgc tacgaaaggg acgggggggtt tacttggacc cccagtccgg  24540
cgaggagctc aacccaatcc ccccgccgcc gcagccctat cagcagcagc cgcgggccct  24600
tgcttcccag gatggcaccc aaaaagaagc tgcagctgcc gccgccaccc acggacgagg  24660
aggaatactg ggacagtcag gcagaggagg ttttggacga ggaggaggag gacatgatgg  24720
aagactggga gagcctagac gaggaagctt ccgaggtcga agaggtgtca gacgaaacac  24780
cgtcaccctc ggtcgcattc ccctcgccgg cgccccagaa atcggcaacc ggttccagca  24840
tggctacaac ctccgctcct caggcgccgc cggcactgcc cgttcgccga cccaaccgta  24900
```

gatgggacac cactggaacc agggccggta agtccaagca gccgccgccg ttagcccaag 24960
agcaacaaca gcgccaaggc taccgctcat ggcgcgggca caagaacgcc atagttgctt 25020
gcttgcaaga ctgtgggggc aacatctcct tcgcccgccg ctttcttctc taccatcacg 25080
gcgtggcctt cccccgtaac atcctgcatt actaccgtca tctctacagc ccatactgca 25140
ccggcggcag cggcagcaac agcagcggcc acacagaagc aaaggcgacc ggatagcaag 25200
actctgacaa agcccaagaa atccacagcg gcggcagcag caggaggagg agcgctgcgt 25260
ctggcgccca acgaacccgt atcgacccgc gagcttagaa acaggatttt tcccactctg 25320
tatgctatat ttcaacagag caggggccaa gaacaagagc tgaaaataaa aaacaggtct 25380
ctgcgatccc tcacccgcag ctgcctgtat cacaaaagcg aagatcagct tcggcgcacg 25440
ctggaagacg cggaggctct cttcagtaaa tactgcgcgc tgactcttaa ggactagttt 25500
cgcgcccttt ctcaaattta agcgcgaaaa ctacgtcatc tccagcggcc acacccggcg 25560
ccagcacctg ttgtcagcgc cattatgagc aaggaaattc ccacgcccta catgtggagt 25620
taccagccac aaatgggact tgcggctgga gctgcccaag actactcaac ccgaataaac 25680
tacatgagcg cgggacccca catgatatcc cgggtcaacg gaatacgcgc ccaccgaaac 25740
cgaattctcc tggaacaggc ggctattacc accacacctc gtaataacct taatccccgt 25800
agttggcccg ctgccctggt gtaccaggaa agtcccgctc ccaccactgt ggtacttccc 25860
agagacgccc aggccgaagt tcagatgact aactcagggg cgcagcttgc gggcggcttt 25920
cgtcacaggg tgcggtcgcc cgggcagggt ataactcacc tgacaatcag agggcgaggt 25980
attcagctca acgacgagtc ggtgagctcc tcgcttggtc tccgtccgga cgggacattt 26040
cagatcggcg gcgccggccg ctcttcattc acgcctcgtc aggcaatcct aactctgcag 26100
acctcgtcct ctgagccgcg ctctggaggc attggaactc tgcaatttat tgaggagttt 26160
gtgccatcgg tctactttaa ccccttctcg ggacctcccg gccactatcc ggatcaattt 26220
attcctaact ttgacgcggt aaaggactcg gcggacggct acgactgaat gttaagtgga 26280
gaggcagagc aactgcgcct gaaacacctg gtccactgtc gccgccacaa gtgctttgcc 26340
cgcgactccg gtgagttttg ctactttgaa ttgcccgagg atcatatcga gggcccggcg 26400
cacggcgtcc ggcttaccgc ccagggagag cttgcccgta gcctgattcg ggagtttacc 26460
cagcgccccc tgctagttga gcgggacagg ggaccctgtg ttctcactgt gatttgcaac 26520
tgtcctaacc ctggattaca tcaagatctt tgttgccatc tctgtgctga gtataataaa 26580
tacagaaatt aaaatatact ggggctccta tcgccatcct gtaaacgcca ccgtcttcac 26640
ccgcccaagc aaaccaaggc gaaccttacc tggtactttt aacatctctc cctctgtgat 26700
ttacaacagt ttcaacccag acggagtgag tctacgagag aacctctccg agctcagcta 26760
ctccatcaga aaaaacacca ccctccttac ctgccgggaa cgtacgagtg cgtcaccggc 26820
cgctgcacca cacctaccgc ctgaccgtaa accagacttt ttccggacag acctcaataa 26880
ctctgtttac cagaacagga ggtgagctta gaaaaccctt agggtattag gccaaaggcg 26940
cagctactgt ggggtttatg aacaattcaa gcaactctac gggctattct aattcaggtt 27000
tctctagaat cggggttggg gttattctct gtcttgtgat tctctttatt cttatactaa 27060
cgcttctctg cctaaggctc gccgcctgct gtgtgcacat ttgcatttat tgtcagcttt 27120
ttaaacgctg ggtcgccac ccaagatgat taggtacata atcctaggtt tactcaccct 27180
tgcgtcagcc cacggtacca cccaaaaggt ggattttaag gagccagcct gtaatgttac 27240
attcgcagct gaagctaatg agtgcaccac tcttataaaa tgcaccacag aacatgaaaa 27300

```
gctgcttatt cgccacaaaa acaaaattgg caagtatgct gtttatgcta tttggcagcc  27360
aggtgacact acagagtata atgttacagt tttccagggt aaaagtcata aaacttttat  27420
gtatactttt ccattttatg aaatgtgcga cattaccatg tacatgagca aacagtataa  27480
gttgtggccc ccacaaaatt gtgtggaaaa cactggcact ttctgctgca ctgctatgct  27540
aattacagtg ctcgctttgg tctgtaccct actctatatt aaatacaaaa gcagacgcag  27600
ctttattgag gaaaagaaaa tgccttaatt tactaagtta caaagctaat gtcaccacta  27660
actgctttac tcgctgcttg caaaacaaat tcaaaaagtt agcattataa ttagaatagg  27720
atttaaaccc cccggtcatt tcctgctcaa taccattccc ctgaacaatt gactctatgt  27780
gggatatgct ccagcgctac aaccttgaag tcaggcttcc tggatgtcag catctgactt  27840
tggccagcac ctgtcccgcg gatttgttcc agtccaacta cagcgaccca ccctaacaga  27900
gatgaccaac acaaccaacg cggccgccgc taccggactt acatctacca caaatacacc  27960
ccaagtttct gcctttgtca ataactggga taacttgggc atgtggtggt tctccatagc  28020
gcttatgttt gtatgcctta ttattatgtg gctcatctgc tgcctaaagc gcaaacgcgc  28080
ccgaccaccc atctatagtc ccatcattgt gctacaccca aacaatgatg gaatccatag  28140
attggacgga ctgaaacaca tgttcttttc tcttacagta tgattaaatg agacatgatt  28200
cctcgagttt ttatattact gacccttgtt gcgctttttt tgtgcgtgct ccacattggc  28260
tgcggtttct cacatcgaag tagactgcat tccagccttc acagtctatt tgctttacgg  28320
atttgtcacc ctcacgctca tctgcagcct catcactgtg gtcatcgcct ttatccagtg  28380
cattgactgg gtctgtgtgc gctttgcata tctcagacac catccccagt acagggacag  28440
gactatagct gagcttctta gaattcttta attatgaaat ttactgtgac ttttctgctg  28500
attatttgca ccctatctgc gttttgttcc ccgacctcca agcctcaaag acatatatca  28560
tgcagattca ctcgtatatg gaatattcca agttgctaca atgaaaaaag cgatctttcc  28620
gaagcctggt tatatgcaat catctctgtt atggtgttct gcagtaccat cttagcccta  28680
gctatatatc cctaccttga cattggctgg aacgcaatag atgccatgaa ccacccaact  28740
ttccccgcgc ccgctatgct tccactgcaa caagttgttg ccggcggctt tgtcccagcc  28800
aatcagcctc gcccaccttc tcccaccccc actgaaatca gctactttaa tctaacagga  28860
ggagatgact gacaccctag atctagaaat ggacggaatt attacagagc agcgcctgct  28920
agaaagacgc agggcagcgg ccgagcaaca gcgcatgaat caagagctcc aagacatggt  28980
taacttgcac cagtgcaaaa ggggtatctt ttgtctggta aagcaggcca aagtcaccta  29040
cgacagtaat accaccggac accgccttag ctacaagttg ccaaccaagc gtcagaaatt  29100
ggtggtcatg gtgggagaaa agcccattac cataactcag cactcggtag aaaccgaagg  29160
ctgcattcac tcaccttgtc aaggacctga ggatctctgc acccttatta agaccctgtg  29220
cggtctcaaa gatcttattc cctttaacta ataaaaaaaa ataataaagc atcacttact  29280
taaaatcagt tagcaaattt ctgtccagtt tattcagcag cacctccttg ccctcctccc  29340
agctctggta ttgcagcttc ctcctggctg caaactttct ccacaatcta aatggaatgt  29400
cagtttcctc ctgttcctgt ccatccgcac ccactatctt catgttgttg cagatgaagc  29460
gcgcaagacc gtctgaagat accttcaacc ccgtgtatcc atatgacacg gaaaccggtc  29520
ctccaactgt gccttttctt actcctccct ttgtatcccc caatgggttt caagagagtc  29580
cccctggggt actctctttg cgcctatccg aacctctagt tacctccaat ggcatgcttg  29640
```

-continued

```
cgctcaaaat gggcaacggc ctctctctgg acgaggccgg caaccttacc tcccaaaatg  29700
taaccactgt gagcccacct ctcaaaaaaa ccaagtcaaa cataaacctg gaaatatctg  29760
cacccctcac agttacctca gaagccctaa ctgtggctgc cgccgcacct ctaatggtcg  29820
cgggcaacac actcaccatg caatcacagg ccccgctaac cgtgcacgac tccaaactta  29880
gcattgccac ccaaggaccc ctcacagtgt cagaaggaaa gctagccctg caaacatcag  29940
gcccccctcac caccaccgat agcagtaccc ttactatcac tgcctcaccc cctctaacta  30000
ctgccactgg tagcttgggc attgacttga aagagcccat ttatacacaa aatggaaaac  30060
taggactaaa gtacggggct cctttgcatg taacagacga cctaaacact ttgaccgtag  30120
caactggtcc aggtgtgact attaataata cttccttgca aactaaagtt actggagcct  30180
tgggttttga ttcacaaggc aatatgcaac ttaatgtagc aggaggacta aggattgatt  30240
ctcaaaacag acgccttata cttgatgtta gttatccgtt tgatgctcaa aaccaactaa  30300
atctaagact aggacagggc cctcttttta taaactcagc ccacaacttg gatattaact  30360
acaacaaagg cctttacttg tttacagctt caaacaattc caaaaagctt gaggttaacc  30420
taagcactgc caaggggttg atgtttgacg ctacagccat agccattaat gcaggagatg  30480
ggcttgaatt tggttcacct aatgcaccaa acacaaatcc cctcaaaaca aaaattggcc  30540
atggcctaga atttgattca aacaaggcta tggttcctaa actaggaact ggccttagtt  30600
ttgacagcac aggtgccatt acagtaggaa acaaaaataa tgataagcta actttgtgga  30660
ccacaccagc tccatctcct aactgtagac taaatgcaga gaaagatgct aaactcactt  30720
tggtcttaac aaaatgtggc agtcaaatac ttgctacagt ttcagttttg gctgttaaag  30780
gcagtttggc tccaatatct ggaacagttc aaagtgctca tcttattata agatttgacg  30840
aaaatggagt gctactaaac aattccttcc tggacccaga atattggaac tttagaaatg  30900
gagatcttac tgaaggcaca gcctatacaa acgctgttgg atttatgcct aacctatcag  30960
cttatccaaa atctcacggt aaaactgcca aaagtaacat tgtcagtcaa gtttacttaa  31020
acggagacaa aactaaacct gtaacactaa ccattacact aaacggtaca caggaaacag  31080
gagacacaac tccaagtgca tactctatgt cattttcatg ggactggtct ggccacaact  31140
acattaatga aatatttgcc acatcctctt acactttttc atacattgcc caagaataaa  31200
gaatcgtttg tgttatgttt caacgtgttt atttttcaat tgcagaaaat ttcaagtcat  31260
ttttcattca gtagtatagc cccaccacca catagcttat acagatcacc gtaccttaat  31320
caaactcaca gaaccctagt attcaacctg ccacctccct cccaacacac agagtacaca  31380
gtcctttctc cccggctggc cttaaaaagc atcatatcat gggtaacaga catattctta  31440
ggtgttatat tccacacggt ttcctgtcga gccaaacgct catcagtgat attaataaac  31500
tccccgggca gctcacttaa gttcatgtcg ctgtccagct gctgagccac aggctgctgt  31560
ccaacttgcg gttgcttaac gggcggcgaa ggagaagtcc acgcctacat gggggtagag  31620
tcataatcgt gcatcaggat agggcggtgg tgctgcagca gcgcgcgaat aaactgctgc  31680
cgccgccgct ccgtcctgca ggaatacaac atggcagtgg tctcctcagc gatgattcgc  31740
accgcccgca gcataaggcg ccttgtcctc cgggcacagc agcgcaccct gatctcactt  31800
aaatcagcac agtaactgca gcacagcacc acaatattgt tcaaaatccc acagtgcaag  31860
gcgctgtatc caaagctcat ggcggggacc acagaaccca cgtggccatc ataccacaag  31920
cgcaggtaga ttaagtggcg acccctcata aacacgctgg acataaacat tacctctttt  31980
ggcatgttgt aattcaccac ctcccggtac catataaacc tctgattaaa catggcgcca  32040
```

```
tccaccacca tcctaaacca gctggccaaa acctgcccgc cggctataca ctgcagggaa  32100
ccgggactgg aacaatgaca gtggagagcc caggactcgt aaccatggat catcatgctc  32160
gtcatgatat caatgttggc acaacacagg cacacgtgca tacacttcct caggattaca  32220
agctcctccc gcgttagaac catatcccag ggaacaaccc attcctgaat cagcgtaaat  32280
cccacactgc agggaagacc tcgcacgtaa ctcacgttgt gcattgtcaa agtgttacat  32340
tcgggcagca gcggatgatc ctccagtatg gtagcgcggg tttctgtctc aaaaggaggt  32400
agacgatccc tactgtacgg agtgcgccga gacaaccgag atcgtgttgg tcgtagtgtc  32460
atgccaaatg gaacgccgga cgtagtcata tttcctgaag caaaaccagg tgcgggcgtg  32520
acaaacagat ctgcgtctcc ggtctcgccg cttagatcgc tctgtgtagt agttgtagta  32580
tatccactct ctcaaagcat ccaggcgccc cctggcttcg ggttctatgt aaactccttc  32640
atgcgccgct gccctgataa catccaccac cgcagaataa gccacaccca gccaacctac  32700
acattcgttc tgcgagtcac acacgggagg agcgggaaga gctggaagaa ccatgttttt  32760
tttttattc caaaagatta tccaaaacct caaaatgaag atctattaag tgaacgcgct  32820
cccctccggt ggcgtggtca aactctacag ccaaagaaca gataatggca tttgtaagat  32880
gttgcacaat ggcttccaaa aggcaaacgg ccctcacgtc caagtggacg taaaggctaa  32940
acccttcagg gtgaatctcc tctataaaca ttccagcacc ttcaaccatg cccaaataat  33000
tctcatctcg ccaccttctc aatatatctc taagcaaatc ccgaatatta agtccggcca  33060
ttgtaaaaat ctgctccaga gcgccctcca ccttcagcct caagcagcga atcatgattg  33120
caaaaattca ggttcctcac agacctgtat aagattcaaa agcggaacat taacaaaaat  33180
accgcgatcc cgtaggtccc ttcgcagggc cagctgaaca taatcgtgca ggtctgcacg  33240
gaccagcgcg gccacttccc cgccaggaac catgacaaaa gaacccacac tgattatgac  33300
acgcatactc ggagctatgc taaccagcgt agccccgatg taagcttgtt gcatgggcgg  33360
cgatataaaa tgcaaggtgc tgctcaaaaa atcaggcaaa gcctcgcgca aaaaagaaag  33420
cacatcgtag tcatgctcat gcagataaag gcaggtaagc tccggaacca ccacagaaaa  33480
agacaccatt tttctctcaa acatgtctgc gggtttctgc ataaacacaa aataaaataa  33540
caaaaaaaca tttaaacatt agaagcctgt cttacaacag gaaaaacaac ccttataagc  33600
ataagacgga ctacggccat gccggcgtga ccgtaaaaaa actggtcacc gtgattaaaa  33660
agcaccaccg acagctcctc ggtcatgtcc ggagtcataa tgtaagactc ggtaaacaca  33720
tcaggttgat tcacatcggt cagtgctaaa aagcgaccga aatagcccgg gggaatacat  33780
acccgcaggc gtagagacaa cattacagcc cccataggag gtataacaaa attaatagga  33840
gagaaaaaca cataaacacc tgaaaaaccc tcctgcctag gcaaaatagc accctcccgc  33900
tccagaacaa catacagcgc ttccacagcg gcagccataa cagtcagcct taccagtaaa  33960
aaagaaaacc tattaaaaaa acaccactcg acacggcacc agctcaatca gtcacagtgt  34020
aaaaaagggc caagtgcaga gcgagtatat ataggactaa aaaatgacgt aacggttaaa  34080
gtccacaaaa aacacccaga aaaccgcacg cgaacctacg cccagaaacg aaagccaaaa  34140
aacccacaac ttcctcaaat cgtcacttcc gttttcccac gttacgtcac ttcccatttt  34200
aagaaaacta caattcccaa cacatacaag ttactccgcc ctaaaaccta cgtcacccgc  34260
cccgttccca cgccccgcgc cacgtcacaa actccacccc ctcattatca tattggcttc  34320
aatccaaaat aaggtatatt attgatgatg                                    34350
```

-continued

<210> SEQ ID NO 2
<211> LENGTH: 590
<212> TYPE: DNA
<213> ORGANISM: Artificial sequence
<220> FEATURE:
<223> OTHER INFORMATION: TNFR portion of the TNFR-Fas chimera (Fas-c)

<400> SEQUENCE: 2
atgggcctct ccaccgtgcc tgacctgctg ctgccgctgg tgctcctgga gctgttggtg 60
ggaatatacc cctcaggggt tattggactg gtccctcacc taggggacag ggagaagaga 120
gatagtgtgt gtccccaagg aaaatatatc caccctcaaa ataattcgat ttgctgtacc 180
aagtgccaca aaggaaccta cttgtacaat gactgtccag gcccggggca ggatacggac 240
tgcagggagt gtgagagcgg ctccttcacc gcttcagaaa accacctcag acactgcctc 300
agctgctcca aatgccgaaa ggaaatgggt caggtggaga tctcttcttg cacagtggac 360
cgggacaccg tgtgtggctg caggaagaac cagtaccggc attattggag tgaaaacctt 420
ttccagtgct tcaattgcag cctctgcctc aatgggaccg tgcacctctc ctgccaggag 480
aaacagaaca ccgtgtgcac ctgccatgca ggtttctttc taagagaaaa cgagtgtgtc 540
tcctgtagta actgtaagaa aagcctggag tgcacgaagt tgtgcctacc 590

<210> SEQ ID NO 3
<211> LENGTH: 511
<212> TYPE: DNA
<213> ORGANISM: Artificial sequence
<220> FEATURE:
<223> OTHER INFORMATION: Fas portion of the TNFR-Fas chimera (Fas-c)

<400> SEQUENCE: 3
aagcttagga tccagatcta acttggggtg gctttgtctt cttcttttgc caattccact 60
aattgtttgg gtgaagagaa aggaagtaca gaaaacatgc agaaagcaca gaaaggaaaa 120
ccaaggttct catgaatctc caaccttaaa tcctgaaaca gtggcaataa atttatctga 180
tgttgacttg agtaaatata tcaccactat tgctggagtc atgacactaa gtcaagttaa 240
aggctttgtt cgaaagaatg gtgtcaatga agccaaaata gatgagatca agaatgacaa 300
tgtccaagac acagcagaac agaaagttca actgcttcgt aattggcatc aacttcatgg 360
aaagaaagaa gcgtatgaca cattgattaa agatctcaaa aaagccaatc tttgtactct 420
tgcagagaaa attcagacta tcatcctcaa ggacattact agtgactcag aaaattcaaa 480
cttcagaaat gaaatccaaa gcttggtcta g 511

<210> SEQ ID NO 4
<211> LENGTH: 1101
<212> TYPE: DNA
<213> ORGANISM: Artificial sequence
<220> FEATURE:
<223> OTHER INFORMATION: TNFR1-Fas chimera (Fas-c) coding sequence

<400> SEQUENCE: 4
atgggcctct ccaccgtgcc tgacctgctg ctgccgctgg tgctcctgga gctgttggtg 60
ggaatatacc cctcaggggt tattggactg gtccctcacc taggggacag ggagaagaga 120
gatagtgtgt gtccccaagg aaaatatatc caccctcaaa ataattcgat ttgctgtacc 180
aagtgccaca aaggaaccta cttgtacaat gactgtccag gcccggggca ggatacggac 240
tgcagggagt gtgagagcgg ctccttcacc gcttcagaaa accacctcag acactgcctc 300
agctgctcca aatgccgaaa ggaaatgggt caggtggaga tctcttcttg cacagtggac 360
cgggacaccg tgtgtggctg caggaagaac cagtaccggc attattggag tgaaaacctt 420
ttccagtgct tcaattgcag cctctgcctc aatgggaccg tgcacctctc ctgccaggag 480
aaacagaaca ccgtgtgcac ctgccatgca ggtttctttc taagagaaaa cgagtgtgtc 540
tcctgtagta actgtaagaa aagcctggag tgcacgaagt tgtgcctacc aagcttagga 600
tccagatcta acttggggtg gctttgtctt cttcttttgc caattccact aattgtttgg 660
gtgaagagaa aggaagtaca gaaaacatgc agaaagcaca gaaaggaaaa ccaaggttct 720
catgaatctc caaccttaaa tcctgaaaca gtggcaataa atttatctga tgttgacttg 780
agtaaatata tcaccactat tgctggagtc atgacactaa gtcaagttaa aggctttgtt 840
cgaaagaatg gtgtcaatga agccaaaata gatgagatca agaatgacaa tgtccaagac 900
acagcagaac agaaagttca actgcttcgt aattggcatc aacttcatgg aaagaaagaa 960
gcgtatgaca cattgattaa agatctcaaa aaagccaatc tttgtactct tgcagagaaa 1020
attcagacta tcatcctcaa ggacattact agtgactcag aaaattcaaa cttcagaaat 1080
gaaatccaaa gcttggtcta g 1101

<210> SEQ ID NO 5
<211> LENGTH: 6
<212> TYPE: DNA
<213> ORGANISM: Artificial sequence
<220> FEATURE:
<223> OTHER INFORMATION: Hypoxia responsive element - E-box

<400> SEQUENCE: 5 gcacgt 6

<210> SEQ ID NO 6
<211> LENGTH: 44
<212> TYPE: DNA
<213> ORGANISM: Artificial sequence
<220> FEATURE:
<223> OTHER INFORMATION: Murine endothelial specific enhancer element

<400> SEQUENCE: 6
gtacttcata cttttcattc caatggggtg actttgcttc tgga 44

<210> SEQ ID NO 7
<211> LENGTH: 143
<212> TYPE: DNA
<213> ORGANISM: Artificial sequence
<220> FEATURE:
<223> OTHER INFORMATION: A triplicate copy of a murine enhancer sequence
originated from the PPE-1 promoter

<400> SEQUENCE: 7
gtacttcata cttttcattc caatggggtg actttgcttc tggagggtga ctttgcttct 60
ggagccagta cttcatactt ttcattgtac ttcatacttt tcattccaat ggggtgactt 120
tgcttctgga ggctagctgc cag 143

<210> SEQ ID NO 8
<211> LENGTH: 47
<212> TYPE: DNA
<213> ORGANISM: Artificial sequence
<220> FEATURE:
<223> OTHER INFORMATION: EDC fragment

<400> SEQUENCE: 8
ctggagggtg actttgcttc tggagccagt acttcatact tttcatt 47

<210> SEQ ID NO 9
<211> LENGTH: 36460
<212> TYPE: DNA
<213> ORGANISM: Artificial sequence
<220> FEATURE:
<223> OTHER INFORMATION: PPE-1-3X-FasC virl construct including repeat sequences
<220> FEATURE:
<221> NAME/KEY: misc_feature
<222> LOCATION: (460)..(1437)
<223> OTHER INFORMATION: A modified murine pre-proendothelin-1 promoter (PPE-1-3X)
<220> FEATURE:
<221> NAME/KEY: misc_feature
<222> LOCATION: (1202)..(1207)
<223> OTHER INFORMATION: Hypoxia response element
<220> FEATURE:
<221> NAME/KEY: misc_feature
<222> LOCATION: (1438)..(1468)
<223> OTHER INFORMATION: Linker containing Restriction sites (NotI, PstI, BamHI)
<220> FEATURE:
<221> NAME/KEY: misc_feature
<222> LOCATION: (1469)..(2058)
<223> OTHER INFORMATION: TNFR portion of the Fas-TNFR-1 chimera (Fas-c)
<220> FEATURE:
<221> NAME/KEY: misc_feature
<222> LOCATION: (2059)..(2569)
<223> OTHER INFORMATION: FAS portion of the Fas-TNFR-1 chimera (Fas-c)
<220> FEATURE:
<221> NAME/KEY: misc_feature
<222> LOCATION: (2801)..(4062)
<223> OTHER INFORMATION: Duplication - copy 1
<220> FEATURE:
<221> NAME/KEY: misc_feature
<222> LOCATION: (4063)..(5315)
<223> OTHER INFORMATION: Duplication - copy 2

<400> SEQUENCE: 9
catcatcaat aatatacctt attttggatt gaagccaata tgataatgag gggtggagt 60 ttgtgacgtg gcgcggggcg tgggaacggg gcgggtgacg tagtagtgtg gcggaagtgt 120
gatgttgcaa gtgtggcgga acacatgtaa gcgacggatg tggcaaaagt gacgtttttg 180
gtgtgcgccg gtgtacacag gaagtgacaa ttttcgcgcg gttttaggcg gatgttgtag 240
taaatttggg cgtaaccgag taagatttgg ccattttcgc gggaaaactg aataagagga 300
agtgaaatct gaataatttt gtgttactca tagcgcgtaa tatttgtcta gggccgcggg 360
gactttgacc gtttacgtgg agactcgccc aggtgttttt ctcaggtgtt ttccgcgttc 420
cgggtcaaag ttggcgtttt attattatag tcagtacgta cgtgtacttc tgatcggcga 480
tactagggag ataaggatgt acctgacaaa accacattgt tgttgttatc attattattt 540
agttttcctt ccttgctaac tcctgacgga atctttctca cctcaaatgc gaagtacttt 600
agtttagaaa agacttggtg gaaggggtgg tggtggaaaa gtagggtgat cttccaaact 660
aatctggttc cccgcccgcc ccagtagctg ggattcaaga gcgaagagtg gggatcgtcc 720
ccttgtttga tcagaaagac ataaaaggaa aatcaagtga acaatgatca gccccacctc 780
caccccaccc ccctgcgcgc gcacaataca atctatttaa ttgtacttca tacttttcat 840
tccaatgggg tgactttgct tctggagaaa ctcttgattc ttgaactctg gggctggcag 900
ctagcctcca gaagcaaagt caccccattg gaatgaaaag tatgaagtac aatgaaaagt 960
atgaagtact ggctccagaa gcaaagtcac cctccagaag caaagtcacc ccattggaat 1020
gaaaagtatg aagtacgcta gcaaaagggg aagcgggctg ctgctctctg caggttctgc 1080
agcggtctct gtctagtggg tgttttcttt ttcttagccc tgcccctgga ttgtcagacg 1140

```
gcgggcgtct gcctctgaag ttagccgtga tttcctctag agccgggtct tatctctggc   1200
tgcacgttgc ctgtgggtga ctaatcacac aataacattg tttagggctg gaataaagtc   1260
agagctgttt acccccactc tataggggtt caatataaaa aggcggcgga gaactgtccg   1320
agtcagaagc gttcctgcac cggcgctgag agcctgaccc ggtctgctcc gctgtccttg   1380
cgcgctgcct cccggctgcc cgcgacgctt tcgccccagt ggaagggcca cttgctgcgg   1440
ccgctaattc tgcagatcgg gatccggcat gggcctctcc accgtgcctg acctgctgct   1500
gccgctggtg ctcctggagc tgttggtggg aatatacccc tcaggggtta ttggactggt   1560
ccctcaccta ggggacaggg agaagagaga tagtgtgtgt ccccaaggaa aatatatcca   1620
ccctcaaaat aattcgattt gctgtaccaa gtgccacaaa ggaacctact tgtacaatga   1680
ctgtccaggc ccggggcagg atacggactg cagggagtgt gagagcggct ccttcaccgc   1740
ttcagaaaac cacctcagac actgcctcag ctgctccaaa tgccgaaagg aaatgggtca   1800
ggtggagatc tcttcttgca cagtggaccg ggacaccgtg tgtggctgca ggaagaacca   1860
gtaccggcat tattggagtg aaaacctttt ccagtgcttc aattgcagcc tctgcctcaa   1920
tgggaccgtg cacctctcct gccaggagaa acagaacacc gtgtgcacct gccatgcagg   1980
tttctttcta agagaaaacg agtgtgtctc ctgtagtaac tgtaagaaaa gcctggagtg   2040
cacgaagttg tgcctaccaa gcttaggatc cagatctaac ttggggtggc tttgtcttct   2100
tcttttgcca attccactaa ttgtttgggt gaagagaaag gaagtacaga aaacatgcag   2160
aaagcacaga aaggaaaacc aaggttctca tgaatctcca accttaaatc ctgaaacagt   2220
ggcaataaat ttatctgatg ttgacttgag taaatatatc accactattg ctggagtcat   2280
gacactaagt caagttaaag gctttgttcg aaagaatggt gtcaatgaag ccaaaataga   2340
tgagatcaag aatgacaatg tccaagacac agcagaacag aaagttcaac tgcttcgtaa   2400
ttggcatcaa cttcatggaa agaaagaagc gtatgacaca ttgattaaag atctcaaaaa   2460
agccaatctt tgtactcttg cagagaaaat tcagactatc atcctcaagg acattactag   2520
tgactcagaa aattcaaact tcagaaatga aatccaaagc ttggtctagc tcgagcatgc   2580
atctaggcgg ccgcatggca gaaattcgcg aattcgctag cgttaacgga tcctctagac   2640
gagatccgaa cttgtttatt gcagcttata atggttacaa ataaagcaat agcatcacaa   2700
atttcacaaa taaagcattt ttttcactgc attctagttg tggtttgtcc aaactcatca   2760
atgtatctta tcatgtctag atctgtactg aaatgtgtgg gcgtggctta agggtgggaa   2820
agaatatata aggtgggggt cttatgtagt tttgtatctg ttttgcagca gccgccgccg   2880
ccatgagcac caactcgttt gatggaagca ttgtgagctc atatttgaca acgcgcatgc   2940
ccccatgggc cggggtgcgt cagaatgtga tgggctccag cattgatggt cgccccgtcc   3000
tgcccgcaaa ctctactacc ttgacctacg agaccgtgtc tggaacgccg ttggagactg   3060
cagcctccgc cgccgcttca gccgctgcag ccaccgcccg cgggattgtg actgactttg   3120
ctttcctgag cccgcttgca agcagtgcag cttcccgttc atccgcccgc gatgacaagt   3180
tgacggctct tttggcacaa ttggattctt tgacccggga acttaatgtc gtttctcagc   3240
agctgttgga tctgcgccag caggtttctg ccctgaaggc ttcctcccct cccaatgcgg   3300
tttaaaacat aaataaaaaa ccagactctg tttggatttg gatcaagcaa gtgtcttgct   3360
gtctttattt aggggttttg cgcgcgcggt aggcccggga ccagcggtct cggtcgttga   3420
gggtcctgtg tatttttttcc aggacgtggt aaaggtgact ctggatgttc agatacatgg   3480
```

-continued gcataagccc gtctctgggg tggaggtagc accactgcag agcttcatgc tgcggggtgg 3540
tgttgtagat gatccagtcg tagcaggagc gctgggcgtg gtgcctaaaa atgtctttca 3600
gtagcaagct gattgccagg ggcaggccct tggtgtaagt gtttacaaag cggttaagct 3660
gggatgggtg catacgtggg gatatgagat gcatcttgga ctgtattttt aggttggcta 3720
tgttcccagc catatccctc cggggattca tgttgtgcag aaccaccagc acagtgtatc 3780
cggtgcactt gggaaatttg tcatgtagct tagaaggaaa tgcgtggaag aacttggaga 3840
cgcccttgtg acctccaaga ttttccatgc attcgtccat aatgatggca atgggcccac 3900
gggcggcggc ctgggcgaag atatttctgg gatcactaac gtcatagttg tgttccagga 3960
tgagatcgtc ataggccatt tttacaaagc gcgggcggag ggtgccagac tgcggtataa 4020
tggttccatc cggcccaggg gcgtagttac cctcacagat ttaagggtgg gaaagaatat 4080
ataaggtggg ggtcttatgt agttttgtat ctgttttgca gcagccgccg ccgccatgag 4140
caccaactcg tttgatggaa gcattgtgag ctcatatttg acaacgcgca tgcccccatg 4200
ggccggggtg cgtcagaatg tgatgggctc cagcattgat ggtcgccccg tcctgcccgc 4260
aaactctact accttgacct acgagaccgt gtctggaacg ccgttggaga ctgcagcctc 4320
cgccgccgct tcagccgctg cagccaccgc ccgcgggatt gtgactgact ttgctttcct 4380
gagcccgctt gcaagcagtg cagcttcccg ttcatccgcc cgcgatgaca agttgacggc 4440
tcttttggca caattggatt ctttgacccg ggaacttaat gtcgtttctc agcagctgtt 4500
ggatctgcgc cagcaggttt ctgccctgaa ggcttcctcc cctcccaatg cggtttaaaa 4560
cataaataaa aaaccagact ctgtttggat ttggatcaag caagtgtctt gctgtcttta 4620
tttaggggtt ttgcgcgcgc ggtaggcccg ggaccagcgg tctcggtcgt tgagggtcct 4680
gtgtattttt tccaggacgt ggtaaaggtg actctggatg ttcagataca tgggcataag 4740
cccgtctctg gggtggaggt agcaccactg cagagcttca tgctgcgggg tggtgttgta 4800
gatgatccag tcgtagcagg agcgctgggc gtggtgccta aaaatgtctt tcagtagcaa 4860
gctgattgcc aggggcaggc ccttggtgta agtgtttaca aagcggttaa gctgggatgg 4920
gtgcatacgt ggggatatga gatgcatctt ggactgtatt tttaggttgg ctatgttccc 4980
agccatatcc ctccggggat tcatgttgtg cagaaccacc agcacagtgt atccggtgca 5040
cttgggaaat ttgtcatgta gcttagaagg aaatgcgtgg aagaacttgg agacgccctt 5100
gtgacctcca agattttcca tgcattcgtc cataatgatg gcaatgggcc cacgggcggc 5160
ggcctgggcg aagatatttc tgggatcact aacgtcatag ttgtgttcca ggatgagatc 5220
gtcataggcc atttttacaa agcgcgggcg gagggtgcca gactgcggta taatggttcc 5280
atccggccca ggggcgtagt taccctcaca gatttgcatt tcccacgctt tgagttcaga 5340
tggggggatc atgtctacct gcggggcgat gaagaaaacg gtttccgggg taggggagat 5400
cagctgggaa gaaagcaggt tcctgagcag ctgcgactta ccgcagccgg tgggcccgta 5460
aatcacacct attaccggct gcaactggta gttaagagag ctgcagctgc cgtcatccct 5520
gagcaggggg gccacttcgt taagcatgtc cctgactcgc atgttttccc tgaccaaatc 5580
cgccagaagg cgctcgccgc ccagcgatag cagttcttgc aaggaagcaa agtttttcaa 5640
cggtttgaga ccgtccgccg taggcatgct tttgagcgtt tgaccaagca gttccaggcg 5700
gtcccacagc tcggtcacct gctctacggc atctcgatcc agcatatctc ctcgtttcgc 5760
gggttggggc ggctttcgct gtacggcagt agtcggtgct cgtccagacg ggccagggtc 5820
atgtctttcc acgggcgcag ggtcctcgtc agcgtagtct gggtcacggt gaaggggtgc 5880

-continued

```
gctccgggct gcgcgctggc cagggtgcgc ttgaggctgg tcctgctggt gctgaagcgc   5940
tgccggtctt cgccctgcgc gtcggccagg tagcatttga ccatggtgtc atagtccagc   6000
ccctccgcgg cgtggccctt ggcgcgcagc ttgcccttgg aggaggcgcc gcacgagggg   6060
cagtgcagac ttttgagggc gtagagcttg ggcgcgagaa ataccgattc cggggagtag   6120
gcatccgcgc cgcaggcccc gcagacggtc tcgcattcca cgagccaggt gagctctggc   6180
cgttcggggt caaaaaccag gtttccccca tgctttttga tgcgtttctt acctctggtt   6240
tccatgagcc ggtgtccacg ctcggtgacg aaaaggctgt ccgtgtcccc gtatacagac   6300
ttgagaggcc tgtcctcgag cggtgttccg cggtcctcct cgtatagaaa ctcggaccac   6360
tctgagacaa aggctcgcgt ccaggccagc acgaaggagg ctaagtggga ggggtagcgg   6420
tcgttgtcca ctagggggtc cactcgctcc agggtgtgaa gacacatgtc gccctcttcg   6480
gcatcaagga aggtgattgg tttgtaggtg taggccacgt gaccgggtgt tcctgaaggg   6540
gggctataaa agggggtggg ggcgcgttcg tcctcactct cttccgcatc gctgtctgcg   6600
agggccagct gttggggtga gtactccctc tgaaaagcgg gcatgacttc tgcgctaaga   6660
ttgtcagttt ccaaaaacga ggaggatttg atattcacct ggcccgcggt gatgcctttg   6720
agggtggccg catccatctg gtcagaaaag acaatctttt tgttgtcaag cttggtggca   6780
aacgacccgt agagggcgtt ggacagcaac ttggcgatgg agcgcagggt ttggtttttg   6840
tcgcgatcgg cgcgctcctt ggccgcgatg tttagctgca cgtattcgcg cgcaacgcac   6900
cgccattcgg gaaagacggt ggtgcgctcg tcgggcacca ggtgcacgcg ccaaccgcgg   6960
ttgtgcaggg tgacaaggtc aacgctggtg gctacctctc cgcgtaggcg ctcgttggtc   7020
cagcagaggc ggccgccctt gcgcgagcag aatggcggta gggggtctag ctgcgtctcg   7080
tccggggggt ctgcgtccac ggtaaagacc ccgggcagca ggcgcgcgtc gaagtagtct   7140
atcttgcatc cttgcaagtc tagcgcctgc tgccatgcgc gggcggcaag cgcgcgctcg   7200
tatgggttga gtgggggacc ccatggcatg gggtgggtga gcgcggaggc gtacatgccg   7260
caaatgtcgt aaacgtagag gggctctctg agtattccaa gatatgtagg gtagcatctt   7320
ccaccgcgga tgctggcgcg cacgtaatcg tatagttcgt gcgagggagc gaggaggtcg   7380
ggaccgaggt tgctacgggc gggctgctct gctcggaaga ctatctgcct gaagatggca   7440
tgtgagttgg atgatatggt tggacgctgg aagacgttga agctggcgtc tgtgagacct   7500
accgcgtcac gcacgaagga ggcgtaggag tcgcgcagct tgttgaccag ctcggcggtg   7560
acctgcacgt ctagggcgca gtagtccagg gtttccttga tgatgtcata cttatcctgt   7620
cccttttttt tccacagctc gcggttgagg acaaactctt cgcggtcttt ccagtactct   7680
tggatcggaa acccgtcggc ctccgaacgg taagagccta gcatgtagaa ctggttgacg   7740
gcctggtagg cgcagcatcc cttttctacg ggtagcgcgt atgcctgcgc ggccttccgg   7800
agcgaggtgt gggtgagcgc aaaggtgtcc ctgaccatga ctttgaggta ctggtatttg   7860
aagtcagtgt cgtcgcatcc gccctgctcc cagagcaaaa agtccgtgcg ctttttggaa   7920
cgcggatttg gcagggcgaa ggtgacatcg ttgaagagta tctttcccgc gcgaggcata   7980
aagttgcgtg tgatgcggaa gggtcccggc acctcggaac ggttgttaat tacctgggcg   8040
gcgagcacga tctcgtcaaa gccgttgatg ttgtggccca caatgtaaag ttccaagaag   8100
cgcgggatgc ccttgatgga aggcaatttt ttaagttcct cgtaggtgag ctcttcaggg   8160
gagctgagcc cgtgctctga aagggcccag tctgcaagat gagggttgga agcgacgaat   8220
```

```
gagctccaca ggtcacgggc cattagcatt tgcaggtggt cgcgaaaggt cctaaactgg   8280
cgacctatgg ccatttttc tggggtgatg cagtagaagg taagcgggtc ttgttcccag   8340
cggtcccatc caaggttcgc ggctaggtct cgcgcggcag tcactagagg ctcatctccg   8400
ccgaacttca tgaccagcat gaagggcacg agctgcttcc caaaggcccc catccaagta   8460
taggtctcta catcgtaggt gacaaagaga cgctcggtgc gaggatgcga gccgatcggg   8520
aagaactgga tctcccgcca ccaattggag gagtggctat tgatgtggtg aaagtagaag   8580
tccctgcgac gggccgaaca ctcgtgctgg cttttgtaaa aacgtgcgca gtactggcag   8640
cggtgcacgg gctgtacatc ctgcacgagg ttgacctgac gaccgcgcac aaggaagcag   8700
agtgggaatt tgagcccctc gcctggcggg tttggctggt ggtcttctac ttcggctgct   8760
tgtccttgac cgtctggctg ctcgagggga gttacggtgg atcggaccac cacgccgcgc   8820
gagcccaaag tccagatgtc cgcgcgcggc ggtcggagct tgatgacaac atcgcgcaga   8880
tgggagctgt ccatggtctg gagctcccgc ggcgtcaggt caggcgggag ctcctgcagg   8940
tttacctcgc atagacgggt cagggcgcgg gctagatcca ggtgatacct aatttccagg   9000
ggctggttgg tggcggcgtc gatggcttgc aagaggccgc atccccgcgg cgcgactacg   9060
gtaccgcgcg gcgggcggtg ggccgcgggg gtgtccttgg atgatgcatc taaaagcggt   9120
gacgcgggcg agcccccgga ggtagggggg gctccggacc cgccgggaga gggggcaggg   9180
gcacgtcggc gccgcgcgcg ggcaggagct ggtgctgcgc gcgtaggttg ctggcgaacg   9240
cgacgacgcg gcggttgatc tcctgaatct ggcgcctctg cgtgaagacg acgggcccgg   9300
tgagcttgaa cctgaaagag agttcgacag aatcaatttc ggtgtcgttg acggcggcct   9360
ggcgcaaaat ctcctgcacg tctcctgagt tgtcttgata ggcgatctcg gccatgaact   9420
gctcgatctc ttcctcctgg agatctccgc gtccggctcg ctccacggtg gcggcgaggt   9480
cgttggaaat gcgggccatg agctgcgaga aggcgttgag gcctccctcg ttccagacgc   9540
ggctgtagac cacgcccccct tcggcatcgc gggcgcgcat gaccacctgc gcgagattga   9600
gctccacgtg ccgggcgaag acggcgtagt ttcgcaggcg ctgaaagagg tagttgaggg   9660
tggtggcggt gtgttctgcc acgaagaagt acataaccca gcgtcgcaac gtggattcgt   9720
tgatatcccc caaggcctca aggcgctcca tggcctcgta gaagtccacg gcgaagttga   9780
aaaactggga gttgcgcgcc gacacggtta actcctcctc cagaagacgg atgagctcgg   9840
cgacagtgtc gcgcacctcg cgctcaaagg ctacaggggc ctcttcttct tcttcaatct   9900
cctcttccat aagggcctcc ccttcttctt cttctggcgg cggtggggga gggggggacac   9960
ggcggcgacg acggcgcacc gggaggcggt cgacaaagcg ctcgatcatc tccccgcggc  10020
gacggcgcat ggtctcggtg acggcgcggc cgttctcgcg gggggcgcagt tggaagacgc  10080
cgcccgtcat gtcccggtta tgggttggcg gggggctgcc atgcggcagg gatacggcgc  10140
taacgatgca tctcaacaat tgttgtgtag gtactccgcc gccgagggac ctgagcgagt  10200
ccgcatcgac cggatcggaa aacctctcga gaaaggcgtc taaccagtca cagtcgcaag  10260
gtaggctgag caccgtggcg ggcggcagcg ggcggcggtc ggggttgttt ctggcggagg  10320
tgctgctgat gatgtaatta aagtaggcgg tcttgagacg gcggatggtc gacagaagca  10380
ccatgtcctt gggtccggcc tgctgaatgc gcaggcggtc ggccatgccc caggcttcgt  10440
tttgacatcg gcgcaggtct ttgtagtagt cttgcatgag cctttctacc ggcacttctt  10500
cttctccttc ctcttgtcct gcatctcttg catctatcgc tgcggcggcg gcggagtttg  10560
gccgtaggtg gcgccctctt cctcccatgc gtgtgacccc gaagcccctc atcggctgaa  10620
```

gcagggctag gtcggcgaca acgcgctcgg ctaatatggc ctgctgcacc tgcgtgaggg 10680
tagactggaa gtcatccatg tccacaaagc ggtggtatgc gcccgtgttg atggtgtaag 10740
tgcagttggc cataacggac cagttaacgg tctggtgacc cggctgcgag agctcggtgt 10800
acctgagacg cgagtaagcc ctcgagtcaa atacgtagtc gttgcaagtc cgcaccaggt 10860
actggtatcc caccaaaaag tgcggcggcg gctggcggta gaggggccag cgtagggtgg 10920
ccggggctcc gggggcgaga tcttccaaca taaggcgatg atatccgtag atgtacctgg 10980
acatccaggt gatgccggcg gcggtggtgg aggcgcgcgg aaagtcgcgg acgcggttcc 11040
agatgttgcg cagcggcaaa aagtgctcca tggtcgggac gctctggccg gtcaggcgcg 11100
cgcaatcgtt gacgctctag accgtgcaaa aggagagcct gtaagcgggc actcttccgt 11160
ggtctggtgg ataaattcgc aagggtatca tggcggacga ccggggttcg agccccgtat 11220
ccggccgtcc gccgtgatcc atgcggttac cgcccgcgtg tcgaacccag gtgtgcgacg 11280
tcagacaacg ggggagtgct ccttttggct tccttccagg cgcggcggct gctgcgctag 11340 ctttttggc cactggccgc gcgcagcgta agcggttagg ctggaaagcg aaagcattaa 11400
gtggctcgct ccctgtagcc ggagggttat tttccaaggg ttgagtcgcg ggacccccgg 11460
ttcgagtctc ggaccggccg gactgcggcg aacgggggtt tgcctccccg tcatgcaaga 11520
ccccgcttgc aaattcctcc ggaaacaggg acgagcccct tttttgcttt tcccagatgc 11580
atccggtgct gcggcagatg cgccccctc ctcagcagcg gcaagagcaa gagcagcggc 11640
agacatgcag ggcaccctcc cctcctccta ccgcgtcagg aggggcgaca tccgcggttg 11700
acgcggcagc agatggtgat tacgaacccc cgcggcgccg ggcccggcac tacctggact 11760
tggaggaggg cgagggcctg gcgcggctag gagcgccctc tcctgagcgg cacccaaggg 11820
tgcagctgaa gcgtgatacg cgtgaggcgt acgtgccgcg gcagaacctg tttcgcgacc 11880
gcgagggaga ggagcccgag gagatgcggg atcgaaagtt ccacgcaggg cgcgagctgc 11940
ggcatggcct gaatcgcgag cggttgctgc gcgaggagga ctttgagccc gacgcgcgaa 12000
ccgggattag tcccgcgcgc gcacacgtgg cggccgccga cctggtaacc gcatacgagc 12060
agacggtgaa ccaggagatt aactttcaaa aaagctttaa caaccacgtg cgtacgcttg 12120
tggcgcgcga ggaggtggct ataggactga tgcatctgtg ggactttgta agcgcgctgg 12180
agcaaaaccc aaatagcaag ccgctcatgg cgcagctgtt ccttatagtg cagcacagca 12240
gggacaacga ggcattcagg gatgcgctgc taaacatagt agagcccgag ggccgctggc 12300
tgctcgattt gataaacatc ctgcagagca tagtggtgca ggagcgcagc ttgagcctgg 12360
ctgacaaggt ggccgccatc aactattcca tgcttagcct gggcaagttt tacgcccgca 12420
agatatacca taccccttac gttcccatag acaaggaggt aaagatcgag gggttctaca 12480
tgcgcatggc gctgaaggtg cttaccttga gcgacgacct gggcgtttat cgcaacgagc 12540
gcatccacaa ggccgtgagc gtgagccggc ggcgcgagct cagcgaccgc gagctgatgc 12600
acagcctgca aagggccctg gctggcacgg gcagcggcga tagagaggcc gagtcctact 12660
ttgacgcggg cgctgacctg cgctgggccc caagccgacg cgccctggag gcagctgggg 12720
ccggacctgg gctggcggtg gcacccgcgc gcgctggcaa cgtcggcggc gtggaggaat 12780
atgacgagga cgatgagtac gagccagagg acggcgagta ctaagcggtg atgtttctga 12840
tcagatgatg caagacgcaa cggacccggc ggtgcgggcg gcgctgcaga gccagccgtc 12900
cggccttaac tccacggacg actggcgcca ggtcatggac cgcatcatgt cgctgactgc 12960
gcgcaatcct gacgcgttcc ggcagcagcc gcaggccaac cggctctccg caattctgga 13020
agcggtggtc ccggcgcgcg caaaccccac gcacgagaag gtgctggcga tcgtaaacgc 13080
gctggccgaa aacagggcca tccggcccga cgaggccggc ctggtctacg acgcgctgct 13140
tcagcgcgtg gctcgttaca acagcggcaa cgtgcagacc aacctggacc ggctggtggg 13200
ggatgtgcgc gaggccgtgg cgcagcgtga gcgcgcgcag cagcagggca acctgggctc 13260
catggttgca ctaaacgcct tcctgagtac acagcccgcc aacgtgccgc ggggacagga 13320
ggactacacc aactttgtga gcgcactgcg gctaatggtg actgagacac cgcaaagtga 13380
ggtgtaccag tctgggccag actatttttt ccagaccagt agacaaggcc tgcagaccgt 13440
aaacctgagc caggctttca aaaacttgca ggggctgtgg ggggtgcggg ctcccacagg 13500
cgaccgcgcg accgtgtcta gcttgctgac gcccaactcg cgcctgttgc tgctgctaat 13560
agcgcccttc acggacagtg gcagcgtgtc ccgggacaca tacctaggtc acttgctgac 13620
actgtaccgc gaggccatag gtcaggcgca tgtggacgag catactttcc aggagattac 13680
aagtgtcagc cgcgcgctgg ggcaggagga cacgggcagc ctggaggcaa ccctaaacta 13740
cctgctgacc aaccggcggc agaagatccc ctcgttgcac agtttaaaca gcgaggagga 13800
gcgcattttg cgctacgtgc agcagagcgt gagccttaac ctgatgcgcg acggggtaac 13860
gcccagcgtg gcgctggaca tgaccgcgcg caacatggaa ccgggcatgt atgcctcaaa 13920
ccggccgttt atcaaccgcc taatggacta cttgcatcgc gcggccgccg tgaaccccga 13980
gtatttcacc aatgccatct tgaacccgca ctggctaccg ccccctggtt tctacaccgg 14040
gggattcgag gtgcccgagg gtaacgatgg attcctctgg gacgacatag acgacagcgt 14100
gttttccccg caaccgcaga ccctgctaga gttgcaacag cgcgagcagg cagaggcggc 14160
gctgcgaaag gaaagcttcc gcaggccaag cagcttgtcc gatctaggcg ctgcggcccc 14220
gcggtcagat gctagtagcc catttccaag cttgataggg tctcttacca gcactcgcac 14280
cacccgcccg cgcctgctgg gcgaggagga gtacctaaac aactcgctgc tgcagccgca 14340
gcgcgaaaaa aacctgcctc cggcatttcc caacaacggg atagagagcc tagtggacaa 14400
gatgagtaga tggaagacgt acgcgcagga gcacagggac gtgccaggcc cgcgcccgcc 14460
cacccgtcgt caaaggcacg accgtcagcg gggtctggtg tgggaggacg atgactcggc 14520
agacgacagc agcgtcctgg atttgggagg gagtggcaac ccgtttgcgc accttcgccc 14580
caggctgggg agaatgtttt aaaaaaaaaa aaagcatgat gcaaaataaa aaactcacca 14640
aggccatggc accgagcgtt ggttttcttg tattcccctt agtatgcggc gcgcggcgat 14700
gtatgaggaa ggtcctcctc cctcctacga gagtgtggtg agcgcggcgc cagtggcggc 14760
ggcgctgggt tctcccttcg atgctcccct ggacccgccg tttgtgcctc cgcggtacct 14820
gcggcctacc ggggggagaa acagcatccg ttactctgag ttggcacccc tattcgacac 14880
cacccgtgtg tacctggtgg acaacaagtc aacggatgtg gcatccctga actaccagaa 14940
cgaccacagc aactttctga ccacggtcat tcaaaacaat gactacagcc cgggggaggc 15000
aagcacacag accatcaatc ttgacgaccg gtcgcactgg ggcggcgacc tgaaaaccat 15060
cctgcatacc aacatgccaa atgtgaacga gttcatgttt accaataagt ttaaggcgcg 15120
ggtgatggtg tcgcgcttgc ctactaagga caatcaggtg gagctgaaat acgagtgggt 15180
ggagttcacg ctgcccgagg gcaactactc cgagaccatg accatagacc ttatgaacaa 15240
cgcgatcgtg gagcactact tgaaagtggg cagacagaac ggggttctgg aaagcgacat 15300
cggggtaaag tttgacaccc gcaacttcag actggggttt gaccccgtca ctggtcttgt 15360

-continued catgcctggg gtatatacaa acgaagcctt ccatccagac atcattttgc tgccaggatg 15420
cggggtggac ttcacccaca gccgcctgag caacttgttg ggcatccgca agcggcaacc 15480
cttccaggag ggctttagga tcacctacga tgatctggag ggtggtaaca ttcccgcact 15540
gttggatgtg gacgcctacc aggcgagctt gaaagatgac accgaacagg gcgggggtgg 15600
cgcaggcggc agcaacagca gtggcagcgg cgcggaagag aactccaacg cggcagccgc 15660
ggcaatgcag ccggtggagg acatgaacga tcatgccatt cgcggcgaca cctttgccac 15720
acgggctgag gagaagcgcg ctgaggccga agcagcggcc gaagctgccg cccccgctgc 15780
gcaacccgag gtcgagaagc ctcagaagaa accggtgatc aaacccctga cagaggacag 15840
caagaaacgc agttacaacc taataagcaa tgacagcacc ttcacccagt accgcagctg 15900
gtaccttgca tacaactacg gcgaccctca gaccggaatc cgctcatgga ccctgctttg 15960
cactcctgac gtaacctgcg gctcggagca ggtctactgg tcgttgccag acatgatgca 16020
agaccccgtg accttccgct ccacgcgcca gatcagcaac tttccggtgg tgggcgccga 16080
gctgttgccc gtgcactcca agagcttcta caacgaccag gccgtctact cccaactcat 16140
ccgccagttt acctctctga cccacgtgtt caatcgcttt cccgagaacc agattttggc 16200
gcgcccgcca gcccccacca tcaccaccgt cagtgaaaac gttcctgctc tcacagatca 16260
cgggacgcta ccgctgcgca acagcatcgg aggagtccag cgagtgacca ttactgacgc 16320
cagacgccgc acctgcccct acgtttacaa ggccctgggc atagtctcgc cgcgcgtcct 16380
atcgagccgc actttttgag caagcatgtc catccttata tcgcccagca ataacacagg 16440
ctggggcctg cgcttcccaa gcaagatgtt tggcggggcc aagaagcgct ccgaccaaca 16500
cccagtgcgc gtgcgcgggc actaccgcgc gccctggggc gcgcacaaac gcggccgcac 16560
tgggcgcacc accgtcgatg acgccatcga cgcggtggtg gaggaggcgc gcaactacac 16620
gcccacgccg ccaccagtgt ccacagtgga cgcggccatt cagaccgtgg tgcgcggagc 16680
ccggcgctat gctaaaatga agagacggcg gaggcgcgta gcacgtcgcc accgccgccg 16740
acccggcact gccgcccaac gcgcggcggc ggccctgctt aaccgcgcac gtcgcaccgg 16800
ccgacgggcg gccatgcggg ccgctcgaag gctggccgcg ggtattgtca ctgtgccccc 16860
caggtccagg cgacgagcgg ccgccgcagc agccgcggcc attagtgcta tgactcaggg 16920
tcgcaggggc aacgtgtatt gggtgcgcga ctcggttagc ggcctgcgcg tgcccgtgcg 16980
cacccgcccc ccgcgcaact agattgcaag aaaaaactac ttagactcgt actgttgtat 17040
gtatccagcg gcggcggcgc gcaacgaagc tatgtccaag cgcaaaatca aagaagagat 17100
gctccaggtc atcgcgccgg agatctatgg ccccccgaag aaggaagagc aggattacaa 17160
gccccgaaag ctaaagcggg tcaaaaagaa aaagaaagat gatgatgatg aacttgacga 17220
cgaggtggaa ctgctgcacg ctaccgcgcc caggcgacgg gtacagtgga aaggtcgacg 17280
cgtaaaacgt gttttgcgac ccggcaccac cgtagtcttt acgcccggtg agcgctccac 17340
ccgcacctac aagcgcgtgt atgatgaggt gtacggcgac gaggacctgc ttgagcaggc 17400
caacgagcgc ctcggggagt ttgcctacgg aaagcggcat aaggacatgc tggcgttgcc 17460
gctggacgag ggcaacccaa cacctagcct aaagcccgta acactgcagc aggtgctgcc 17520
cgcgcttgca ccgtccgaag aaaagcgcgg cctaaagcgc gagtctggtg acttggcacc 17580
caccgtgcag ctgatggtac ccaagcgcca gcgactggaa gatgtcttgg aaaaaatgac 17640
cgtggaacct gggctggagc ccgaggtccg cgtgcggcca atcaagcagg tggcgccggg 17700

-continued actgggcgtg cagaccgtgg acgttcagat acccactacc agtagcacca gtattgccac 17760
cgccacagag ggcatggaga cacaaacgtc cccggttgcc tcagcggtgg cggatgccgc 17820
ggtgcaggcg gtcgctgcgg ccgcgtccaa gacctctacg gaggtgcaaa cggacccgtg 17880
gatgtttcgc gtttcagccc cccggcgccc gcgccgttcg aggaagtacg gcgccgccag 17940
cgcgctactg cccgaatatg ccctacatcc ttccattgcg cctacccccg gctatcgtgg 18000
ctacacctac cgccccagaa gacgagcaac tacccgacgc cgaaccacca ctggaacccg 18060
ccgccgccgt cgccgtcgcc agcccgtgct ggccccgatt tccgtgcgca gggtggctcg 18120
cgaaggaggc aggaccctgg tgctgccaac agcgcgctac caccccagca tcgtttaaaa 18180
gccggtcttt gtggttcttg cagatatggc cctcacctgc cgcctccgtt tcccggtgcc 18240
gggattccga ggaagaatgc accgtaggag gggcatggcc ggccacggcc tgacgggcgg 18300
catgcgtcgt gcgcaccacc ggcggcggcg cgcgtcgcac cgtcgcatgc gcggcggtat 18360
cctgcccctc cttattccac tgatcgccgc ggcgattggc gccgtgcccg gaattgcatc 18420
cgtggccttg caggcgcaga gacactgatt aaaaacaagt tgcatgtgga aaaatcaaaa 18480
taaaaagtct ggactctcac gctcgcttgg tcctgtaact attttgtaga atggaagaca 18540
tcaactttgc gtctctggcc ccgcgacacg gctcgcgccc gttcatggga aactggcaag 18600
atatcggcac cagcaatatg agcggtggcg ccttcagctg gggctcgctg tggagcggca 18660
ttaaaaattt cggttccacc gttaagaact atggcagcaa ggcctggaac agcagcacag 18720
gccagatgct gagggataag ttgaaagagc aaaatttcca acaaaaggtg gtagatggcc 18780
tggcctctgg cattagcggg gtggtggacc tggccaacca ggcagtgcaa aataagatta 18840
acagtaagct tgatccccgc cctcccgtag aggagcctcc accggccgtg gagacagtgt 18900
ctccagaggg gcgtggcgaa aagcgtccgc gccccgacag ggaagaaact ctggtgacgc 18960
aaatagacga gcctccctcg tacgaggagg cactaaagca aggcctgccc accacccgtc 19020
ccatcgcgcc catggctacc ggagtgctgg gccagcacac acccgtaacg ctggacctgc 19080
ctccccccgc cgacacccag cagaaacctg tgctgccagg cccgaccgcc gttgttgtaa 19140
cccgtcctag ccgcgcgtcc ctgcgccgcg ccgccagcgg tccgcgatcg ttgcggcccg 19200
tagccagtgg caactggcaa agcacactga acagcatcgt gggtctgggg gtgcaatccc 19260
tgaagcgccg acgatgcttc tgatagctaa cgtgtcgtat gtgtgtcatg tatgcgtcca 19320
tgtcgccgcc agaggagctg ctgagccgcc gcgcgcccgc tttccaagat ggctacccct 19380
tcgatgatgc cgcagtggtc ttacatgcac atctcgggcc aggacgcctc ggagtacctg 19440
agccccgggc tggtgcagtt tgcccgcgcc accgagacgt acttcagcct gaataacaag 19500
tttagaaacc ccacggtggc gcctacgcac gacgtgacca cagaccggtc ccagcgtttg 19560
acgctgcggt tcatccctgt ggaccgtgag gatactgcgt actcgtacaa ggcgcggttc 19620
accctagctg tgggtgataa ccgtgtgctg gacatggctt ccacgtactt tgacatccgc 19680
ggcgtgctgg acaggggccc tacttttaag ccctactctg gcactgccta caacgccctg 19740
gctcccaagg gtgccccaaa tccttgcgaa tgggatgaag ctgctactgc tcttgaaata 19800
aacctagaag aagaggacga tgacaacgaa gacgaagtag acgagcaagc tgagcagcaa 19860
aaaactcacg tatttgggca ggcgccttat tctggtataa atattacaaa ggagggtatt 19920
caaataggtg tcgaaggtca aacacctaaa tatgccgata aaacatttca acctgaacct 19980
caaataggag aatctcagtg gtacgaaaca gaaattaatc atgcagctgg gagagtccta 20040
aaaaagacta ccccaatgaa accatgttac ggttcatatg caaaacccac aaatgaaaat 20100
ggagggcaag gcattcttgt aaagcaacaa aatggaaagc tagaaagtca agtggaaatg 20160
caatttttct caactactga ggcagccgca ggcaatggtg ataacttgac tcctaaagtg 20220
gtattgtaca gtgaagatgt agatatagaa accccagaca ctcatatttc ttacatgccc 20280
actattaagg aaggtaactc acgagaacta atgggccaac aatctatgcc caacaggcct 20340
aattacattg cttttaggga caattttatt ggtctaatgt attacaacag cacgggtaat 20400
atgggtgttc tggcgggcca agcatcgcag ttgaatgctg ttgtagattt gcaagacaga 20460
aacacagagc tttcatacca gcttttgctt gattccattg gtgatagaac caggtacttt 20520
tctatgtgga atcaggctgt tgacagctat gatccagatg ttagaattat tgaaaatcat 20580
ggaactgaag atgaacttcc aaattactgc tttccactgg gaggtgtgat taatacagag 20640
actcttacca aggtaaaacc taaaacaggt caggaaaatg gatgggaaaa agatgctaca 20700
gaattttcag ataaaaatga aataagagtt ggaaataatt ttgccatgga aatcaatcta 20760
aatgccaacc tgtggagaaa tttcctgtac tccaacatag cgctgtattt gcccgacaag 20820
ctaaagtaca gtccttccaa cgtaaaaatt tctgataacc caaacaccta cgactacatg 20880
aacaagcgag tggtggctcc cgggctagtg gactgctaca ttaaccttgg agcacgctgg 20940
tcccttgact atatggacaa cgtcaaccca tttaaccacc accgcaatgc tggcctgcgc 21000
taccgctcaa tgttgctggg caatggtcgc tatgtgccct tccacatcca ggtgcctcag 21060
aagttctttg ccattaaaaa cctccttctc ctgccgggct catacaccta cgagtggaac 21120
ttcaggaagg atgttaacat ggttctgcag agctccctag gaaatgacct aagggttgac 21180
ggagccagca ttaagtttga tagcatttgc ctttacgcca ccttcttccc catggcccac 21240
aacaccgcct ccacgcttga ggccatgctt agaaacgaca ccaacgacca gtcctttaac 21300
gactatctct ccgccgccaa catgctctac cctatacccg ccaacgctac caacgtgccc 21360
atatccatcc cctcccgcaa ctgggcggct ttccgcggct gggccttcac gcgccttaag 21420
actaaggaaa ccccatcact gggctcgggc tacgaccctt attacaccta ctctggctct 21480
ataccctacc tagatggaac cttttacctc aaccacacct ttaagaaggt ggccattacc 21540
tttgactctt ctgtcagctg gcctggcaat gaccgcctgc ttacccccaa cgagtttgaa 21600
attaagcgct cagttgacgg ggagggttac aacgttgccc agtgtaacat gaccaaagac 21660
tggttcctgg tacaaatgct agctaactat aacattggct accagggctt ctatatccca 21720
gagagctaca aggaccgcat gtactccttc tttagaaact tccagcccat gagccgtcag 21780
gtggtggatg atactaaata caaggactac caacaggtgg gcatcctaca ccaacacaac 21840
aactctggat ttgttggcta ccttgccccc accatgcgcg aaggacaggc ctaccctgct 21900
aacttcccct atccgcttat aggcaagacc gcagttgaca gcattaccca gaaaaagttt 21960
ctttgcgatc gcaccctttg gcgcatccca ttctccagta actttatgtc catgggcgca 22020
ctcacagacc tgggccaaaa ccttctctac gccaactccg cccacgcgct agacatgact 22080
tttgaggtgg atcccatgga cgagcccacc cttctttatg ttttgtttga agtctttgac 22140
gtggtccgtg tgcaccagcc gcaccgcggc gtcatcgaaa ccgtgtacct gcgcacgccc 22200
ttctcggccg gcaacgccac aacataaaga agcaagcaac atcaacaaca gctgccgcca 22260
tgggctccag tgagcaggaa ctgaaagcca ttgtcaaaga tcttggttgt gggccatatt 22320
ttttgggcac ctatgacaag cgctttccag gctttgtttc tccacacaag ctcgcctgcg 22380
ccatagtcaa tacggccggt cgcgagactg gggcgtaca ctggatggcc tttgcctgga 22440

-continued acccgcactc aaaaacatgc tacctctttg agccctttgg cttttctgac cagcgactca 22500
agcaggttta ccagtttgag tacgagtcac tcctgcgccg tagcgccatt gcttcttccc 22560
ccgaccgctg tataacgctg gaaaagtcca cccaaagcgt acaggggccc aactcggccg 22620
cctgtggact attctgctgc atgtttctcc acgcctttgc caactggccc caaactccca 22680
tggatcacaa ccccaccatg aaccttatta ccggggtacc caactccatg ctcaacagtc 22740
cccaggtaca gcccaccctg cgtcgcaacc aggaacagct ctacagcttc ctggagcgcc 22800
actcgcccta cttccgcagc cacagtgcgc agattaggag cgccacttct ttttgtcact 22860
tgaaaaacat gtaaaaataa tgtactagag acactttcaa taaaggcaaa tgcttttatt 22920
tgtacactct cgggtgatta tttacccccca cccttgccgt ctgcgccgtt taaaaatcaa 22980
aggggttctg ccgcgcatcg ctatgcgcca ctggcaggga cacgttgcga tactggtgtt 23040
tagtgctcca cttaaactca ggcacaacca tccgcggcag ctcggtgaag ttttcactcc 23100
acaggctgcg caccatcacc aacgcgttta gcaggtcggg cgccgatatc ttgaagtcgc 23160
agttggggcc tccgccctgc gcgcgcgagt tgcgatacac agggttgcag cactggaaca 23220
ctatcagcgc cgggtggtgc acgctggcca gcacgctctt gtcggagatc agatccgcgt 23280
ccaggtcctc cgcgttgctc agggcgaacg gagtcaactt tggtagctgc cttcccaaaa 23340
agggcgcgtg cccaggcttt gagttgcact cgcaccgtag tggcatcaaa aggtgaccgt 23400
gcccggtctg ggcgttagga tacagcgcct gcataaaagc cttgatctgc ttaaaagcca 23460
cctgagcctt tgcgccttca gagaagaaca tgccgcaaga cttgccggaa aactgattgg 23520
ccggacaggc cgcgtcgtgc acgcagcacc ttgcgtcggt gttggagatc tgcaccacat 23580
ttcggcccca ccggttcttc acgatcttgg ccttgctaga ctgctccttc agcgcgcgct 23640
gcccgttttc gctcgtcaca tccatttcaa tcacgtgctc cttatttatc ataatgcttc 23700
cgtgtagaca cttaagctcg ccttcgatct cagcgcagcg gtgcagccac aacgcgcagc 23760
ccgtgggctc gtgatgcttg taggtcacct ctgcaaacga ctgcaggtac gcctgcagga 23820
atcgccccat catcgtcaca aaggtcttgt tgctggtgaa ggtcagctgc aacccgcggt 23880
gctcctcgtt cagccaggtc ttgcatacgg ccgccagagc ttccacttgg tcaggcagta 23940
gtttgaagtt cgcctttaga tcgttatcca cgtggtactt gtccatcagc gcgcgcgcag 24000
cctccatgcc cttctcccac gcagacacga tcggcacact cagcgggttc atcaccgtaa 24060
tttcactttc cgcttcgctg ggctcttcct cttcctcttg cgtccgcata ccacgcgcca 24120
ctgggtcgtc ttcattcagc cgccgcactg tgcgcttacc tcctttgcca tgcttgatta 24180
gcaccggtgg gttgctgaaa cccaccattt gtagcgccac atcttctctt tcttcctcgc 24240
tgtccacgat tacctctggt gatggcgggc gctcgggctt gggagaaggg cgcttctttt 24300
tcttcttggg cgcaatggcc aaatccgccg ccgaggtcga tggccgcggg ctgggtgtgc 24360
gcggcaccag cgcgtcttgt gatgagtctt cctcgtcctc ggactcgata cgccgcctca 24420
tccgcttttt tgggggcgcc cggggaggcg gcggcgacgg ggacggggac gacacgtcct 24480
ccatggttgg gggacgtcgc gccgcaccgc gtccgcgctc gggggtggtt tcgcgctgct 24540
cctcttcccg actggccatt tccttctcct ataggcagaa aaagatcatg gagtcagtcg 24600
agaagaagga cagcctaacc gccccctctg agttcgccac caccgcctcc accgatgccg 24660
ccaacgcgcc taccaccttc cccgtcgagg cacccccgct tgaggaggag gaagtgatta 24720
tcgagcagga cccaggtttt gtaagcgaag acgacgagga ccgctcagta ccaacagagg 24780
ataaaaagca agaccaggac aacgcagagg caaacgagga acaagtcggg cggggggacg 24840
aaaggcatgg cgactaccta gatgtgggag acgacgtgct gttgaagcat ctgcagcgcc 24900
agtgcgccat tatctgcgac gcgttgcaag agcgcagcga tgtgcccctc gccatagcgg 24960
atgtcagcct tgcctacgaa cgccacctat tctcaccgcg cgtacccccc aaacgccaag 25020
aaaacggcac atgcgagccc aacccgcgcc tcaacttcta ccccgtattt gccgtgccag 25080
aggtgcttgc cacctatcac atctttttcc aaaactgcaa gataccccta tcctgccgtg 25140
ccaaccgcag ccgagcggac aagcagctgg ccttgcggca gggcgctgtc atacctgata 25200
tcgcctcgct caacgaagtg ccaaaaatct ttgagggtct tggacgcgac gagaagcgcg 25260
cggcaaacgc tctgcaacag gaaaacagcg aaaatgaaag tcactctgga gtgttggtgg 25320
aactcgaggg tgacaacgcg cgcctagccg tactaaaacg cagcatcgag gtcacccact 25380
ttgcctaccc ggcacttaac ctacccccca aggtcatgag cacagtcatg agtgagctga 25440
tcgtgcgccg tgcgcagccc ctggagaggg atgcaaattt gcaagaacaa acagaggagg 25500
gcctacccgc agttggcgac gagcagctag cgcgctggct tcaaacgcgc gagcctgccg 25560
acttggagga gcgacgcaaa ctaatgatgg ccgcagtgct cgttaccgtg gagcttgagt 25620
gcatgcagcg gttctttgct gacccggaga tgcagcgcaa gctagaggaa acattgcact 25680
acacctttcg acagggctac gtacgccagg cctgcaagat ctccaacgtg gagctctgca 25740
acctggtctc ctaccttgga attttgcacg aaaaccgcct tgggcaaaac gtgcttcatt 25800
ccacgctcaa gggcgaggcg cgccgcgact acgtccgcga ctgcgtttac ttatttctat 25860
gctacacctg gcagacggcc atgggcgttt ggcagcagtg cttggaggag tgcaacctca 25920
aggagctgca gaaactgcta aagcaaaact tgaaggacct atggacggcc ttcaacgagc 25980
gctccgtggc cgcgcacctg gcggacatca ttttccccga acgcctgctt aaaaccctgc 26040
aacagggtct gccagacttc accagtcaaa gcatgttgca gaactttagg aactttatcc 26100
tagagcgctc aggaatcttg cccgccacct gctgtgcact tcctagcgac tttgtgccca 26160
ttaagtaccg cgaatgccct ccgccgcttt ggggccactg ctaccttctg cagctagcca 26220
actaccttgc ctaccactct gacataatgg aagacgtgag cggtgacggt ctactggagt 26280
gtcactgtcg ctgcaaccta tgcaccccgc accgctccct ggtttgcaat tcgcagctgc 26340
ttaacgaaag tcaaattatc ggtacctttg agctgcaggg tccctcgcct gacgaaaagt 26400
ccgcggctcc ggggttgaaa ctcactccgg ggctgtggac gtcggcttac cttcgcaaat 26460
ttgtacctga ggactaccac gcccacgaga ttaggttcta cgaagaccaa tcccgcccgc 26520
ctaatgcgga gcttaccgcc tgcgtcatta cccagggcca cattcttggc caattgcaag 26580
ccatcaacaa agcccgccaa gagtttctgc tacgaaaggg acgggggtt tacttggacc 26640
cccagtccgg cgaggagctc aacccaatcc ccccgccgcc gcagccctat cagcagcagc 26700
cgcgggccct tgcttcccag gatggcaccc aaaaagaagc tgcagctgcc gccgccaccc 26760
acggacgagg aggaatactg ggacagtcag gcagaggagg ttttggacga ggaggaggag 26820
gacatgatgg aagactggga gagcctagac gaggaagctt ccgaggtcga agaggtgtca 26880
gacgaaacac cgtcaccctc ggtcgcattc ccctcgccgg cgccccagaa atcggcaacc 26940
ggttccagca tggctacaac ctccgctcct caggcgccgc cggcactgcc cgttcgccga 27000
cccaaccgta gatgggacac cactggaacc agggccggta agtccaagca gccgccgccg 27060
ttagcccaag agcaacaaca gcgccaaggc taccgctcat ggcgcgggca caagaacgcc 27120
atagttgctt gcttgcaaga ctgtgggggc aacatctcct tcgcccgccg ctttcttctc 27180

-continued

```
taccatcacg gcgtggcctt cccccgtaac atcctgcatt actaccgtca tctctacagc  27240
ccatactgca ccggcggcag cggcagcaac agcagcggcc acacagaagc aaaggcgacc  27300
ggatagcaag actctgacaa agcccaagaa atccacagcg gcggcagcag caggaggagg  27360
agcgctgcgt ctggcgccca acgaacccgt atcgacccgc gagcttagaa acaggatttt  27420
tcccactctg tatgctatat ttcaacagag caggggccaa gaacaagagc tgaaaataaa  27480
aaacaggtct ctgcgatccc tcacccgcag ctgcctgtat cacaaaagcg aagatcagct  27540
tcggcgcacg ctggaagacg cggaggctct cttcagtaaa tactgcgcgc tgactcttaa  27600
ggactagttt cgcgcccttt ctcaaattta agcgcgaaaa ctacgtcatc tccagcggcc  27660
acacccggcg ccagcacctg ttgtcagcgc cattatgagc aaggaaattc ccacgcccta  27720
catgtggagt taccagccac aaatgggact tgcggctgga gctgcccaag actactcaac  27780
ccgaataaac tacatgagcg cgggacccca catgatatcc cgggtcaacg gaatacgcgc  27840
ccaccgaaac cgaattctcc tggaacaggc ggctattacc accacacctc gtaataacct  27900
taatccccgt agttggcccg ctgccctggt gtaccaggaa agtcccgctc ccaccactgt  27960
ggtacttccc agagacgccc aggccgaagt tcagatgact aactcagggg cgcagcttgc  28020
gggcggcttt cgtcacaggg tgcggtcgcc cgggcagggt ataactcacc tgacaatcag  28080
agggcgaggt attcagctca acgacgagtc ggtgagctcc tcgcttggtc tccgtccgga  28140
cgggacattt cagatcggcg gcgccggccg ctcttcattc acgcctcgtc aggcaatcct  28200
aactctgcag acctcgtcct ctgagccgcg ctctggaggc attggaactc tgcaatttat  28260
tgaggagttt gtgccatcgg tctactttaa ccccttctcg ggacctcccg gccactatcc  28320
ggatcaattt attcctaact ttgacgcggt aaaggactcg gcggacggct acgactgaat  28380
gttaagtgga gaggcagagc aactgcgcct gaaacacctg gtccactgtc gccgccacaa  28440
gtgctttgcc cgcgactccg gtgagttttg ctactttgaa ttgcccgagg atcatatcga  28500
gggcccggcg cacggcgtcc ggcttaccgc ccagggagag cttgcccgta gcctgattcg  28560
ggagtttacc cagcgccccc tgctagttga gcgggacagg ggaccctgtg ttctcactgt  28620
gatttgcaac tgtcctaacc ctggattaca tcaagatctt tgttgccatc tctgtgctga  28680
gtataataaa tacagaaatt aaaatatact ggggctccta tcgccatcct gtaaacgcca  28740
ccgtcttcac ccgcccaagc aaaccaaggc gaaccttacc tggtactttt aacatctctc  28800
cctctgtgat ttacaacagt ttcaacccag acggagtgag tctacgagag aacctctccg  28860
agctcagcta ctccatcaga aaaaacacca ccctccttac ctgccgggaa cgtacgagtg  28920
cgtcaccggc cgctgcacca cacctaccgc ctgaccgtaa accagacttt ttccggacag  28980
acctcaataa ctctgtttac cagaacagga ggtgagctta gaaaaccctt agggtattag  29040
gccaaaggcg cagctactgt ggggtttatg aacaattcaa gcaactctac gggctattct  29100
aattcaggtt tctctagaat cggggttggg gttattctct gtcttgtgat tctctttatt  29160
cttatactaa cgcttctctg cctaaggctc gccgcctgct gtgtgcacat ttgcatttat  29220
tgtcagcttt ttaaacgctg ggtcgccac ccaagatgat taggtacata atcctaggtt  29280
tactcaccct tgcgtcagcc cacggtacca cccaaaaggt ggattttaag gagccagcct  29340
gtaatgttac attcgcagct gaagctaatg agtgcaccac tcttataaaa tgcaccacag  29400
aacatgaaaa gctgcttatt cgccacaaaa acaaaattgg caagtatgct gtttatgcta  29460
tttggcagcc aggtgacact acagagtata atgttacagt tttccagggt aaaagtcata  29520
aaacttttat gtatactttt ccattttatg aaatgtgcga cattaccatg tacatgagca  29580
```

aacagtataa gttgtggccc ccacaaaatt gtgtggaaaa cactggcact ttctgctgca 29640
ctgctatgct aattacagtg ctcgctttgg tctgtaccct actctatatt aaatacaaaa 29700
gcagacgcag ctttattgag gaaaagaaaa tgccttaatt tactaagtta caaagctaat 29760
gtcaccacta actgctttac tcgctgcttg caaaacaaat tcaaaaagtt agcattataa 29820
ttagaatagg atttaaaccc cccggtcatt tcctgctcaa taccattccc ctgaacaatt 29880
gactctatgt gggatatgct ccagcgctac aaccttgaag tcaggcttcc tggatgtcag 29940
catctgactt tggccagcac ctgtcccgcg gatttgttcc agtccaacta cagcgaccca 30000
ccctaacaga gatgaccaac acaaccaacg cggccgccgc taccggactt acatctacca 30060
caaatacacc ccaagtttct gcctttgtca ataactggga taacttgggc atgtggtggt 30120
tctccatagc gcttatgttt gtatgcctta ttattatgtg gctcatctgc tgcctaaagc 30180
gcaaacgcgc ccgaccaccc atctatagtc ccatcattgt gctacaccca aacaatgatg 30240
gaatccatag attggacgga ctgaaacaca tgttcttttc tcttacagta tgattaaatg 30300
agacatgatt cctcgagttt ttatattact gacccttgtt gcgctttttt tgtgcgtgct 30360
ccacattggc tgcggtttct cacatcgaag tagactgcat tccagccttc acagtctatt 30420
tgctttacgg atttgtcacc ctcacgctca tctgcagcct catcactgtg gtcatcgcct 30480
ttatccagtg cattgactgg gtctgtgtgc gctttgcata tctcagacac catccccagt 30540
acagggacag gactatagct gagcttctta gaattcttta attatgaaat ttactgtgac 30600
ttttctgctg attatttgca ccctatctgc gttttgttcc ccgacctcca agcctcaaag 30660
acatatatca tgcagattca ctcgtatatg gaatattcca agttgctaca atgaaaaaag 30720
cgatctttcc gaagcctggt tatatgcaat catctctgtt atggtgttct gcagtaccat 30780
cttagcccta gctatatatc cctaccttga cattggctgg aacgcaatag atgccatgaa 30840
ccacccaact ttccccgcgc ccgctatgct tccactgcaa caagttgttg ccggcggctt 30900
tgtcccagcc aatcagcctc gcccaccttc tcccaccccc actgaaatca gctactttaa 30960
tctaacagga ggagatgact gacaccctag atctagaaat ggacggaatt attacagagc 31020
agcgcctgct agaaagacgc agggcagcgg ccgagcaaca gcgcatgaat caagagctcc 31080
aagacatggt taacttgcac cagtgcaaaa ggggtatctt ttgtctggta aagcaggcca 31140
aagtcaccta cgacagtaat accaccggac accgccttag ctacaagttg ccaaccaagc 31200
gtcagaaatt ggtggtcatg gtgggagaaa agcccattac cataactcag cactcggtag 31260
aaaccgaagg ctgcattcac tcaccttgtc aaggacctga ggatctctgc acccttatta 31320
agaccctgtg cggtctcaaa gatcttattc cctttaacta ataaaaaaaa ataataaagc 31380
atcacttact taaaatcagt tagcaaattt ctgtccagtt tattcagcag cacctccttg 31440
ccctcctccc agctctggta ttgcagcttc ctcctggctg caaactttct ccacaatcta 31500
aatggaatgt cagtttcctc ctgttcctgt ccatccgcac ccactatctt catgttgttg 31560
cagatgaagc gcgcaagacc gtctgaagat accttcaacc ccgtgtatcc atatgacacg 31620
gaaaccggtc ctccaactgt gccttttctt actcctccct ttgtatcccc caatgggttt 31680
caagagagtc cccctggggt actctctttg cgcctatccg aacctctagt tacctccaat 31740
ggcatgcttg cgctcaaaat gggcaacggc ctctctctgg acgaggccgg caaccttacc 31800
tcccaaaatg taaccactgt gagcccacct ctcaaaaaaa ccaagtcaaa cataaacctg 31860
gaaatatctg cacccctcac agttacctca gaagccctaa ctgtggctgc cgccgcacct 31920

```
ctaatggtcg cgggcaacac actcaccatg caatcacagg ccccgctaac cgtgcacgac  31980
tccaaactta gcattgccac ccaaggaccc ctcacagtgt cagaaggaaa gctagccctg  32040
caaacatcag gcccccctcac caccaccgat agcagtaccc ttactatcac tgcctcaccc  32100
cctctaacta ctgccactgg tagcttgggc attgacttga aagagcccat ttatacacaa  32160
aatggaaaac taggactaaa gtacggggct cctttgcatg taacagacga cctaaacact  32220
ttgaccgtag caactggtcc aggtgtgact attaataata cttccttgca aactaaagtt  32280
actggagcct tgggttttga ttcacaaggc aatatgcaac ttaatgtagc aggaggacta  32340
aggattgatt ctcaaaacag acgccttata cttgatgtta gttatccgtt tgatgctcaa  32400
aaccaactaa atctaagact aggacagggc cctcttttta taaactcagc ccacaacttg  32460
gatattaact acaacaaagg cctttacttg tttacagctt caaacaattc caaaaagctt  32520
gaggttaacc taagcactgc caaggggttg atgtttgacg ctacagccat agccattaat  32580
gcaggagatg ggcttgaatt tggttcacct aatgcaccaa acacaaatcc cctcaaaaca  32640
aaaattggcc atggcctaga atttgattca aacaaggcta tggttcctaa actaggaact  32700
ggccttagtt ttgacagcac aggtgccatt acagtaggaa acaaaaataa tgataagcta  32760
actttgtgga ccacaccagc tccatctcct aactgtagac taaatgcaga gaaagatgct  32820
aaactcactt tggtcttaac aaaatgtggc agtcaaatac ttgctacagt ttcagttttg  32880
gctgttaaag gcagtttggc tccaatatct ggaacagttc aaagtgctca tcttattata  32940
agatttgacg aaaatggagt gctactaaac aattccttcc tggacccaga atattggaac  33000
tttagaaatg gagatcttac tgaaggcaca gcctatacaa acgctgttgg atttatgcct  33060
aacctatcag cttatccaaa atctcacggt aaaactgcca aaagtaacat tgtcagtcaa  33120
gtttacttaa acggagacaa aactaaacct gtaacactaa ccattacact aaacggtaca  33180
caggaaacag gagacacaac tccaagtgca tactctatgt cattttcatg ggactggtct  33240
ggccacaact acattaatga aatatttgcc acatcctctt acactttttc atacattgcc  33300
caagaataaa gaatcgtttg tgttatgttt caacgtgttt atttttcaat tgcagaaaat  33360
ttcaagtcat ttttcattca gtagtatagc cccaccacca catagcttat acagatcacc  33420
gtaccttaat caaactcaca gaaccctagt attcaacctg ccacctccct cccaacacac  33480
agagtacaca gtcctttctc cccggctggc cttaaaaagc atcatatcat gggtaacaga  33540
catattctta ggtgttatat tccacacggt ttcctgtcga gccaaacgct catcagtgat  33600
attaataaac tccccgggca gctcacttaa gttcatgtcg ctgtccagct gctgagccac  33660
aggctgctgt ccaacttgcg gttgcttaac gggcggcgaa ggagaagtcc acgcctacat  33720
gggggtagag tcataatcgt gcatcaggat agggcggtgg tgctgcagca gcgcgcgaat  33780
aaactgctgc cgccgccgct ccgtcctgca ggaatacaac atggcagtgg tctcctcagc  33840
gatgattcgc accgcccgca gcataaggcg ccttgtcctc cgggcacagc agcgcaccct  33900
gatctcactt aaatcagcac agtaactgca gcacagcacc acaatattgt tcaaaatccc  33960
acagtgcaag gcgctgtatc caaagctcat ggcggggacc acagaaccca cgtggccatc  34020
ataccacaag cgcaggtaga ttaagtggcg acccctcata aacacgctgg acataaacat  34080
tacctctttt ggcatgttgt aattcaccac ctcccggtac catataaacc tctgattaaa  34140
catggcgcca tccaccacca tcctaaacca gctggccaaa acctgcccgc cggctataca  34200
ctgcagggaa ccgggactgg aacaatgaca gtggagagcc caggactcgt aaccatggat  34260
catcatgctc gtcatgatat caatgttggc acaacacagg cacacgtgca tacacttcct  34320
```

caggattaca agctcctccc gcgttagaac catatcccag ggaacaaccc attcctgaat 34380
cagcgtaaat cccacactgc agggaagacc tcgcacgtaa ctcacgttgt gcattgtcaa 34440
agtgttacat tcgggcagca gcggatgatc ctccagtatg gtagcgcggg tttctgtctc 34500
aaaaggaggt agacgatccc tactgtacgg agtgcgccga gacaaccgag atcgtgttgg 34560
tcgtagtgtc atgccaaatg gaacgccgga cgtagtcata tttcctgaag caaaaccagg 34620
tgcgggcgtg acaaacagat ctgcgtctcc ggtctcgccg cttagatcgc tctgtgtagt 34680
agttgtagta tatccactct ctcaaagcat ccaggcgccc cctggcttcg ggttctatgt 34740
aaactccttc atgcgccgct gccctgataa catccaccac cgcagaataa gccacaccca 34800
gccaacctac acattcgttc tgcgagtcac acacgggagg agcgggaaga gctggaagaa 34860
ccatgttttt tttttattc caaaagatta tccaaaacct caaaatgaag atctattaag 34920
tgaacgcgct cccctccggt ggcgtggtca aactctacag ccaaagaaca gataatggca 34980
tttgtaagat gttgcacaat ggcttccaaa aggcaaacgg ccctcacgtc caagtggacg 35040
taaaggctaa acccttcagg gtgaatctcc tctataaaca ttccagcacc ttcaaccatg 35100
cccaaataat tctcatctcg ccaccttctc aatatatctc taagcaaatc ccgaatatta 35160
agtccggcca ttgtaaaaat ctgctccaga gcgccctcca ccttcagcct caagcagcga 35220
atcatgattg caaaaattca ggttcctcac agacctgtat aagattcaaa agcggaacat 35280
taacaaaaat accgcgatcc cgtaggtccc ttcgcagggc cagctgaaca taatcgtgca 35340
ggtctgcacg gaccagcgcg gccacttccc cgccaggaac catgacaaaa gaacccacac 35400
tgattatgac acgcatactc ggagctatgc taaccagcgt agccccgatg taagcttgtt 35460
gcatgggcgg cgatataaaa tgcaaggtgc tgctcaaaaa atcaggcaaa gcctcgcgca 35520
aaaaagaaag cacatcgtag tcatgctcat gcagataaag gcaggtaagc tccggaacca 35580
ccacagaaaa agacaccatt tttctctcaa acatgtctgc gggtttctgc ataaacacaa 35640
aataaaataa caaaaaaaca tttaaacatt agaagcctgt cttacaacag gaaaaacaac 35700
ccttataagc ataagacgga ctacggccat gccggcgtga ccgtaaaaaa actggtcacc 35760
gtgattaaaa agcaccaccg acagctcctc ggtcatgtcc ggagtcataa tgtaagactc 35820
ggtaaacaca tcaggttgat tcacatcggt cagtgctaaa aagcgaccga aatagcccgg 35880
gggaatacat acccgcaggc gtagagacaa cattacagcc cccataggag gtataacaaa 35940
attaatagga gagaaaaaca cataaacacc tgaaaaaccc tcctgcctag gcaaaatagc 36000
accctcccgc tccagaacaa catacagcgc ttccacagcg gcagccataa cagtcagcct 36060
taccagtaaa aaagaaaacc tattaaaaaa acaccactcg acacggcacc agctcaatca 36120
gtcacagtgt aaaaaagggc caagtgcaga gcgagtatat ataggactaa aaaatgacgt 36180
aacggttaaa gtccacaaaa aacacccaga aaaccgcacg cgaacctacg cccagaaacg 36240
aaagccaaaa aacccacaac ttcctcaaat cgtcacttcc gttttcccac gttacgtcac 36300
ttcccatttt aagaaaacta caattcccaa cacatacaag ttactccgcc ctaaaaccta 36360
cgtcacccgc cccgttccca cgccccgcgc cacgtcacaa actccacccc ctcattatca 36420
tattggcttc aatccaaaat aaggtatatt attgatgatg 36460

<210> SEQ ID NO 10
<211> LENGTH: 35203
<212> TYPE: DNA
<213> ORGANISM: Artificial sequence
<220> FEATURE:

-continued

<223> OTHER INFORMATION: PPE-1-3X-FasC virl construct (lacking repeats)
<220> FEATURE:
<221> NAME/KEY: misc_feature
<222> LOCATION: (460)..(1437)
<223> OTHER INFORMATION: A modified murine pre-proendothelin-1 promoter (PPE-1-3X)
<220> FEATURE:
<221> NAME/KEY: misc_feature
<222> LOCATION: (1202)..(1207)
<223> OTHER INFORMATION: Hypoxia response element
<220> FEATURE:
<221> NAME/KEY: misc_feature
<222> LOCATION: (1438)..(1468)
<223> OTHER INFORMATION: Linker
<220> FEATURE:
<221> NAME/KEY: misc_feature
<222> LOCATION: (1469)..(2058)
<223> OTHER INFORMATION: TNFR portion of the Fas-TNFR-1 chimera (Fas-c)
<220> FEATURE:
<221> NAME/KEY: misc_feature
<222> LOCATION: (2059)..(2569)
<223> OTHER INFORMATION: FAS portion of the Fas-TNFR-1 chimera (Fas-c)

<400> SEQUENCE: 10
catcatcaat aatatacctt attttggatt gaagccaata tgataatgag gggtggagt 60 ttgtgacgtg gcgcggggcg tgggaacggg gcgggtgacg tagtagtgtg gcggaagtgt 120
gatgttgcaa gtgtggcgga acacatgtaa gcgacggatg tggcaaaagt gacgtttttg 180
gtgtgcgccg gtgtacacag gaagtgacaa ttttcgcgcg gttttaggcg gatgttgtag 240
taaatttggg cgtaaccgag taagatttgg ccattttcgc gggaaaactg aataagagga 300
agtgaaatct gaataatttt gtgttactca tagcgcgtaa tatttgtcta gggccgcggg 360
gactttgacc gtttacgtgg agactcgccc aggtgttttt ctcaggtgtt ttccgcgttc 420
cgggtcaaag ttggcgtttt attattatag tcagtacgta cgtgtacttc tgatcggcga 480
tactagggag ataaggatgt acctgacaaa accacattgt tgttgttatc attattattt 540
agttttcctt ccttgctaac tcctgacgga atctttctca cctcaaatgc gaagtacttt 600
agtttagaaa agacttggtg gaaggggtgg tggtggaaaa gtagggtgat cttccaaact 660
aatctggttc cccgcccgcc ccagtagctg ggattcaaga gcgaagagtg gggatcgtcc 720
ccttgtttga tcagaaagac ataaaaggaa aatcaagtga acaatgatca gccccacctc 780
caccccaccc ccctgcgcgc gcacaataca atctatttaa ttgtacttca tacttttcat 840
tccaatgggg tgactttgct tctggagaaa ctcttgattc ttgaactctg gggctggcag 900
ctagcctcca gaagcaaagt caccccattg gaatgaaaag tatgaagtac aatgaaaagt 960
atgaagtact ggctccagaa gcaaagtcac cctccagaag caaagtcacc ccattggaat 1020
gaaaagtatg aagtacgcta gcaaaagggg aagcgggctg ctgctctctg caggttctgc 1080
agcggtctct gtctagtggg tgttttcttt ttcttagccc tgcccctgga ttgtcagacg 1140
gcgggcgtct gcctctgaag ttagccgtga tttcctctag agccgggtct tatctctggc 1200
tgcacgttgc ctgtgggtga ctaatcacac aataacattg tttagggctg gaataaagtc 1260
agagctgttt acccccactc tataggggtt caatataaaa aggcggcgga gaactgtccg 1320
agtcagaagc gttcctgcac cggcgctgag agcctgaccc ggtctgctcc gctgtccttg 1380
cgcgctgcct cccggctgcc cgcgacgctt tcgccccagt ggaagggcca cttgctgcgg 1440
ccgctaattc tgcagatcgg gatccggcat gggcctctcc accgtgcctg acctgctgct 1500
gccgctggtg ctcctggagc tgttggtggg aatatacccc tcaggggtta ttggactggt 1560
ccctcaccta ggggacaggg agaagagaga tagtgtgtgt ccccaaggaa aatatatcca 1620

```
ccctcaaaat aattcgattt gctgtaccaa gtgccacaaa ggaacctact tgtacaatga   1680
ctgtccaggc ccggggcagg atacggactg cagggagtgt gagagcggct ccttcaccgc   1740
ttcagaaaac cacctcagac actgcctcag ctgctccaaa tgccgaaagg aaatgggtca   1800
ggtggagatc tcttcttgca cagtggaccg ggacaccgtg tgtggctgca ggaagaacca   1860
gtaccggcat tattggagtg aaaacctttt ccagtgcttc aattgcagcc tctgcctcaa   1920
tgggaccgtg cacctctcct gccaggagaa acagaacacc gtgtgcacct gccatgcagg   1980
tttctttcta agagaaaacg agtgtgtctc ctgtagtaac tgtaagaaaa gcctggagtg   2040
cacgaagttg tgcctaccaa gcttaggatc cagatctaac ttggggtggc tttgtcttct   2100
tcttttgcca attccactaa ttgtttgggt gaagagaaag gaagtacaga aaacatgcag   2160
aaagcacaga aaggaaaacc aaggttctca tgaatctcca accttaaatc ctgaaacagt   2220
ggcaataaat ttatctgatg ttgacttgag taaatatatc accactattg ctggagtcat   2280
gacactaagt caagttaaag gctttgttcg aaagaatggt gtcaatgaag ccaaaataga   2340
tgagatcaag aatgacaatg tccaagacac agcagaacag aaagttcaac tgcttcgtaa   2400
ttggcatcaa cttcatggaa agaaagaagc gtatgacaca ttgattaaag atctcaaaaa   2460
agccaatctt tgtactcttg cagagaaaat tcagactatc atcctcaagg acattactag   2520
tgactcagaa aattcaaact tcagaaatga aatccaaagc ttggtctagc tcgagcatgc   2580
atctaggcgg ccgcatggca gaaattcgcg aattcgctag cgttaacgga tcctctagac   2640
gagatccgaa cttgtttatt gcagcttata atggttacaa ataaagcaat agcatcacaa   2700
atttcacaaa taaagcattt ttttcactgc attctagttg tggtttgtcc aaactcatca   2760
atgtatctta tcatgtctag atctgtactg aaatgtgtgg gcgtggctta agggtgggaa   2820
agaatatata aggtgggggt cttatgtagt tttgtatctg ttttgcagca gccgccgccg   2880
ccatgagcac caactcgttt gatggaagca ttgtgagctc atatttgaca acgcgcatgc   2940
ccccatgggc cggggtgcgt cagaatgtga tgggctccag cattgatggt cgccccgtcc   3000
tgcccgcaaa ctctactacc ttgacctacg agaccgtgtc tggaacgccg ttggagactg   3060
cagcctccgc cgccgcttca gccgctgcag ccaccgcccg cgggattgtg actgactttg   3120
ctttcctgag cccgcttgca agcagtgcag cttcccgttc atccgcccgc gatgacaagt   3180
tgacggctct tttggcacaa ttggattctt tgacccggga acttaatgtc gtttctcagc   3240
agctgttgga tctgcgccag caggtttctg ccctgaaggc ttcctcccct cccaatgcgg   3300
tttaaaacat aaataaaaaa ccagactctg tttggatttg gatcaagcaa gtgtcttgct   3360
gtctttattt aggggttttg cgcgcgcggt aggcccggga ccagcggtct cggtcgttga   3420
gggtcctgtg tatttttttcc aggacgtggt aaaggtgact ctggatgttc agatacatgg   3480
gcataagccc gtctctgggg tggaggtagc accactgcag agcttcatgc tgcggggtgg   3540
tgttgtagat gatccagtcg tagcaggagc gctgggcgtg gtgcctaaaa atgtctttca   3600
gtagcaagct gattgccagg ggcaggccct tggtgtaagt gtttacaaag cggttaagct   3660
gggatgggtg catacgtggg gatatgagat gcatcttgga ctgtattttt aggttggcta   3720
tgttcccagc catatccctc cggggattca tgttgtgcag aaccaccagc acagtgtatc   3780
cggtgcactt gggaaatttg tcatgtagct tagaaggaaa tgcgtggaag aacttggaga   3840
cgcccttgtg acctccaaga ttttccatgc attcgtccat aatgatggca atgggcccac   3900
gggcggcggc ctgggcgaag atatttctgg gatcactaac gtcatagttg tgttccagga   3960
tgagatcgtc ataggccatt tttacaaagc gcgggcggag ggtgccagac tgcggtataa   4020
```

tggttccatc cggcccaggg gcgtagttac cctcacagat ttgcatttcc cacgctttga 4080
gttcagatgg ggggatcatg tctacctgcg gggcgatgaa gaaaacggtt tccggggtag 4140
gggagatcag ctgggaagaa agcaggttcc tgagcagctg cgacttaccg cagccggtgg 4200
gcccgtaaat cacacctatt accggctgca actggtagtt aagagagctg cagctgccgt 4260
catccctgag caggggggcc acttcgttaa gcatgtccct gactcgcatg ttttccctga 4320
ccaaatccgc cagaaggcgc tcgccgccca gcgatagcag ttcttgcaag gaagcaaagt 4380
ttttcaacgg tttgagaccg tccgccgtag gcatgctttt gagcgtttga ccaagcagtt 4440
ccaggcggtc ccacagctcg gtcacctgct ctacggcatc tcgatccagc atatctcctc 4500
gtttcgcggg ttggggcggc tttcgctgta cggcagtagt cggtgctcgt ccagacgggc 4560
cagggtcatg tctttccacg ggcgcagggt cctcgtcagc gtagtctggg tcacggtgaa 4620
ggggtgcgct ccgggctgcg cgctggccag ggtgcgcttg aggctggtcc tgctggtgct 4680
gaagcgctgc cggtcttcgc cctgcgcgtc ggccaggtag catttgacca tggtgtcata 4740
gtccagcccc tccgcggcgt ggcccttggc gcgcagcttg cccttggagg aggcgccgca 4800
cgaggggcag tgcagacttt tgagggcgta gagcttgggc gcgagaaata ccgattccgg 4860
ggagtaggca tccgcgccgc aggccccgca gacggtctcg cattccacga gccaggtgag 4920
ctctggccgt tcggggtcaa aaaccaggtt tcccccatgc tttttgatgc gtttcttacc 4980
tctggtttcc atgagccggt gtccacgctc ggtgacgaaa aggctgtccg tgtccccgta 5040
tacagacttg agaggcctgt cctcgagcgg tgttccgcgg tcctcctcgt atagaaactc 5100
ggaccactct gagacaaagg ctcgcgtcca ggccagcacg aaggaggcta agtgggaggg 5160
gtagcggtcg ttgtccacta gggggtccac tcgctccagg gtgtgaagac acatgtcgcc 5220
ctcttcggca tcaaggaagg tgattggttt gtaggtgtag gccacgtgac cgggtgttcc 5280
tgaagggggg ctataaaagg gggtgggggc gcgttcgtcc tcactctctt ccgcatcgct 5340
gtctgcgagg gccagctgtt ggggtgagta ctccctctga aaagcgggca tgacttctgc 5400
gctaagattg tcagtttcca aaaacgagga ggatttgata ttcacctggc ccgcggtgat 5460
gcctttgagg gtggccgcat ccatctggtc agaaaagaca atctttttgt tgtcaagctt 5520
ggtggcaaac gacccgtaga gggcgttgga cagcaacttg gcgatggagc gcagggtttg 5580
gtttttgtcg cgatcggcgc gctccttggc cgcgatgttt agctgcacgt attcgcgcgc 5640
aacgcaccgc cattcgggaa agacggtggt gcgctcgtcg ggcaccaggt gcacgcgcca 5700
accgcggttg tgcagggtga caaggtcaac gctggtggct acctctccgc gtaggcgctc 5760
gttggtccag cagaggcggc cgcccttgcg cgagcagaat ggcggtaggg ggtctagctg 5820
cgtctcgtcc ggggggtctg cgtccacggt aaagaccccg ggcagcaggc gcgcgtcgaa 5880
gtagtctatc ttgcatcctt gcaagtctag cgcctgctgc catgcgcggg cggcaagcgc 5940
gcgctcgtat gggttgagtg gggaccccca tggcatgggg tgggtgagcg cggaggcgta 6000
catgccgcaa atgtcgtaaa cgtagagggg ctctctgagt attccaagat atgtagggta 6060
gcatcttcca ccgcggatgc tggcgcgcac gtaatcgtat agttcgtgcg agggagcgag 6120
gaggtcggga ccgaggttgc tacgggcggg ctgctctgct cggaagacta tctgcctgaa 6180
gatggcatgt gagttggatg atatggttgg acgctggaag acgttgaagc tggcgtctgt 6240
gagacctacc gcgtcacgca cgaaggaggc gtaggagtcg cgcagcttgt tgaccagctc 6300
ggcggtgacc tgcacgtcta gggcgcagta gtccagggtt tccttgatga tgtcatactt 6360
atcctgtccc ttttttttcc acagctcgcg gttgaggaca aactcttcgc ggtctttcca 6420
gtactcttgg atcggaaacc cgtcggcctc cgaacggtaa gagcctagca tgtagaactg 6480
gttgacggcc tggtaggcgc agcatccctt ttctacgggt agcgcgtatg cctgcgcggc 6540
cttccggagc gaggtgtggg tgagcgcaaa ggtgtccctg accatgactt tgaggtactg 6600
gtatttgaag tcagtgtcgt cgcatccgcc ctgctcccag agcaaaaagt ccgtgcgctt 6660
tttggaacgc ggatttggca gggcgaaggt gacatcgttg aagagtatct ttcccgcgcg 6720
aggcataaag ttgcgtgtga tgcggaaggg tcccggcacc tcggaacggt tgttaattac 6780
ctgggcggcg agcacgatct cgtcaaagcc gttgatgttg tggcccacaa tgtaaagttc 6840
caagaagcgc gggatgccct tgatggaagg caattttta agttcctcgt aggtgagctc 6900
ttcaggggag ctgagcccgt gctctgaaag ggcccagtct gcaagatgag ggttggaagc 6960
gacgaatgag ctccacaggt cacgggccat tagcatttgc aggtggtcgc gaaaggtcct 7020
aaactggcga cctatggcca tttttctgg ggtgatgcag tagaaggtaa gcgggtcttg 7080
ttcccagcgg tcccatccaa ggttcgcggc taggtctcgc gcggcagtca ctagaggctc 7140
atctccgccg aacttcatga ccagcatgaa gggcacgagc tgcttcccaa aggcccccat 7200
ccaagtatag gtctctacat cgtaggtgac aaagagacgc tcggtgcgag gatgcgagcc 7260
gatcgggaag aactggatct cccgccacca attggaggag tggctattga tgtggtgaaa 7320
gtagaagtcc ctgcgacggg ccgaacactc gtgctggctt ttgtaaaaac gtgcgcagta 7380
ctggcagcgg tgcacgggct gtacatcctg cacgaggttg acctgacgac cgcgcacaag 7440
gaagcagagt gggaatttga gcccctcgcc tggcgggttt ggctggtggt cttctacttc 7500
ggctgcttgt ccttgaccgt ctggctgctc gaggggagtt acggtggatc ggaccaccac 7560
gccgcgcgag cccaaagtcc agatgtccgc gcgcggcggt cggagcttga tgacaacatc 7620
gcgcagatgg gagctgtcca tggtctggag ctcccgcggc gtcaggtcag gcgggagctc 7680
ctgcaggttt acctcgcata gacgggtcag ggcgcgggct agatccaggt gatacctaat 7740
ttccaggggc tggttggtgg cggcgtcgat ggcttgcaag aggccgcatc cccgcggcgc 7800
gactacggta ccgcgcggcg ggcggtgggc cgcgggggtg tccttggatg atgcatctaa 7860
aagcggtgac gcgggcgagc ccccggaggt agggggggct ccggacccgc cgggagaggg 7920
ggcaggggca cgtcggcgcc gcgcgcgggc aggagctggt gctgcgcgcg taggttgctg 7980
gcgaacgcga cgacgcggcg gttgatctcc tgaatctggc gcctctgcgt gaagacgacg 8040
ggcccggtga gcttgaacct gaaagagagt tcgacagaat caatttcggt gtcgttgacg 8100
gcggcctggc gcaaaatctc ctgcacgtct cctgagttgt cttgataggc gatctcggcc 8160
atgaactgct cgatctcttc ctcctggaga tctccgcgtc cggctcgctc cacggtggcg 8220
gcgaggtcgt tggaaatgcg ggccatgagc tgcgagaagg cgttgaggcc tccctcgttc 8280
cagacgcggc tgtagaccac gccccttcg gcatcgcggg cgcgcatgac cacctgcgcg 8340
agattgagct ccacgtgccg ggcgaagacg gcgtagtttc gcaggcgctg aaagaggtag 8400
ttgagggtgg tggcggtgtg ttctgccacg aagaagtaca taacccagcg tcgcaacgtg 8460
gattcgttga tatcccccaa ggcctcaagg cgctccatgg cctcgtagaa gtccacggcg 8520
aagttgaaaa actgggagtt gcgcgccgac acggttaact cctcctccag aagacggatg 8580
agctcggcga cagtgtcgcg cacctcgcgc tcaaaggcta caggggcctc ttcttcttct 8640
tcaatctcct cttccataag ggcctcccct tcttcttctt ctggcggcgg tgggggaggg 8700
gggacacggc ggcgacgacg gcgcaccggg aggcggtcga caaagcgctc gatcatctcc 8760
ccgcggcgac ggcgcatggt ctcggtgacg gcgcggccgt tctcgcgggg gcgcagttgg 8820
aagacgccgc ccgtcatgtc ccggttatgg gttggcgggg ggctgccatg cggcagggat 8880
acggcgctaa cgatgcatct caacaattgt tgtgtaggta ctccgccgcc gagggacctg 8940
agcgagtccg catcgaccgg atcggaaaac ctctcgagaa aggcgtctaa ccagtcacag 9000
tcgcaaggta ggctgagcac cgtggcgggc ggcagcgggc ggcggtcggg gttgtttctg 9060
gcggaggtgc tgctgatgat gtaattaaag taggcggtct tgagacggcg gatggtcgac 9120
agaagcacca tgtccttggg tccggcctgc tgaatgcgca ggcggtcggc catgccccag 9180
gcttcgtttt gacatcggcg caggtctttg tagtagtctt gcatgagcct ttctaccggc 9240
acttcttctt ctccttcctc ttgtcctgca tctcttgcat ctatcgctgc ggcggcggcg 9300
gagtttggcc gtaggtggcg ccctcttcct cccatgcgtg tgaccccgaa gcccctcatc 9360
ggctgaagca gggctaggtc ggcgacaacg cgctcggcta atatggcctg ctgcacctgc 9420
gtgagggtag actggaagtc atccatgtcc acaaagcggt ggtatgcgcc cgtgttgatg 9480
gtgtaagtgc agttggccat aacggaccag ttaacggtct ggtgacccgg ctgcgagagc 9540
tcggtgtacc tgagacgcga gtaagccctc gagtcaaata cgtagtcgtt gcaagtccgc 9600
accaggtact ggtatcccac caaaaagtgc ggcggcggct ggcggtagag gggccagcgt 9660
agggtggccg gggctccggg ggcgagatct tccaacataa ggcgatgata tccgtagatg 9720
tacctggaca tccaggtgat gccggcggcg gtggtggagg cgcgcggaaa gtcgcggacg 9780
cggttccaga tgttgcgcag cggcaaaaag tgctccatgg tcgggacgct ctggccggtc 9840
aggcgcgcgc aatcgttgac gctctagacc gtgcaaaagg agagcctgta agcgggcact 9900
cttccgtggt ctggtggata aattcgcaag ggtatcatgg cggacgaccg gggttcgagc 9960
cccgtatccg gccgtccgcc gtgatccatg cggttaccgc ccgcgtgtcg aacccaggtg 10020
tgcgacgtca gacaacgggg gagtgctcct tttggcttcc ttccaggcgc ggcggctgct 10080
gcgctagctt ttttggccac tggccgcgcg cagcgtaagc ggttaggctg gaaagcgaaa 10140
gcattaagtg gctcgctccc tgtagccgga gggttatttt ccaagggttg agtcgcggga 10200
cccccggttc gagtctcgga ccggccggac tgcggcgaac gggggtttgc ctccccgtca 10260
tgcaagaccc cgcttgcaaa ttcctccgga aacagggacg agcccctttt ttgcttttcc 10320
cagatgcatc cggtgctgcg gcagatgcgc ccccctcctc agcagcggca agagcaagag 10380
cagcggcaga catgcagggc accctcccct cctcctaccg cgtcaggagg ggcgacatcc 10440
gcggttgacg cggcagcaga tggtgattac gaaccccgc ggcgccgggc ccggcactac 10500
ctggacttgg aggagggcga gggcctggcg cggctaggag cgccctctcc tgagcggcac 10560
ccaagggtgc agctgaagcg tgatacgcgt gaggcgtacg tgccgcggca gaacctgttt 10620
cgcgaccgcg agggagagga gcccgaggag atgcgggatc gaaagttcca cgcagggcgc 10680
gagctgcggc atggcctgaa tcgcgagcgg ttgctgcgcg aggaggactt tgagcccgac 10740
gcgcgaaccg ggattagtcc cgcgcgcgca cacgtggcgg ccgccgacct ggtaaccgca 10800
tacgagcaga cggtgaacca ggagattaac tttcaaaaaa gctttaacaa ccacgtgcgt 10860
acgcttgtgg cgcgcgagga ggtggctata ggactgatgc atctgtggga ctttgtaagc 10920
gcgctggagc aaaacccaaa tagcaagccg ctcatggcgc agctgttcct tatagtgcag 10980
cacagcaggg acaacgaggc attcagggat gcgctgctaa acatagtaga gcccgagggc 11040
cgctggctgc tcgatttgat aaacatcctg cagagcatag tggtgcagga gcgcagcttg 11100

-continued agcctggctg acaaggtggc cgccatcaac tattccatgc ttagcctggg caagttttac 11160
gcccgcaaga tataccatac cccttacgtt cccatagaca aggaggtaaa gatcgagggg 11220
ttctacatgc gcatggcgct gaaggtgctt accttgagcg acgacctggg cgtttatcgc 11280
aacgagcgca tccacaaggc cgtgagcgtg agccggcggc gcgagctcag cgaccgcgag 11340
ctgatgcaca gcctgcaaag ggccctggct ggcacgggca gcggcgatag agaggccgag 11400
tcctactttg acgcgggcgc tgacctgcgc tgggccccaa gccgacgcgc cctggaggca 11460
gctggggccg gacctgggct ggcggtggca cccgcgcgcg ctggcaacgt cggcggcgtg 11520
gaggaatatg acgaggacga tgagtacgag ccagaggacg gcgagtacta agcggtgatg 11580
tttctgatca gatgatgcaa gacgcaacgg acccggcggt gcgggcggcg ctgcagagcc 11640
agccgtccgg ccttaactcc acggacgact ggcgccaggt catggaccgc atcatgtcgc 11700
tgactgcgcg caatcctgac gcgttccggc agcagccgca ggccaaccgg ctctccgcaa 11760
ttctggaagc ggtggtcccg gcgcgcgcaa accccacgca cgagaaggtg ctggcgatcg 11820
taaacgcgct ggccgaaaac agggccatcc ggcccgacga ggccggcctg gtctacgacg 11880
cgctgcttca gcgcgtggct cgttacaaca gcggcaacgt gcagaccaac ctggaccggc 11940
tggtggggga tgtgcgcgag gccgtggcgc agcgtgagcg cgcgcagcag cagggcaacc 12000
tgggctccat ggttgcacta aacgccttcc tgagtacaca gcccgccaac gtgccgcggg 12060
gacaggagga ctacaccaac tttgtgagcg cactgcggct aatggtgact gagacaccgc 12120
aaagtgaggt gtaccagtct gggccagact atttttttcca gaccagtaga caaggcctgc 12180
agaccgtaaa cctgagccag gctttcaaaa acttgcaggg gctgtggggg gtgcgggctc 12240
ccacaggcga ccgcgcgacc gtgtctagct tgctgacgcc caactcgcgc ctgttgctgc 12300
tgctaatagc gcccttcacg gacagtggca gcgtgtcccg ggacacatac ctaggtcact 12360
tgctgacact gtaccgcgag gccataggtc aggcgcatgt ggacgagcat actttccagg 12420
agattacaag tgtcagccgc gcgctggggc aggaggacac gggcagcctg gaggcaaccc 12480
taaactacct gctgaccaac cggcggcaga agatcccctc gttgcacagt ttaaacagcg 12540
aggaggagcg cattttgcgc tacgtgcagc agagcgtgag ccttaacctg atgcgcgacg 12600 ggtaacgcc cagcgtggcg ctggacatga ccgcgcgcaa catggaaccg ggcatgtatg 12660
cctcaaaccg gccgtttatc aaccgcctaa tggactactt gcatcgcgcg gccgccgtga 12720
accccgagta tttcaccaat gccatcttga acccgcactg gctaccgccc cctggtttct 12780
acaccggggg attcgaggtg cccgagggta acgatggatt cctctgggac gacatagacg 12840
acagcgtgtt ttccccgcaa ccgcagaccc tgctagagtt gcaacagcgc gagcaggcag 12900
aggcggcgct gcgaaaggaa agcttccgca ggccaagcag cttgtccgat ctaggcgctg 12960
cggccccgcg gtcagatgct agtagcccat ttccaagctt gatagggtct cttaccagca 13020
ctcgcaccac ccgcccgcgc ctgctgggcg aggaggagta cctaaacaac tcgctgctgc 13080
agccgcagcg cgaaaaaaac ctgcctccgg catttcccaa caacgggata gagagcctag 13140
tggacaagat gagtagatgg aagacgtacg cgcaggagca cagggacgtg ccaggcccgc 13200
gcccgcccac ccgtcgtcaa aggcacgacc gtcagcgggg tctggtgtgg gaggacgatg 13260
actcggcaga cgacagcagc gtcctggatt tgggagggag tggcaacccg tttgcgcacc 13320
ttcgccccag gctggggaga atgttttaaa aaaaaaaaaa gcatgatgca aaataaaaaa 13380
ctcaccaagg ccatggcacc gagcgttggt tttcttgtat tccccttagt atgcggcgcg 13440
cggcgatgta tgaggaaggt cctcctccct cctacgagag tgtggtgagc gcggcgccag 13500
tggcggcggc gctgggttct cccttcgatg ctcccctgga cccgccgttt gtgcctccgc 13560
ggtacctgcg gcctaccggg gggagaaaca gcatccgtta ctctgagttg gcacccctat 13620
tcgacaccac ccgtgtgtac ctggtggaca acaagtcaac ggatgtggca tccctgaact 13680
accagaacga ccacagcaac tttctgacca cggtcattca aaacaatgac tacagcccgg 13740
gggaggcaag cacacagacc atcaatcttg acgaccggtc gcactggggc ggcgacctga 13800
aaaccatcct gcataccaac atgccaaatg tgaacgagtt catgtttacc aataagttta 13860
aggcgcgggt gatggtgtcg cgcttgccta ctaaggacaa tcaggtggag ctgaaatacg 13920
agtgggtgga gttcacgctg cccgagggca actactccga gaccatgacc atagacctta 13980
tgaacaacgc gatcgtggag cactacttga aagtgggcag acagaacggg gttctggaaa 14040
gcgacatcgg ggtaaagttt gacacccgca acttcagact ggggtttgac cccgtcactg 14100
gtcttgtcat gcctggggta tatacaaacg aagccttcca tccagacatc attttgctgc 14160
caggatgcgg ggtggacttc acccacagcc gcctgagcaa cttgttgggc atccgcaagc 14220
ggcaaccctt ccaggagggc tttaggatca cctacgatga tctggagggt ggtaacattc 14280
ccgcactgtt ggatgtggac gcctaccagg cgagcttgaa agatgacacc gaacagggcg 14340
ggggtggcgc aggcggcagc aacagcagtg gcagcggcgc ggaagagaac tccaacgcgg 14400
cagccgcggc aatgcagccg gtggaggaca tgaacgatca tgccattcgc ggcgacacct 14460
ttgccacacg ggctgaggag aagcgcgctg aggccgaagc agcggccgaa gctgccgccc 14520
ccgctgcgca acccgaggtc gagaagcctc agaagaaacc ggtgatcaaa cccctgacag 14580
aggacagcaa gaaacgcagt tacaacctaa taagcaatga cagcaccttc acccagtacc 14640
gcagctggta ccttgcatac aactacggcg accctcagac cggaatccgc tcatggaccc 14700
tgctttgcac tcctgacgta acctgcggct cggagcaggt ctactggtcg ttgccagaca 14760
tgatgcaaga ccccgtgacc ttccgctcca cgcgccagat cagcaacttt ccggtggtgg 14820
gcgccgagct gttgcccgtg cactccaaga gcttctacaa cgaccaggcc gtctactccc 14880
aactcatccg ccagtttacc tctctgaccc acgtgttcaa tcgctttccc gagaaccaga 14940
ttttggcgcg cccgccagcc cccaccatca ccaccgtcag tgaaaacgtt cctgctctca 15000
cagatcacgg gacgctaccg ctgcgcaaca gcatcggagg agtccagcga gtgaccatta 15060
ctgacgccag acgccgcacc tgcccctacg tttacaaggc cctgggcata gtctcgccgc 15120
gcgtcctatc gagccgcact ttttgagcaa gcatgtccat ccttatatcg cccagcaata 15180
acacaggctg gggcctgcgc ttcccaagca agatgtttgg cggggccaag aagcgctccg 15240
accaacaccc agtgcgcgtg cgcgggcact accgcgcgcc ctggggcgcg cacaaacgcg 15300
gccgcactgg gcgcaccacc gtcgatgacg ccatcgacgc ggtggtggag gaggcgcgca 15360
actacacgcc cacgccgcca ccagtgtcca cagtggacgc ggccattcag accgtggtgc 15420
gcggagcccg gcgctatgct aaaatgaaga gacggcggag gcgcgtagca cgtcgccacc 15480
gccgccgacc cggcactgcc gcccaacgcg cggcggcggc cctgcttaac cgcgcacgtc 15540
gcaccggccg acgggcggcc atgcgggccg ctcgaaggct ggccgcgggt attgtcactg 15600
tgccccccag gtccaggcga cgagcggccg ccgcagcagc cgcggccatt agtgctatga 15660
ctcagggtcg caggggcaac gtgtattggg tgcgcgactc ggttagcggc ctgcgcgtgc 15720
ccgtgcgcac ccgccccccg cgcaactaga ttgcaagaaa aaactactta gactcgtact 15780
gttgtatgta tccagcggcg gcggcgcgca acgaagctat gtccaagcgc aaaatcaaag 15840
aagagatgct ccaggtcatc gcgccggaga tctatggccc cccgaagaag gaagagcagg 15900
attacaagcc ccgaaagcta aagcgggtca aaaagaaaaa gaaagatgat gatgatgaac 15960
ttgacgacga ggtggaactg ctgcacgcta ccgcgcccag gcgacgggta cagtggaaag 16020
gtcgacgcgt aaaacgtgtt ttgcgacccg gcaccaccgt agtctttacg cccggtgagc 16080
gctccacccg cacctacaag cgcgtgtatg atgaggtgta cggcgacgag gacctgcttg 16140
agcaggccaa cgagcgcctc ggggagtttg cctacggaaa gcggcataag gacatgctgg 16200
cgttgccgct ggacgagggc aacccaacac ctagcctaaa gcccgtaaca ctgcagcagg 16260
tgctgcccgc gcttgcaccg tccgaagaaa agcgcggcct aaagcgcgag tctggtgact 16320
tggcacccac cgtgcagctg atggtaccca agcgccagcg actggaagat gtcttggaaa 16380
aaatgaccgt ggaacctggg ctggagcccg aggtccgcgt gcggccaatc aagcaggtgg 16440
cgccgggact gggcgtgcag accgtggacg ttcagatacc cactaccagt agcaccagta 16500
ttgccaccgc cacagagggc atggagacac aaacgtcccc ggttgcctca gcggtggcgg 16560
atgccgcggt gcaggcggtc gctgcggccg cgtccaagac ctctacggag gtgcaaacgg 16620
acccgtggat gtttcgcgtt tcagcccccc ggcgcccgcg ccgttcgagg aagtacggcg 16680
ccgccagcgc gctactgccc gaatatgccc tacatccttc cattgcgcct acccccggct 16740
atcgtggcta cacctaccgc cccagaagac gagcaactac ccgacgccga accaccactg 16800
gaacccgccg ccgccgtcgc cgtcgccagc ccgtgctggc cccgatttcc gtgcgcaggg 16860
tggctcgcga aggaggcagg accctggtgc tgccaacagc gcgctaccac cccagcatcg 16920
tttaaaagcc ggtctttgtg gttcttgcag atatggccct cacctgccgc ctccgtttcc 16980
cggtgccggg attccgagga agaatgcacc gtaggagggg catggccggc cacggcctga 17040
cgggcggcat gcgtcgtgcg caccaccggc ggcggcgcgc gtcgcaccgt cgcatgcgcg 17100
gcggtatcct gcccctcctt attccactga tcgccgcggc gattggcgcc gtgcccggaa 17160
ttgcatccgt ggccttgcag gcgcagagac actgattaaa aacaagttgc atgtggaaaa 17220
atcaaaataa aaagtctgga ctctcacgct cgcttggtcc tgtaactatt ttgtagaatg 17280
gaagacatca actttgcgtc tctggccccg cgacacggct cgcgcccgtt catgggaaac 17340
tggcaagata tcggcaccag caatatgagc ggtggcgcct tcagctgggg ctcgctgtgg 17400
agcggcatta aaaatttcgg ttccaccgtt aagaactatg gcagcaaggc ctggaacagc 17460
agcacaggcc agatgctgag ggataagttg aaagagcaaa atttccaaca aaaggtggta 17520
gatggcctgg cctctggcat tagcggggtg gtggacctgg ccaaccaggc agtgcaaaat 17580
aagattaaca gtaagcttga tccccgccct cccgtagagg agcctccacc ggccgtggag 17640
acagtgtctc cagaggggcg tggcgaaaag cgtccgcgcc ccgacaggga agaaactctg 17700
gtgacgcaaa tagacgagcc tccctcgtac gaggaggcac taaagcaagg cctgcccacc 17760
acccgtccca tcgcgcccat ggctaccgga gtgctgggcc agcacacacc cgtaacgctg 17820
gacctgcctc cccccgccga cacccagcag aaacctgtgc tgccaggccc gaccgccgtt 17880
gttgtaaccc gtcctagccg cgcgtccctg cgccgcgccg ccagcggtcc gcgatcgttg 17940
cggcccgtag ccagtggcaa ctggcaaagc acactgaaca gcatcgtggg tctgggggtg 18000
caatccctga agcgccgacg atgcttctga tagctaacgt gtcgtatgtg tgtcatgtat 18060
gcgtccatgt cgccgccaga ggagctgctg agccgccgcg cgcccgcttt ccaagatggc 18120
taccccttcg atgatgccgc agtggtctta catgcacatc tcgggccagg acgcctcgga 18180
gtacctgagc cccgggctgg tgcagtttgc ccgcgccacc gagacgtact tcagcctgaa 18240

```
taacaagttt agaaacccca cggtggcgcc tacgcacgac gtgaccacag accggtccca  18300
gcgtttgacg ctgcggttca tccctgtgga ccgtgaggat actgcgtact cgtacaaggc  18360
gcggttcacc ctagctgtgg gtgataaccg tgtgctggac atggcttcca cgtactttga  18420
catccgcggc gtgctggaca ggggccctac ttttaagccc tactctggca ctgcctacaa  18480
cgccctggct cccaagggtg ccccaaatcc ttgcgaatgg gatgaagctg ctactgctct  18540
tgaaataaac ctagaagaag aggacgatga caacgaagac gaagtagacg agcaagctga  18600
gcagcaaaaa actcacgtat ttgggcaggc gccttattct ggtataaata ttacaaagga  18660
gggtattcaa ataggtgtcg aaggtcaaac acctaaatat gccgataaaa catttcaacc  18720
tgaacctcaa ataggagaat ctcagtggta cgaaacagaa attaatcatg cagctgggag  18780
agtcctaaaa aagactaccc caatgaaacc atgttacggt tcatatgcaa aacccacaaa  18840
tgaaaatgga gggcaaggca ttcttgtaaa gcaacaaaat ggaaagctag aaagtcaagt  18900
ggaaatgcaa tttttctcaa ctactgaggc agccgcaggc aatggtgata acttgactcc  18960
taaagtggta ttgtacagtg aagatgtaga tatagaaacc ccagacactc atatttctta  19020
catgcccact attaaggaag gtaactcacg agaactaatg ggccaacaat ctatgcccaa  19080
caggcctaat tacattgctt ttagggacaa ttttattggt ctaatgtatt acaacagcac  19140
gggtaatatg ggtgttctgg cgggccaagc atcgcagttg aatgctgttg tagatttgca  19200
agacagaaac acagagcttt cataccagct tttgcttgat tccattggtg atagaaccag  19260
gtacttttct atgtggaatc aggctgttga cagctatgat ccagatgtta gaattattga  19320
aaatcatgga actgaagatg aacttccaaa ttactgcttt ccactgggag gtgtgattaa  19380
tacagagact cttaccaagg taaaacctaa aacaggtcag gaaaatggat gggaaaaaga  19440
tgctacagaa ttttcagata aaaatgaaat aagagttgga aataattttg ccatggaaat  19500
caatctaaat gccaacctgt ggagaaattt cctgtactcc aacatagcgc tgtatttgcc  19560
cgacaagcta aagtacagtc cttccaacgt aaaaatttct gataacccaa acacctacga  19620
ctacatgaac aagcgagtgg tggctcccgg gctagtggac tgctacatta accttggagc  19680
acgctggtcc cttgactata tggacaacgt caacccattt aaccaccacc gcaatgctgg  19740
cctgcgctac cgctcaatgt tgctgggcaa tggtcgctat gtgcccttcc acatccaggt  19800
gcctcagaag ttctttgcca ttaaaaacct ccttctcctg ccgggctcat acacctacga  19860
gtggaacttc aggaaggatg ttaacatggt tctgcagagc tccctaggaa atgacctaag  19920
ggttgacgga gccagcatta agtttgatag catttgcctt tacgccacct tcttccccat  19980
ggcccacaac accgcctcca cgcttgaggc catgcttaga aacgacacca acgaccagtc  20040
ctttaacgac tatctctccg ccgccaacat gctctaccct atacccgcca acgctaccaa  20100
cgtgcccata tccatcccct cccgcaactg ggcggctttc cgcggctggg ccttcacgcg  20160
ccttaagact aaggaaaccc catcactggg ctcgggctac gacccttatt acacctactc  20220
tggctctata ccctacctag atggaacctt ttacctcaac cacaccttta agaaggtggc  20280
cattaccttt gactcttctg tcagctggcc tggcaatgac cgcctgctta cccccaacga  20340
gtttgaaatt aagcgctcag ttgacgggga gggttacaac gttgcccagt gtaacatgac  20400
caaagactgg ttcctggtac aaatgctagc taactataac attggctacc agggcttcta  20460
tatcccagag agctacaagg accgcatgta ctccttcttt agaaacttcc agcccatgag  20520
ccgtcaggtg gtggatgata ctaaatacaa ggactaccaa caggtgggca tcctacacca  20580
```

acacaacaac tctggatttg ttggctacct tgcccccacc atgcgcgaag gacaggccta 20640
ccctgctaac ttcccctatc cgcttatagg caagaccgca gttgacagca ttacccagaa 20700
aaagtttctt tgcgatcgca ccctttggcg catcccattc tccagtaact ttatgtccat 20760
gggcgcactc acagacctgg gccaaaacct tctctacgcc aactccgccc acgcgctaga 20820
catgactttt gaggtggatc ccatggacga gcccaccctt ctttatgttt tgtttgaagt 20880
ctttgacgtg gtccgtgtgc accagccgca ccgcggcgtc atcgaaaccg tgtacctgcg 20940
cacgcccttc tcggccggca acgccacaac ataaagaagc aagcaacatc aacaacagct 21000
gccgccatgg gctccagtga gcaggaactg aaagccattg tcaaagatct tggttgtggg 21060
ccatattttt tgggcaccta tgacaagcgc tttccaggct ttgtttctcc acacaagctc 21120
gcctgcgcca tagtcaatac ggccggtcgc gagactgggg gcgtacactg gatggccttt 21180
gcctggaacc cgcactcaaa aacatgctac ctctttgagc cctttggctt ttctgaccag 21240
cgactcaagc aggtttacca gtttgagtac gagtcactcc tgcgccgtag cgccattgct 21300
tcttccccccg accgctgtat aacgctggaa aagtccaccc aaagcgtaca ggggcccaac 21360
tcggccgcct gtggactatt ctgctgcatg tttctccacg cctttgccaa ctggccccaa 21420
actcccatgg atcacaaccc caccatgaac cttattaccg gggtacccaa ctccatgctc 21480
aacagtcccc aggtacagcc caccctgcgt cgcaaccagg aacagctcta cagcttcctg 21540
gagcgccact cgccctactt ccgcagccac agtgcgcaga ttaggagcgc cacttctttt 21600
tgtcacttga aaaacatgta aaaataatgt actagagaca ctttcaataa aggcaaatgc 21660
ttttatttgt acactctcgg gtgattattt acccccaccc ttgccgtctg cgccgtttaa 21720
aaatcaaagg ggttctgccg cgcatcgcta tgcgccactg gcagggacac gttgcgatac 21780
tggtgtttag tgctccactt aaactcaggc acaaccatcc gcggcagctc ggtgaagttt 21840
tcactccaca ggctgcgcac catcaccaac gcgtttagca ggtcgggcgc cgatatcttg 21900
aagtcgcagt tggggcctcc gccctgcgcg cgcgagttgc gatacacagg gttgcagcac 21960
tggaacacta tcagcgccgg gtggtgcacg ctggccagca cgctcttgtc ggagatcaga 22020
tccgcgtcca ggtcctccgc gttgctcagg gcgaacggag tcaactttgg tagctgcctt 22080
cccaaaaagg gcgcgtgccc aggctttgag ttgcactcgc accgtagtgg catcaaaagg 22140
tgaccgtgcc cggtctgggc gttaggatac agcgcctgca taaaagcctt gatctgctta 22200
aaagccacct gagcctttgc gccttcagag aagaacatgc cgcaagactt gccggaaaac 22260
tgattggccg gacaggccgc gtcgtgcacg cagcaccttg cgtcggtgtt ggagatctgc 22320
accacatttc ggccccaccg gttcttcacg atcttggcct tgctagactg ctccttcagc 22380
gcgcgctgcc cgttttcgct cgtcacatcc atttcaatca cgtgctcctt atttatcata 22440
atgcttccgt gtagacactt aagctcgcct tcgatctcag cgcagcggtg cagccacaac 22500
gcgcagcccg tgggctcgtg atgcttgtag gtcacctctg caaacgactg caggtacgcc 22560
tgcaggaatc gccccatcat cgtcacaaag gtcttgttgc tggtgaaggt cagctgcaac 22620
ccgcggtgct cctcgttcag ccaggtcttg catacggccg ccagagcttc cacttggtca 22680
ggcagtagtt tgaagttcgc ctttagatcg ttatccacgt ggtacttgtc catcagcgcg 22740
cgcgcagcct ccatgccctt ctcccacgca gacacgatcg gcacactcag cgggttcatc 22800
accgtaattt cactttccgc ttcgctgggc tcttcctctt cctcttgcgt ccgcatacca 22860
cgcgccactg ggtcgtcttc attcagccgc cgcactgtgc gcttacctcc tttgccatgc 22920
ttgattagca ccggtgggtt gctgaaaccc accatttgta gcgccacatc ttctctttct 22980

-continued

```
tcctcgctgt ccacgattac ctctggtgat ggcgggcgct cgggcttggg agaagggcgc  23040
ttctttttct tcttgggcgc aatggccaaa tccgccgccg aggtcgatgg ccgcgggctg  23100
ggtgtgcgcg gcaccagcgc gtcttgtgat gagtcttcct cgtcctcgga ctcgatacgc  23160
cgcctcatcc gctttttgg gggcgcccgg ggaggcggcg gcgacgggga cggggacgac  23220
acgtcctcca tggttggggg acgtcgcgcc gcaccgcgtc cgcgctcggg ggtggtttcg  23280
cgctgctcct cttcccgact ggccatttcc ttctcctata ggcagaaaaa gatcatggag  23340
tcagtcgaga agaaggacag cctaaccgcc ccctctgagt tcgccaccac cgcctccacc  23400
gatgccgcca acgcgcctac caccttcccc gtcgaggcac ccccgcttga ggaggaggaa  23460
gtgattatcg agcaggaccc aggttttgta agcgaagacg acgaggaccg ctcagtacca  23520
acagaggata aaaagcaaga ccaggacaac gcagaggcaa acgaggaaca agtcgggcgg  23580
ggggacgaaa ggcatggcga ctacctagat gtgggagacg acgtgctgtt gaagcatctg  23640
cagcgccagt gcgccattat ctgcgacgcg ttgcaagagc gcagcgatgt gcccctcgcc  23700
atagcggatg tcagccttgc ctacgaacgc cacctattct caccgcgcgt acccccaaa  23760
cgccaagaaa acggcacatg cgagcccaac ccgcgcctca acttctaccc cgtatttgcc  23820
gtgccagagg tgcttgccac ctatcacatc tttttccaaa actgcaagat acccctatcc  23880
tgccgtgcca accgcagccg agcggacaag cagctggcct tgcggcaggg cgctgtcata  23940
cctgatatcg cctcgctcaa cgaagtgcca aaaatctttg agggtcttgg acgcgacgag  24000
aagcgcgcgg caaacgctct gcaacaggaa aacagcgaaa atgaaagtca ctctggagtg  24060
ttggtggaac tcgagggtga caacgcgcgc ctagccgtac taaaacgcag catcgaggtc  24120
acccactttg cctacccggc acttaaccta ccccccaagg tcatgagcac agtcatgagt  24180
gagctgatcg tgcgccgtgc gcagcccctg gagagggatg caaatttgca agaacaaaca  24240
gaggagggcc tacccgcagt tggcgacgag cagctagcgc gctggcttca aacgcgcgag  24300
cctgccgact tggaggagcg acgcaaacta atgatggccg cagtgctcgt taccgtggag  24360
cttgagtgca tgcagcggtt ctttgctgac ccggagatgc agcgcaagct agaggaaaca  24420
ttgcactaca cctttcgaca gggctacgta cgccaggcct gcaagatctc caacgtggag  24480
ctctgcaacc tggtctccta ccttggaatt ttgcacgaaa accgccttgg gcaaaacgtg  24540
cttcattcca cgctcaaggg cgaggcgcgc cgcgactacg tccgcgactg cgtttactta  24600
tttctatgct acacctggca gacggccatg ggcgtttggc agcagtgctt ggaggagtgc  24660
aacctcaagg agctgcagaa actgctaaag caaaacttga aggacctatg gacggccttc  24720
aacgagcgct ccgtggccgc gcacctggcg gacatcattt tccccgaacg cctgcttaaa  24780
accctgcaac agggtctgcc agacttcacc agtcaaagca tgttgcagaa ctttaggaac  24840
tttatcctag agcgctcagg aatcttgccc gccacctgct gtgcacttcc tagcgacttt  24900
gtgcccatta agtaccgcga atgccctccg ccgctttggg gccactgcta ccttctgcag  24960
ctagccaact accttgccta ccactctgac ataatggaag acgtgagcgg tgacggtcta  25020
ctggagtgtc actgtcgctg caacctatgc accccgcacc gctccctggt ttgcaattcg  25080
cagctgctta acgaaagtca aattatcggt acctttgagc tgcagggtcc ctcgcctgac  25140
gaaaagtccg cggctccggg gttgaaactc actccggggc tgtggacgtc ggcttacctt  25200
cgcaaatttg tacctgagga ctaccacgcc cacgagatta ggttctacga agaccaatcc  25260
cgcccgccta atgcggagct taccgcctgc gtcattaccc agggccacat tcttggccaa  25320
```

```
ttgcaagcca tcaacaaagc ccgccaagag tttctgctac gaaagggacg gggggtttac  25380
ttggacccccc agtccggcga ggagctcaac ccaatccccc cgccgccgca gccctatcag  25440
cagcagccgc gggcccttgc ttcccaggat ggcacccaaa aagaagctgc agctgccgcc  25500
gccacccacg gacgaggagg aatactggga cagtcaggca gaggaggttt tggacgagga  25560
ggaggaggac atgatggaag actgggagag cctagacgag gaagcttccg aggtcgaaga  25620
ggtgtcagac gaaacaccgt caccctcggt cgcattcccc tcgccggcgc cccagaaatc  25680
ggcaaccggt tccagcatgg ctacaacctc cgctcctcag gcgccgccgg cactgcccgt  25740
tcgccgaccc aaccgtagat gggacaccac tggaaccagg gccggtaagt ccaagcagcc  25800
gccgccgtta gcccaagagc aacaacagcg ccaaggctac cgctcatggc gcgggcacaa  25860
gaacgccata gttgcttgct tgcaagactg tgggggcaac atctccttcg cccgccgctt  25920
tcttctctac catcacggcg tggccttccc ccgtaacatc ctgcattact accgtcatct  25980
ctacagccca tactgcaccg gcggcagcgg cagcaacagc agcggccaca cagaagcaaa  26040
ggcgaccgga tagcaagact ctgacaaagc ccaagaaatc cacagcggcg gcagcagcag  26100
gaggaggagc gctgcgtctg gcgcccaacg aacccgtatc gacccgcgag cttagaaaca  26160
ggatttttcc cactctgtat gctatatttc aacagagcag gggccaagaa caagagctga  26220
aaataaaaaa caggtctctg cgatccctca cccgcagctg cctgtatcac aaaagcgaag  26280
atcagcttcg gcgcacgctg gaagacgcgg aggctctctt cagtaaatac tgcgcgctga  26340
ctcttaagga ctagtttcgc gccctttctc aaatttaagc gcgaaaacta cgtcatctcc  26400
agcggccaca cccggcgcca gcacctgttg tcagcgccat tatgagcaag gaaattccca  26460
cgccctacat gtggagttac cagccacaaa tgggacttgc ggctggagct gcccaagact  26520
actcaacccg aataaactac atgagcgcgg gaccccacat gatatcccgg gtcaacggaa  26580
tacgcgccca ccgaaaccga attctcctgg aacaggcggc tattaccacc acacctcgta  26640
ataaccttaa tccccgtagt tggcccgctg ccctggtgta ccaggaaagt cccgctccca  26700
ccactgtggt acttcccaga gacgcccagg ccgaagttca gatgactaac tcaggggcgc  26760
agcttgcggg cggctttcgt cacagggtgc ggtcgcccgg gcagggtata actcacctga  26820
caatcagagg gcgaggtatt cagctcaacg acgagtcggt gagctcctcg cttggtctcc  26880
gtccggacgg gacatttcag atcggcggcg ccggccgctc ttcattcacg cctcgtcagg  26940
caatcctaac tctgcagacc tcgtcctctg agccgcgctc tggaggcatt ggaactctgc  27000
aatttattga ggagtttgtg ccatcggtct actttaaccc cttctcggga cctcccggcc  27060
actatccgga tcaatttatt cctaactttg acgcggtaaa ggactcggcg gacggctacg  27120
actgaatgtt aagtggagag gcagagcaac tgcgcctgaa acacctggtc cactgtcgcc  27180
gccacaagtg ctttgcccgc gactccggtg agttttgcta ctttgaattg cccgaggatc  27240
atatcgaggg cccggcgcac ggcgtccggc ttaccgccca gggagagctt gcccgtagcc  27300
tgattcggga gtttacccag cgccccctgc tagttgagcg ggacagggga ccctgtgttc  27360
tcactgtgat ttgcaactgt cctaaccctg gattacatca agatctttgt tgccatctct  27420
gtgctgagta taataaatac agaaattaaa atatactggg gctcctatcg ccatcctgta  27480
aacgccaccg tcttcacccg cccaagcaaa ccaaggcgaa ccttacctgg tacttttaac  27540
atctctccct ctgtgattta caacagtttc aacccagacg gagtgagtct acgagagaac  27600
ctctccgagc tcagctactc catcagaaaa aacaccaccc tccttacctg ccgggaacgt  27660
acgagtgcgt caccggccgc tgcaccacac ctaccgcctg accgtaaacc agactttttc  27720
```

```
cggacagacc tcaataactc tgtttaccag aacaggaggt gagcttagaa aacccttagg  27780
gtattaggcc aaaggcgcag ctactgtggg gtttatgaac aattcaagca actctacggg  27840
ctattctaat tcaggtttct ctagaatcgg ggttggggtt attctctgtc ttgtgattct  27900
ctttattctt atactaacgc ttctctgcct aaggctcgcc gcctgctgtg tgcacatttg  27960
catttattgt cagcttttta aacgctgggg tcgccaccca agatgattag gtacataatc  28020
ctaggtttac tcacccttgc gtcagcccac ggtaccaccc aaaaggtgga ttttaaggag  28080
ccagcctgta atgttacatt cgcagctgaa gctaatgagt gcaccactct tataaaatgc  28140
accacagaac atgaaaagct gcttattcgc cacaaaaaca aaattggcaa gtatgctgtt  28200
tatgctattt ggcagccagg tgacactaca gagtataatg ttacagtttt ccagggtaaa  28260
agtcataaaa cttttatgta tacttttcca ttttatgaaa tgtgcgacat taccatgtac  28320
atgagcaaac agtataagtt gtggccccca caaaattgtg tggaaaacac tggcactttc  28380
tgctgcactg ctatgctaat tacagtgctc gctttggtct gtaccctact ctatattaaa  28440
tacaaaagca gacgcagctt tattgaggaa aagaaaatgc cttaatttac taagttacaa  28500
agctaatgtc accactaact gctttactcg ctgcttgcaa aacaaattca aaaagttagc  28560
attataatta gaataggatt taaacccccc ggtcatttcc tgctcaatac cattcccctg  28620
aacaattgac tctatgtggg atatgctcca gcgctacaac cttgaagtca ggcttcctgg  28680
atgtcagcat ctgactttgg ccagcacctg tcccgcggat ttgttccagt ccaactacag  28740
cgacccaccc taacagagat gaccaacaca accaacgcgg ccgccgctac cggacttaca  28800
tctaccacaa atacacccca agtttctgcc tttgtcaata actgggataa cttgggcatg  28860
tggtggttct ccatagcgct tatgtttgta tgccttatta ttatgtggct catctgctgc  28920
ctaaagcgca aacgcgcccg accacccatc tatagtccca tcattgtgct acacccaaac  28980
aatgatggaa tccatagatt ggacggactg aaacacatgt tcttttctct tacagtatga  29040
ttaaatgaga catgattcct cgagttttta tattactgac ccttgttgcg cttttttgt   29100
gcgtgctcca cattggctgc ggtttctcac atcgaagtag actgcattcc agccttcaca  29160
gtctatttgc tttacggatt tgtcaccctc acgctcatct gcagcctcat cactgtggtc  29220
atcgccttta tccagtgcat tgactgggtc tgtgtgcgct ttgcatatct cagacaccat  29280
ccccagtaca gggacaggac tatagctgag cttcttagaa ttctttaatt atgaaattta  29340
ctgtgacttt tctgctgatt atttgcaccc tatctgcgtt ttgttccccg acctccaagc  29400
ctcaaagaca tatatcatgc agattcactc gtatatggaa tattccaagt tgctacaatg  29460
aaaaaagcga tctttccgaa gcctggttat atgcaatcat ctctgttatg gtgttctgca  29520
gtaccatctt agccctagct atatatccct accttgacat tggctggaac gcaatagatg  29580
ccatgaacca cccaactttc cccgcgcccg ctatgcttcc actgcaacaa gttgttgccg  29640
gcggctttgt cccagccaat cagcctcgcc caccttctcc cacccccact gaaatcagct  29700
actttaatct aacaggagga gatgactgac accctagatc tagaaatgga cggaattatt  29760
acagagcagc gcctgctaga aagacgcagg gcagcggccg agcaacagcg catgaatcaa  29820
gagctccaag acatggttaa cttgcaccag tgcaaaaggg gtatcttttg tctggtaaag  29880
caggccaaag tcacctacga cagtaatacc accggacacc gccttagcta caagttgcca  29940
accaagcgtc agaaattggt ggtcatggtg ggagaaaagc ccattaccat aactcagcac  30000
tcggtagaaa ccgaaggctg cattcactca ccttgtcaag gacctgagga tctctgcacc  30060
```

-continued

```
cttattaaga ccctgtgcgg tctcaaagat cttattccct ttaactaata aaaaaaaata  30120
ataaagcatc acttacttaa aatcagttag caaatttctg tccagtttat tcagcagcac  30180
ctccttgccc tcctcccagc tctggtattg cagcttcctc ctggctgcaa actttctcca  30240
caatctaaat ggaatgtcag tttcctcctg ttcctgtcca tccgcaccca ctatcttcat  30300
gttgttgcag atgaagcgcg caagaccgtc tgaagatacc ttcaaccccg tgtatccata  30360
tgacacggaa accggtcctc caactgtgcc ttttcttact cctccctttg tatcccccaa  30420
tgggtttcaa gagagtcccc ctggggtact ctctttgcgc ctatccgaac ctctagttac  30480
ctccaatggc atgcttgcgc tcaaaatggg caacggcctc tctctggacg aggccggcaa  30540
ccttacctcc caaaatgtaa ccactgtgag cccacctctc aaaaaaacca agtcaaacat  30600
aaacctggaa atatctgcac ccctcacagt tacctcagaa gccctaactg tggctgccgc  30660
cgcacctcta atggtcgcgg gcaacacact caccatgcaa tcacaggccc cgctaaccgt  30720
gcacgactcc aaacttagca ttgccaccca aggacccctc acagtgtcag aaggaaagct  30780
agccctgcaa acatcaggcc ccctcaccac caccgatagc agtaccctta ctatcactgc  30840
ctcacccccct ctaactactg ccactggtag cttgggcatt gacttgaaag agcccattta  30900
tacacaaaat ggaaaactag gactaaagta cggggctcct ttgcatgtaa cagacgacct  30960
aaacactttg accgtagcaa ctggtccagg tgtgactatt aataatactt ccttgcaaac  31020
taaagttact ggagccttgg gttttgattc acaaggcaat atgcaactta atgtagcagg  31080
aggactaagg attgattctc aaaacagacg ccttatactt gatgttagtt atccgtttga  31140
tgctcaaaac caactaaatc taagactagg acagggccct ctttttataa actcagccca  31200
caacttggat attaactaca acaaaggcct ttacttgttt acagcttcaa acaattccaa  31260
aaagcttgag gttaacctaa gcactgccaa ggggttgatg tttgacgcta cagccatagc  31320
cattaatgca ggagatgggc ttgaatttgg ttcacctaat gcaccaaaca caaatcccct  31380
caaaacaaaa attggccatg gcctagaatt tgattcaaac aaggctatgg ttcctaaact  31440
aggaactggc cttagttttg acagcacagg tgccattaca gtaggaaaca aaaataatga  31500
taagctaact ttgtggacca caccagctcc atctcctaac tgtagactaa atgcagagaa  31560
agatgctaaa ctcactttgg tcttaacaaa atgtggcagt caaatacttg ctacagtttc  31620
agttttggct gttaaaggca gtttggctcc aatatctgga acagttcaaa gtgctcatct  31680
tattataaga tttgacgaaa atggagtgct actaaacaat tccttcctgg acccagaata  31740
ttggaacttt agaaatggag atcttactga aggcacagcc tatacaaacg ctgttggatt  31800
tatgcctaac ctatcagctt atccaaaatc tcacggtaaa actgccaaaa gtaacattgt  31860
cagtcaagtt tacttaaacg gagacaaaac taaacctgta acactaacca ttacactaaa  31920
cggtacacag gaaacaggag acacaactcc aagtgcatac tctatgtcat tttcatggga  31980
ctggtctggc cacaactaca ttaatgaaat atttgccaca tcctcttaca ctttttcata  32040
cattgcccaa gaataaagaa tcgtttgtgt tatgtttcaa cgtgtttatt tttcaattgc  32100
agaaaatttc aagtcatttt tcattcagta gtatagcccc accaccacat agcttataca  32160
gatcaccgta ccttaatcaa actcacagaa ccctagtatt caacctgcca cctccctccc  32220
aacacacaga gtacacagtc ctttctcccc ggctggcctt aaaaagcatc atatcatggg  32280
taacagacat attcttaggt gttatattcc acacggtttc ctgtcgagcc aaacgctcat  32340
cagtgatatt aataaactcc ccgggcagct cacttaagtt catgtcgctg tccagctgct  32400
gagccacagg ctgctgtcca acttgcggtt gcttaacggg cggcgaagga gaagtccacg  32460
```

```
cctacatggg ggtagagtca taatcgtgca tcaggatagg gcggtggtgc tgcagcagcg  32520
cgcgaataaa ctgctgccgc cgccgctccg tcctgcagga atacaacatg gcagtggtct  32580
cctcagcgat gattcgcacc gcccgcagca taaggcgcct tgtcctccgg gcacagcagc  32640
gcaccctgat ctcacttaaa tcagcacagt aactgcagca cagcaccaca atattgttca  32700
aaatcccaca gtgcaaggcg ctgtatccaa agctcatggc ggggaccaca gaacccacgt  32760
ggccatcata ccacaagcgc aggtagatta agtggcgacc cctcataaac acgctggaca  32820
taaacattac ctcttttggc atgttgtaat tcaccacctc ccggtaccat ataaacctct  32880
gattaaacat ggcgccatcc accaccatcc taaaccagct ggccaaaacc tgcccgccgg  32940
ctatacactg cagggaaccg ggactggaac aatgacagtg gagagcccag gactcgtaac  33000
catggatcat catgctcgtc atgatatcaa tgttggcaca acacaggcac acgtgcatac  33060
acttcctcag gattacaagc tcctcccgcg ttagaaccat atcccaggga acaacccatt  33120
cctgaatcag cgtaaatccc acactgcagg gaagacctcg cacgtaactc acgttgtgca  33180
ttgtcaaagt gttacattcg ggcagcagcg gatgatcctc cagtatggta gcgcgggttt  33240
ctgtctcaaa aggaggtaga cgatccctac tgtacggagt gcgccgagac aaccgagatc  33300
gtgttggtcg tagtgtcatg ccaaatggaa cgccggacgt agtcatattt cctgaagcaa  33360
aaccaggtgc gggcgtgaca aacagatctg cgtctccggt ctcgccgctt agatcgctct  33420
gtgtagtagt tgtagtatat ccactctctc aaagcatcca ggcgccccct ggcttcgggt  33480
tctatgtaaa ctccttcatg cgccgctgcc ctgataacat ccaccaccgc agaataagcc  33540
acacccagcc aacctacaca ttcgttctgc gagtcacaca cgggaggagc gggaagagct  33600
ggaagaacca tgtttttttt tttattccaa aagattatcc aaaacctcaa aatgaagatc  33660
tattaagtga acgcgctccc ctccggtggc gtggtcaaac tctacagcca aagaacagat  33720
aatggcattt gtaagatgtt gcacaatggc ttccaaaagg caaacggccc tcacgtccaa  33780
gtggacgtaa aggctaaacc cttcagggtg aatctcctct ataaacattc cagcaccttc  33840
aaccatgccc aaataattct catctcgcca ccttctcaat atatctctaa gcaaatcccg  33900
aatattaagt ccggccattg taaaaatctg ctccagagcg ccctccacct tcagcctcaa  33960
gcagcgaatc atgattgcaa aaattcaggt tcctcacaga cctgtataag attcaaaagc  34020
ggaacattaa caaaaatacc gcgatcccgt aggtcccttc gcagggccag ctgaacataa  34080
tcgtgcaggt ctgcacggac cagcgcggcc acttccccgc caggaaccat gacaaaagaa  34140
cccacactga ttatgacacg catactcgga gctatgctaa ccagcgtagc cccgatgtaa  34200
gcttgttgca tgggcggcga tataaaatgc aaggtgctgc tcaaaaaatc aggcaaagcc  34260
tcgcgcaaaa aagaaagcac atcgtagtca tgctcatgca gataaaggca ggtaagctcc  34320
ggaaccacca cagaaaaaga caccattttt ctctcaaaca tgtctgcggg tttctgcata  34380
aacacaaaat aaaataacaa aaaaacattt aaacattaga agcctgtctt acaacaggaa  34440
aaacaaccct tataagcata agacggacta cggccatgcc ggcgtgaccg taaaaaaact  34500
ggtcaccgtg attaaaaagc accaccgaca gctcctcggt catgtccgga gtcataatgt  34560
aagactcggt aaacacatca ggttgattca catcggtcag tgctaaaaag cgaccgaaat  34620
agcccggggg aatacatacc cgcaggcgta gagacaacat tacagccccc ataggaggta  34680
taacaaaatt aataggagag aaaaacacat aaacacctga aaaaccctcc tgcctaggca  34740
aaatagcacc ctcccgctcc agaacaacat acagcgcttc cacagcggca gccataacag  34800
```

tcagccttac cagtaaaaaa gaaaacctat taaaaaaaca ccactcgaca cggcaccagc 34860
tcaatcagtc acagtgtaaa aaagggccaa gtgcagagcg agtatatata ggactaaaaa 34920
atgacgtaac ggttaaagtc cacaaaaaac acccagaaaa ccgcacgcga acctacgccc 34980
agaaacgaaa gccaaaaaac ccacaacttc ctcaaatcgt cacttccgtt ttcccacgtt 35040
acgtcacttc ccattttaag aaaactacaa ttcccaacac atacaagtta ctccgcccta 35100
aaacctacgt cacccgcccc gttcccacgc cccgcgccac gtcacaaact ccaccccctc 35160
attatcatat tggcttcaat ccaaaataag gtatattatt gat 35203

<210> SEQ ID NO 11
<211> LENGTH: 33093
<212> TYPE: DNA
<213> ORGANISM: Artificial sequence
<220> FEATURE:
<223> OTHER INFORMATION: Empty Ad5 vector sequence (repeats included)

<400> SEQUENCE: 11
catcatcaat aatatacctt attttggatt gaagccaata tgataatgag ggggtggagt 60
ttgtgacgtg gcgcggggcg tgggaacggg gcgggtgacg tagtagtgtg gcggaagtgt 120
gatgttgcaa gtgtggcgga acacatgtaa gcgacggatg tggcaaaagt gacgtttttg 180
gtgtgcgccg gtgtacacag gaagtgacaa ttttcgcgcg gttttaggcg gatgttgtag 240
taaatttggg cgtaaccgag taagatttgg ccattttcgc gggaaaactg aataagagga 300
agtgaaatct gaataatttt gtgttactca tagcgcgtaa tatttgtcta gggccgcggg 360
gactttgacc gtttacgtgg agactcgccc aggtgttttt ctcaggtgtt ttccgcgttc 420
cgggtcaaag ttggcgtttt attattatag tcagtacgtc tcgagcatgc atctaggcgg 480
ccgcatggca gaaattcgcg aattcgctag cgttaacgga tcctctagac gagatccgaa 540
cttgtttatt gcagcttata atggttacaa ataaagcaat agcatcacaa atttcacaaa 600
taaagcattt ttttcactgc attctagttg tggtttgtcc aaactcatca atgtatctta 660
tcatgtctag atctgtactg aaatgtgtgg gcgtggctta agggtgggaa agaatatata 720
aggtgggggt cttatgtagt tttgtatctg ttttgcagca gccgccgccg ccatgagcac 780
caactcgttt gatggaagca ttgtgagctc atatttgaca acgcgcatgc ccccatgggc 840
cggggtgcgt cagaatgtga tgggctccag cattgatggt cgccccgtcc tgcccgcaaa 900
ctctactacc ttgacctacg agaccgtgtc tggaacgccg ttggagactg cagcctccgc 960
cgccgcttca gccgctgcag ccaccgcccg cgggattgtg actgactttg ctttcctgag 1020
cccgcttgca agcagtgcag cttcccgttc atccgcccgc gatgacaagt tgacggctct 1080
tttggcacaa ttggattctt tgacccggga acttaatgtc gtttctcagc agctgttgga 1140
tctgcgccag caggtttctg ccctgaaggc ttcctcccct cccaatgcgg tttaaaacat 1200
aaataaaaaa ccagactctg tttggatttg gatcaagcaa gtgtcttgct gtctttattt 1260
aggggttttg cgcgcgcggt aggcccggga ccagcggtct cggtcgttga gggtcctgtg 1320 tatttttcc aggacgtggt aaaggtgact ctggatgttc agatacatgg gcataagccc 1380
gtctctgggg tggaggtagc accactgcag agcttcatgc tgcggggtgg tgttgtagat 1440
gatccagtcg tagcaggagc gctgggcgtg gtgcctaaaa atgtctttca gtagcaagct 1500
gattgccagg ggcaggccct tggtgtaagt gtttacaaag cggttaagct gggatgggtg 1560
catacgtggg gatatgagat gcatcttgga ctgtattttt aggttggcta tgttcccagc 1620
catatccctc cggggattca tgttgtgcag aaccaccagc acagtgtatc cggtgcactt 1680

-continued

```
gggaaatttg tcatgtagct tagaaggaaa tgcgtggaag aacttggaga cgcccttgtg   1740
acctccaaga ttttccatgc attcgtccat aatgatggca atgggcccac gggcggcggc   1800
ctgggcgaag atatttctgg gatcactaac gtcatagttg tgttccagga tgagatcgtc   1860
ataggccatt tttacaaagc gcgggcggag ggtgccagac tgcggtataa tggttccatc   1920
cggcccaggg gcgtagttac cctcacagat ttgcatttcc cacgctttga gttcagatgg   1980
ggggatcatg tctacctgcg gggcgatgaa gaaaacggtt tccggggtag gggagatcag   2040
ctgggaagaa agcaggttcc tgagcagctg cgacttaccg cagccggtgg gcccgtaaat   2100
cacacctatt accggctgca actggtagtt aagagagctg cagctgccgt catccctgag   2160
caggggggcc acttcgttaa gcatgtccct gactcgcatg ttttccctga ccaaatccgc   2220
cagaaggcgc tcgccgccca gcgatagcag ttcttgcaag gaagcaaagt ttttcaacgg   2280
tttgagaccg tccgccgtag gcatgctttt gagcgtttga ccaagcagtt ccaggcggtc   2340
ccacagctcg gtcacctgct ctacggcatc tcgatccagc atatctcctc gtttcgcggg   2400
ttggggcggc tttcgctgta cggcagtagt cggtgctcgt ccagacgggc cagggtcatg   2460
tctttccacg ggcgcagggt cctcgtcagc gtagtctggg tcacggtgaa ggggtgcgct   2520
ccgggctgcg cgctggccag ggtgcgcttg aggctggtcc tgctggtgct gaagcgctgc   2580
cggtcttcgc cctgcgcgtc ggccaggtag catttgacca tggtgtcata gtccagcccc   2640
tccgcggcgt ggcccttggc gcgcagcttg cccttggagg aggcgccgca cgaggggcag   2700
tgcagacttt tgagggcgta gagcttgggc gcgagaaata ccgattccgg ggagtaggca   2760
tccgcgccgc aggccccgca gacggtctcg cattccacga gccaggtgag ctctggccgt   2820
tcggggtcaa aaaccaggtt tcccccatgc tttttgatgc gtttcttacc tctggtttcc   2880
atgagccggt gtccacgctc ggtgacgaaa aggctgtccg tgtccccgta tacagacttg   2940
agaggcctgt cctcgagcgg tgttccgcgg tcctcctcgt atagaaactc ggaccactct   3000
gagacaaagg ctcgcgtcca ggccagcacg aaggaggcta agtgggaggg gtagcggtcg   3060
ttgtccacta gggggtccac tcgctccagg gtgtgaagac acatgtcgcc ctcttcggca   3120
tcaaggaagg tgattggttt gtaggtgtag gccacgtgac cgggtgttcc tgaagggggg   3180
ctataaaagg gggtgggggc gcgttcgtcc tcactctctt ccgcatcgct gtctgcgagg   3240
gccagctgtt ggggtgagta ctccctctga aaagcgggca tgacttctgc gctaagattg   3300
tcagtttcca aaaacgagga ggatttgata ttcacctggc ccgcggtgat gcctttgagg   3360
gtggccgcat ccatctggtc agaaaagaca atctttttgt tgtcaagctt ggtggcaaac   3420
gacccgtaga gggcgttgga cagcaacttg gcgatggagc gcagggtttg gtttttgtcg   3480
cgatcggcgc gctccttggc cgcgatgttt agctgcacgt attcgcgcgc aacgcaccgc   3540
cattcgggaa agacggtggt gcgctcgtcg ggcaccaggt gcacgcgcca accgcggttg   3600
tgcagggtga caaggtcaac gctggtggct acctctccgc gtaggcgctc gttggtccag   3660
cagaggcggc cgcccttgcg cgagcagaat ggcggtaggg ggtctagctg cgtctcgtcc   3720
ggggggtctg cgtccacggt aaagaccccg ggcagcaggc gcgcgtcgaa gtagtctatc   3780
ttgcatcctt gcaagtctag cgcctgctgc catgcgcggg cggcaagcgc gcgctcgtat   3840
gggttgagtg gggaccccca tggcatgggg tgggtgagcg cggaggcgta catgccgcaa   3900
atgtcgtaaa cgtagagggg ctctctgagt attccaagat atgtagggta gcatcttcca   3960
ccgcggatgc tggcgcgcac gtaatcgtat agttcgtgcg agggagcgag gaggtcggga   4020
```

```
ccgaggttgc tacgggcggg ctgctctgct cggaagacta tctgcctgaa gatggcatgt   4080
gagttggatg atatggttgg acgctggaag acgttgaagc tggcgtctgt gagacctacc   4140
gcgtcacgca cgaaggaggc gtaggagtcg cgcagcttgt tgaccagctc ggcggtgacc   4200
tgcacgtcta gggcgcagta gtccagggtt tccttgatga tgtcatactt atcctgtccc   4260
ttttttttcc acagctcgcg gttgaggaca aactcttcgc ggtctttcca gtactcttgg   4320
atcggaaacc cgtcggcctc cgaacggtaa gagcctagca tgtagaactg gttgacggcc   4380
tggtaggcgc agcatccctt ttctacgggt agcgcgtatg cctgcgcggc cttccggagc   4440
gaggtgtggg tgagcgcaaa ggtgtccctg accatgactt tgaggtactg gtatttgaag   4500
tcagtgtcgt cgcatccgcc ctgctcccag agcaaaaagt ccgtgcgctt tttggaacgc   4560
ggatttggca gggcgaaggt gacatcgttg aagagtatct ttcccgcgcg aggcataaag   4620
ttgcgtgtga tgcggaaggg tcccggcacc tcggaacggt tgttaattac ctgggcggcg   4680
agcacgatct cgtcaaagcc gttgatgttg tggcccacaa tgtaaagttc caagaagcgc   4740
gggatgccct tgatggaagg caattttta agttcctcgt aggtgagctc ttcaggggag   4800
ctgagcccgt gctctgaaag ggcccagtct gcaagatgag ggttggaagc gacgaatgag   4860
ctccacaggt cacgggccat tagcatttgc aggtggtcgc gaaaggtcct aaactggcga   4920
cctatggcca ttttttctgg ggtgatgcag tagaaggtaa gcgggtcttg ttcccagcgg   4980
tcccatccaa ggttcgcggc taggtctcgc gcggcagtca ctagaggctc atctccgccg   5040
aacttcatga ccagcatgaa gggcacgagc tgcttcccaa aggcccccat ccaagtatag   5100
gtctctacat cgtaggtgac aaagagacgc tcggtgcgag gatgcgagcc gatcgggaag   5160
aactggatct cccgccacca attggaggag tggctattga tgtggtgaaa gtagaagtcc   5220
ctgcgacggg ccgaacactc gtgctggctt ttgtaaaaac gtgcgcagta ctggcagcgg   5280
tgcacgggct gtacatcctg cacgaggttg acctgacgac cgcgcacaag gaagcagagt   5340
gggaatttga gcccctcgcc tggcgggttt ggctggtggt cttctacttc ggctgcttgt   5400
ccttgaccgt ctggctgctc gaggggagtt acggtggatc ggaccaccac gccgcgcgag   5460
cccaaagtcc agatgtccgc gcgcggcggt cggagcttga tgacaacatc gcgcagatgg   5520
gagctgtcca tggtctggag ctcccgcggc gtcaggtcag gcgggagctc ctgcaggttt   5580
acctcgcata gacgggtcag ggcgcgggct agatccaggt gatacctaat ttccaggggc   5640
tggttggtgg cggcgtcgat ggcttgcaag aggccgcatc cccgcggcgc gactacggta   5700
ccgcgcggcg ggcggtgggc cgcgggggtg tccttggatg atgcatctaa aagcggtgac   5760
gcgggcgagc cccggaggt agggggggct ccggacccgc cgggagaggg ggcaggggca   5820
cgtcggcgcc gcgcgcgggc aggagctggt gctgcgcgcg taggttgctg gcgaacgcga   5880
cgacgcggcg gttgatctcc tgaatctggc gcctctgcgt gaagacgacg ggcccggtga   5940
gcttgaacct gaaagagagt tcgacagaat caatttcggt gtcgttgacg gcggcctggc   6000
gcaaaatctc ctgcacgtct cctgagttgt cttgataggc gatctcggcc atgaactgct   6060
cgatctcttc ctcctggaga tctccgcgtc cggctcgctc cacggtggcg gcgaggtcgt   6120
tggaaatgcg ggccatgagc tgcgagaagg cgttgaggcc tccctcgttc cagacgcggc   6180
tgtagaccac gcccccttcg gcatcgcggg cgcgcatgac cacctgcgcg agattgagct   6240
ccacgtgccg ggcgaagacg gcgtagtttc gcaggcgctg aaagaggtag ttgagggtgg   6300
tggcggtgtg ttctgccacg aagaagtaca taacccagcg tcgcaacgtg gattcgttga   6360
tatcccccaa ggcctcaagg cgctccatgg cctcgtagaa gtccacggcg aagttgaaaa   6420
```

-continued

```
actgggagtt gcgcgccgac acggttaact cctcctccag aagacggatg agctcggcga   6480
cagtgtcgcg cacctcgcgc tcaaaggcta caggggcctc ttcttcttct tcaatctcct   6540
cttccataag ggcctcccct tcttcttctt ctggcggcgg tgggggaggg gggacacggc   6600
ggcgacgacg gcgcaccggg aggcggtcga caaagcgctc gatcatctcc ccgcggcgac   6660
ggcgcatggt ctcggtgacg gcgcggccgt tctcgcgggg gcgcagttgg aagacgccgc   6720
ccgtcatgtc ccggttatgg gttggcgggg ggctgccatg cggcagggat acggcgctaa   6780
cgatgcatct caacaattgt tgtgtaggta ctccgccgcc gagggacctg agcgagtccg   6840
catcgaccgg atcggaaaac ctctcgagaa aggcgtctaa ccagtcacag tcgcaaggta   6900
ggctgagcac cgtggcgggc ggcagcgggc ggcggtcggg gttgtttctg gcggaggtgc   6960
tgctgatgat gtaattaaag taggcggtct tgagacggcg gatggtcgac agaagcacca   7020
tgtccttggg tccggcctgc tgaatgcgca ggcggtcggc catgccccag gcttcgtttt   7080
gacatcggcg caggtctttg tagtagtctt gcatgagcct ttctaccggc acttcttctt   7140
ctccttcctc ttgtcctgca tctcttgcat ctatcgctgc ggcggcggcg gagtttggcc   7200
gtaggtggcg ccctcttcct cccatgcgtg tgaccccgaa gcccctcatc ggctgaagca   7260
gggctaggtc ggcgacaacg cgctcggcta atatggcctg ctgcacctgc gtgagggtag   7320
actggaagtc atccatgtcc acaaagcggt ggtatgcgcc cgtgttgatg gtgtaagtgc   7380
agttggccat aacggaccag ttaacggtct ggtgacccgg ctgcgagagc tcggtgtacc   7440
tgagacgcga gtaagccctc gagtcaaata cgtagtcgtt gcaagtccgc accaggtact   7500
ggtatcccac caaaaagtgc ggcggcggct ggcggtagag gggccagcgt agggtggccg   7560
gggctccggg ggcgagatct tccaacataa ggcgatgata tccgtagatg tacctggaca   7620
tccaggtgat gccggcggcg gtggtggagg cgcgcggaaa gtcgcggacg cggttccaga   7680
tgttgcgcag cggcaaaaag tgctccatgg tcgggacgct ctggccggtc aggcgcgcgc   7740
aatcgttgac gctctagacc gtgcaaaagg agagcctgta agcgggcact cttccgtggt   7800
ctggtggata aattcgcaag ggtatcatgg cggacgaccg gggttcgagc cccgtatccg   7860
gccgtccgcc gtgatccatg cggttaccgc ccgcgtgtcg aacccaggtg tgcgacgtca   7920
gacaacgggg gagtgctcct tttggcttcc ttccaggcgc ggcggctgct gcgctagctt   7980
ttttggccac tggccgcgcg cagcgtaagc ggttaggctg gaaagcgaaa gcattaagtg   8040
gctcgctccc tgtagccgga gggttatttt ccaagggttg agtcgcggga cccccggttc   8100
gagtctcgga ccggccggac tgcggcgaac gggggtttgc ctccccgtca tgcaagaccc   8160
cgcttgcaaa ttcctccgga aacagggacg agcccctttt ttgcttttcc cagatgcatc   8220
cggtgctgcg gcagatgcgc ccccctcctc agcagcggca agagcaagag cagcggcaga   8280
catgcagggc accctcccct cctcctaccg cgtcaggagg ggcgacatcc gcggttgacg   8340
cggcagcaga tggtgattac gaaccccccgc ggcgccgggc ccggcactac ctggacttgg   8400
aggagggcga gggcctggcg cggctaggag cgccctctcc tgagcggcac ccaagggtgc   8460
agctgaagcg tgatacgcgt gaggcgtacg tgccgcggca gaacctgttt cgcgaccgcg   8520
agggagagga gcccgaggag atgcgggatc gaaagttcca cgcagggcgc gagctgcggc   8580
atggcctgaa tcgcgagcgg ttgctgcgcg aggaggactt tgagcccgac gcgcgaaccg   8640
ggattagtcc cgcgcgcgca cacgtggcgg ccgccgacct ggtaaccgca tacgagcaga   8700
cggtgaacca ggagattaac tttcaaaaaa gctttaacaa ccacgtgcgt acgcttgtgg   8760
```

-continued

```
cgcgcgagga ggtggctata ggactgatgc atctgtggga ctttgtaagc gcgctggagc   8820
aaaacccaaa tagcaagccg ctcatggcgc agctgttcct tatagtgcag cacagcaggg   8880
acaacgaggc attcagggat gcgctgctaa acatagtaga gcccgagggc cgctggctgc   8940
tcgatttgat aaacatcctg cagagcatag tggtgcagga gcgcagcttg agcctggctg   9000
acaaggtggc cgccatcaac tattccatgc ttagcctggg caagttttac gcccgcaaga   9060
tataccatac cccttacgtt cccatagaca aggaggtaaa gatcgagggg ttctacatgc   9120
gcatggcgct gaaggtgctt accttgagcg acgacctggg cgtttatcgc aacgagcgca   9180
tccacaaggc cgtgagcgtg agccggcggc gcgagctcag cgaccgcgag ctgatgcaca   9240
gcctgcaaag ggccctggct ggcacgggca gcggcgatag agaggccgag tcctactttg   9300
acgcgggcgc tgacctgcgc tgggccccaa gccgacgcgc cctggaggca gctggggccg   9360
gacctgggct ggcggtggca cccgcgcgcg ctggcaacgt cggcggcgtg gaggaatatg   9420
acgaggacga tgagtacgag ccagaggacg gcgagtacta agcggtgatg tttctgatca   9480
gatgatgcaa gacgcaacgg acccggcggt gcgggcggcg ctgcagagcc agccgtccgg   9540
ccttaactcc acggacgact ggcgccaggt catggaccgc atcatgtcgc tgactgcgcg   9600
caatcctgac gcgttccggc agcagccgca ggccaaccgg ctctccgcaa ttctggaagc   9660
ggtggtcccg gcgcgcgcaa accccacgca cgagaaggtg ctggcgatcg taaacgcgct   9720
ggccgaaaac agggccatcc ggcccgacga ggccggcctg gtctacgacg cgctgcttca   9780
gcgcgtggct cgttacaaca gcggcaacgt gcagaccaac ctggaccggc tggtgggga    9840
tgtgcgcgag gccgtggcgc agcgtgagcg cgcgcagcag cagggcaacc tgggctccat   9900
ggttgcacta aacgccttcc tgagtacaca gcccgccaac gtgccgcggg gacaggagga   9960
ctacaccaac tttgtgagcg cactgcggct aatggtgact gagacaccgc aaagtgaggt  10020
gtaccagtct gggccagact attttttcca gaccagtaga caaggcctgc agaccgtaaa  10080
cctgagccag gctttcaaaa acttgcaggg gctgtggggg gtgcgggctc ccacaggcga  10140
ccgcgcgacc gtgtctagct tgctgacgcc caactcgcgc ctgttgctgc tgctaatagc  10200
gcccttcacg gacagtggca gcgtgtcccg ggacacatac ctaggtcact tgctgacact  10260
gtaccgcgag gccataggtc aggcgcatgt ggacgagcat actttccagg agattacaag  10320
tgtcagccgc gcgctggggc aggaggacac gggcagcctg gaggcaaccc taaactacct  10380
gctgaccaac cggcggcaga agatcccctc gttgcacagt ttaaacagcg aggaggagcg  10440
cattttgcgc tacgtgcagc agagcgtgag ccttaacctg atgcgcgacg ggtaacgcc   10500
cagcgtggcg ctggacatga ccgcgcgcaa catggaaccg ggcatgtatg cctcaaaccg  10560
gccgtttatc aaccgcctaa tggactactt gcatcgcgcg gccgccgtga accccgagta  10620
tttcaccaat gccatcttga acccgcactg gctaccgccc cctggtttct acaccggggg  10680
attcgaggtg cccgagggta acgatggatt cctctgggac gacatagacg acagcgtgtt  10740
ttccccgcaa ccgcagaccc tgctagagtt gcaacagcgc gagcaggcag aggcggcgct  10800
gcgaaaggaa agcttccgca ggccaagcag cttgtccgat ctaggcgctg cggccccgcg  10860
gtcagatgct agtagcccat ttccaagctt gatagggtct cttaccagca ctcgcaccac  10920
ccgcccgcgc ctgctgggcg aggaggagta cctaaacaac tcgctgctgc agccgcagcg  10980
cgaaaaaaac ctgcctccgg catttcccaa caacgggata gagagcctag tggacaagat  11040
gagtagatgg aagacgtacg cgcaggagca cagggacgtg ccaggcccgc gcccgcccac  11100
ccgtcgtcaa aggcacgacc gtcagcgggg tctggtgtgg gaggacgatg actcggcaga  11160
```

cgacagcagc gtcctggatt tgggagggag tggcaacccg tttgcgcacc ttcgccccag 11220
gctggggaga atgttttaaa aaaaaaaaaa gcatgatgca aaataaaaaa ctcaccaagg 11280
ccatggcacc gagcgttggt tttcttgtat tccccttagt atgcggcgcg cggcgatgta 11340
tgaggaaggt cctcctccct cctacgagag tgtggtgagc gcggcgccag tggcggcggc 11400
gctgggttct cccttcgatg ctcccctgga cccgccgttt gtgcctccgc ggtacctgcg 11460
gcctaccggg gggagaaaca gcatccgtta ctctgagttg gcacccctat tcgacaccac 11520
ccgtgtgtac ctggtggaca acaagtcaac ggatgtggca tccctgaact accagaacga 11580
ccacagcaac tttctgacca cggtcattca aaacaatgac tacagcccgg gggaggcaag 11640
cacacagacc atcaatcttg acgaccggtc gcactggggc ggcgacctga aaaccatcct 11700
gcataccaac atgccaaatg tgaacgagtt catgtttacc aataagttta aggcgcgggt 11760
gatggtgtcg cgcttgccta ctaaggacaa tcaggtggag ctgaaatacg agtgggtgga 11820
gttcacgctg cccgagggca actactccga gaccatgacc atagacctta tgaacaacgc 11880
gatcgtggag cactacttga aagtgggcag acagaacggg gttctggaaa gcgacatcgg 11940
ggtaaagttt gacacccgca acttcagact ggggtttgac ccgtcactg gtcttgtcat 12000
gcctggggta tatacaaacg aagccttcca tccagacatc attttgctgc caggatgcgg 12060
ggtggacttc acccacagcc gcctgagcaa cttgttgggc atccgcaagc ggcaaccctt 12120
ccaggagggc tttaggatca cctacgatga tctggagggt ggtaacattc ccgcactgtt 12180
ggatgtggac gcctaccagg cgagcttgaa agatgacacc gaacagggcg ggggtggcgc 12240
aggcggcagc aacagcagtg gcagcggcgc ggaagagaac tccaacgcgg cagccgcggc 12300
aatgcagccg gtggaggaca tgaacgatca tgccattcgc ggcgacacct ttgccacacg 12360
ggctgaggag aagcgcgctg aggccgaagc agcggccgaa gctgccgccc ccgctgcgca 12420
acccgaggtc gagaagcctc agaagaaacc ggtgatcaaa cccctgacag aggacagcaa 12480
gaaacgcagt tacaacctaa taagcaatga cagcaccttc acccagtacc gcagctggta 12540
ccttgcatac aactacggcg accctcagac cggaatccgc tcatggaccc tgctttgcac 12600
tcctgacgta acctgcggct cggagcaggt ctactggtcg ttgccagaca tgatgcaaga 12660
ccccgtgacc ttccgctcca cgcgccagat cagcaacttt ccggtggtgg gcgccgagct 12720
gttgcccgtg cactccaaga gcttctacaa cgaccaggcc gtctactccc aactcatccg 12780
ccagtttacc tctctgaccc acgtgttcaa tcgctttccc gagaaccaga ttttggcgcg 12840
cccgccagcc cccaccatca ccaccgtcag tgaaaacgtt cctgctctca cagatcacgg 12900
gacgctaccg ctgcgcaaca gcatcggagg agtccagcga gtgaccatta ctgacgccag 12960
acgccgcacc tgcccctacg tttacaaggc cctgggcata gtctcgccgc gcgtcctatc 13020
gagccgcact ttttgagcaa gcatgtccat ccttatatcg cccagcaata acacaggctg 13080
gggcctgcgc ttcccaagca agatgtttgg cggggccaag aagcgctccg accaacaccc 13140
agtgcgcgtg cgcgggcact accgcgcgcc ctggggcgcg cacaaacgcg gccgcactgg 13200
gcgcaccacc gtcgatgacg ccatcgacgc ggtggtggag gaggcgcgca actacacgcc 13260
cacgccgcca ccagtgtcca cagtggacgc ggccattcag accgtggtgc gcggagcccg 13320
gcgctatgct aaaatgaaga gacggcggag gcgcgtagca cgtcgccacc gccgccgacc 13380
cggcactgcc gcccaacgcg cggcggcggc cctgcttaac cgcgcacgtc gcaccggccg 13440
acgggcggcc atgcgggccg ctcgaaggct ggccgcgggt attgtcactg tgccccccag 13500
gtccaggcga cgagcggccg ccgcagcagc cgcggccatt agtgctatga ctcagggtcg 13560
caggggcaac gtgtattggg tgcgcgactc ggttagcggc ctgcgcgtgc ccgtgcgcac 13620
ccgccccccg cgcaactaga ttgcaagaaa aaactactta gactcgtact gttgtatgta 13680
tccagcggcg gcggcgcgca acgaagctat gtccaagcgc aaaatcaaag aagagatgct 13740
ccaggtcatc gcgccggaga tctatggccc cccgaagaag gaagagcagg attacaagcc 13800
ccgaaagcta aagcgggtca aaaagaaaaa gaaagatgat gatgatgaac ttgacgacga 13860
ggtggaactg ctgcacgcta ccgcgcccag gcgacgggta cagtggaaag gtcgacgcgt 13920
aaaacgtgtt ttgcgacccg gcaccaccgt agtctttacg cccggtgagc gctccacccg 13980
cacctacaag cgcgtgtatg atgaggtgta cggcgacgag gacctgcttg agcaggccaa 14040
cgagcgcctc ggggagtttg cctacggaaa gcggcataag gacatgctgg cgttgccgct 14100
ggacgagggc aacccaacac ctagcctaaa gcccgtaaca ctgcagcagg tgctgcccgc 14160
gcttgcaccg tccgaagaaa agcgcggcct aaagcgcgag tctggtgact tggcacccac 14220
cgtgcagctg atggtaccca agcgccagcg actggaagat gtcttggaaa aaatgaccgt 14280
ggaacctggg ctggagcccg aggtccgcgt gcggccaatc aagcaggtgg cgccgggact 14340
gggcgtgcag accgtggacg ttcagatacc cactaccagt agcaccagta ttgccaccgc 14400
cacagagggc atggagacac aaacgtcccc ggttgcctca gcggtggcgg atgccgcggt 14460
gcaggcggtc gctgcggccg cgtccaagac ctctacggag gtgcaaacgg acccgtggat 14520
gtttcgcgtt tcagcccccc ggcgcccgcg ccgttcgagg aagtacggcg ccgccagcgc 14580
gctactgccc gaatatgccc tacatccttc cattgcgcct acccccggct atcgtggcta 14640
cacctaccgc cccagaagac gagcaactac ccgacgccga accaccactg gaacccgccg 14700
ccgccgtcgc cgtcgccagc ccgtgctggc cccgatttcc gtgcgcaggg tggctcgcga 14760
aggaggcagg accctggtgc tgccaacagc gcgctaccac cccagcatcg tttaaaagcc 14820
ggtctttgtg gttcttgcag atatggccct cacctgccgc ctccgtttcc cggtgccggg 14880
attccgagga agaatgcacc gtaggagggg catggccggc cacggcctga cgggcggcat 14940
gcgtcgtgcg caccaccggc ggcggcgcgc gtcgcaccgt cgcatgcgcg gcggtatcct 15000
gcccctcctt attccactga tcgccgcggc gattggcgcc gtgcccggaa ttgcatccgt 15060
ggccttgcag gcgcagagac actgattaaa aacaagttgc atgtggaaaa atcaaaataa 15120
aaagtctgga ctctcacgct cgcttggtcc tgtaactatt ttgtagaatg gaagacatca 15180
actttgcgtc tctggccccg cgacacggct cgcgcccgtt catgggaaac tggcaagata 15240
tcggcaccag caatatgagc ggtggcgcct tcagctgggg ctcgctgtgg agcggcatta 15300
aaaatttcgg ttccaccgtt aagaactatg gcagcaaggc ctggaacagc agcacaggcc 15360
agatgctgag ggataagttg aaagagcaaa atttccaaca aaaggtggta gatggcctgg 15420
cctctggcat tagcggggtg gtggacctgg ccaaccaggc agtgcaaaat aagattaaca 15480
gtaagcttga tccccgccct cccgtagagg agcctccacc ggccgtggag acagtgtctc 15540
cagaggggcg tggcgaaaag cgtccgcgcc ccgacaggga agaaactctg gtgacgcaaa 15600
tagacgagcc tccctcgtac gaggaggcac taaagcaagg cctgcccacc acccgtccca 15660
tcgcgcccat ggctaccgga gtgctgggcc agcacacacc cgtaacgctg gacctgcctc 15720
cccccgccga cacccagcag aaacctgtgc tgccaggccc gaccgccgtt gttgtaaccc 15780
gtcctagccg cgcgtccctg cgccgcgccg ccagcggtcc gcgatcgttg cggcccgtag 15840
ccagtggcaa ctggcaaagc acactgaaca gcatcgtggg tctgggggtg caatccctga 15900

-continued

```
agcgccgacg atgcttctga tagctaacgt gtcgtatgtg tgtcatgtat gcgtccatgt  15960
cgccgccaga ggagctgctg agccgccgcg cgcccgcttt ccaagatggc taccccttcg  16020
atgatgccgc agtggtctta catgcacatc tcgggccagg acgcctcgga gtacctgagc  16080
cccgggctgg tgcagtttgc ccgcgccacc gagacgtact tcagcctgaa taacaagttt  16140
agaaacccca cggtggcgcc tacgcacgac gtgaccacag accggtccca gcgtttgacg  16200
ctgcggttca tccctgtgga ccgtgaggat actgcgtact cgtacaaggc gcggttcacc  16260
ctagctgtgg gtgataaccg tgtgctggac atggcttcca cgtactttga catccgcggc  16320
gtgctggaca ggggccctac ttttaagccc tactctggca ctgcctacaa cgccctggct  16380
cccaagggtg ccccaaatcc ttgcgaatgg gatgaagctg ctactgctct tgaaataaac  16440
ctagaagaag aggacgatga caacgaagac gaagtagacg agcaagctga gcagcaaaaa  16500
actcacgtat ttgggcaggc gccttattct ggtataaata ttacaaagga gggtattcaa  16560
ataggtgtcg aaggtcaaac acctaaatat gccgataaaa catttcaacc tgaacctcaa  16620
ataggagaat ctcagtggta cgaaacagaa attaatcatg cagctgggag agtcctaaaa  16680
aagactaccc caatgaaacc atgttacggt tcatatgcaa aacccacaaa tgaaaatgga  16740
gggcaaggca ttcttgtaaa gcaacaaaat ggaaagctag aaagtcaagt ggaaatgcaa  16800
tttttctcaa ctactgaggc agccgcaggc aatggtgata acttgactcc taaagtggta  16860
ttgtacagtg aagatgtaga tatagaaacc ccagacactc atatttctta catgcccact  16920
attaaggaag gtaactcacg agaactaatg ggccaacaat ctatgcccaa caggcctaat  16980
tacattgctt ttagggacaa ttttattggt ctaatgtatt acaacagcac gggtaatatg  17040
ggtgttctgg cgggccaagc atcgcagttg aatgctgttg tagatttgca agacagaaac  17100
acagagcttt cataccagct tttgcttgat tccattggtg atagaaccag gtacttttct  17160
atgtggaatc aggctgttga cagctatgat ccagatgtta gaattattga aaatcatgga  17220
actgaagatg aacttccaaa ttactgcttt ccactgggag gtgtgattaa tacagagact  17280
cttaccaagg taaaacctaa aacaggtcag gaaaatggat gggaaaaaga tgctacagaa  17340
ttttcagata aaaatgaaat aagagttgga aataattttg ccatggaaat caatctaaat  17400
gccaacctgt ggagaaattt cctgtactcc aacatagcgc tgtatttgcc cgacaagcta  17460
aagtacagtc cttccaacgt aaaaatttct gataacccaa acacctacga ctacatgaac  17520
aagcgagtgg tggctcccgg gctagtggac tgctacatta accttggagc acgctggtcc  17580
cttgactata tggacaacgt caacccattt aaccaccacc gcaatgctgg cctgcgctac  17640
cgctcaatgt tgctgggcaa tggtcgctat gtgcccttcc acatccaggt gcctcagaag  17700
ttctttgcca ttaaaaacct ccttctcctg ccgggctcat acacctacga gtggaacttc  17760
aggaaggatg ttaacatggt tctgcagagc tccctaggaa atgacctaag ggttgacgga  17820
gccagcatta agtttgatag catttgcctt tacgccacct tcttccccat ggcccacaac  17880
accgcctcca cgcttgaggc catgcttaga aacgacacca acgaccagtc ctttaacgac  17940
tatctctccg ccgccaacat gctctaccct atacccgcca acgctaccaa cgtgcccata  18000
tccatcccct cccgcaactg ggcggctttc cgcggctggg ccttcacgcg ccttaagact  18060
aaggaaaccc catcactggg ctcgggctac gacccttatt acacctactc tggctctata  18120
ccctacctag atggaacctt ttacctcaac cacaccttta agaaggtggc cattaccttt  18180
gactcttctg tcagctggcc tggcaatgac cgcctgctta cccccaacga gtttgaaatt  18240
```

-continued

```
aagcgctcag ttgacgggga gggttacaac gttgcccagt gtaacatgac caaagactgg  18300
ttcctggtac aaatgctagc taactataac attggctacc agggcttcta tatcccagag  18360
agctacaagg accgcatgta ctccttcttt agaaacttcc agcccatgag ccgtcaggtg  18420
gtggatgata ctaaatacaa ggactaccaa caggtgggca tcctacacca acacaacaac  18480
tctggatttg ttggctacct tgcccccacc atgcgcgaag gacaggccta ccctgctaac  18540
ttcccctatc cgcttatagg caagaccgca gttgacagca ttacccagaa aaagtttctt  18600
tgcgatcgca ccctttggcg catcccattc tccagtaact ttatgtccat gggcgcactc  18660
acagacctgg gccaaaacct tctctacgcc aactccgccc acgcgctaga catgactttt  18720
gaggtggatc ccatggacga gcccaccctt ctttatgttt tgtttgaagt ctttgacgtg  18780
gtccgtgtgc accagccgca ccgcggcgtc atcgaaaccg tgtacctgcg cacgcccttc  18840
tcggccggca acgccacaac ataaagaagc aagcaacatc aacaacagct gccgccatgg  18900
gctccagtga gcaggaactg aaagccattg tcaaagatct tggttgtggg ccatattttt  18960
tgggcaccta tgacaagcgc tttccaggct ttgtttctcc acacaagctc gcctgcgcca  19020
tagtcaatac ggccggtcgc gagactgggg gcgtacactg gatggccttt gcctggaacc  19080
cgcactcaaa aacatgctac ctctttgagc cctttggctt ttctgaccag cgactcaagc  19140
aggtttacca gtttgagtac gagtcactcc tgcgccgtag cgccattgct tcttcccccg  19200
accgctgtat aacgctggaa aagtccaccc aaagcgtaca ggggcccaac tcggccgcct  19260
gtggactatt ctgctgcatg tttctccacg cctttgccaa ctggccccaa actcccatgg  19320
atcacaaccc caccatgaac cttattaccg gggtacccaa ctccatgctc aacagtcccc  19380
aggtacagcc caccctgcgt cgcaaccagg aacagctcta cagcttcctg gagcgccact  19440
cgccctactt ccgcagccac agtgcgcaga ttaggagcgc cacttctttt tgtcacttga  19500
aaaacatgta aaaataatgt actagagaca ctttcaataa aggcaaatgc ttttatttgt  19560
acactctcgg gtgattattt acccccaccc ttgccgtctg cgccgtttaa aaatcaaagg  19620
ggttctgccg cgcatcgcta tgcgccactg gcagggacac gttgcgatac tggtgtttag  19680
tgctccactt aaactcaggc acaaccatcc gcggcagctc ggtgaagttt tcactccaca  19740
ggctgcgcac catcaccaac gcgtttagca ggtcgggcgc cgatatcttg aagtcgcagt  19800
tggggcctcc gccctgcgcg cgcgagttgc gatacacagg gttgcagcac tggaacacta  19860
tcagcgccgg gtggtgcacg ctggccagca cgctcttgtc ggagatcaga tccgcgtcca  19920
ggtcctccgc gttgctcagg gcgaacggag tcaactttgg tagctgcctt cccaaaaagg  19980
gcgcgtgccc aggctttgag ttgcactcgc accgtagtgg catcaaaagg tgaccgtgcc  20040
cggtctgggc gttaggatac agcgcctgca taaaagcctt gatctgctta aaagccacct  20100
gagcctttgc gccttcagag aagaacatgc cgcaagactt gccggaaaac tgattggccg  20160
gacaggccgc gtcgtgcacg cagcaccttg cgtcggtgtt ggagatctgc accacatttc  20220
ggccccaccg gttcttcacg atcttggcct tgctagactg ctccttcagc gcgcgctgcc  20280
cgttttcgct cgtcacatcc atttcaatca cgtgctcctt atttatcata atgcttccgt  20340
gtagacactt aagctcgcct tcgatctcag cgcagcggtg cagccacaac gcgcagcccg  20400
tgggctcgtg atgcttgtag gtcacctctg caaacgactg caggtacgcc tgcaggaatc  20460
gccccatcat cgtcacaaag gtcttgttgc tggtgaaggt cagctgcaac ccgcggtgct  20520
cctcgttcag ccaggtcttg catacggccg ccagagcttc cacttggtca ggcagtagtt  20580
tgaagttcgc ctttagatcg ttatccacgt ggtacttgtc catcagcgcg cgcgcagcct  20640
```

```
ccatgccctt ctcccacgca gacacgatcg gcacactcag cgggttcatc accgtaattt  20700
cactttccgc ttcgctgggc tcttcctctt cctcttgcgt ccgcatacca cgcgccactg  20760
ggtcgtcttc attcagccgc cgcactgtgc gcttacctcc tttgccatgc ttgattagca  20820
ccggtgggtt gctgaaaccc accatttgta gcgccacatc ttctctttct tcctcgctgt  20880
ccacgattac ctctggtgat ggcgggcgct cgggcttggg agaagggcgc ttctttttct  20940
tcttgggcgc aatggccaaa tccgccgccg aggtcgatgg ccgcgggctg ggtgtgcgcg  21000
gcaccagcgc gtcttgtgat gagtcttcct cgtcctcgga ctcgatacgc cgcctcatcc  21060
gcttttttgg gggcgcccgg ggaggcggcg gcgacgggga cggggacgac acgtcctcca  21120
tggttggggg acgtcgcgcc gcaccgcgtc cgcgctcggg ggtggtttcg cgctgctcct  21180
cttcccgact ggccatttcc ttctcctata ggcagaaaaa gatcatggag tcagtcgaga  21240
agaaggacag cctaaccgcc ccctctgagt tcgccaccac cgcctccacc gatgccgcca  21300
acgcgcctac caccttcccc gtcgaggcac ccccgcttga ggaggaggaa gtgattatcg  21360
agcaggaccc aggttttgta agcgaagacg acgaggaccg ctcagtacca acagaggata  21420
aaaagcaaga ccaggacaac gcagaggcaa acgaggaaca agtcgggcgg ggggacgaaa  21480
ggcatggcga ctacctagat gtgggagacg acgtgctgtt gaagcatctg cagcgccagt  21540
gcgccattat ctgcgacgcg ttgcaagagc gcagcgatgt gcccctcgcc atagcggatg  21600
tcagccttgc ctacgaacgc cacctattct caccgcgcgt acccccaaa cgccaagaaa  21660
acggcacatg cgagcccaac ccgcgcctca acttctaccc cgtatttgcc gtgccagagg  21720
tgcttgccac ctatcacatc tttttccaaa actgcaagat acccctatcc tgccgtgcca  21780
accgcagccg agcggacaag cagctggcct tgcggcaggg cgctgtcata cctgatatcg  21840
cctcgctcaa cgaagtgcca aaaatctttg agggtcttgg acgcgacgag aagcgcgcgg  21900
caaacgctct gcaacaggaa aacagcgaaa atgaaagtca ctctggagtg ttggtggaac  21960
tcgagggtga caacgcgcgc ctagccgtac taaaacgcag catcgaggtc acccactttg  22020
cctacccggc acttaaccta ccccccaagg tcatgagcac agtcatgagt gagctgatcg  22080
tgcgccgtgc gcagcccctg gagagggatg caaatttgca agaacaaaca gaggagggcc  22140
tacccgcagt tggcgacgag cagctagcgc gctggcttca aacgcgcgag cctgccgact  22200
tggaggagcg acgcaaacta atgatggccg cagtgctcgt taccgtggag cttgagtgca  22260
tgcagcggtt ctttgctgac ccggagatgc agcgcaagct agaggaaaca ttgcactaca  22320
cctttcgaca gggctacgta cgccaggcct gcaagatctc caacgtggag ctctgcaacc  22380
tggtctccta ccttggaatt ttgcacgaaa accgccttgg gcaaaacgtg cttcattcca  22440
cgctcaaggg cgaggcgcgc cgcgactacg tccgcgactg cgtttactta tttctatgct  22500
acacctggca gacggccatg ggcgtttggc agcagtgctt ggaggagtgc aacctcaagg  22560
agctgcagaa actgctaaag caaaacttga aggacctatg gacggccttc aacgagcgct  22620
ccgtggccgc gcacctggcg gacatcattt tccccgaacg cctgcttaaa accctgcaac  22680
agggtctgcc agacttcacc agtcaaagca tgttgcagaa ctttaggaac tttatcctag  22740
agcgctcagg aatcttgccc gccacctgct gtgcacttcc tagcgacttt gtgcccatta  22800
agtaccgcga atgccctccg ccgctttggg gccactgcta ccttctgcag ctagccaact  22860
accttgccta ccactctgac ataatggaag acgtgagcgg tgacggtcta ctggagtgtc  22920
actgtcgctg caacctatgc accccgcacc gctccctggt ttgcaattcg cagctgctta  22980
```

acgaaagtca aattatcggt acctttgagc tgcagggtcc ctcgcctgac gaaaagtccg 23040
cggctccggg gttgaaactc actccggggc tgtggacgtc ggcttacctt cgcaaatttg 23100
tacctgagga ctaccacgcc cacgagatta ggttctacga agaccaatcc cgcccgccta 23160
atgcggagct taccgcctgc gtcattaccc agggccacat tcttggccaa ttgcaagcca 23220
tcaacaaagc ccgccaagag tttctgctac gaaagggacg gggggtttac ttggaccccc 23280
agtccggcga ggagctcaac ccaatccccc cgccgccgca gccctatcag cagcagccgc 23340
gggcccttgc ttcccaggat ggcacccaaa aagaagctgc agctgccgcc gccacccacg 23400
gacgaggagg aatactggga cagtcaggca gaggaggttt tggacgagga ggaggaggac 23460
atgatggaag actgggagag cctagacgag gaagcttccg aggtcgaaga ggtgtcagac 23520
gaaacaccgt caccctcggt cgcattcccc tcgccggcgc cccagaaatc ggcaaccggt 23580
tccagcatgg ctacaacctc cgctcctcag gcgccgccgg cactgcccgt tcgccgaccc 23640
aaccgtagat gggacaccac tggaaccagg gccggtaagt ccaagcagcc gccgccgtta 23700
gcccaagagc aacaacagcg ccaaggctac cgctcatggc gcgggcacaa gaacgccata 23760
gttgcttgct tgcaagactg tgggggcaac atctccttcg cccgccgctt tcttctctac 23820
catcacggcg tggccttccc ccgtaacatc ctgcattact accgtcatct ctacagccca 23880
tactgcaccg gcggcagcgg cagcaacagc agcggccaca cagaagcaaa ggcgaccgga 23940
tagcaagact ctgacaaagc ccaagaaatc cacagcggcg gcagcagcag gaggaggagc 24000
gctgcgtctg gcgcccaacg aacccgtatc gacccgcgag cttagaaaca ggatttttcc 24060
cactctgtat gctatatttc aacagagcag gggccaagaa caagagctga aaataaaaaa 24120
caggtctctg cgatccctca cccgcagctg cctgtatcac aaaagcgaag atcagcttcg 24180
gcgcacgctg gaagacgcgg aggctctctt cagtaaatac tgcgcgctga ctcttaagga 24240
ctagtttcgc gccctttctc aaatttaagc gcgaaaacta cgtcatctcc agcggccaca 24300
cccggcgcca gcacctgttg tcagcgccat tatgagcaag gaaattccca cgccctacat 24360
gtggagttac cagccacaaa tgggacttgc ggctggagct gcccaagact actcaacccg 24420
aataaactac atgagcgcgg gaccccacat gatatcccgg gtcaacggaa tacgcgccca 24480
ccgaaaccga attctcctgg aacaggcggc tattaccacc acacctcgta ataaccttaa 24540
tccccgtagt tggcccgctg ccctggtgta ccaggaaagt cccgctccca ccactgtggt 24600
acttcccaga gacgcccagg ccgaagttca gatgactaac tcaggggcgc agcttgcggg 24660
cggctttcgt cacagggtgc ggtcgcccgg gcagggtata actcacctga caatcagagg 24720
gcgaggtatt cagctcaacg acgagtcggt gagctcctcg cttggtctcc gtccggacgg 24780
gacatttcag atcggcggcg ccggccgctc ttcattcacg cctcgtcagg caatcctaac 24840
tctgcagacc tcgtcctctg agccgcgctc tggaggcatt ggaactctgc aatttattga 24900
ggagtttgtg ccatcggtct actttaaccc cttctcggga cctcccggcc actatccgga 24960
tcaatttatt cctaactttg acgcggtaaa ggactcggcg gacggctacg actgaatgtt 25020
aagtggagag gcagagcaac tgcgcctgaa acacctggtc cactgtcgcc gccacaagtg 25080
ctttgcccgc gactccggtg agttttgcta ctttgaattg cccgaggatc atatcgaggg 25140
cccggcgcac ggcgtccggc ttaccgccca gggagagctt gcccgtagcc tgattcggga 25200
gtttacccag cgcccccctgc tagttgagcg ggacagggga ccctgtgttc tcactgtgat 25260
ttgcaactgt cctaaccctg gattacatca agatctttgt tgccatctct gtgctgagta 25320
taataaatac agaaattaaa atatactggg gctcctatcg ccatcctgta aacgccaccg 25380

```
tcttcacccg cccaagcaaa ccaaggcgaa ccttacctgg tacttttaac atctctccct  25440
ctgtgattta caacagtttc aacccagacg gagtgagtct acgagagaac ctctccgagc  25500
tcagctactc catcagaaaa aacaccaccc tccttacctg ccgggaacgt acgagtgcgt  25560
caccggccgc tgcaccacac ctaccgcctg accgtaaacc agactttttc cggacagacc  25620
tcaataactc tgtttaccag aacaggaggt gagcttagaa aacccttagg gtattaggcc  25680
aaaggcgcag ctactgtggg gtttatgaac aattcaagca actctacggg ctattctaat  25740
tcaggtttct ctagaatcgg ggttggggtt attctctgtc ttgtgattct ctttattctt  25800
atactaacgc ttctctgcct aaggctcgcc gcctgctgtg tgcacatttg catttattgt  25860
cagcttttta aacgctgggg tcgccaccca agatgattag gtacataatc ctaggtttac  25920
tcacccttgc gtcagcccac ggtaccaccc aaaaggtgga ttttaaggag ccagcctgta  25980
atgttacatt cgcagctgaa gctaatgagt gcaccactct tataaaatgc accacagaac  26040
atgaaaagct gcttattcgc cacaaaaaca aaattggcaa gtatgctgtt tatgctattt  26100
ggcagccagg tgacactaca gagtataatg ttacagtttt ccagggtaaa agtcataaaa  26160
cttttatgta tacttttcca ttttatgaaa tgtgcgacat taccatgtac atgagcaaac  26220
agtataagtt gtggccccca caaaattgtg tggaaaacac tggcactttc tgctgcactg  26280
ctatgctaat tacagtgctc gctttggtct gtaccctact ctatattaaa tacaaaagca  26340
gacgcagctt tattgaggaa aagaaaatgc cttaatttac taagttacaa agctaatgtc  26400
accactaact gctttactcg ctgcttgcaa aacaaattca aaaagttagc attataatta  26460
gaataggatt taaacccccc ggtcatttcc tgctcaatac cattcccctg aacaattgac  26520
tctatgtggg atatgctcca gcgctacaac cttgaagtca ggcttcctgg atgtcagcat  26580
ctgactttgg ccagcacctg tcccgcggat ttgttccagt ccaactacag cgacccaccc  26640
taacagagat gaccaacaca accaacgcgg ccgccgctac cggacttaca tctaccacaa  26700
atacacccca agtttctgcc tttgtcaata actgggataa cttgggcatg tggtggttct  26760
ccatagcgct tatgtttgta tgccttatta ttatgtggct catctgctgc ctaaagcgca  26820
aacgcgcccg accacccatc tatagtccca tcattgtgct acacccaaac aatgatggaa  26880
tccatagatt ggacggactg aaacacatgt tcttttctct tacagtatga ttaaatgaga  26940
catgattcct cgagttttta tattactgac ccttgttgcg cttttttgt gcgtgctcca  27000
cattggctgc ggtttctcac atcgaagtag actgcattcc agccttcaca gtctatttgc  27060
tttacggatt tgtcaccctc acgctcatct gcagcctcat cactgtggtc atcgccttta  27120
tccagtgcat tgactgggtc tgtgtgcgct ttgcatatct cagacaccat ccccagtaca  27180
gggacaggac tatagctgag cttcttagaa ttctttaatt atgaaattta ctgtgacttt  27240
tctgctgatt atttgcaccc tatctgcgtt ttgttccccg acctccaagc ctcaaagaca  27300
tatatcatgc agattcactc gtatatggaa tattccaagt tgctacaatg aaaaaagcga  27360
tctttccgaa gcctggttat atgcaatcat ctctgttatg gtgttctgca gtaccatctt  27420
agccctagct atatatccct accttgacat tggctggaac gcaatagatg ccatgaacca  27480
cccaactttc cccgcgcccg ctatgcttcc actgcaacaa gttgttgccg gcggctttgt  27540
cccagccaat cagcctcgcc caccttctcc cacccccact gaaatcagct actttaatct  27600
aacaggagga gatgactgac accctagatc tagaaatgga cggaattatt acagagcagc  27660
gcctgctaga aagacgcagg gcagcggccg agcaacagcg catgaatcaa gagctccaag  27720
```

-continued

```
acatggttaa cttgcaccag tgcaaaaggg gtatcttttg tctggtaaag caggccaaag  27780
tcacctacga cagtaatacc accggacacc gccttagcta caagttgcca accaagcgtc  27840
agaaattggt ggtcatggtg ggagaaaagc ccattaccat aactcagcac tcggtagaaa  27900
ccgaaggctg cattcactca ccttgtcaag gacctgagga tctctgcacc cttattaaga  27960
ccctgtgcgg tctcaaagat cttattccct ttaactaata aaaaaaaata ataaagcatc  28020
acttacttaa aatcagttag caaatttctg tccagtttat tcagcagcac ctccttgccc  28080
tcctcccagc tctggtattg cagcttcctc ctggctgcaa actttctcca caatctaaat  28140
ggaatgtcag tttcctcctg ttcctgtcca tccgcaccca ctatcttcat gttgttgcag  28200
atgaagcgcg caagaccgtc tgaagatacc ttcaaccccg tgtatccata tgacacggaa  28260
accggtcctc caactgtgcc ttttcttact cctccctttg tatcccccaa tgggtttcaa  28320
gagagtcccc ctggggtact ctctttgcgc ctatccgaac ctctagttac ctccaatggc  28380
atgcttgcgc tcaaaatggg caacggcctc tctctggacg aggccggcaa ccttacctcc  28440
caaaatgtaa ccactgtgag cccacctctc aaaaaaacca agtcaaacat aaacctggaa  28500
atatctgcac ccctcacagt tacctcagaa gccctaactg tggctgccgc cgcacctcta  28560
atggtcgcgg gcaacacact caccatgcaa tcacaggccc cgctaaccgt gcacgactcc  28620
aaacttagca ttgccaccca aggacccctc acagtgtcag aaggaaagct agccctgcaa  28680
acatcaggcc ccctcaccac caccgatagc agtaccctta ctatcactgc ctcacccccct  28740
ctaactactg ccactggtag cttgggcatt gacttgaaag agcccattta tacacaaaat  28800
ggaaaactag gactaaagta cggggctcct ttgcatgtaa cagacgacct aaacactttg  28860
accgtagcaa ctggtccagg tgtgactatt aataatactt ccttgcaaac taaagttact  28920
ggagccttgg gttttgattc acaaggcaat atgcaactta atgtagcagg aggactaagg  28980
attgattctc aaaacagacg ccttatactt gatgttagtt atccgtttga tgctcaaaac  29040
caactaaatc taagactagg acagggccct ctttttataa actcagccca caacttggat  29100
attaactaca acaaaggcct ttacttgttt acagcttcaa acaattccaa aaagcttgag  29160
gttaacctaa gcactgccaa ggggttgatg tttgacgcta cagccatagc cattaatgca  29220
ggagatgggc ttgaatttgg ttcacctaat gcaccaaaca caaatcccct caaaacaaaa  29280
attggccatg gcctagaatt tgattcaaac aaggctatgg ttcctaaact aggaactggc  29340
cttagttttg acagcacagg tgccattaca gtaggaaaca aaaataatga taagctaact  29400
ttgtggacca caccagctcc atctcctaac tgtagactaa atgcagagaa agatgctaaa  29460
ctcactttgg tcttaacaaa atgtggcagt caaatacttg ctacagtttc agttttggct  29520
gttaaaggca gtttggctcc aatatctgga acagttcaaa gtgctcatct tattataaga  29580
tttgacgaaa atggagtgct actaaacaat tccttcctgg acccagaata ttggaacttt  29640
agaaatggag atcttactga aggcacagcc tatacaaacg ctgttggatt tatgcctaac  29700
ctatcagctt atccaaaatc tcacggtaaa actgccaaaa gtaacattgt cagtcaagtt  29760
tacttaaacg gagacaaaac taaacctgta acactaacca ttacactaaa cggtacacag  29820
gaaacaggag acacaactcc aagtgcatac tctatgtcat tttcatggga ctggtctggc  29880
cacaactaca ttaatgaaat atttgccaca tcctcttaca ctttttcata cattgcccaa  29940
gaataaagaa tcgtttgtgt tatgtttcaa cgtgtttatt tttcaattgc agaaaatttc  30000
aagtcatttt tcattcagta gtatagcccc accaccacat agcttataca gatcaccgta  30060
ccttaatcaa actcacagaa ccctagtatt caacctgcca cctccctccc aacacacaga  30120
```

-continued

```
gtacacagtc ctttctcccc ggctggcctt aaaaagcatc atatcatggg taacagacat  30180
attcttaggt gttatattcc acacggtttc ctgtcgagcc aaacgctcat cagtgatatt  30240
aataaactcc ccgggcagct cacttaagtt catgtcgctg tccagctgct gagccacagg  30300
ctgctgtcca acttgcggtt gcttaacggg cggcgaagga gaagtccacg cctacatggg  30360
ggtagagtca taatcgtgca tcaggatagg gcggtggtgc tgcagcagcg cgcgaataaa  30420
ctgctgccgc cgccgctccg tcctgcagga atacaacatg gcagtggtct cctcagcgat  30480
gattcgcacc gcccgcagca taaggcgcct tgtcctccgg gcacagcagc gcaccctgat  30540
ctcacttaaa tcagcacagt aactgcagca cagcaccaca atattgttca aaatcccaca  30600
gtgcaaggcg ctgtatccaa agctcatggc ggggaccaca gaacccacgt ggccatcata  30660
ccacaagcgc aggtagatta agtggcgacc cctcataaac acgctggaca taaacattac  30720
ctcttttggc atgttgtaat tcaccacctc ccggtaccat ataaacctct gattaaacat  30780
ggcgccatcc accaccatcc taaaccagct ggccaaaacc tgcccgccgg ctatacactg  30840
cagggaaccg ggactggaac aatgacagtg gagagcccag gactcgtaac catggatcat  30900
catgctcgtc atgatatcaa tgttggcaca acacaggcac acgtgcatac acttcctcag  30960
gattacaagc tcctcccgcg ttagaaccat atcccaggga acaacccatt cctgaatcag  31020
cgtaaatccc acactgcagg gaagacctcg cacgtaactc acgttgtgca ttgtcaaagt  31080
gttacattcg ggcagcagcg gatgatcctc cagtatggta gcgcgggttt ctgtctcaaa  31140
aggaggtaga cgatccctac tgtacggagt gcgccgagac aaccgagatc gtgttggtcg  31200
tagtgtcatg ccaaatggaa cgccggacgt agtcatattt cctgaagcaa aaccaggtgc  31260
gggcgtgaca aacagatctg cgtctccggt ctcgccgctt agatcgctct gtgtagtagt  31320
tgtagtatat ccactctctc aaagcatcca ggcgccccct ggcttcgggt tctatgtaaa  31380
ctccttcatg cgccgctgcc ctgataacat ccaccaccgc agaataagcc acacccagcc  31440
aacctacaca ttcgttctgc gagtcacaca cgggaggagc gggaagagct ggaagaacca  31500
tgtttttttt tttattccaa aagattatcc aaaacctcaa aatgaagatc tattaagtga  31560
acgcgctccc ctccggtggc gtggtcaaac tctacagcca aagaacagat aatggcattt  31620
gtaagatgtt gcacaatggc ttccaaaagg caaacggccc tcacgtccaa gtggacgtaa  31680
aggctaaacc cttcagggtg aatctcctct ataaacattc cagcaccttc aaccatgccc  31740
aaataattct catctcgcca ccttctcaat atatctctaa gcaaatcccg aatattaagt  31800
ccggccattg taaaaatctg ctccagagcg ccctccacct tcagcctcaa gcagcgaatc  31860
atgattgcaa aaattcaggt tcctcacaga cctgtataag attcaaaagc ggaacattaa  31920
caaaaatacc gcgatcccgt aggtcccttc gcagggccag ctgaacataa tcgtgcaggt  31980
ctgcacggac cagcgcggcc acttccccgc caggaaccat gacaaaagaa cccacactga  32040
ttatgacacg catactcgga gctatgctaa ccagcgtagc cccgatgtaa gcttgttgca  32100
tgggcggcga tataaaatgc aaggtgctgc tcaaaaaatc aggcaaagcc tcgcgcaaaa  32160
aagaaagcac atcgtagtca tgctcatgca gataaaggca ggtaagctcc ggaaccacca  32220
cagaaaaaga caccattttt ctctcaaaca tgtctgcggg tttctgcata aacacaaaat  32280
aaaataacaa aaaaacattt aaacattaga agcctgtctt acaacaggaa aaacaaccct  32340
tataagcata agacggacta cggccatgcc ggcgtgaccg taaaaaaact ggtcaccgtg  32400
attaaaaagc accaccgaca gctcctcggt catgtccgga gtcataatgt aagactcggt  32460
```

aaacacatca ggttgattca catcggtcag tgctaaaaag cgaccgaaat agcccggggg 32520
aatacatacc cgcaggcgta gagacaacat tacagccccc ataggaggta taacaaaatt 32580
aataggagag aaaaacacat aaacacctga aaaaccctcc tgcctaggca aaatagcacc 32640
ctcccgctcc agaacaacat acagcgcttc cacagcggca gccataacag tcagccttac 32700
cagtaaaaaa gaaaacctat taaaaaaaca ccactcgaca cggcaccagc tcaatcagtc 32760
acagtgtaaa aaagggccaa gtgcagagcg agtatatata ggactaaaaa atgacgtaac 32820
ggttaaagtc cacaaaaaac acccagaaaa ccgcacgcga acctacgccc agaaacgaaa 32880
gccaaaaaac ccacaacttc ctcaaatcgt cacttccgtt ttcccacgtt acgtcacttc 32940
ccattttaag aaaactacaa ttcccaacac atacaagtta ctccgcccta aaacctacgt 33000
cacccgcccc gttcccacgc cccgcgccac gtcacaaact ccaccccctc attatcatat 33060
tggcttcaat ccaaaataag gtatattatt gat 33093

<210> SEQ ID NO 12
<211> LENGTH: 978
<212> TYPE: DNA
<213> ORGANISM: Artificial sequence
<220> FEATURE:
<223> OTHER INFORMATION: PPE-1-3X promoter

<400> SEQUENCE: 12
acgtgtactt ctgatcggcg atactaggga gataaggatg tacctgacaa aaccacattg 60
ttgttgttat cattattatt tagttttcct tccttgctaa ctcctgacgg aatctttctc 120
acctcaaatg cgaagtactt tagtttagaa aagacttggt ggaaggggtg gtggtggaaa 180
agtagggtga tcttccaaac taatctggtt ccccgcccgc cccagtagct gggattcaag 240
agcgaagagt ggggatcgtc cccttgtttg atcagaaaga cataaaagga aaatcaagtg 300
aacaatgatc agccccacct ccaccccacc cccctgcgcg cgcacaatac aatctattta 360
attgtacttc atacttttca ttccaatggg gtgactttgc ttctggagaa actcttgatt 420
cttgaactct ggggctggca gctagcctcc agaagcaaag tcaccccatt ggaatgaaaa 480
gtatgaagta caatgaaaag tatgaagtac tggctccaga agcaaagtca ccctccagaa 540
gcaaagtcac cccattggaa tgaaaagtat gaagtacgct agcaaaaggg gaagcgggct 600
gctgctctct gcaggttctg cagcggtctc tgtctagtgg gtgttttctt tttcttagcc 660
ctgcccctgg attgtcagac ggcgggcgtc tgcctctgaa gttagccgtg atttcctcta 720
gagccgggtc ttatctctgg ctgcacgttg cctgtgggtg actaatcaca caataacatt 780
gtttagggct ggaataaagt cagagctgtt tacccccact ctataggggt tcaatataaa 840
aaggcggcgg agaactgtcc gagtcagaag cgttcctgca ccggcgctga gagcctgacc 900
cggtctgctc cgctgtcctt gcgcgctgcc tcccggctgc ccgcgacgct ttcgccccag 960
tggaagggcc acttgctg 978

<210> SEQ ID NO 13
<211> LENGTH: 1334
<212> TYPE: DNA
<213> ORGANISM: Mus musculus

<400> SEQUENCE: 13
gtgtgtgtgt gtgtgtgtgt gtgtgtgtgt gtgtgtgtgt gtgtagtgta cttctgatcg 60
gcgatactag ggagataagg atgtacctga caaaaccaca ttgttgttgt tatcattatt 120
atttagtttt ccttccttgc taactcctga cggaatcttt ctcacctcaa atgcgaagta 180

```
ctttagttta gaaaagactt ggtggaaggg gtggtggtgg aaaagtaggg tgatcttcca    240

aactaatctg gttccccgcc cgccccagta gctgggattc aagagcgaag agtggggatc    300

gtccccttgt ttgatcagaa agacataaaa ggaaaatcaa gtgaacaatg atcagcccca    360

cctccacccc accccccctgc gcgcgcacaa tacaatctat ttaattgtac ttcatacttt    420

tcattccaat ggggtgactt tgcttctgga gaaactcttg attcttgaac tctggggctg    480

gcagctagca aaaggggaag cgggctgctg ctctctgcag gttctgcagc ggtctctgtc    540

tagtgggtgt tttctttttc ttagccctgc ccctggattg tcagacggcg ggcgtctgcc    600

tctgaagtta gccgtgattt cctctagagc cgggtcttat ctctggctgc acgttgcctg    660

tgggtgacta atcacacaat aacattgttt agggctggaa taaagtcaga gctgtttacc    720

cccactctat aggggttcaa tataaaaagg cggcggagaa ctgtccgagt cagacgcgtt    780

cctgcaccgg cgctgagagc ctgacccggt ctgctccgct gtccttgcgc gctgcctccc    840

ggctgcccgc gacgctttcg ccccagtgga agggccactt gctgaggacc gcgctgagat    900

ctaaaaaaaa aacaaaaaac aaaaaacaaa aaaacccaga ggcgatcaga gcgaccagac    960

accgtcctct tcgttttgca ttgagttcca tttgcaaccg agtttctttt ttttcctttt   1020

tccccactct tctgacccct ttgcagaatg gattattttc ccgtgatctt ctctctgctg   1080

ttcgtgactt tccaaggagc tccagaaaca ggtaggcgcc acttgcgaat ctttctactt   1140

cagcgcagca gttatcgctt ctgttttcca cttttctttc tttcttttct ttcattcttt   1200

ccttttttatt tatttttta attactgaag ctccagcagc aagtgcctta caattaatta   1260

acttctgtgt gaagcgaaag aaataaaacc cctgtttgaa tacagctgac tacaaccgag   1320

tatcgcatag cttc                                                     1334
```

<210> SEQ ID NO 14
<211> LENGTH: 5
<212> TYPE: DNA
<213> ORGANISM: Artificial sequence
<220> FEATURE:
<223> OTHER INFORMATION: wild type element M9

<400> SEQUENCE: 14

```
ctgga                                                                  5
```

<210> SEQ ID NO 15
<211> LENGTH: 5
<212> TYPE: DNA
<213> ORGANISM: Artificial sequence
<220> FEATURE:
<223> OTHER INFORMATION: wild type element M4

<400> SEQUENCE: 15

```
cattc                                                                  5
```

<210> SEQ ID NO 16
<211> LENGTH: 5
<212> TYPE: DNA
<213> ORGANISM: Artificial sequence
<220> FEATURE:
<223> OTHER INFORMATION: wild type element M5

<400> SEQUENCE: 16

```
caatg                                                                  5
```

<210> SEQ ID NO 17

<211> LENGTH: 5
<212> TYPE: DNA
<213> ORGANISM: Artificial sequence
<220> FEATURE:
<223> OTHER INFORMATION: wild type element M6

<400> SEQUENCE: 17 gggtg 5

<210> SEQ ID NO 18
<211> LENGTH: 5
<212> TYPE: DNA
<213> ORGANISM: Artificial sequence
<220> FEATURE:
<223> OTHER INFORMATION: wild type element M7

<400> SEQUENCE: 18 acttt 5

<210> SEQ ID NO 19
<211> LENGTH: 5
<212> TYPE: DNA
<213> ORGANISM: Artificial sequence
<220> FEATURE:
<223> OTHER INFORMATION: wild type element M8

<400> SEQUENCE: 19 gcttc 5

<210> SEQ ID NO 20
<211> LENGTH: 5
<212> TYPE: DNA
<213> ORGANISM: Artificial sequence
<220> FEATURE:
<223> OTHER INFORMATION: wild type element M1
<220> FEATURE:
<221> NAME/KEY: misc_feature
<222> LOCATION: (1)..(6)
<223> OTHER INFORMATION: n is a, c, g, or t

<400> SEQUENCE: 20 gtact 5

<210> SEQ ID NO 21
<211> LENGTH: 5
<212> TYPE: DNA
<213> ORGANISM: Artificial sequence
<220> FEATURE:
<223> OTHER INFORMATION: wild type element M3
<220> FEATURE:
<221> NAME/KEY: misc_feature
<222> LOCATION: (1)..(6)
<223> OTHER INFORMATION: n is a, c, g, or t

<400> SEQUENCE: 21 ctttt 5

<210> SEQ ID NO 22
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 22
gggtgacttt gcttctgga 19

<210> SEQ ID NO 23
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(15)
<223> OTHER INFORMATION: At least one residue mutated or absent

<400> SEQUENCE: 23
gggtgacttt gcttctgga 19

<210> SEQ ID NO 24
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (12)..(16)
<223> OTHER INFORMATION: At least one residue mutated or absent

<400> SEQUENCE: 24
ggggtgactt tgcttctgg 19

<210> SEQ ID NO 25
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(15)
<223> OTHER INFORMATION: At least one residue mutated or absent

<400> SEQUENCE: 25
caatggggtg gcttctgga 19

<210> SEQ ID NO 26
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (12)..(16)
<223> OTHER INFORMATION: At least one residue mutated or absent

<400> SEQUENCE: 26
ccaatggggt ggcttctgg 19

<210> SEQ ID NO 27
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(15)
<223> OTHER INFORMATION: At least one residue mutated or absent

<400> SEQUENCE: 27
gggtgacttt gcttctgga 19

<210> SEQ ID NO 28
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (12)..(16)
<223> OTHER INFORMATION: At least one residue mutated or absent

<400> SEQUENCE: 28
ggggtgactt tgcttctgg 19

<210> SEQ ID NO 29
<211> LENGTH: 44
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (36)..(40)
<223> OTHER INFORMATION: At least one residue mutated or absent

<400> SEQUENCE: 29
gtacttcata cttttcattc caatggggtg actttgcttc tgga 44

<210> SEQ ID NO 30
<211> LENGTH: 39
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (31)..(35)
<223> OTHER INFORMATION: At least one residue mutated or absent

<400> SEQUENCE: 30
gtactctttt cattccaatg gggtgacttt gcttctgga 39

<210> SEQ ID NO 31
<211> LENGTH: 39
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (31)..(35)
<223> OTHER INFORMATION: At least one residue mutated or absent

<400> SEQUENCE: 31
gtacttcata cattccaatg gggtgacttt gcttctgga 39

<210> SEQ ID NO 32
<211> LENGTH: 39
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (31)..(35)
<223> OTHER INFORMATION: At least one residue mutated or absent

<400> SEQUENCE: 32
gtacttcata cttttcaatg gggtgacttt gcttctgga 39

<210> SEQ ID NO 33
<211> LENGTH: 39
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (31)..(35)
<223> OTHER INFORMATION: At least one residue mutated or absent

<400> SEQUENCE: 33
gtacttcata cttttcattc gggtgacttt gcttctgga 39

<210> SEQ ID NO 34
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (26)..(30)
<223> OTHER INFORMATION: At least one residue mutated or absent

<400> SEQUENCE: 34
gtactcattc caatggggtg actttgcttc tgga 34

<210> SEQ ID NO 35
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (21)..(25)
<223> OTHER INFORMATION: At least one residue mutated or absent

<400> SEQUENCE: 35
gtactcaatg gggtgacttt gcttctgga 29

<210> SEQ ID NO 36
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (16)..(20)
<223> OTHER INFORMATION: At least one residue mutated or absent

<400> SEQUENCE: 36
gtactgggtg actttgcttc tgga 24

<210> SEQ ID NO 37
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (26)..(30)

<223> OTHER INFORMATION: At least one residue mutated or absent

<400> SEQUENCE: 37
gtacttcata caatggggtg actttgcttc tgga 34

<210> SEQ ID NO 38
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (21)..(25)
<223> OTHER INFORMATION: At least one residue mutated or absent

<400> SEQUENCE: 38
gtacttcata gggtgacttt gcttctgga 29

<210> SEQ ID NO 39
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (26)..(30)
<223> OTHER INFORMATION: At least one residue mutated or absent

<400> SEQUENCE: 39
gtacttcata cttttgggtg actttgcttc tgga 34

<210> SEQ ID NO 40
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (26)..(30)
<223> OTHER INFORMATION: At least one residue mutated or absent

<400> SEQUENCE: 40
gtactctttt caatggggtg actttgcttc tgga 34

<210> SEQ ID NO 41
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (26)..(30)
<223> OTHER INFORMATION: At least one residue mutated or absent

<400> SEQUENCE: 41
gtacttcata cattcgggtg actttgcttc tgga 34

<210> SEQ ID NO 42
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature

```
<222> LOCATION: (26)..(30)
<223> OTHER INFORMATION: At least one residue mutated or absent

<400> SEQUENCE: 42

gtactctttt cattcgggtg actttgcttc tgga                              34

<210> SEQ ID NO 43
<211> LENGTH: 44
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (36)..(40)
<223> OTHER INFORMATION: At least one residue mutated or absent

<400> SEQUENCE: 43

gtacttcata cttttcattc caatggggtg actttgcttc tgga                   44

<210> SEQ ID NO 44
<211> LENGTH: 39
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (31)..(35)
<223> OTHER INFORMATION: At least one residue mutated or absent

<400> SEQUENCE: 44

gtactctttt cattccaatg gggtgacttt gcttctgga                         39

<210> SEQ ID NO 45
<211> LENGTH: 39
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (31)..(35)
<223> OTHER INFORMATION: At least one residue mutated or absent

<400> SEQUENCE: 45

gtacttcata cattccaatg gggtgacttt gcttctgga                         39

<210> SEQ ID NO 46
<211> LENGTH: 39
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (31)..(35)
<223> OTHER INFORMATION: At least one residue mutated or absent

<400> SEQUENCE: 46

gtacttcata cttttcaatg gggtgacttt gcttctgga                         39

<210> SEQ ID NO 47
<211> LENGTH: 39
<212> TYPE: DNA
<213> ORGANISM: Artificial sequence
<220> FEATURE:
<223> OTHER INFORMATION: Exemplary element X variant
<220> FEATURE:
```

<221> NAME/KEY: misc_feature
<222> LOCATION: (31)..(35)
<223> OTHER INFORMATION: At least one residue mutated or absent

<400> SEQUENCE: 47
gtacttcata cttttcattc gggtgacttt gcttctgga 39

<210> SEQ ID NO 48
<211> LENGTH: 39
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (31)..(35)
<223> OTHER INFORMATION: At least one residue mutated or absent

<400> SEQUENCE: 48
gtacttcata cttttcattc caatgacttt gcttctgga 39

<210> SEQ ID NO 49
<211> LENGTH: 39
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (31)..(35)
<223> OTHER INFORMATION: At least one residue mutated or absent

<400> SEQUENCE: 49
gtacttcata cttttcattc caatggggtg gcttctgga 39

<210> SEQ ID NO 50
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (26)..(30)
<223> OTHER INFORMATION: At least one residue mutated or absent

<400> SEQUENCE: 50
gtactcattc caatggggtg actttgcttc tgga 34

<210> SEQ ID NO 51
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (21)..(25)
<223> OTHER INFORMATION: At least one residue mutated or absent

<400> SEQUENCE: 51
gtactcaatg gggtgacttt gcttctgga 29

<210> SEQ ID NO 52
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (16)..(20)
<223> OTHER INFORMATION: At least one residue mutated or absent

<400> SEQUENCE: 52
gtactgggtg actttgcttc tgga 24

<210> SEQ ID NO 53
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(15)
<223> OTHER INFORMATION: At least one residue mutated or absent

<400> SEQUENCE: 53
gtactacttt gcttctgga 19

<210> SEQ ID NO 54
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (26)..(30)
<223> OTHER INFORMATION: At least one residue mutated or absent

<400> SEQUENCE: 54
gtacttcata caatggggtg actttgcttc tgga 34

<210> SEQ ID NO 55
<211> LENGTH: 28
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (21)..(25)
<223> OTHER INFORMATION: At least one residue mutated or absent

<400> SEQUENCE: 55
cattccaatg gggtgacttt gcttctgg 28

<210> SEQ ID NO 56
<211> LENGTH: 23
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (16)..(20)
<223> OTHER INFORMATION: At least one residue mutated or absent

<400> SEQUENCE: 56
cattcgggtg actttgcttc tgg 23

<210> SEQ ID NO 57
<211> LENGTH: 19
<212> TYPE: DNA
<213> ORGANISM: Artificial sequence
<220> FEATURE:

<223> OTHER INFORMATION: Exemplary element X variant
<220> FEATURE:
<221> NAME/KEY: misc_feature
<222> LOCATION: (11)..(15)
<223> OTHER INFORMATION: At least one residue mutated or absent

<400> SEQUENCE: 57
cattcacttt gcttctgga 19

<210> SEQ ID NO 58
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(15)
<223> OTHER INFORMATION: At least one residue mutated or absent

<400> SEQUENCE: 58
cttttcattc gcttctgga 19

<210> SEQ ID NO 59
<211> LENGTH: 23
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (16)..(20)
<223> OTHER INFORMATION: At least one residue mutated or absent

<400> SEQUENCE: 59
cattccaatg actttgcttc tgg 23

<210> SEQ ID NO 60
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(15)
<223> OTHER INFORMATION: At least one residue mutated or absent

<400> SEQUENCE: 60
cattccaatg gcttctgga 19

<210> SEQ ID NO 61
<211> LENGTH: 23
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (16)..(20)
<223> OTHER INFORMATION: At least one residue mutated or absent

<400> SEQUENCE: 61
cattccaatg gggtggcttc tgg 23

<210> SEQ ID NO 62
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(15)
<223> OTHER INFORMATION: At least one residue mutated or absent

<400> SEQUENCE: 62
cattcgggtg gcttctgga 19

<210> SEQ ID NO 63
<211> LENGTH: 23
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (16)..(20)
<223> OTHER INFORMATION: At least one residue mutated or absent

<400> SEQUENCE: 63
caatggggtg actttgcttc tgg 23

<210> SEQ ID NO 64
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(15)
<223> OTHER INFORMATION: At least one residue mutated or absent

<400> SEQUENCE: 64
caatggggtg gcttctgga 19

<210> SEQ ID NO 65
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(15)
<223> OTHER INFORMATION: At least one residue mutated or absent

<400> SEQUENCE: 65
caatgacttt gcttctgga 19

<210> SEQ ID NO 66
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(15)
<223> OTHER INFORMATION: At least one residue mutated or absent

<400> SEQUENCE: 66
cattccaatg gcttctgga 19

<210> SEQ ID NO 67
<211> LENGTH: 28
<212> TYPE: DNA

<213> ORGANISM: Artificial sequence
<220> FEATURE:
<223> OTHER INFORMATION: Exemplary element X variant
<220> FEATURE:
<221> NAME/KEY: misc_feature
<222> LOCATION: (21)..(25)
<223> OTHER INFORMATION: At least one residue mutated or absent

<400> SEQUENCE: 67
cattccaatg gggtgacttt gcttctgg 28

<210> SEQ ID NO 68
<211> LENGTH: 23
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (16)..(20)
<223> OTHER INFORMATION: At least one residue mutated or absent

<400> SEQUENCE: 68
cattccaatg actttgcttc tgg 23

<210> SEQ ID NO 69
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(15)
<223> OTHER INFORMATION: At least one residue mutated or absent

<400> SEQUENCE: 69
cattccaatg gcttctgga 19

<210> SEQ ID NO 70
<211> LENGTH: 23
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (16)..(20)
<223> OTHER INFORMATION: At least one residue mutated or absent

<400> SEQUENCE: 70
cattccaatg gggtggcttc tgg 23

<210> SEQ ID NO 71
<211> LENGTH: 43
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (36)..(40)
<223> OTHER INFORMATION: At least one residue mutated or absent

<400> SEQUENCE: 71
gtacttcata cttttcattc caatggggtg actttgcttc tgg 43

<210> SEQ ID NO 72
<211> LENGTH: 43
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (36)..(40)
<223> OTHER INFORMATION: At least one residue mutated or absent

<400> SEQUENCE: 72
gtacttcata cttttcattc caatggggtg actttgcttc tgg 43

<210> SEQ ID NO 73
<211> LENGTH: 38
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (31)..(35)
<223> OTHER INFORMATION: At least one residue mutated or absent

<400> SEQUENCE: 73
gtactctttt cattccaatg gggtgacttt gcttctgg 38

<210> SEQ ID NO 74
<211> LENGTH: 38
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (31)..(35)
<223> OTHER INFORMATION: At least one residue mutated or absent

<400> SEQUENCE: 74
gtacttcata cattccaatg gggtgacttt gcttctgg 38

<210> SEQ ID NO 75
<211> LENGTH: 33
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (26)..(30)
<223> OTHER INFORMATION: At least one residue mutated or absent

<400> SEQUENCE: 75
gtactcattc caatggggtg actttgcttc tgg 33

<210> SEQ ID NO 76
<211> LENGTH: 43
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (36)..(40)
<223> OTHER INFORMATION: At least one residue mutated or absent

<400> SEQUENCE: 76
gtacttcata cttttcattc caatggggtg actttgcttc tgg 43

<210> SEQ ID NO 77
<211> LENGTH: 38
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (31)..(35)
<223> OTHER INFORMATION: At least one residue mutated or absent

<400> SEQUENCE: 77
gtacttcata cttttcattc gggtgacttt gcttctgg 38

<210> SEQ ID NO 78
<211> LENGTH: 38
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (31)..(35)
<223> OTHER INFORMATION: At least one residue mutated or absent

<400> SEQUENCE: 78
gtacttcata cttttcattc caatgacttt gcttctgg 38

<210> SEQ ID NO 79
<211> LENGTH: 38
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (31)..(35)
<223> OTHER INFORMATION: At least one residue mutated or absent

<400> SEQUENCE: 79
gtacttcata cttttcattc caatggggtg gcttctgg 38

<210> SEQ ID NO 80
<211> LENGTH: 33
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (26)..(30)
<223> OTHER INFORMATION: At least one residue mutated or absent

<400> SEQUENCE: 80
gtacttcata cttttcattc actttgcttc tgg 33

<210> SEQ ID NO 81
<211> LENGTH: 33
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (26)..(30)
<223> OTHER INFORMATION: At least one residue mutated or absent

<400> SEQUENCE: 81
gtacttcata cttttcattc gggtggcttc tgg 33

<210> SEQ ID NO 82
<211> LENGTH: 28
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (21)..(25)
<223> OTHER INFORMATION: At least one residue mutated or absent

<400> SEQUENCE: 82
gtacttcata cttttcattc gcttctgg 28

<210> SEQ ID NO 83
<211> LENGTH: 33
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (26)..(30)
<223> OTHER INFORMATION: At least one residue mutated or absent

<400> SEQUENCE: 83
gtacttcata cttttcattc caatggcttc tgg 33

<210> SEQ ID NO 84
<211> LENGTH: 33
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (26)..(30)
<223> OTHER INFORMATION: At least one residue mutated or absent

<400> SEQUENCE: 84
gtacttcata cattcgggtg actttgcttc tgg 33

<210> SEQ ID NO 85
<211> LENGTH: 33
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (26)..(30)
<223> OTHER INFORMATION: At least one residue mutated or absent

<400> SEQUENCE: 85
gtacttcata cattccaatg actttgcttc tgg 33

<210> SEQ ID NO 86
<211> LENGTH: 33
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (26)..(30)
<223> OTHER INFORMATION: At least one residue mutated or absent

<400> SEQUENCE: 86
gtacttcata cattccaatg gggtggcttc tgg 33

<210> SEQ ID NO 87
<211> LENGTH: 28
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (21)..(25)
<223> OTHER INFORMATION: At least one residue mutated or absent

<400> SEQUENCE: 87
gtacttcata cattcacttt gcttctgg 28

<210> SEQ ID NO 88
<211> LENGTH: 28
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (21)..(25)
<223> OTHER INFORMATION: At least one residue mutated or absent

<400> SEQUENCE: 88
gtacttcata cattcgggtg gcttctgg 28

<210> SEQ ID NO 89
<211> LENGTH: 23
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (16)..(20)
<223> OTHER INFORMATION: At least one residue mutated or absent

<400> SEQUENCE: 89
gtacttcata cattcgcttc tgg 23

<210> SEQ ID NO 90
<211> LENGTH: 28
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (21)..(25)
<223> OTHER INFORMATION: At least one residue mutated or absent

<400> SEQUENCE: 90
gtacttcata cattccaatg gcttctgg 28

<210> SEQ ID NO 91
<211> LENGTH: 38
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (31)..(35)

<223> OTHER INFORMATION: At least one residue mutated or absent

<400> SEQUENCE: 91
gtactctttt cattccaatg gggtgacttt gcttctgg 38

<210> SEQ ID NO 92
<211> LENGTH: 33
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (26)..(30)
<223> OTHER INFORMATION: At least one residue mutated or absent

<400> SEQUENCE: 92
gtactctttt cattcgggtg actttgcttc tgg 33

<210> SEQ ID NO 93
<211> LENGTH: 33
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (26)..(30)
<223> OTHER INFORMATION: At least one residue mutated or absent

<400> SEQUENCE: 93
gtactctttt cattccaatg actttgcttc tgg 33

<210> SEQ ID NO 94
<211> LENGTH: 33
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (26)..(30)
<223> OTHER INFORMATION: At least one residue mutated or absent

<400> SEQUENCE: 94
gtactctttt cattccaatg gggtggcttc tgg 33

<210> SEQ ID NO 95
<211> LENGTH: 28
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (21)..(25)
<223> OTHER INFORMATION: At least one residue mutated or absent

<400> SEQUENCE: 95
gtactctttt cattcacttt gcttctgg 28

<210> SEQ ID NO 96
<211> LENGTH: 28
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (21)..(25)
<223> OTHER INFORMATION: At least one residue mutated or absent

<400> SEQUENCE: 96
gtactctttt cattcgggtg gcttctgg 28

<210> SEQ ID NO 97
<211> LENGTH: 23
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (16)..(20)
<223> OTHER INFORMATION: At least one residue mutated or absent

<400> SEQUENCE: 97
gtactctttt cattcgcttc tgg 23

<210> SEQ ID NO 98
<211> LENGTH: 28
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (21)..(25)
<223> OTHER INFORMATION: At least one residue mutated or absent

<400> SEQUENCE: 98
gtactctttt cattccaatg gcttctgg 28

<210> SEQ ID NO 99
<211> LENGTH: 33
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:

<221> NAME/KEY: misc_feature
<222> LOCATION: (26)..(30)
<223> OTHER INFORMATION: At least one residue mutated or absent

<400> SEQUENCE: 99
gtactcattc caatggggtg actttgcttc tgg 33

<210> SEQ ID NO 100
<211> LENGTH: 28
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (21)..(25)
<223> OTHER INFORMATION: At least one residue mutated or absent

<400> SEQUENCE: 100
gtactcattc gggtgacttt gcttctgg 28

<210> SEQ ID NO 101
<211> LENGTH: 28
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (21)..(25)
<223> OTHER INFORMATION: At least one residue mutated or absent

<400> SEQUENCE: 101
gtactcattc caatgacttt gcttctgg 28

<210> SEQ ID NO 102
<211> LENGTH: 28
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (21)..(25)
<223> OTHER INFORMATION: At least one residue mutated or absent

<400> SEQUENCE: 102
gtactcattc caatggggtg gcttctgg 28

<210> SEQ ID NO 103
<211> LENGTH: 23
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (16)..(20)
<223> OTHER INFORMATION: At least one residue mutated or absent

<400> SEQUENCE: 103
gtactcattc actttgcttc tgg 23

<210> SEQ ID NO 104
<211> LENGTH: 23
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (16)..(20)
<223> OTHER INFORMATION: At least one residue mutated or absent

<400> SEQUENCE: 104
gtactcattc gggtggcttc tgg 23

<210> SEQ ID NO 105
<211> LENGTH: 23
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (16)..(20)
<223> OTHER INFORMATION: At least one residue mutated or absent

<400> SEQUENCE: 105
gtactcattc caatggcttc tgg 23

<210> SEQ ID NO 106
<211> LENGTH: 43
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (36)..(40)
<223> OTHER INFORMATION: At least one residue mutated or absent

<400> SEQUENCE: 106
gtacttcata cttttcattc caatggggtg actttgcttc tgg 43

<210> SEQ ID NO 107
<211> LENGTH: 38
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)

<223> OTHER INFORMATION: At least one residue mutated or absent
<220> FEATURE:
<221> NAME/KEY: misc_feature
<222> LOCATION: (31)..(35)
<223> OTHER INFORMATION: At least one residue mutated or absent

<400> SEQUENCE: 107
gtactctttt cattccaatg gggtgacttt gcttctgg 38

<210> SEQ ID NO 108
<211> LENGTH: 38
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (31)..(35)
<223> OTHER INFORMATION: At least one residue mutated or absent

<400> SEQUENCE: 108
gtacttcata cattccaatg gggtgacttt gcttctgg 38

<210> SEQ ID NO 109
<211> LENGTH: 38
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (31)..(35)
<223> OTHER INFORMATION: At least one residue mutated or absent

<400> SEQUENCE: 109
gtacttcata cttttcaatg gggtgacttt gcttctgg 38

<210> SEQ ID NO 110
<211> LENGTH: 33
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (26)..(30)
<223> OTHER INFORMATION: At least one residue mutated or absent

<400> SEQUENCE: 110
gtactcattc caatggggtg actttgcttc tgg 33

<210> SEQ ID NO 111
<211> LENGTH: 33
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (26)..(30)
<223> OTHER INFORMATION: At least one residue mutated or absent

<400> SEQUENCE: 111
gtacttcata caatggggtg actttgcttc tgg 33

<210> SEQ ID NO 112
<211> LENGTH: 33
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (26)..(30)
<223> OTHER INFORMATION: At least one residue mutated or absent

<400> SEQUENCE: 112
gtactctttt caatggggtg actttgcttc tgg 33

<210> SEQ ID NO 113
<211> LENGTH: 28
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (21)..(25)
<223> OTHER INFORMATION: At least one residue mutated or absent

<400> SEQUENCE: 113
gtactcaatg gggtgacttt gcttctgg 28

<210> SEQ ID NO 114
<211> LENGTH: 38
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (31)..(35)
<223> OTHER INFORMATION: At least one residue mutated or absent

<400> SEQUENCE: 114
gtacttcata cttttcattc caatgacttt gcttctgg 38

<210> SEQ ID NO 115
<211> LENGTH: 38
<212> TYPE: DNA
<213> ORGANISM: Artificial sequence
<220> FEATURE:
<223> OTHER INFORMATION: Exemplary element X variant
<220> FEATURE:

<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (31)..(35)
<223> OTHER INFORMATION: At least one residue mutated or absent

<400> SEQUENCE: 115
gtacttcata cttttcattc caatggggtg gcttctgg 38

<210> SEQ ID NO 116
<211> LENGTH: 33
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (26)..(30)
<223> OTHER INFORMATION: At least one residue mutated or absent

<400> SEQUENCE: 116
gtacttcata cttttcattc caatggcttc tgg 33

<210> SEQ ID NO 117
<211> LENGTH: 33
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (26)..(30)
<223> OTHER INFORMATION: At least one residue mutated or absent

<400> SEQUENCE: 117
gtactctttt cattccaatg actttgcttc tgg 33

<210> SEQ ID NO 118
<211> LENGTH: 33
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (26)..(30)
<223> OTHER INFORMATION: At least one residue mutated or absent

<400> SEQUENCE: 118
gtacttcata cattccaatg actttgcttc tgg 33

<210> SEQ ID NO 119
<211> LENGTH: 33
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (26)..(30)
<223> OTHER INFORMATION: At least one residue mutated or absent

<400> SEQUENCE: 119
gtacttcata cttttcaatg actttgcttc tgg 33

<210> SEQ ID NO 120
<211> LENGTH: 28
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (21)..(25)
<223> OTHER INFORMATION: At least one residue mutated or absent

<400> SEQUENCE: 120
gtactcattc caatgacttt gcttctgg 28

<210> SEQ ID NO 121
<211> LENGTH: 28
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (21)..(25)
<223> OTHER INFORMATION: At least one residue mutated or absent

<400> SEQUENCE: 121
gtacttcata caatgacttt gcttctgg 28

<210> SEQ ID NO 122
<211> LENGTH: 28
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (21)..(25)
<223> OTHER INFORMATION: At least one residue mutated or absent

<400> SEQUENCE: 122
gtactctttt caatgacttt gcttctgg 28

<210> SEQ ID NO 123
<211> LENGTH: 23
<212> TYPE: DNA
<213> ORGANISM: Artificial sequence
<220> FEATURE:

<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (16)..(20)
<223> OTHER INFORMATION: At least one residue mutated or absent

<400> SEQUENCE: 123
gtactcaatg actttgcttc tgg 23

<210> SEQ ID NO 124
<211> LENGTH: 33
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (26)..(30)
<223> OTHER INFORMATION: At least one residue mutated or absent

<400> SEQUENCE: 124
gtactctttt cattccaatg gggtggcttc tgg 33

<210> SEQ ID NO 125
<211> LENGTH: 33
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (26)..(30)
<223> OTHER INFORMATION: At least one residue mutated or absent

<400> SEQUENCE: 125
gtacttcata cattccaatg gggtggcttc tgg 33

<210> SEQ ID NO 126
<211> LENGTH: 33
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (26)..(30)
<223> OTHER INFORMATION: At least one residue mutated or absent

<400> SEQUENCE: 126
gtacttcata cttttcaatg gggtggcttc tgg 33

<210> SEQ ID NO 127
<211> LENGTH: 28
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (21)..(25)
<223> OTHER INFORMATION: At least one residue mutated or absent

<400> SEQUENCE: 127
gtactcattc caatggggtg gcttctgg 28

<210> SEQ ID NO 128
<211> LENGTH: 28
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (21)..(25)
<223> OTHER INFORMATION: At least one residue mutated or absent

<400> SEQUENCE: 128
gtacttcata caatggggtg gcttctgg 28

<210> SEQ ID NO 129
<211> LENGTH: 28
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (21)..(25)
<223> OTHER INFORMATION: At least one residue mutated or absent

<400> SEQUENCE: 129
gtactctttt caatggggtg gcttctgg 28

<210> SEQ ID NO 130
<211> LENGTH: 23
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (16)..(20)
<223> OTHER INFORMATION: At least one residue mutated or absent

<400> SEQUENCE: 130
gtactcaatg gggtggcttc tgg 23

<210> SEQ ID NO 131
<211> LENGTH: 28
<212> TYPE: DNA

<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (21)..(25)
<223> OTHER INFORMATION: At least one residue mutated or absent

<400> SEQUENCE: 131
gtactctttt cattccaatg gcttctgg 28

<210> SEQ ID NO 132
<211> LENGTH: 28
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (21)..(25)
<223> OTHER INFORMATION: At least one residue mutated or absent

<400> SEQUENCE: 132
gtacttcata cattccaatg gcttctgg 28

<210> SEQ ID NO 133
<211> LENGTH: 28
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (21)..(25)
<223> OTHER INFORMATION: At least one residue mutated or absent

<400> SEQUENCE: 133
gtacttcata cttttcaatg gcttctgg 28

<210> SEQ ID NO 134
<211> LENGTH: 23
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (16)..(20)
<223> OTHER INFORMATION: At least one residue mutated or absent

<400> SEQUENCE: 134
gtactcattc caatggcttc tgg 23

<210> SEQ ID NO 135
<211> LENGTH: 23

<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (16)..(20)
<223> OTHER INFORMATION: At least one residue mutated or absent

<400> SEQUENCE: 135
gtacttcata caatggcttc tgg 23

<210> SEQ ID NO 136
<211> LENGTH: 23
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (16)..(20)
<223> OTHER INFORMATION: At least one residue mutated or absent

<400> SEQUENCE: 136
gtactctttt caatggcttc tgg 23

<210> SEQ ID NO 137
<211> LENGTH: 43
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (36)..(40)
<223> OTHER INFORMATION: At least one residue mutated or absent

<400> SEQUENCE: 137
gtacttcata cttttcattc caatggggtg actttgcttc tgg 43

<210> SEQ ID NO 138
<211> LENGTH: 38
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (31)..(35)
<223> OTHER INFORMATION: At least one residue mutated or absent

<400> SEQUENCE: 138
gtactctttt cattccaatg gggtgacttt gcttctgg 38

<210> SEQ ID NO 139

<211> LENGTH: 38
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (31)..(35)
<223> OTHER INFORMATION: At least one residue mutated or absent

<400> SEQUENCE: 139
gtacttcata cattccaatg gggtgacttt gcttctgg 38

<210> SEQ ID NO 140
<211> LENGTH: 33
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (26)..(30)
<223> OTHER INFORMATION: At least one residue mutated or absent

<400> SEQUENCE: 140
gtactcattc caatggggtg actttgcttc tgg 33

<210> SEQ ID NO 141
<211> LENGTH: 38
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (31)..(35)
<223> OTHER INFORMATION: At least one residue mutated or absent

<400> SEQUENCE: 141
gtacttcata cttttcattc caatgacttt gcttctgg 38

<210> SEQ ID NO 142
<211> LENGTH: 38
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (31)..(35)
<223> OTHER INFORMATION: At least one residue mutated or absent

<400> SEQUENCE: 142
gtacttcata cttttcattc caatggggtg gcttctgg 38

<210> SEQ ID NO 143
<211> LENGTH: 33
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (26)..(30)
<223> OTHER INFORMATION: At least one residue mutated or absent

<400> SEQUENCE: 143
gtacttcata cttttcattc caatggcttc tgg 33

<210> SEQ ID NO 144
<211> LENGTH: 33
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (26)..(30)
<223> OTHER INFORMATION: At least one residue mutated or absent

<400> SEQUENCE: 144
gtactctttt cattccaatg actttgcttc tgg 33

<210> SEQ ID NO 145
<211> LENGTH: 33
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (26)..(30)
<223> OTHER INFORMATION: At least one residue mutated or absent

<400> SEQUENCE: 145
gtacttcata cattccaatg actttgcttc tgg 33

<210> SEQ ID NO 146
<211> LENGTH: 28
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (21)..(25)
<223> OTHER INFORMATION: At least one residue mutated or absent

<400> SEQUENCE: 146
gtactcattc caatgacttt gcttctgg 28

<210> SEQ ID NO 147
<211> LENGTH: 33
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (26)..(30)
<223> OTHER INFORMATION: At least one residue mutated or absent

<400> SEQUENCE: 147
gtactctttt cattccaatg gggtggcttc tgg 33

<210> SEQ ID NO 148
<211> LENGTH: 33
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (26)..(30)
<223> OTHER INFORMATION: At least one residue mutated or absent

<400> SEQUENCE: 148
gtacttcata cattccaatg gggtggcttc tgg 33

<210> SEQ ID NO 149
<211> LENGTH: 28
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (21)..(25)
<223> OTHER INFORMATION: At least one residue mutated or absent

<400> SEQUENCE: 149
gtactcattc caatggggtg gcttctgg 28

<210> SEQ ID NO 150
<211> LENGTH: 28
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (21)..(25)
<223> OTHER INFORMATION: At least one residue mutated or absent

<400> SEQUENCE: 150
gtactctttt cattccaatg gcttctgg 28

<210> SEQ ID NO 151
<211> LENGTH: 28
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (21)..(25)
<223> OTHER INFORMATION: At least one residue mutated or absent

<400> SEQUENCE: 151
gtacttcata cattccaatg gcttctgg 28

<210> SEQ ID NO 152
<211> LENGTH: 23
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(5)
<223> OTHER INFORMATION: At least one residue mutated or absent
<220> FEATURE:
<221> NAME/KEY: misc_feature
<222> LOCATION: (16)..(20)
<223> OTHER INFORMATION: At least one residue mutated or absent

<400> SEQUENCE: 152
gtactcattc caatggcttc tgg 23

<210> SEQ ID NO 153
<211> LENGTH: 43
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (16)..(20)
<223> OTHER INFORMATION: At least one residue mutated or absent

<400> SEQUENCE: 153
gtacttcata cttttcattc caatggggtg actttgcttc tgg 43

<210> SEQ ID NO 154
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(11)
<223> OTHER INFORMATION: At least one residue mutated or absent

<400> SEQUENCE: 154
acttttcatt ccaatgggg 19

<210> SEQ ID NO 155
<211> LENGTH: 19
<212> TYPE: DNA
<213> ORGANISM: Artificial sequence
<220> FEATURE:

<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 155
cttttcattc caatggggt 19

<210> SEQ ID NO 156
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(9)
<223> OTHER INFORMATION: At least one residue mutated or absent

<400> SEQUENCE: 156
ttttcattcc aatggggtg 19

<210> SEQ ID NO 157
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(8)
<223> OTHER INFORMATION: At least one residue mutated or absent

<400> SEQUENCE: 157
tttcattcca atggggtga 19

<210> SEQ ID NO 158
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(12)
<223> OTHER INFORMATION: At least one residue mutated or absent

<400> SEQUENCE: 158
tacttttcat tccaatggg 19

<210> SEQ ID NO 159
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(13)
<223> OTHER INFORMATION: At least one residue mutated or absent

<400> SEQUENCE: 159
atacttttca ttccaatgg 19

<210> SEQ ID NO 160
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(14)
<223> OTHER INFORMATION: At least one residue mutated or absent

<400> SEQUENCE: 160
catacttttc attccaatg 19

<210> SEQ ID NO 161
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(15)
<223> OTHER INFORMATION: At least one residue mutated or absent

<400> SEQUENCE: 161
tcatactttt cattccaat 19

<210> SEQ ID NO 162
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (12)..(16)
<223> OTHER INFORMATION: At least one residue mutated or absent

<400> SEQUENCE: 162
ttcatacttt tcattccaa 19

<210> SEQ ID NO 163
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(8)
<223> OTHER INFORMATION: At least one residue mutated or absent

<400> SEQUENCE: 163
ttccaatggg gtgactttg 19

<210> SEQ ID NO 164
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(9)
<223> OTHER INFORMATION: At least one residue mutated or absent

<400> SEQUENCE: 164
attccaatgg ggtgacttt 19

<210> SEQ ID NO 165
<211> LENGTH: 19
<212> TYPE: DNA

<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 165
cattccaatg gggtgactt 19

<210> SEQ ID NO 166
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(11)
<223> OTHER INFORMATION: At least one residue mutated or absent

<400> SEQUENCE: 166
tcattccaat ggggtgact 19

<210> SEQ ID NO 167
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(12)
<223> OTHER INFORMATION: At least one residue mutated or absent

<400> SEQUENCE: 167
ttcattccaa tggggtgac 19

<210> SEQ ID NO 168
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(13)
<223> OTHER INFORMATION: At least one residue mutated or absent

<400> SEQUENCE: 168
tttcattcca atggggtga 19

<210> SEQ ID NO 169
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(14)
<223> OTHER INFORMATION: At least one residue mutated or absent

<400> SEQUENCE: 169
ttttcattcc aatggggtg 19

<210> SEQ ID NO 170
<211> LENGTH: 19

<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(15)
<223> OTHER INFORMATION: At least one residue mutated or absent

<400> SEQUENCE: 170
cttttcattc caatggggt 19

<210> SEQ ID NO 171
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (12)..(16)
<223> OTHER INFORMATION: At least one residue mutated or absent

<400> SEQUENCE: 171
acttttcatt ccaatgggg 19

<210> SEQ ID NO 172
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(13)
<223> OTHER INFORMATION: At least one residue mutated or absent

<400> SEQUENCE: 172
tttcattcca atggggtgac tttg 24

<210> SEQ ID NO 173
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(14)
<223> OTHER INFORMATION: At least one residue mutated or absent

<400> SEQUENCE: 173
ttttcattcc aatggggtga cttt 24

<210> SEQ ID NO 174
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(15)
<223> OTHER INFORMATION: At least one residue mutated or absent

<400> SEQUENCE: 174
cttttcattc caatggggtg actt 24

<210> SEQ ID NO 175

<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(16)
<223> OTHER INFORMATION: At least one residue mutated or absent

<400> SEQUENCE: 175
acttttcatt ccaatggggt gact 24

<210> SEQ ID NO 176
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(17)
<223> OTHER INFORMATION: At least one residue mutated or absent

<400> SEQUENCE: 176
tacttttcat tccaatgggg tgac 24

<210> SEQ ID NO 177
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(18)
<223> OTHER INFORMATION: At least one residue mutated or absent

<400> SEQUENCE: 177
atacttttca ttccaatggg gtga 24

<210> SEQ ID NO 178
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(19)
<223> OTHER INFORMATION: At least one residue mutated or absent

<400> SEQUENCE: 178
catacttttc attccaatgg ggtg 24

<210> SEQ ID NO 179
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(20)
<223> OTHER INFORMATION: At least one residue mutated or absent

<400> SEQUENCE: 179
tcatactttt cattccaatg gggt 24

<210> SEQ ID NO 180
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(21)
<223> OTHER INFORMATION: At least one residue mutated or absent

<400> SEQUENCE: 180
ttcatacttt tcattccaat gggg 24

<210> SEQ ID NO 181
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(9)
<223> OTHER INFORMATION: At least one residue mutated or absent

<400> SEQUENCE: 181
ttttcattcc aatggggtg 19

<210> SEQ ID NO 182
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(8)
<223> OTHER INFORMATION: At least one residue mutated or absent

<400> SEQUENCE: 182
tttcattcca atggggtga 19

<210> SEQ ID NO 183
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(9)
<223> OTHER INFORMATION: At least one residue mutated or absent

<400> SEQUENCE: 183
attccaatgg ggtgacttt 19

<210> SEQ ID NO 184
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(8)
<223> OTHER INFORMATION: At least one residue mutated or absent

<400> SEQUENCE: 184
ttccaatggg gtgactttg 19

<210> SEQ ID NO 185
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 185
cattccaatg gggtgactt 19

<210> SEQ ID NO 186
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(11)
<223> OTHER INFORMATION: At least one residue mutated or absent

<400> SEQUENCE: 186
tcattccaat ggggtgact 19

<210> SEQ ID NO 187
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(12)
<223> OTHER INFORMATION: At least one residue mutated or absent

<400> SEQUENCE: 187
ttcattccaa tggggtgac 19

<210> SEQ ID NO 188
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(13)
<223> OTHER INFORMATION: At least one residue mutated or absent

<400> SEQUENCE: 188
tttcattcca atggggtga 19

<210> SEQ ID NO 189
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(14)
<223> OTHER INFORMATION: At least one residue mutated or absent

<400> SEQUENCE: 189
ttttcattcc aatggggtg 19

<210> SEQ ID NO 190
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(14)
<223> OTHER INFORMATION: At least one residue mutated or absent

<400> SEQUENCE: 190
ttttcattcc aatggggtga cttt 24

<210> SEQ ID NO 191
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(20)
<223> OTHER INFORMATION: At least one residue mutated or absent

<400> SEQUENCE: 191
tcatactttt cattccaatg gggtg 25

<210> SEQ ID NO 192
<211> LENGTH: 23
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(8)
<223> OTHER INFORMATION: At least one residue mutated or absent

<400> SEQUENCE: 192
tttcattcca atggggtgac ttt 23

<210> SEQ ID NO 193
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(9)
<223> OTHER INFORMATION: At least one residue mutated or absent

<400> SEQUENCE: 193
ttttcattcg ggtgacttt 19

<210> SEQ ID NO 194
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(9)
<223> OTHER INFORMATION: At least one residue mutated or absent

<400> SEQUENCE: 194
ttttcattcc aatgactttg cttc 24

<210> SEQ ID NO 195
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(9)
<223> OTHER INFORMATION: At least one residue mutated or absent

<400> SEQUENCE: 195
ttttcattca ctttgcttc 19

<210> SEQ ID NO 196
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(9)
<223> OTHER INFORMATION: At least one residue mutated or absent

<400> SEQUENCE: 196
attccaatgg ggtgacttt 19

<210> SEQ ID NO 197
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(9)
<223> OTHER INFORMATION: At least one residue mutated or absent

<400> SEQUENCE: 197
attccaatga ctttgcttc 19

<210> SEQ ID NO 198
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(8)
<223> OTHER INFORMATION: At least one residue mutated or absent

<400> SEQUENCE: 198
ttccaatgac tttgcttct 19

<210> SEQ ID NO 199
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(13)
<223> OTHER INFORMATION: At least one residue mutated or absent

<400> SEQUENCE: 199
tttcattcca atggggtgac tttg 24

<210> SEQ ID NO 200
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(14)
<223> OTHER INFORMATION: At least one residue mutated or absent

<400> SEQUENCE: 200
ttttcattcc aatggggtga cttt 24

<210> SEQ ID NO 201
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(15)
<223> OTHER INFORMATION: At least one residue mutated or absent

<400> SEQUENCE: 201
cttttcattc caatggggtg acttt 25

<210> SEQ ID NO 202
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(14)
<223> OTHER INFORMATION: At least one residue mutated or absent

<400> SEQUENCE: 202
ttttcattcc aatgactttg cttc 24

<210> SEQ ID NO 203
<211> LENGTH: 23
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(8)
<223> OTHER INFORMATION: At least one residue mutated or absent

<400> SEQUENCE: 203
tttcattcca atggggtgac ttt 23

<210> SEQ ID NO 204
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(9)
<223> OTHER INFORMATION: At least one residue mutated or absent

<400> SEQUENCE: 204
ttttcattcg ggtgacttt 19

<210> SEQ ID NO 205
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(8)
<223> OTHER INFORMATION: At least one residue mutated or absent

<400> SEQUENCE: 205
tttcattcgg gtgactttg 19

<210> SEQ ID NO 206
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(9)
<223> OTHER INFORMATION: At least one residue mutated or absent

<400> SEQUENCE: 206
attccaatgg ggtgacttt 19

<210> SEQ ID NO 207
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(8)
<223> OTHER INFORMATION: At least one residue mutated or absent

<400> SEQUENCE: 207
ttccaatggg gtgactttg 19

<210> SEQ ID NO 208
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(14)
<223> OTHER INFORMATION: At least one residue mutated or absent

<400> SEQUENCE: 208
ttttcattcc aatggggtga cttt 24

<210> SEQ ID NO 209
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(13)
<223> OTHER INFORMATION: At least one residue mutated or absent

<400> SEQUENCE: 209
tttcattcca atggggtgac tttg 24

<210> SEQ ID NO 210
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(8)
<223> OTHER INFORMATION: At least one residue mutated or absent
<220> FEATURE:
<221> NAME/KEY: misc_feature
<222> LOCATION: (14)..(18)
<223> OTHER INFORMATION: At least one residue mutated or absent

<400> SEQUENCE: 210
tttcattcca atggggtgac tttg 24

<210> SEQ ID NO 211
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(9)
<223> OTHER INFORMATION: At least one residue mutated or absent
<220> FEATURE:
<221> NAME/KEY: misc_feature
<222> LOCATION: (15)..(19)
<223> OTHER INFORMATION: At least one residue mutated or absent

<400> SEQUENCE: 211
ttttcattcc aatggggtga cttt 24

<210> SEQ ID NO 212
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent
<220> FEATURE:
<221> NAME/KEY: misc_feature
<222> LOCATION: (16)..(20)
<223> OTHER INFORMATION: At least one residue mutated or absent

<400> SEQUENCE: 212
cttttcattc caatggggtg actt 24

<210> SEQ ID NO 213
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(11)
<223> OTHER INFORMATION: At least one residue mutated or absent
<220> FEATURE:
<221> NAME/KEY: misc_feature
<222> LOCATION: (17)..(21)

<223> OTHER INFORMATION: At least one residue mutated or absent

<400> SEQUENCE: 213
acttttcatt ccaatggggt gact 24

<210> SEQ ID NO 214
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(13)
<223> OTHER INFORMATION: At least one residue mutated or absent

<400> SEQUENCE: 214
ttccaatggg gtgactttgc ttct 24

<210> SEQ ID NO 215
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(14)
<223> OTHER INFORMATION: At least one residue mutated or absent

<400> SEQUENCE: 215
attccaatgg ggtgactttg cttc 24

<210> SEQ ID NO 216
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(15)
<223> OTHER INFORMATION: At least one residue mutated or absent

<400> SEQUENCE: 216
cattccaatg gggtgacttt gctt 24

<210> SEQ ID NO 217
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(16)
<223> OTHER INFORMATION: At least one residue mutated or absent

<400> SEQUENCE: 217
tcattccaat ggggtgactt tgct 24

<210> SEQ ID NO 218
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(17)
<223> OTHER INFORMATION: At least one residue mutated or absent

<400> SEQUENCE: 218
ttcattccaa tggggtgact ttgc 24

<210> SEQ ID NO 219
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(18)
<223> OTHER INFORMATION: At least one residue mutated or absent

<400> SEQUENCE: 219
tttcattcca atggggtgac tttg 24

<210> SEQ ID NO 220
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(19)
<223> OTHER INFORMATION: At least one residue mutated or absent

<400> SEQUENCE: 220
ttttcattcc aatggggtga cttt 24

<210> SEQ ID NO 221
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(20)
<223> OTHER INFORMATION: At least one residue mutated or absent

<400> SEQUENCE: 221
cttttcattc caatggggtg actt 24

<210> SEQ ID NO 222
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (12)..(21)
<223> OTHER INFORMATION: At least one residue mutated or absent

<400> SEQUENCE: 222
acttttcatt ccaatggggt gact 24

<210> SEQ ID NO 223
<211> LENGTH: 29
<212> TYPE: DNA
<213> ORGANISM: Artificial sequence
<220> FEATURE:
<223> OTHER INFORMATION: Exemplary element X variant
<220> FEATURE:

<221> NAME/KEY: misc_feature
<222> LOCATION: (4)..(18)
<223> OTHER INFORMATION: At least one residue mutated or absent

<400> SEQUENCE: 223
tttcattcca atggggtgac tttgcttct 29

<210> SEQ ID NO 224
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(19)
<223> OTHER INFORMATION: At least one residue mutated or absent

<400> SEQUENCE: 224
ttttcattcc aatggggtga ctttgcttc 29

<210> SEQ ID NO 225
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(20)
<223> OTHER INFORMATION: At least one residue mutated or absent

<400> SEQUENCE: 225
cttttcattc caatggggtg actttgctt 29

<210> SEQ ID NO 226
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(21)
<223> OTHER INFORMATION: At least one residue mutated or absent

<400> SEQUENCE: 226
acttttcatt ccaatggggt gactttgct 29

<210> SEQ ID NO 227
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(22)
<223> OTHER INFORMATION: At least one residue mutated or absent

<400> SEQUENCE: 227
tacttttcat tccaatgggg tgactttgc 29

<210> SEQ ID NO 228
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(23)
<223> OTHER INFORMATION: At least one residue mutated or absent

<400> SEQUENCE: 228
atacttttca ttccaatggg gtgactttg 29

<210> SEQ ID NO 229
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(24)
<223> OTHER INFORMATION: At least one residue mutated or absent

<400> SEQUENCE: 229
catacttttc attccaatgg ggtgacttt 29

<210> SEQ ID NO 230
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(25)
<223> OTHER INFORMATION: At least one residue mutated or absent

<400> SEQUENCE: 230
tcatactttt cattccaatg gggtgactt 29

<210> SEQ ID NO 231
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (12)..(26)
<223> OTHER INFORMATION: At least one residue mutated or absent

<400> SEQUENCE: 231
ttcatacttt tcattccaat ggggtgact 29

<210> SEQ ID NO 232
<211> LENGTH: 26
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(8)
<223> OTHER INFORMATION: At least one residue mutated or absent
<220> FEATURE:
<221> NAME/KEY: misc_feature
<222> LOCATION: (19)..(23)
<223> OTHER INFORMATION: At least one residue mutated or absent

<400> SEQUENCE: 232
tttcattcca atggggtgac tttgct 26

<210> SEQ ID NO 233

<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent
<220> FEATURE:
<221> NAME/KEY: misc_feature
<222> LOCATION: (16)..(20)
<223> OTHER INFORMATION: At least one residue mutated or absent

<400> SEQUENCE: 233
cttttcattc caatgacttt gctt 24

<210> SEQ ID NO 234
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent
<220> FEATURE:
<221> NAME/KEY: misc_feature
<222> LOCATION: (16)..(20)
<223> OTHER INFORMATION: At least one residue mutated or absent

<400> SEQUENCE: 234
cttttcattc gggtgacttt gctt 24

<210> SEQ ID NO 235
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(9)
<223> OTHER INFORMATION: At least one residue mutated or absent
<220> FEATURE:
<221> NAME/KEY: misc_feature
<222> LOCATION: (15)..(19)
<223> OTHER INFORMATION: At least one residue mutated or absent

<400> SEQUENCE: 235
ttttcattcc aatgactttg cttc 24

<210> SEQ ID NO 236
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(9)
<223> OTHER INFORMATION: At least one residue mutated or absent
<220> FEATURE:
<221> NAME/KEY: misc_feature
<222> LOCATION: (15)..(19)
<223> OTHER INFORMATION: At least one residue mutated or absent

<400> SEQUENCE: 236
ttttcattcg ggtgactttg cttc 24

<210> SEQ ID NO 237
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(9)
<223> OTHER INFORMATION: At least one residue mutated or absent
<220> FEATURE:
<221> NAME/KEY: misc_feature
<222> LOCATION: (15)..(19)
<223> OTHER INFORMATION: At least one residue mutated or absent

<400> SEQUENCE: 237
attccaatgg ggtgactttg cttc 24

<210> SEQ ID NO 238
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(8)
<223> OTHER INFORMATION: At least one residue mutated or absent
<220> FEATURE:
<221> NAME/KEY: misc_feature
<222> LOCATION: (14)..(18)
<223> OTHER INFORMATION: At least one residue mutated or absent

<400> SEQUENCE: 238
ttccaatggg gtgactttgc ttct 24

<210> SEQ ID NO 239
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent
<220> FEATURE:
<221> NAME/KEY: misc_feature
<222> LOCATION: (16)..(20)
<223> OTHER INFORMATION: At least one residue mutated or absent

<400> SEQUENCE: 239
cattccaatg gggtgacttt gctt 24

<210> SEQ ID NO 240
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(11)
<223> OTHER INFORMATION: At least one residue mutated or absent
<220> FEATURE:
<221> NAME/KEY: misc_feature
<222> LOCATION: (17)..(21)
<223> OTHER INFORMATION: At least one residue mutated or absent

<400> SEQUENCE: 240
tcattccaat ggggtgactt tgct 24

<210> SEQ ID NO 241
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(13)
<223> OTHER INFORMATION: At least one residue mutated or absent
<220> FEATURE:
<221> NAME/KEY: misc_feature
<222> LOCATION: (19)..(23)
<223> OTHER INFORMATION: At least one residue mutated or absent

<400> SEQUENCE: 241
tttcattcca atggggtgac tttgcttct 29

<210> SEQ ID NO 242
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(14)
<223> OTHER INFORMATION: At least one residue mutated or absent
<220> FEATURE:
<221> NAME/KEY: misc_feature
<222> LOCATION: (20)..(24)
<223> OTHER INFORMATION: At least one residue mutated or absent

<400> SEQUENCE: 242
ttttcattcc aatggggtga ctttgcttc 29

<210> SEQ ID NO 243
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(15)
<223> OTHER INFORMATION: At least one residue mutated or absent
<220> FEATURE:
<221> NAME/KEY: misc_feature
<222> LOCATION: (21)..(25)
<223> OTHER INFORMATION: At least one residue mutated or absent

<400> SEQUENCE: 243
cttttcattc caatggggtg actttgctt 29

<210> SEQ ID NO 244
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(25)
<223> OTHER INFORMATION: At least one residue mutated or absent

<400> SEQUENCE: 244
tcatactttt cattccaatg actttgctt 29

<210> SEQ ID NO 245
<211> LENGTH: 29

<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(24)
<223> OTHER INFORMATION: At least one residue mutated or absent

<400> SEQUENCE: 245 catactttc attccaatga ctttgcttc 29

<210> SEQ ID NO 246
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(23)
<223> OTHER INFORMATION: At least one residue mutated or absent

<400> SEQUENCE: 246
atacttttca ttccaatgac tttgcttct 29

<210> SEQ ID NO 247
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(22)
<223> OTHER INFORMATION: At least one residue mutated or absent

<400> SEQUENCE: 247
tacttttcat tccaatgact ttgcttctg 29

<210> SEQ ID NO 248
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(21)
<223> OTHER INFORMATION: At least one residue mutated or absent

<400> SEQUENCE: 248
acttttcatt ccaatgactt tgcttctgg 29

<210> SEQ ID NO 249
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(8)
<223> OTHER INFORMATION: At least one residue mutated or absent
<220> FEATURE:
<221> NAME/KEY: misc_feature
<222> LOCATION: (14)..(23)
<223> OTHER INFORMATION: At least one residue mutated or absent

<400> SEQUENCE: 249
tttcattcca atggggtgac tttgcttct 29

<210> SEQ ID NO 250
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(9)
<223> OTHER INFORMATION: At least one residue mutated or absent
<220> FEATURE:
<221> NAME/KEY: misc_feature
<222> LOCATION: (15)..(24)
<223> OTHER INFORMATION: At least one residue mutated or absent

<400> SEQUENCE: 250
ttttcattcc aatggggtga ctttgcttc 29

<210> SEQ ID NO 251
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent
<220> FEATURE:
<221> NAME/KEY: misc_feature
<222> LOCATION: (16)..(25)
<223> OTHER INFORMATION: At least one residue mutated or absent

<400> SEQUENCE: 251
cttttcattc caatggggtg actttgctt 29

<210> SEQ ID NO 252
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(11)
<223> OTHER INFORMATION: At least one residue mutated or absent
<220> FEATURE:
<221> NAME/KEY: misc_feature
<222> LOCATION: (17)..(26)
<223> OTHER INFORMATION: At least one residue mutated or absent

<400> SEQUENCE: 252
acttttcatt ccaatggggt gactttgct 29

<210> SEQ ID NO 253
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (12)..(26)
<223> OTHER INFORMATION: At least one residue mutated or absent

<400> SEQUENCE: 253
ttcatacttt tcattcgggt gactttgct 29

<210> SEQ ID NO 254
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(25)
<223> OTHER INFORMATION: At least one residue mutated or absent

<400> SEQUENCE: 254
tcatactttt cattcgggtg actttgctt 29

<210> SEQ ID NO 255
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(24)
<223> OTHER INFORMATION: At least one residue mutated or absent

<400> SEQUENCE: 255
catacttttc attcgggtga ctttgcttc 29

<210> SEQ ID NO 256
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(23)
<223> OTHER INFORMATION: At least one residue mutated or absent

<400> SEQUENCE: 256
atacttttca ttcgggtgac tttgcttct 29

<210> SEQ ID NO 257
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(22)
<223> OTHER INFORMATION: At least one residue mutated or absent

<400> SEQUENCE: 257
tacttttcat tcgggtgact ttgcttctg 29

<210> SEQ ID NO 258
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(21)
<223> OTHER INFORMATION: At least one residue mutated or absent

<400> SEQUENCE: 258
acttttcatt cgggtgactt tgcttctgg 29

<210> SEQ ID NO 259
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (12)..(26)
<223> OTHER INFORMATION: At least one residue mutated or absent

<400> SEQUENCE: 259
acttttcatt ccaatggggt gactttgct 29

<210> SEQ ID NO 260
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(25)
<223> OTHER INFORMATION: At least one residue mutated or absent

<400> SEQUENCE: 260
cttttcattc caatggggtg actttgctt 29

<210> SEQ ID NO 261
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(24)
<223> OTHER INFORMATION: At least one residue mutated or absent

<400> SEQUENCE: 261
ttttcattcc aatggggtga ctttgcttc 29

<210> SEQ ID NO 262
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(23)
<223> OTHER INFORMATION: At least one residue mutated or absent

<400> SEQUENCE: 262
tttcattcca atggggtgac tttgcttct 29

<210> SEQ ID NO 263
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(22)
<223> OTHER INFORMATION: At least one residue mutated or absent

<400> SEQUENCE: 263
ttcattccaa tggggtgact ttgcttctg 29

<210> SEQ ID NO 264
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(21)
<223> OTHER INFORMATION: At least one residue mutated or absent

<400> SEQUENCE: 264
tcattccaat ggggtgactt tgcttctgg 29

<210> SEQ ID NO 265
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (12)..(31)
<223> OTHER INFORMATION: At least one residue mutated or absent

<400> SEQUENCE: 265
ttcatacttt tcattccaat ggggtgactt tgct 34

<210> SEQ ID NO 266
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(30)
<223> OTHER INFORMATION: At least one residue mutated or absent

<400> SEQUENCE: 266
tcatactttt cattccaatg gggtgacttt gctt 34

<210> SEQ ID NO 267
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(29)
<223> OTHER INFORMATION: At least one residue mutated or absent

<400> SEQUENCE: 267
catacttttc attccaatgg ggtgactttg cttc 34

<210> SEQ ID NO 268
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(28)
<223> OTHER INFORMATION: At least one residue mutated or absent

<400> SEQUENCE: 268
atacttttca ttccaatggg gtgactttgc ttct 34

<210> SEQ ID NO 269
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(27)
<223> OTHER INFORMATION: At least one residue mutated or absent

<400> SEQUENCE: 269
tacttttcat tccaatgggg tgactttgct tctg 34

<210> SEQ ID NO 270
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(26)
<223> OTHER INFORMATION: At least one residue mutated or absent

<400> SEQUENCE: 270
acttttcatt ccaatggggt gactttgctt ctgg 34

<210> SEQ ID NO 271
<211> LENGTH: 28
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(8)
<223> OTHER INFORMATION: At least one residue mutated or absent

<400> SEQUENCE: 271
tttcattcca atggggtgac tttgcttc 28

<210> SEQ ID NO 272
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(9)
<223> OTHER INFORMATION: At least one residue mutated or absent

<400> SEQUENCE: 272
ttttcattcg ggtgactttg cttc 24

<210> SEQ ID NO 273
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(9)
<223> OTHER INFORMATION: At least one residue mutated or absent

<400> SEQUENCE: 273
ttttcattcc aatgactttg cttc                                              24

<210> SEQ ID NO 274
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(9)
<223> OTHER INFORMATION: At least one residue mutated or absent

<400> SEQUENCE: 274
ttttcattcc aatgggggtgg cttc                                             24

<210> SEQ ID NO 275
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 275
cttttcattc caatggggtg gcttc                                             25

<210> SEQ ID NO 276
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(14)
<223> OTHER INFORMATION: At least one residue mutated or absent

<400> SEQUENCE: 276
catacttttc attcgggtgg cttc                                              24

<210> SEQ ID NO 277
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(14)
<223> OTHER INFORMATION: At least one residue mutated or absent

<400> SEQUENCE: 277
catacttttc attcactttg cttc                                              24

<210> SEQ ID NO 278
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(14)
<223> OTHER INFORMATION: At least one residue mutated or absent

<400> SEQUENCE: 278
catacttttc attccaatgg cttc 24

<210> SEQ ID NO 279
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (15)..(19)
<223> OTHER INFORMATION: At least one residue mutated or absent

<400> SEQUENCE: 279
tacttcatac ttttcattcg cttc 24

<210> SEQ ID NO 280
<211> LENGTH: 23
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(8)
<223> OTHER INFORMATION: At least one residue mutated or absent

<400> SEQUENCE: 280
ttccaatggg gtgactttgc ttc 23

<210> SEQ ID NO 281
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(8)
<223> OTHER INFORMATION: At least one residue mutated or absent

<400> SEQUENCE: 281
ttccaatgac tttgcttct 19

<210> SEQ ID NO 282
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(8)
<223> OTHER INFORMATION: At least one residue mutated or absent

<400> SEQUENCE: 282
ttccaatggg gtggcttct 19

<210> SEQ ID NO 283
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(13)
<223> OTHER INFORMATION: At least one residue mutated or absent

<400> SEQUENCE: 283
tttcattcca atggcttct 19

<210> SEQ ID NO 284
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(14)
<223> OTHER INFORMATION: At least one residue mutated or absent

<400> SEQUENCE: 284
ttttcattcc aatggcttc 19

<210> SEQ ID NO 285
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(9)
<223> OTHER INFORMATION: At least one residue mutated or absent

<400> SEQUENCE: 285
attccaatgg ggtgactttg cttc 24

<210> SEQ ID NO 286
<211> LENGTH: 20
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(9)
<223> OTHER INFORMATION: At least one residue mutated or absent

<400> SEQUENCE: 286
attccaatga ctttgcttct 20

<210> SEQ ID NO 287
<211> LENGTH: 20
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(9)
<223> OTHER INFORMATION: At least one residue mutated or absent

<400> SEQUENCE: 287
attccaatgg ggtggcttct 20

<210> SEQ ID NO 288
<211> LENGTH: 28
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(13)

<223> OTHER INFORMATION: At least one residue mutated or absent

<400> SEQUENCE: 288
tttcattcca atggggtgac tttgcttc 28

<210> SEQ ID NO 289
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(14)
<223> OTHER INFORMATION: At least one residue mutated or absent

<400> SEQUENCE: 289
ttttcattcc aatgactttg cttc 24

<210> SEQ ID NO 290
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(14)
<223> OTHER INFORMATION: At least one residue mutated or absent

<400> SEQUENCE: 290
ttttcattcc aatggggtgg cttc 24

<210> SEQ ID NO 291
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(19)
<223> OTHER INFORMATION: At least one residue mutated or absent

<400> SEQUENCE: 291 catactttc attccaatgg cttc 24

<210> SEQ ID NO 292
<211> LENGTH: 28
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(13)
<223> OTHER INFORMATION: At least one residue mutated or absent

<400> SEQUENCE: 292
tttcattcca atggggtgac tttgcttc 28

<210> SEQ ID NO 293
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(14)
<223> OTHER INFORMATION: At least one residue mutated or absent

<400> SEQUENCE: 293
ttttcattcc aatgactttg cttc 24

<210> SEQ ID NO 294
<211> LENGTH: 28
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(8)
<223> OTHER INFORMATION: At least one residue mutated or absent

<400> SEQUENCE: 294
tttcattcca atggggtgac tttgcttc 28

<210> SEQ ID NO 295
<211> LENGTH: 23
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(8)
<223> OTHER INFORMATION: At least one residue mutated or absent

<400> SEQUENCE: 295
tttcattcca atggggtggc ttc 23

<210> SEQ ID NO 296
<211> LENGTH: 23
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(8)
<223> OTHER INFORMATION: At least one residue mutated or absent

<400> SEQUENCE: 296
tttcattcgg gtgactttgc ttc 23

<210> SEQ ID NO 297
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(8)
<223> OTHER INFORMATION: At least one residue mutated or absent

<400> SEQUENCE: 297
tttcattcgg gtggcttct 19

<210> SEQ ID NO 298
<211> LENGTH: 19
<212> TYPE: DNA
<213> ORGANISM: Artificial sequence
<220> FEATURE:
<223> OTHER INFORMATION: Exemplary element X variant
<220> FEATURE:

<221> NAME/KEY: misc_feature
<222> LOCATION: (5)..(9)
<223> OTHER INFORMATION: At least one residue mutated or absent

<400> SEQUENCE: 298
ttttcattcg ggtggcttc 19

<210> SEQ ID NO 299
<211> LENGTH: 23
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(8)
<223> OTHER INFORMATION: At least one residue mutated or absent

<400> SEQUENCE: 299
ttccaatggg gtgactttgc ttc 23

<210> SEQ ID NO 300
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(9)
<223> OTHER INFORMATION: At least one residue mutated or absent

<400> SEQUENCE: 300
attccaatgg ggtggcttc 19

<210> SEQ ID NO 301
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(8)
<223> OTHER INFORMATION: At least one residue mutated or absent

<400> SEQUENCE: 301
attcaatggg gtggcttct 19

<210> SEQ ID NO 302
<211> LENGTH: 28
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(13)
<223> OTHER INFORMATION: At least one residue mutated or absent

<400> SEQUENCE: 302
tttcattcca atggggtgac tttgcttc 28

<210> SEQ ID NO 303
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(14)
<223> OTHER INFORMATION: At least one residue mutated or absent

<400> SEQUENCE: 303
ttttcattcc aatggggtgg cttc 24

<210> SEQ ID NO 304
<211> LENGTH: 28
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(8)
<223> OTHER INFORMATION: At least one residue mutated or absent

<400> SEQUENCE: 304
tttcattcca atggggtgac tttgcttc 28

<210> SEQ ID NO 305
<211> LENGTH: 23
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(8)
<223> OTHER INFORMATION: At least one residue mutated or absent

<400> SEQUENCE: 305
tttcattcgg gtgactttgc ttc 23

<210> SEQ ID NO 306
<211> LENGTH: 23
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(8)
<223> OTHER INFORMATION: At least one residue mutated or absent

<400> SEQUENCE: 306
tttcattcca atgactttgc ttc 23

<210> SEQ ID NO 307
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(9)
<223> OTHER INFORMATION: At least one residue mutated or absent

<400> SEQUENCE: 307
ttttcattca ctttgcttc 19

<210> SEQ ID NO 308
<211> LENGTH: 19
<212> TYPE: DNA
<213> ORGANISM: Artificial sequence
<220> FEATURE:

<223> OTHER INFORMATION: Exemplary element X variant
<220> FEATURE:
<221> NAME/KEY: misc_feature
<222> LOCATION: (4)..(8)
<223> OTHER INFORMATION: At least one residue mutated or absent

<400> SEQUENCE: 308
tttcattcac tttgcttct 19

<210> SEQ ID NO 309
<211> LENGTH: 23
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(8)
<223> OTHER INFORMATION: At least one residue mutated or absent

<400> SEQUENCE: 309
ttccaatggg gtgactttgc ttc 23

<210> SEQ ID NO 310
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(8)
<223> OTHER INFORMATION: At least one residue mutated or absent

<400> SEQUENCE: 310
ttccaatgac tttgcttct 19

<210> SEQ ID NO 311
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(9)
<223> OTHER INFORMATION: At least one residue mutated or absent

<400> SEQUENCE: 311
attccaatga ctttgcttc 19

<210> SEQ ID NO 312
<211> LENGTH: 28
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(13)
<223> OTHER INFORMATION: At least one residue mutated or absent

<400> SEQUENCE: 312
tttcattcca atggggtgac tttgcttc 28

<210> SEQ ID NO 313
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(14)
<223> OTHER INFORMATION: At least one residue mutated or absent

<400> SEQUENCE: 313
ttttcattcc aatgactttg cttc 24

<210> SEQ ID NO 314
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(13)
<223> OTHER INFORMATION: At least one residue mutated or absent

<400> SEQUENCE: 314
tttcattcca atgactttgc ttct 24

<210> SEQ ID NO 315
<211> LENGTH: 28
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(8)
<223> OTHER INFORMATION: At least one residue mutated or absent

<400> SEQUENCE: 315
tttcattcca atggggtgac tttgcttc 28

<210> SEQ ID NO 316
<211> LENGTH: 23
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(8)
<223> OTHER INFORMATION: At least one residue mutated or absent

<400> SEQUENCE: 316
tttcattcgg gtgactttgc ttc 23

<210> SEQ ID NO 317
<211> LENGTH: 23
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(8)
<223> OTHER INFORMATION: At least one residue mutated or absent

<400> SEQUENCE: 317
ttccaatggg gtgactttgc ttc 23

<210> SEQ ID NO 318
<211> LENGTH: 28
<212> TYPE: DNA

<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(13)
<223> OTHER INFORMATION: At least one residue mutated or absent

<400> SEQUENCE: 318
tttcattcca atggggtgac tttgcttc 28

<210> SEQ ID NO 319
<211> LENGTH: 28
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(8)
<223> OTHER INFORMATION: At least one residue mutated or absent
<220> FEATURE:
<221> NAME/KEY: misc_feature
<222> LOCATION: (14)..(18)
<223> OTHER INFORMATION: At least one residue mutated or absent

<400> SEQUENCE: 319
tttcattcca atggggtgac tttgcttc 28

<210> SEQ ID NO 320
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(13)
<223> OTHER INFORMATION: At least one residue mutated or absent

<400> SEQUENCE: 320
ttttcattcg ggtgactttg cttc 24

<210> SEQ ID NO 321
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(9)
<223> OTHER INFORMATION: At least one residue mutated or absent
<220> FEATURE:
<221> NAME/KEY: misc_feature
<222> LOCATION: (15)..(19)
<223> OTHER INFORMATION: At least one residue mutated or absent

<400> SEQUENCE: 321
ttttcattcc aatggggtgg cttc 24

<210> SEQ ID NO 322
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(19)
<223> OTHER INFORMATION: At least one residue mutated or absent

<400> SEQUENCE: 322
catacttttc attcgggtgg cttc 24

<210> SEQ ID NO 323
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(13)
<223> OTHER INFORMATION: At least one residue mutated or absent

<400> SEQUENCE: 323
tttcattcgg gtgactttgc ttct 24

<210> SEQ ID NO 324
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(8)
<223> OTHER INFORMATION: At least one residue mutated or absent
<220> FEATURE:
<221> NAME/KEY: misc_feature
<222> LOCATION: (14)..(18)
<223> OTHER INFORMATION: At least one residue mutated or absent

<400> SEQUENCE: 324
tttcattcca atggggtggc ttct 24

<210> SEQ ID NO 325
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(18)
<223> OTHER INFORMATION: At least one residue mutated or absent

<400> SEQUENCE: 325
atacttttca ttcgggtggc ttct 24

<210> SEQ ID NO 326
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(17)
<223> OTHER INFORMATION: At least one residue mutated or absent

<400> SEQUENCE: 326
tacttttcat tcgggtggct tctg 24

<210> SEQ ID NO 327
<211> LENGTH: 24
<212> TYPE: DNA
<213> ORGANISM: Artificial sequence
<220> FEATURE:

<223> OTHER INFORMATION: Exemplary element X variant
<220> FEATURE:
<221> NAME/KEY: misc_feature
<222> LOCATION: (7)..(16)
<223> OTHER INFORMATION: At least one residue mutated or absent

<400> SEQUENCE: 327
acttttcatt cgggtggctt ctgg 24

<210> SEQ ID NO 328
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(13)
<223> OTHER INFORMATION: At least one residue mutated or absent

<400> SEQUENCE: 328
ttccaatggg gtgactttgc ttct 24

<210> SEQ ID NO 329
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(14)
<223> OTHER INFORMATION: At least one residue mutated or absent

<400> SEQUENCE: 329
attccaatgg ggtgactttg cttc 24

<210> SEQ ID NO 330
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(19)
<223> OTHER INFORMATION: At least one residue mutated or absent

<400> SEQUENCE: 330
ttttcattcc aatggggtgg cttc 24

<210> SEQ ID NO 331
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(18)
<223> OTHER INFORMATION: At least one residue mutated or absent

<400> SEQUENCE: 331
tttcattcca atggggtggc ttct 24

<210> SEQ ID NO 332
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(17)
<223> OTHER INFORMATION: At least one residue mutated or absent

<400> SEQUENCE: 332
ttcattccaa tggggtggct tctg 24

<210> SEQ ID NO 333
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(16)
<223> OTHER INFORMATION: At least one residue mutated or absent

<400> SEQUENCE: 333
tcattccaat ggggtgactt tgcttctgg 29

<210> SEQ ID NO 334
<211> LENGTH: 28
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(18)
<223> OTHER INFORMATION: At least one residue mutated or absent

<400> SEQUENCE: 334
tttcattcca atggggtgac tttgcttc 28

<210> SEQ ID NO 335
<211> LENGTH: 30
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(19)
<223> OTHER INFORMATION: At least one residue mutated or absent

<400> SEQUENCE: 335
ttttcattcc aatggggtga ctttgcttct 30

<210> SEQ ID NO 336
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(23)
<223> OTHER INFORMATION: At least one residue mutated or absent

<400> SEQUENCE: 336
atacttttca ttccaatggg gtggcttct 29

<210> SEQ ID NO 337
<211> LENGTH: 29
<212> TYPE: DNA

<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(24)
<223> OTHER INFORMATION: At least one residue mutated or absent

<400> SEQUENCE: 337 catactttc attccaatgg ggtggcttc 29

<210> SEQ ID NO 338
<211> LENGTH: 28
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(8)
<223> OTHER INFORMATION: At least one residue mutated or absent
<220> FEATURE:
<221> NAME/KEY: misc_feature
<222> LOCATION: (19)..(23)
<223> OTHER INFORMATION: At least one residue mutated or absent

<400> SEQUENCE: 338
tttcattcca atggggtgac tttgcttc 28

<210> SEQ ID NO 339
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(9)
<223> OTHER INFORMATION: At least one residue mutated or absent
<220> FEATURE:
<221> NAME/KEY: misc_feature
<222> LOCATION: (15)..(19)
<223> OTHER INFORMATION: At least one residue mutated or absent

<400> SEQUENCE: 339
ttttcattcc aatgactttg cttc 24

<210> SEQ ID NO 340
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(9)
<223> OTHER INFORMATION: At least one residue mutated or absent
<220> FEATURE:
<221> NAME/KEY: misc_feature
<222> LOCATION: (15)..(19)
<223> OTHER INFORMATION: At least one residue mutated or absent

<400> SEQUENCE: 340
ttttcattcg ggtgactttg cttc 24

<210> SEQ ID NO 341
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(19)
<223> OTHER INFORMATION: At least one residue mutated or absent

<400> SEQUENCE: 341 catactttc attcactttg cttc 24

<210> SEQ ID NO 342
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(18)
<223> OTHER INFORMATION: At least one residue mutated or absent

<400> SEQUENCE: 342
atacttttca ttcactttgc ttct 24

<210> SEQ ID NO 343
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(17)
<223> OTHER INFORMATION: At least one residue mutated or absent

<400> SEQUENCE: 343
tacttttcat tcactttgct tctg 24

<210> SEQ ID NO 344
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(16)
<223> OTHER INFORMATION: At least one residue mutated or absent

<400> SEQUENCE: 344
acttttcatt cactttgctt ctgg 24

<210> SEQ ID NO 345
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(8)
<223> OTHER INFORMATION: At least one residue mutated or absent
<220> FEATURE:
<221> NAME/KEY: misc_feature
<222> LOCATION: (14)..(18)
<223> OTHER INFORMATION: At least one residue mutated or absent

<400> SEQUENCE: 345
ttccaatggg gtgactttgc ttct 24

<210> SEQ ID NO 346

<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(9)
<223> OTHER INFORMATION: At least one residue mutated or absent
<220> FEATURE:
<221> NAME/KEY: misc_feature
<222> LOCATION: (15)..(19)
<223> OTHER INFORMATION: At least one residue mutated or absent

<400> SEQUENCE: 346
attccaatgg ggtgactttg cttc 24

<210> SEQ ID NO 347
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(18)
<223> OTHER INFORMATION: At least one residue mutated or absent

<400> SEQUENCE: 347
tttcattcca atgactttgc ttct 24

<210> SEQ ID NO 348
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(19)
<223> OTHER INFORMATION: At least one residue mutated or absent

<400> SEQUENCE: 348
ttttcattcc aatgactttg cttc 24

<210> SEQ ID NO 349
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(14)
<223> OTHER INFORMATION: At least one residue mutated or absent
<220> FEATURE:
<221> NAME/KEY: misc_feature
<222> LOCATION: (20)..(24)
<223> OTHER INFORMATION: At least one residue mutated or absent

<400> SEQUENCE: 349
ttttcattcc aatggggtga ctttgcttc 29

<210> SEQ ID NO 350
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(13)
<223> OTHER INFORMATION: At least one residue mutated or absent
<220> FEATURE:
<221> NAME/KEY: misc_feature
<222> LOCATION: (19)..(23)
<223> OTHER INFORMATION: At least one residue mutated or absent

<400> SEQUENCE: 350
tttcattcca atggggtgac tttgcttct 29

<210> SEQ ID NO 351
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(24)
<223> OTHER INFORMATION: At least one residue mutated or absent

<400> SEQUENCE: 351
catacttttc attccaatga ctttgcttc 29

<210> SEQ ID NO 352
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(23)
<223> OTHER INFORMATION: At least one residue mutated or absent

<400> SEQUENCE: 352
atacttttca ttccaatgac tttgcttct 29

<210> SEQ ID NO 353
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(22)
<223> OTHER INFORMATION: At least one residue mutated or absent

<400> SEQUENCE: 353
tacttttcat tccaatgact ttgcttctg 29

<210> SEQ ID NO 354
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(21)
<223> OTHER INFORMATION: At least one residue mutated or absent

<400> SEQUENCE: 354
acttttcatt ccaatgactt tgcttctgg 29

<210> SEQ ID NO 355
<211> LENGTH: 29
<212> TYPE: DNA

<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(9)
<223> OTHER INFORMATION: At least one residue mutated or absent
<220> FEATURE:
<221> NAME/KEY: misc_feature
<222> LOCATION: (15)..(24)
<223> OTHER INFORMATION: At least one residue mutated or absent

<400> SEQUENCE: 355
ttttcattcc aatggggtga ctttgcttc 29

<210> SEQ ID NO 356
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (5)..(9)
<223> OTHER INFORMATION: At least one residue mutated or absent
<220> FEATURE:
<221> NAME/KEY: misc_feature
<222> LOCATION: (15)..(24)
<223> OTHER INFORMATION: At least one residue mutated or absent

<400> SEQUENCE: 356
ttttcattcc aatggggtga ctttgcttc 29

<210> SEQ ID NO 357
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (4)..(18)
<223> OTHER INFORMATION: At least one residue mutated or absent

<400> SEQUENCE: 357
tttcattcgg gtgactttgc ttct 24

<210> SEQ ID NO 358
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(24)
<223> OTHER INFORMATION: At least one residue mutated or absent

<400> SEQUENCE: 358 catactttc attcgggtga ctttgcttc 29

<210> SEQ ID NO 359
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(23)
<223> OTHER INFORMATION: At least one residue mutated or absent

<400> SEQUENCE: 359
atacttttca ttcgggtgac tttgcttct 29

<210> SEQ ID NO 360
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(22)
<223> OTHER INFORMATION: At least one residue mutated or absent

<400> SEQUENCE: 360
tacttttcat tcgggtgact ttgcttctg 29

<210> SEQ ID NO 361
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(21)
<223> OTHER INFORMATION: At least one residue mutated or absent

<400> SEQUENCE: 361
acttttcatt cgggtgactt tgcttctgg 29

<210> SEQ ID NO 362
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(24)
<223> OTHER INFORMATION: At least one residue mutated or absent

<400> SEQUENCE: 362
ttttcattcc aatggggtga ctttgcttc 29

<210> SEQ ID NO 363
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(23)
<223> OTHER INFORMATION: At least one residue mutated or absent

<400> SEQUENCE: 363
tttcattcca atggggtgac tttgcttct 29

<210> SEQ ID NO 364
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(22)

<223> OTHER INFORMATION: At least one residue mutated or absent

<400> SEQUENCE: 364
ttcattccaa tggggtgact ttgcttctg 29

<210> SEQ ID NO 365
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(21)
<223> OTHER INFORMATION: At least one residue mutated or absent

<400> SEQUENCE: 365
tcattccaat ggggtgactt tgcttctgg 29

<210> SEQ ID NO 366
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(26)
<223> OTHER INFORMATION: At least one residue mutated or absent

<400> SEQUENCE: 366
acttttcatt ccaatggggt gactttgctt ctgg 34

<210> SEQ ID NO 367
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(27)
<223> OTHER INFORMATION: At least one residue mutated or absent

<400> SEQUENCE: 367
tacttttcat tccaatgggg tgactttgct tctg 34

<210> SEQ ID NO 368
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(28)
<223> OTHER INFORMATION: At least one residue mutated or absent

<400> SEQUENCE: 368
atacttttca ttccaatggg gtgactttgc ttct 34

<210> SEQ ID NO 369
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(29)
<223> OTHER INFORMATION: At least one residue mutated or absent

<400> SEQUENCE: 369
catacttttc attccaatgg ggtgactttg cttc 34

<210> SEQ ID NO 370
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(15)
<223> OTHER INFORMATION: At least one residue mutated or absent

<400> SEQUENCE: 370
cttttcattc caatggggtg acttt 25

<210> SEQ ID NO 371
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(16)
<223> OTHER INFORMATION: At least one residue mutated or absent

<400> SEQUENCE: 371
acttttcatt ccaatggggt gactt 25

<210> SEQ ID NO 372
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(17)
<223> OTHER INFORMATION: At least one residue mutated or absent

<400> SEQUENCE: 372
tacttttcat tccaatgggg tgact 25

<210> SEQ ID NO 373
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(18)
<223> OTHER INFORMATION: At least one residue mutated or absent

<400> SEQUENCE: 373
atacttttca ttccaatggg gtgac 25

<210> SEQ ID NO 374
<211> LENGTH: 25
<212> TYPE: DNA
<213> ORGANISM: Artificial sequence
<220> FEATURE:
<223> OTHER INFORMATION: Exemplary element X variant
<220> FEATURE:

<221> NAME/KEY: misc_feature
<222> LOCATION: (10)..(19)
<223> OTHER INFORMATION: At least one residue mutated or absent

<400> SEQUENCE: 374
catacttttc attccaatgg ggtga 25

<210> SEQ ID NO 375
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(20)
<223> OTHER INFORMATION: At least one residue mutated or absent

<400> SEQUENCE: 375
tcatactttt cattccaatg gggtg 25

<210> SEQ ID NO 376
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (12)..(21)
<223> OTHER INFORMATION: At least one residue mutated or absent

<400> SEQUENCE: 376
ttcatacttt tcattccaat ggggt 25

<210> SEQ ID NO 377
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (13)..(22)
<223> OTHER INFORMATION: At least one residue mutated or absent

<400> SEQUENCE: 377
cttcatactt ttcattccaa tgggg 25

<210> SEQ ID NO 378
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (12)..(16)
<223> OTHER INFORMATION: At least one residue mutated or absent

<400> SEQUENCE: 378
ttcatacttt tcattccaa 19

<210> SEQ ID NO 379
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(15)
<223> OTHER INFORMATION: At least one residue mutated or absent

<400> SEQUENCE: 379
tcatactttt cattccaat 19

<210> SEQ ID NO 380
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(14)
<223> OTHER INFORMATION: At least one residue mutated or absent

<400> SEQUENCE: 380
catacttttc attccaatg 19

<210> SEQ ID NO 381
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(13)
<223> OTHER INFORMATION: At least one residue mutated or absent

<400> SEQUENCE: 381
atacttttca ttccaatgg 19

<210> SEQ ID NO 382
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(12)
<223> OTHER INFORMATION: At least one residue mutated or absent

<400> SEQUENCE: 382
tacttttcat tccaatggg 19

<210> SEQ ID NO 383
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(11)
<223> OTHER INFORMATION: At least one residue mutated or absent

<400> SEQUENCE: 383
acttttcatt ccaatgggg 19

<210> SEQ ID NO 384
<211> LENGTH: 19
<212> TYPE: DNA
<213> ORGANISM: Artificial sequence
<220> FEATURE:

<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 384
cttttcattc caatggggt 19

<210> SEQ ID NO 385
<211> LENGTH: 20
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 385
cttttcattc caatggggtg 20

<210> SEQ ID NO 386
<211> LENGTH: 20
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(14)
<223> OTHER INFORMATION: At least one residue mutated or absent

<400> SEQUENCE: 386
catacttttc attcgggtga 20

<210> SEQ ID NO 387
<211> LENGTH: 20
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(13)
<223> OTHER INFORMATION: At least one residue mutated or absent

<400> SEQUENCE: 387
atacttttca ttcgggtgac 20

<210> SEQ ID NO 388
<211> LENGTH: 20
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(12)
<223> OTHER INFORMATION: At least one residue mutated or absent

<400> SEQUENCE: 388
tacttttcat tcgggtgact 20

<210> SEQ ID NO 389
<211> LENGTH: 20
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(11)
<223> OTHER INFORMATION: At least one residue mutated or absent

<400> SEQUENCE: 389
acttttcatt cgggtgactt 20

<210> SEQ ID NO 390
<211> LENGTH: 20
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 390
cttttcattc gggtgacttt 20

<210> SEQ ID NO 391
<211> LENGTH: 20
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(15)
<223> OTHER INFORMATION: At least one residue mutated or absent

<400> SEQUENCE: 391
cttttcattc caatggggtg 20

<210> SEQ ID NO 392
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(14)
<223> OTHER INFORMATION: At least one residue mutated or absent

<400> SEQUENCE: 392
catacttttc aatggggtg 19

<210> SEQ ID NO 393
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(13)
<223> OTHER INFORMATION: At least one residue mutated or absent

<400> SEQUENCE: 393
atacttttca atggggtga 19

<210> SEQ ID NO 394
<211> LENGTH: 19
<212> TYPE: DNA

<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(12)
<223> OTHER INFORMATION: At least one residue mutated or absent

<400> SEQUENCE: 394
tacttttcaa tggggtgac 19

<210> SEQ ID NO 395
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(11)
<223> OTHER INFORMATION: At least one residue mutated or absent

<400> SEQUENCE: 395
acttttcaat ggggtgact 19

<210> SEQ ID NO 396
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 396
cttttcaatg gggtgactt 19

<210> SEQ ID NO 397
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(19)
<223> OTHER INFORMATION: At least one residue mutated or absent

<400> SEQUENCE: 397
catacttttc attccaatgg ggtg 24

<210> SEQ ID NO 398
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(18)
<223> OTHER INFORMATION: At least one residue mutated or absent

<400> SEQUENCE: 398
atacttttca ttccaatggg gtga 24

<210> SEQ ID NO 399
<211> LENGTH: 24

<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(17)
<223> OTHER INFORMATION: At least one residue mutated or absent

<400> SEQUENCE: 399
tacttttcat tccaatgggg tgac 24

<210> SEQ ID NO 400
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(16)
<223> OTHER INFORMATION: At least one residue mutated or absent

<400> SEQUENCE: 400
acttttcatt ccaatggggt gact 24

<210> SEQ ID NO 401
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(15)
<223> OTHER INFORMATION: At least one residue mutated or absent

<400> SEQUENCE: 401
cttttcattc caatggggtg actt 24

<210> SEQ ID NO 402
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 402
cttttcattc caatggggtg acttt 25

<210> SEQ ID NO 403
<211> LENGTH: 20
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 403
cttttcattc caatgacttt 20

<210> SEQ ID NO 404

<211> LENGTH: 20
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 404
cttttcattc gggtgacttt 20

<210> SEQ ID NO 405
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(14)
<223> OTHER INFORMATION: At least one residue mutated or absent

<400> SEQUENCE: 405
catacttttc attcacttt 19

<210> SEQ ID NO 406
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(13)
<223> OTHER INFORMATION: At least one residue mutated or absent

<400> SEQUENCE: 406
atacttttca ttcactttg 19

<210> SEQ ID NO 407
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(12)
<223> OTHER INFORMATION: At least one residue mutated or absent

<400> SEQUENCE: 407
tacttttcat tcactttgc 19

<210> SEQ ID NO 408
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(11)
<223> OTHER INFORMATION: At least one residue mutated or absent

<400> SEQUENCE: 408
acttttcatt cactttgct 19

<210> SEQ ID NO 409
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 409
cttttcattc actttgctt 19

<210> SEQ ID NO 410
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(15)
<223> OTHER INFORMATION: At least one residue mutated or absent

<400> SEQUENCE: 410
cttttcattc caatggggtg acttt 25

<210> SEQ ID NO 411
<211> LENGTH: 20
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(15)
<223> OTHER INFORMATION: At least one residue mutated or absent

<400> SEQUENCE: 411
cttttcattc caatgacttt 20

<210> SEQ ID NO 412
<211> LENGTH: 20
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 412
cttttcaatg gggtgacttt 20

<210> SEQ ID NO 413
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(14)
<223> OTHER INFORMATION: At least one residue mutated or absent

<400> SEQUENCE: 413
catacttttc aatgacttt 19

<210> SEQ ID NO 414
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(13)
<223> OTHER INFORMATION: At least one residue mutated or absent

<400> SEQUENCE: 414
atacttttca atgactttg 19

<210> SEQ ID NO 415
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(12)
<223> OTHER INFORMATION: At least one residue mutated or absent

<400> SEQUENCE: 415
tacttttcaa tgactttgc 19

<210> SEQ ID NO 416
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(11)
<223> OTHER INFORMATION: At least one residue mutated or absent

<400> SEQUENCE: 416
acttttcaat gactttgct 19

<210> SEQ ID NO 417
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 417
cttttcaatg actttgctt 19

<210> SEQ ID NO 418
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(15)
<223> OTHER INFORMATION: At least one residue mutated or absent

<400> SEQUENCE: 418
cttttcattc caatggggtg acttt 25

<210> SEQ ID NO 419
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(19)
<223> OTHER INFORMATION: At least one residue mutated or absent

<400> SEQUENCE: 419 catactttc attccaatga cttt 24

<210> SEQ ID NO 420
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(18)
<223> OTHER INFORMATION: At least one residue mutated or absent

<400> SEQUENCE: 420
atacttttca ttccaatgac tttg 24

<210> SEQ ID NO 421
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(17)
<223> OTHER INFORMATION: At least one residue mutated or absent

<400> SEQUENCE: 421
tacttttcat tccaatgact ttgc 24

<210> SEQ ID NO 422
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(16)
<223> OTHER INFORMATION: At least one residue mutated or absent

<400> SEQUENCE: 422
acttttcatt ccaatgactt tgct 24

<210> SEQ ID NO 423
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(15)
<223> OTHER INFORMATION: At least one residue mutated or absent

<400> SEQUENCE: 423
cttttcattc caatgacttt gctt 24

<210> SEQ ID NO 424
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 424
cttttcattc caatggggtg acttt 25

<210> SEQ ID NO 425
<211> LENGTH: 20
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 425
cttttcattc gggtgacttt 20

<210> SEQ ID NO 426
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(15)
<223> OTHER INFORMATION: At least one residue mutated or absent

<400> SEQUENCE: 426
cttttcattc caatggggtg acttt 25

<210> SEQ ID NO 427
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent
<220> FEATURE:
<221> NAME/KEY: misc_feature
<222> LOCATION: (16)..(20)
<223> OTHER INFORMATION: At least one residue mutated or absent

<400> SEQUENCE: 427
cttttcattc caatggggtg actt 24

<210> SEQ ID NO 428
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(11)
<223> OTHER INFORMATION: At least one residue mutated or absent
<220> FEATURE:
<221> NAME/KEY: misc_feature
<222> LOCATION: (17)..(21)
<223> OTHER INFORMATION: At least one residue mutated or absent

<400> SEQUENCE: 428
acttttcatt ccaatggggt gact 24

<210> SEQ ID NO 429
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (12)..(21)
<223> OTHER INFORMATION: At least one residue mutated or absent

<400> SEQUENCE: 429
ttcatacttt tcattcgggt gact 24

<210> SEQ ID NO 430
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(20)
<223> OTHER INFORMATION: At least one residue mutated or absent

<400> SEQUENCE: 430
tcatactttt cattcgggtg actt 24

<210> SEQ ID NO 431
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(19)
<223> OTHER INFORMATION: At least one residue mutated or absent

<400> SEQUENCE: 431
catacttttc attcgggtga cttt 24

<210> SEQ ID NO 432
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(18)
<223> OTHER INFORMATION: At least one residue mutated or absent

<400> SEQUENCE: 432
atacttttca ttcgggtgac tttg 24

<210> SEQ ID NO 433
<211> LENGTH: 24
<212> TYPE: DNA

<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(17)
<223> OTHER INFORMATION: At least one residue mutated or absent

<400> SEQUENCE: 433
tacttttcat tcgggtgact ttgc 24

<210> SEQ ID NO 434
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(16)
<223> OTHER INFORMATION: At least one residue mutated or absent

<400> SEQUENCE: 434
acttttcatt cgggtgactt tgct 24

<210> SEQ ID NO 435
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(15)
<223> OTHER INFORMATION: At least one residue mutated or absent

<400> SEQUENCE: 435
cttttcattc gggtgacttt gctt 24

<210> SEQ ID NO 436
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(20)
<223> OTHER INFORMATION: At least one residue mutated or absent

<400> SEQUENCE: 436
cttttcattc caatggggtg actt 24

<210> SEQ ID NO 437
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (12)..(21)
<223> OTHER INFORMATION: At least one residue mutated or absent

<400> SEQUENCE: 437
acttttcatt ccaatggggt gact 24

<210> SEQ ID NO 438
<211> LENGTH: 24

<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (12)..(21)
<223> OTHER INFORMATION: At least one residue mutated or absent

<400> SEQUENCE: 438
ttcatacttt tcaatggggt gact 24

<210> SEQ ID NO 439
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(20)
<223> OTHER INFORMATION: At least one residue mutated or absent

<400> SEQUENCE: 439
tcatactttt caatggggtg actt 24

<210> SEQ ID NO 440
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(19)
<223> OTHER INFORMATION: At least one residue mutated or absent

<400> SEQUENCE: 440
catacttttc aatggggtga cttt 24

<210> SEQ ID NO 441
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(18)
<223> OTHER INFORMATION: At least one residue mutated or absent

<400> SEQUENCE: 441
atacttttca atggggtgac tttg 24

<210> SEQ ID NO 442
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(17)
<223> OTHER INFORMATION: At least one residue mutated or absent

<400> SEQUENCE: 442
tacttttcaa tggggtgact ttgc 24

<210> SEQ ID NO 443

<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(16)
<223> OTHER INFORMATION: At least one residue mutated or absent

<400> SEQUENCE: 443
acttttcaat ggggtgactt tgct 24

<210> SEQ ID NO 444
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(15)
<223> OTHER INFORMATION: At least one residue mutated or absent

<400> SEQUENCE: 444
cttttcaatg gggtgacttt gctt 24

<210> SEQ ID NO 445
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (12)..(26)
<223> OTHER INFORMATION: At least one residue mutated or absent

<400> SEQUENCE: 445
ttcatacttt tcattccaat ggggtgact 29

<210> SEQ ID NO 446
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(25)
<223> OTHER INFORMATION: At least one residue mutated or absent

<400> SEQUENCE: 446
tcatactttt cattccaatg gggtgactt 29

<210> SEQ ID NO 447
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(24)
<223> OTHER INFORMATION: At least one residue mutated or absent

<400> SEQUENCE: 447
catacttttc attccaatgg ggtgacttt 29

<210> SEQ ID NO 448
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(23)
<223> OTHER INFORMATION: At least one residue mutated or absent

<400> SEQUENCE: 448 atactttca ttccaatggg gtgactttg 29

<210> SEQ ID NO 449
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(22)
<223> OTHER INFORMATION: At least one residue mutated or absent

<400> SEQUENCE: 449
tacttttcat tccaatgggg tgactttgc 29

<210> SEQ ID NO 450
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(21)
<223> OTHER INFORMATION: At least one residue mutated or absent

<400> SEQUENCE: 450
acttttcatt ccaatggggt gactttgct 29

<210> SEQ ID NO 451
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(20)
<223> OTHER INFORMATION: At least one residue mutated or absent

<400> SEQUENCE: 451
cttttcattc caatggggtg actttgctt 29

<210> SEQ ID NO 452
<211> LENGTH: 28
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent
<220> FEATURE:
<221> NAME/KEY: misc_feature
<222> LOCATION: (21)..(25)
<223> OTHER INFORMATION: At least one residue mutated or absent

<400> SEQUENCE: 452
cttttcattc caatggggtg actttgct 28

<210> SEQ ID NO 453
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent
<220> FEATURE:
<221> NAME/KEY: misc_feature
<222> LOCATION: (16)..(20)
<223> OTHER INFORMATION: At least one residue mutated or absent

<400> SEQUENCE: 453
cttttcattc gggtgacttt gctt 24

<210> SEQ ID NO 454
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent
<220> FEATURE:
<221> NAME/KEY: misc_feature
<222> LOCATION: (16)..(20)
<223> OTHER INFORMATION: At least one residue mutated or absent

<400> SEQUENCE: 454
cttttcattc caatgacttt gctt 24

<210> SEQ ID NO 455
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(20)
<223> OTHER INFORMATION: At least one residue mutated or absent

<400> SEQUENCE: 455
tcatactttt cattcacttt gctt 24

<210> SEQ ID NO 456
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(11)
<223> OTHER INFORMATION: At least one residue mutated or absent
<220> FEATURE:
<221> NAME/KEY: misc_feature
<222> LOCATION: (17)..(21)
<223> OTHER INFORMATION: At least one residue mutated or absent

<400> SEQUENCE: 456
acttttcatt cgggtgactt tgct 24

<210> SEQ ID NO 457
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(11)
<223> OTHER INFORMATION: At least one residue mutated or absent
<220> FEATURE:
<221> NAME/KEY: misc_feature
<222> LOCATION: (17)..(21)
<223> OTHER INFORMATION: At least one residue mutated or absent

<400> SEQUENCE: 457
acttttcatt ccaatgactt tgct                                              24

<210> SEQ ID NO 458
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (12)..(21)
<223> OTHER INFORMATION: At least one residue mutated or absent

<400> SEQUENCE: 458
ttcatacttt tcattcactt tgct                                              24

<210> SEQ ID NO 459
<211> LENGTH: 28
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(15)
<223> OTHER INFORMATION: At least one residue mutated or absent
<220> FEATURE:
<221> NAME/KEY: misc_feature
<222> LOCATION: (21)..(25)
<223> OTHER INFORMATION: At least one residue mutated or absent

<400> SEQUENCE: 459
cttttcattc caatggggtg actttgct                                          28

<210> SEQ ID NO 460
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent
<220> FEATURE:
<221> NAME/KEY: misc_feature
<222> LOCATION: (16)..(20)
<223> OTHER INFORMATION: At least one residue mutated or absent

<400> SEQUENCE: 460
cttttcaatg gggtgacttt gctt                                              24

<210> SEQ ID NO 461

<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(20)
<223> OTHER INFORMATION: At least one residue mutated or absent

<400> SEQUENCE: 461
cttttcattc caatgacttt gctt 24

<210> SEQ ID NO 462
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(20)
<223> OTHER INFORMATION: At least one residue mutated or absent

<400> SEQUENCE: 462
tcatactttt caatgacttt gctt 24

<210> SEQ ID NO 463
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(11)
<223> OTHER INFORMATION: At least one residue mutated or absent
<220> FEATURE:
<221> NAME/KEY: misc_feature
<222> LOCATION: (17)..(21)
<223> OTHER INFORMATION: At least one residue mutated or absent

<400> SEQUENCE: 463
acttttcaat ggggtgactt tgct 24

<210> SEQ ID NO 464
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (12)..(21)
<223> OTHER INFORMATION: At least one residue mutated or absent

<400> SEQUENCE: 464
acttttcatt ccaatgactt tgct 24

<210> SEQ ID NO 465
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (12)..(21)
<223> OTHER INFORMATION: At least one residue mutated or absent

<400> SEQUENCE: 465
ttcatacttt tcaatgactt tgct 24

<210> SEQ ID NO 466
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(15)
<223> OTHER INFORMATION: At least one residue mutated or absent
<220> FEATURE:
<221> NAME/KEY: misc_feature
<222> LOCATION: (21)..(25)
<223> OTHER INFORMATION: At least one residue mutated or absent

<400> SEQUENCE: 466
cttttcattc caatggggtg actttgctt 29

<210> SEQ ID NO 467
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(16)
<223> OTHER INFORMATION: At least one residue mutated or absent
<220> FEATURE:
<221> NAME/KEY: misc_feature
<222> LOCATION: (22)..(26)
<223> OTHER INFORMATION: At least one residue mutated or absent

<400> SEQUENCE: 467
acttttcatt ccaatggggt gactttgct 29

<210> SEQ ID NO 468
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(21)
<223> OTHER INFORMATION: At least one residue mutated or absent

<400> SEQUENCE: 468
acttttcatt ccaatgactt tgcttctgg 29

<210> SEQ ID NO 469
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(20)
<223> OTHER INFORMATION: At least one residue mutated or absent

<400> SEQUENCE: 469
cttttcattc caatgacttt gcttctgga 29

<210> SEQ ID NO 470
<211> LENGTH: 29
<212> TYPE: DNA

<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(25)
<223> OTHER INFORMATION: At least one residue mutated or absent

<400> SEQUENCE: 470
tcatactttt cattccaatg actttgctt 29

<210> SEQ ID NO 471
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (12)..(26)
<223> OTHER INFORMATION: At least one residue mutated or absent

<400> SEQUENCE: 471
ttcatacttt tcattccaat gactttgct 29

<210> SEQ ID NO 472
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(25)
<223> OTHER INFORMATION: At least one residue mutated or absent

<400> SEQUENCE: 472
cttttcattc caatggggtg actttgctt 29

<210> SEQ ID NO 473
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (12)..(26)
<223> OTHER INFORMATION: At least one residue mutated or absent

<400> SEQUENCE: 473
acttttcatt ccaatggggt gactttgct 29

<210> SEQ ID NO 474
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(21)
<223> OTHER INFORMATION: At least one residue mutated or absent

<400> SEQUENCE: 474
acttttcaat ggggtgactt tgcttctgg 29

<210> SEQ ID NO 475
<211> LENGTH: 29

<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(20)
<223> OTHER INFORMATION: At least one residue mutated or absent

<400> SEQUENCE: 475
cttttcaatg gggtgacttt gcttctgga 29

<210> SEQ ID NO 476
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(25)
<223> OTHER INFORMATION: At least one residue mutated or absent

<400> SEQUENCE: 476
tcatactttt caatggggtg actttgctt 29

<210> SEQ ID NO 477
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (12)..(26)
<223> OTHER INFORMATION: At least one residue mutated or absent

<400> SEQUENCE: 477
ttcatacttt tcaatggggt gactttgct 29

<210> SEQ ID NO 478
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(26)
<223> OTHER INFORMATION: At least one residue mutated or absent

<400> SEQUENCE: 478
acttttcatt ccaatggggt gactttgctt ctgg 34

<210> SEQ ID NO 479
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(27)
<223> OTHER INFORMATION: At least one residue mutated or absent

<400> SEQUENCE: 479
tacttttcat tccaatgggg tgactttgct tctg 34

<210> SEQ ID NO 480

<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(28)
<223> OTHER INFORMATION: At least one residue mutated or absent

<400> SEQUENCE: 480
atacttttca ttccaatggg gtgactttgc ttct 34

<210> SEQ ID NO 481
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(29)
<223> OTHER INFORMATION: At least one residue mutated or absent

<400> SEQUENCE: 481
catacttttc attccaatgg ggtgactttg cttc 34

<210> SEQ ID NO 482
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(30)
<223> OTHER INFORMATION: At least one residue mutated or absent

<400> SEQUENCE: 482
tcatactttt cattccaatg gggtgacttt gctt 34

<210> SEQ ID NO 483
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (12)..(31)
<223> OTHER INFORMATION: At least one residue mutated or absent

<400> SEQUENCE: 483
ttcatacttt tcattccaat ggggtgactt tgct 34

<210> SEQ ID NO 484
<211> LENGTH: 30
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 484
cttttcattc caatggggtg actttgcttc 30

<210> SEQ ID NO 485
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 485
cttttcattc gggtgacttt gcttc 25

<210> SEQ ID NO 486
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 486
cttttcattc caatgacttt gcttc 25

<210> SEQ ID NO 487
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 487
cttttcattc caatggggtg gcttc 25

<210> SEQ ID NO 488
<211> LENGTH: 20
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 488
cttttcattc actttgcttc 20

<210> SEQ ID NO 489
<211> LENGTH: 20
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 489
cttttcattc caatggcttc 20

<210> SEQ ID NO 490
<211> LENGTH: 20
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 490
cttttcattc gggtggcttc 20

<210> SEQ ID NO 491
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 491
cttttcattc gcttctgga 19

<210> SEQ ID NO 492
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(11)
<223> OTHER INFORMATION: At least one residue mutated or absent

<400> SEQUENCE: 492
acttttcatt cgcttctgg 19

<210> SEQ ID NO 493
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(12)
<223> OTHER INFORMATION: At least one residue mutated or absent

<400> SEQUENCE: 493
tacttttcat tcgcttctg 19

<210> SEQ ID NO 494
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(13)
<223> OTHER INFORMATION: At least one residue mutated or absent

<400> SEQUENCE: 494
atacttttca ttcgcttct 19

<210> SEQ ID NO 495
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(14)
<223> OTHER INFORMATION: At least one residue mutated or absent

<400> SEQUENCE: 495 catactttc attcgcttc 19

<210> SEQ ID NO 496
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 496
cttttcaatg gggtgacttt gcttc 25

<210> SEQ ID NO 497
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(15)
<223> OTHER INFORMATION: At least one residue mutated or absent

<400> SEQUENCE: 497
cttttcattc caatgacttt gcttc 25

<210> SEQ ID NO 498
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(15)
<223> OTHER INFORMATION: At least one residue mutated or absent

<400> SEQUENCE: 498
cttttcattc caatggggtg gcttc 25

<210> SEQ ID NO 499
<211> LENGTH: 20
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 499
cttttcaatg actttgcttc 20

<210> SEQ ID NO 500
<211> LENGTH: 20
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 500
cttttcaatg gggtggcttc 20

<210> SEQ ID NO 501
<211> LENGTH: 20
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(15)
<223> OTHER INFORMATION: At least one residue mutated or absent

<400> SEQUENCE: 501
cttttcattc caatggcttc 20

<210> SEQ ID NO 502
<211> LENGTH: 30
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(15)
<223> OTHER INFORMATION: At least one residue mutated or absent

<400> SEQUENCE: 502
cttttcattc caatggggtg actttgcttc 30

<210> SEQ ID NO 503
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 503
cttttcaatg gcttctgga 19

<210> SEQ ID NO 504
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (67)..(11)
<223> OTHER INFORMATION: At least one residue mutated or absent

<400> SEQUENCE: 504
acttttcaat ggcttctgg                                              19

<210> SEQ ID NO 505
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(12)
<223> OTHER INFORMATION: At least one residue mutated or absent

<400> SEQUENCE: 505
tacttttcaa tggcttctg                                              19

<210> SEQ ID NO 506
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(13)
<223> OTHER INFORMATION: At least one residue mutated or absent

<400> SEQUENCE: 506
atacttttca atggcttct                                              19

<210> SEQ ID NO 507
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(14)
<223> OTHER INFORMATION: At least one residue mutated or absent

<400> SEQUENCE: 507
catacttttc aatggcttc                                              19

<210> SEQ ID NO 508
<211> LENGTH: 30
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(15)
<223> OTHER INFORMATION: At least one residue mutated or absent

<400> SEQUENCE: 508
cttttcattc caatggggtg actttgcttc                                  30

<210> SEQ ID NO 509
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(15)
<223> OTHER INFORMATION: At least one residue mutated or absent

<400> SEQUENCE: 509
cttttcattc caatgacttt gcttc 25

<210> SEQ ID NO 510
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(15)
<223> OTHER INFORMATION: At least one residue mutated or absent

<400> SEQUENCE: 510
cttttcattc caatggggtg gcttc 25

<210> SEQ ID NO 511
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(15)
<223> OTHER INFORMATION: At least one residue mutated or absent

<400> SEQUENCE: 511
cttttcattc caatggcttc tgga 24

<210> SEQ ID NO 512
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(16)
<223> OTHER INFORMATION: At least one residue mutated or absent

<400> SEQUENCE: 512
acttttcatt ccaatggctt ctgg 24

<210> SEQ ID NO 513
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(17)
<223> OTHER INFORMATION: At least one residue mutated or absent

<400> SEQUENCE: 513
tacttttcat tccaatggct tctg 24

<210> SEQ ID NO 514
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(18)
<223> OTHER INFORMATION: At least one residue mutated or absent

<400> SEQUENCE: 514
atacttttca ttccaatggc ttct 24

<210> SEQ ID NO 515
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(19)
<223> OTHER INFORMATION: At least one residue mutated or absent

<400> SEQUENCE: 515
catacttttc attccaatgg cttc 24

<210> SEQ ID NO 516
<211> LENGTH: 30
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 516
cttttcattc caatggggtg actttgcttc 30

<210> SEQ ID NO 517
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 517
cttttcattc gggtgacttt gcttc 25

<210> SEQ ID NO 518
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 518
cttttcattc caatggggtg gcttc 25

<210> SEQ ID NO 519
<211> LENGTH: 20
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)

<223> OTHER INFORMATION: At least one residue mutated or absent

<400> SEQUENCE: 519
cttttcattc gggtggcttc 20

<210> SEQ ID NO 520
<211> LENGTH: 30
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(15)
<223> OTHER INFORMATION: At least one residue mutated or absent

<400> SEQUENCE: 520
cttttcattc caatggggtg actttgcttc 30

<210> SEQ ID NO 521
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 521
cttttcaatg gggtgacttt gcttc 25

<210> SEQ ID NO 522
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(15)
<223> OTHER INFORMATION: At least one residue mutated or absent

<400> SEQUENCE: 522
cttttcattc caatggggtg gcttc 25

<210> SEQ ID NO 523
<211> LENGTH: 20
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 523
cttttcaatg gggtggcttc 20

<210> SEQ ID NO 524
<211> LENGTH: 30
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(15)
<223> OTHER INFORMATION: At least one residue mutated or absent

<400> SEQUENCE: 524
cttttcattc caatggggtg actttgcttc 30

<210> SEQ ID NO 525
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(15)
<223> OTHER INFORMATION: At least one residue mutated or absent

<400> SEQUENCE: 525
cttttcattc caatggggtg gcttc 25

<210> SEQ ID NO 526
<211> LENGTH: 30
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 526
cttttcattc caatggggtg actttgcttc 30

<210> SEQ ID NO 527
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 527
cttttcattc gggtgacttt gcttc 25

<210> SEQ ID NO 528
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 528
cttttcattc caatgacttt gcttc 25

<210> SEQ ID NO 529
<211> LENGTH: 20
<212> TYPE: DNA
<213> ORGANISM: Artificial sequence
<220> FEATURE:
<223> OTHER INFORMATION: Exemplary element X variant
<220> FEATURE:

<221> NAME/KEY: misc_feature
<222> LOCATION: (6)..(10)
<223> OTHER INFORMATION: At least one residue mutated or absent

<400> SEQUENCE: 529
cttttcattc actttgcttc 20

<210> SEQ ID NO 530
<211> LENGTH: 30
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(15)
<223> OTHER INFORMATION: At least one residue mutated or absent

<400> SEQUENCE: 530
cttttcattc caatggggtg actttgcttc 30

<210> SEQ ID NO 531
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 531
cttttcaatg gggtgacttt gcttc 25

<210> SEQ ID NO 532
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(15)
<223> OTHER INFORMATION: At least one residue mutated or absent

<400> SEQUENCE: 532
cttttcattc caatgacttt gcttc 25

<210> SEQ ID NO 533
<211> LENGTH: 20
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 533
cttttcaatg actttgcttc 20

<210> SEQ ID NO 534
<211> LENGTH: 30
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(15)
<223> OTHER INFORMATION: At least one residue mutated or absent

<400> SEQUENCE: 534
cttttcattc caatggggtg actttgcttc 30

<210> SEQ ID NO 535
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(15)
<223> OTHER INFORMATION: At least one residue mutated or absent

<400> SEQUENCE: 535
cttttcattc caatgacttt gcttc 25

<210> SEQ ID NO 536
<211> LENGTH: 30
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 536
cttttcattc caatggggtg actttgcttc 30

<210> SEQ ID NO 537
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 537
cttttcattc gggtgacttt gcttc 25

<210> SEQ ID NO 538
<211> LENGTH: 30
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(15)
<223> OTHER INFORMATION: At least one residue mutated or absent

<400> SEQUENCE: 538
cttttcattc caatggggtg actttgcttc 30

<210> SEQ ID NO 539
<211> LENGTH: 25
<212> TYPE: DNA
<213> ORGANISM: Artificial sequence
<220> FEATURE:

<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent

<400> SEQUENCE: 539
cttttcaatg gggtgacttt gcttc 25

<210> SEQ ID NO 540
<211> LENGTH: 30
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(15)
<223> OTHER INFORMATION: At least one residue mutated or absent

<400> SEQUENCE: 540
cttttcattc caatggggtg actttgcttc 30

<210> SEQ ID NO 541
<211> LENGTH: 30
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent
<220> FEATURE:
<221> NAME/KEY: misc_feature
<222> LOCATION: (16)..(20)
<223> OTHER INFORMATION: At least one residue mutated or absent

<400> SEQUENCE: 541
cttttcattc caatggggtg actttgcttc 30

<210> SEQ ID NO 542
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(15)
<223> OTHER INFORMATION: At least one residue mutated or absent

<400> SEQUENCE: 542
cttttcattc gggtgacttt gcttc 25

<210> SEQ ID NO 543
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent
<220> FEATURE:
<221> NAME/KEY: misc_feature
<222> LOCATION: (16)..(20)
<223> OTHER INFORMATION: At least one residue mutated or absent

<400> SEQUENCE: 543
cttttcattc caatggggtg gcttc 25

<210> SEQ ID NO 544
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(18)
<223> OTHER INFORMATION: At least one residue mutated or absent

<400> SEQUENCE: 544
atacttttca ttcgggtggc ttct 24

<210> SEQ ID NO 545
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(17)
<223> OTHER INFORMATION: At least one residue mutated or absent

<400> SEQUENCE: 545
tacttttcat tcgggtggct tctg 24

<210> SEQ ID NO 546
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(16)
<223> OTHER INFORMATION: At least one residue mutated or absent

<400> SEQUENCE: 546
acttttcatt cgggtggctt ctgg 24

<210> SEQ ID NO 547
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(15)
<223> OTHER INFORMATION: At least one residue mutated or absent

<400> SEQUENCE: 547
cttttcattc gggtggcttc tgga 24

<210> SEQ ID NO 548
<211> LENGTH: 30
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(20)
<223> OTHER INFORMATION: At least one residue mutated or absent

<400> SEQUENCE: 548
cttttcattc caatggggtg actttgcttc 30

<210> SEQ ID NO 549
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(15)
<223> OTHER INFORMATION: At least one residue mutated or absent

<400> SEQUENCE: 549
cttttcaatg gggtgacttt gcttc 25

<210> SEQ ID NO 550
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(20)
<223> OTHER INFORMATION: At least one residue mutated or absent

<400> SEQUENCE: 550
cttttcattc caatggggtg gcttc 25

<210> SEQ ID NO 551
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(18)
<223> OTHER INFORMATION: At least one residue mutated or absent

<400> SEQUENCE: 551
atacttttca atggggtggc ttct 24

<210> SEQ ID NO 552
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(17)
<223> OTHER INFORMATION: At least one residue mutated or absent

<400> SEQUENCE: 552
tacttttcaa tggggtggct tctg 24

<210> SEQ ID NO 553
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(16)
<223> OTHER INFORMATION: At least one residue mutated or absent

<400> SEQUENCE: 553
acttttcaat ggggtggctt ctgg 24

<210> SEQ ID NO 554
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(15)
<223> OTHER INFORMATION: At least one residue mutated or absent

<400> SEQUENCE: 554
cttttcaatg gggtggcttc tgga 24

<210> SEQ ID NO 555
<211> LENGTH: 30
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(20)
<223> OTHER INFORMATION: At least one residue mutated or absent

<400> SEQUENCE: 555
cttttcattc caatggggtg actttgcttc 30

<210> SEQ ID NO 556
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(23)
<223> OTHER INFORMATION: At least one residue mutated or absent

<400> SEQUENCE: 556
atacttttca ttccaatggg gtggcttct 29

<210> SEQ ID NO 557
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(22)
<223> OTHER INFORMATION: At least one residue mutated or absent

<400> SEQUENCE: 557
tacttttcat tccaatgggg tggcttctg 29

<210> SEQ ID NO 558
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(21)

<223> OTHER INFORMATION: At least one residue mutated or absent

<400> SEQUENCE: 558
acttttcatt ccaatggggt ggcttctgg 29

<210> SEQ ID NO 559
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(20)
<223> OTHER INFORMATION: At least one residue mutated or absent

<400> SEQUENCE: 559
cttttcattc caatggggtg gcttctgga 29

<210> SEQ ID NO 560
<211> LENGTH: 30
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent
<220> FEATURE:
<221> NAME/KEY: misc_feature
<222> LOCATION: (21)..(25)
<223> OTHER INFORMATION: At least one residue mutated or absent

<400> SEQUENCE: 560
cttttcattc caatggggtg actttgcttc 30

<210> SEQ ID NO 561
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent
<220> FEATURE:
<221> NAME/KEY: misc_feature
<222> LOCATION: (16)..(20)
<223> OTHER INFORMATION: At least one residue mutated or absent

<400> SEQUENCE: 561
cttttcattc gggtgacttt gcttc 25

<210> SEQ ID NO 562
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent
<220> FEATURE:
<221> NAME/KEY: misc_feature
<222> LOCATION: (16)..(20)
<223> OTHER INFORMATION: At least one residue mutated or absent

<400> SEQUENCE: 562
cttttcattc caatgacttt gcttc 25

<210> SEQ ID NO 563
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(18)
<223> OTHER INFORMATION: At least one residue mutated or absent

<400> SEQUENCE: 563
atacttttca ttcactttgc ttct 24

<210> SEQ ID NO 564
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(17)
<223> OTHER INFORMATION: At least one residue mutated or absent

<400> SEQUENCE: 564
tacttttcat tcactttgct tctg 24

<210> SEQ ID NO 565
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(16)
<223> OTHER INFORMATION: At least one residue mutated or absent

<400> SEQUENCE: 565
acttttcatt cactttgctt ctgg 24

<210> SEQ ID NO 566
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(15)
<223> OTHER INFORMATION: At least one residue mutated or absent

<400> SEQUENCE: 566
cttttcattc actttgcttc tgga 24

<210> SEQ ID NO 567
<211> LENGTH: 30
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(15)
<223> OTHER INFORMATION: At least one residue mutated or absent
<220> FEATURE:

<221> NAME/KEY: misc_feature
<222> LOCATION: (21)..(25)
<223> OTHER INFORMATION: At least one residue mutated or absent

<400> SEQUENCE: 567
cttttcattc caatggggtg actttgcttc 30

<210> SEQ ID NO 568
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent
<220> FEATURE:
<221> NAME/KEY: misc_feature
<222> LOCATION: (16)..(20)
<223> OTHER INFORMATION: At least one residue mutated or absent

<400> SEQUENCE: 568
cttttcaatg gggtgacttt gcttc 25

<210> SEQ ID NO 569
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(20)
<223> OTHER INFORMATION: At least one residue mutated or absent

<400> SEQUENCE: 569
cttttcattc caatgacttt gcttc 25

<210> SEQ ID NO 570
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(18)
<223> OTHER INFORMATION: At least one residue mutated or absent

<400> SEQUENCE: 570
atacttttca atgactttgc ttct 24

<210> SEQ ID NO 571
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(17)
<223> OTHER INFORMATION: At least one residue mutated or absent

<400> SEQUENCE: 571
tacttttcaa tgactttgct tctg 24

<210> SEQ ID NO 572
<211> LENGTH: 24

<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(16)
<223> OTHER INFORMATION: At least one residue mutated or absent

<400> SEQUENCE: 572
acttttcaat gactttgctt ctgg 24

<210> SEQ ID NO 573
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(15)
<223> OTHER INFORMATION: At least one residue mutated or absent

<400> SEQUENCE: 573
cttttcaatg actttgcttc tgga 24

<210> SEQ ID NO 574
<211> LENGTH: 30
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(15)
<223> OTHER INFORMATION: At least one residue mutated or absent
<220> FEATURE:
<221> NAME/KEY: misc_feature
<222> LOCATION: (21)..(25)
<223> OTHER INFORMATION: At least one residue mutated or absent

<400> SEQUENCE: 574
cttttcattc caatggggtg actttgcttc 30

<210> SEQ ID NO 575
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(23)
<223> OTHER INFORMATION: At least one residue mutated or absent

<400> SEQUENCE: 575
atacttttca ttccaatgac tttgcttct 29

<210> SEQ ID NO 576
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(22)
<223> OTHER INFORMATION: At least one residue mutated or absent

<400> SEQUENCE: 576
tacttttcat tccaatgact ttgcttctg 29

<210> SEQ ID NO 577
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(21)
<223> OTHER INFORMATION: At least one residue mutated or absent

<400> SEQUENCE: 577
acttttcatt ccaatgactt tgcttctgg 29

<210> SEQ ID NO 578
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(20)
<223> OTHER INFORMATION: At least one residue mutated or absent

<400> SEQUENCE: 578
cttttcattc caatgacttt gcttctgga 29

<210> SEQ ID NO 579
<211> LENGTH: 30
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(10)
<223> OTHER INFORMATION: At least one residue mutated or absent
<220> FEATURE:
<221> NAME/KEY: misc_feature
<222> LOCATION: (16)..(25)
<223> OTHER INFORMATION: At least one residue mutated or absent

<400> SEQUENCE: 579
cttttcattc caatggggtg actttgcttc 30

<210> SEQ ID NO 580
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(23)
<223> OTHER INFORMATION: At least one residue mutated or absent

<400> SEQUENCE: 580
atacttttca ttcgggtgac tttgcttct 29

<210> SEQ ID NO 581
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(22)
<223> OTHER INFORMATION: At least one residue mutated or absent

<400> SEQUENCE: 581
tacttttcat tcgggtgact ttgcttctg 29

<210> SEQ ID NO 582
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(21)
<223> OTHER INFORMATION: At least one residue mutated or absent

<400> SEQUENCE: 582
acttttcatt cgggtgactt tgcttctgg 29

<210> SEQ ID NO 583
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(20)
<223> OTHER INFORMATION: At least one residue mutated or absent

<400> SEQUENCE: 583
cttttcattc gggtgacttt gcttctgga 29

<210> SEQ ID NO 584
<211> LENGTH: 30
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(25)
<223> OTHER INFORMATION: At least one residue mutated or absent

<400> SEQUENCE: 584
cttttcattc caatggggtg actttgcttc 30

<210> SEQ ID NO 585
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(23)
<223> OTHER INFORMATION: At least one residue mutated or absent

<400> SEQUENCE: 585
atacttttca atggggtgac tttgcttct 29

<210> SEQ ID NO 586
<211> LENGTH: 29
<212> TYPE: DNA
<213> ORGANISM: Artificial sequence
<220> FEATURE:
<223> OTHER INFORMATION: Exemplary element X variant
<220> FEATURE:

<221> NAME/KEY: misc_feature
<222> LOCATION: (8)..(22)
<223> OTHER INFORMATION: At least one residue mutated or absent

<400> SEQUENCE: 586
tacttttcaa tggggtgact ttgcttctg 29

<210> SEQ ID NO 587
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(21)
<223> OTHER INFORMATION: At least one residue mutated or absent

<400> SEQUENCE: 587
acttttcaat ggggtgactt tgcttctgg 29

<210> SEQ ID NO 588
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(20)
<223> OTHER INFORMATION: At least one residue mutated or absent

<400> SEQUENCE: 588
cttttcaatg gggtgacttt gcttctgga 29

<210> SEQ ID NO 589
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(28)
<223> OTHER INFORMATION: At least one residue mutated or absent

<400> SEQUENCE: 589
atacttttca ttccaatggg gtgactttgc ttct 34

<210> SEQ ID NO 590
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(27)
<223> OTHER INFORMATION: At least one residue mutated or absent

<400> SEQUENCE: 590
tacttttcat tccaatgggg tgactttgct tctg 34

<210> SEQ ID NO 591
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(26)
<223> OTHER INFORMATION: At least one residue mutated or absent

<400> SEQUENCE: 591
acttttcatt ccaatggggt gactttgctt ctgg 34

<210> SEQ ID NO 592
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (6)..(25)
<223> OTHER INFORMATION: At least one residue mutated or absent

<400> SEQUENCE: 592
cttttcattc caatggggtg actttgcttc tgga 34

<210> SEQ ID NO 593
<211> LENGTH: 30
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (16)..(25)
<223> OTHER INFORMATION: At least one residue mutated or absent

<400> SEQUENCE: 593
cttttcattc caatggggtg actttgcttc 30

<210> SEQ ID NO 594
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(20)
<223> OTHER INFORMATION: At least one residue mutated or absent

<400> SEQUENCE: 594
cttttcaatg gggtgacttt gcttc 25

<210> SEQ ID NO 595
<211> LENGTH: 25
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(20)
<223> OTHER INFORMATION: At least one residue mutated or absent

<400> SEQUENCE: 595
cttttcattc gggtgacttt gcttc 25

<210> SEQ ID NO 596
<211> LENGTH: 24
<212> TYPE: DNA
<213> ORGANISM: Artificial sequence
<220> FEATURE:

<223> OTHER INFORMATION: Exemplary element X variant
<220> FEATURE:
<221> NAME/KEY: misc_feature
<222> LOCATION: (6)..(15)
<223> OTHER INFORMATION: At least one residue mutated or absent

<400> SEQUENCE: 596
cttttgggtg actttgcttc tgga 24

<210> SEQ ID NO 597
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (7)..(16)
<223> OTHER INFORMATION: At least one residue mutated or absent

<400> SEQUENCE: 597
acttttgggt gactttgctt ctgg 24

<210> SEQ ID NO 598
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (8)..(17)
<223> OTHER INFORMATION: At least one residue mutated or absent

<400> SEQUENCE: 598
tacttttggg tgactttgct tctg 24

<210> SEQ ID NO 599
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (9)..(18)
<223> OTHER INFORMATION: At least one residue mutated or absent

<400> SEQUENCE: 599
atacttttgg gtgactttgc ttct 24

<210> SEQ ID NO 600
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (10)..(19)
<223> OTHER INFORMATION: At least one residue mutated or absent

<400> SEQUENCE: 600
catacttttg ggtgactttg cttc 24

<210> SEQ ID NO 601
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (21)..(25)
<223> OTHER INFORMATION: At least one residue mutated or absent

<400> SEQUENCE: 601
gtacttcata gggtgacttt gcttctgga 29

<210> SEQ ID NO 602
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (16)..(20)
<223> OTHER INFORMATION: At least one residue mutated or absent

<400> SEQUENCE: 602
gtacttcata actttgcttc tgga 24

<210> SEQ ID NO 603
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(15)
<223> OTHER INFORMATION: At least one residue mutated or absent

<400> SEQUENCE: 603
gtacttcata gcttctgga 19

<210> SEQ ID NO 604
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (26)..(30)
<223> OTHER INFORMATION: At least one residue mutated or absent

<400> SEQUENCE: 604
gtacttcata cttttgggtg actttgcttc tgga 34

<210> SEQ ID NO 605
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (21)..(25)
<223> OTHER INFORMATION: At least one residue mutated or absent

<400> SEQUENCE: 605
gtacttcata cttttacttt gcttctgga 29

<210> SEQ ID NO 606
<211> LENGTH: 24
<212> TYPE: DNA

<213> ORGANISM: Artificial sequence
<220> FEATURE:
<223> OTHER INFORMATION: Exemplary element X variant
<220> FEATURE:
<221> NAME/KEY: misc_feature
<222> LOCATION: (16)..(20)
<223> OTHER INFORMATION: At least one residue mutated or absent

<400> SEQUENCE: 606
gtacttcata cttttgcttc tgga 24

<210> SEQ ID NO 607
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (26)..(30)
<223> OTHER INFORMATION: At least one residue mutated or absent

<400> SEQUENCE: 607
gtacttcata cttttcattc actttgcttc tgga 34

<210> SEQ ID NO 608
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (21)..(25)
<223> OTHER INFORMATION: At least one residue mutated or absent

<400> SEQUENCE: 608
gtacttcata cttttcattc gcttctgga 29

<210> SEQ ID NO 609
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (26)..(30)
<223> OTHER INFORMATION: At least one residue mutated or absent

<400> SEQUENCE: 609
gtacttcata cttttcattc caatggcttc tgga 34

<210> SEQ ID NO 610
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (26)..(30)
<223> OTHER INFORMATION: At least one residue mutated or absent

<400> SEQUENCE: 610
gtactctttt caatggggtg actttgcttc tgga 34

<210> SEQ ID NO 611
<211> LENGTH: 29

<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (21)..(25)
<223> OTHER INFORMATION: At least one residue mutated or absent

<400> SEQUENCE: 611
gtactctttt gggtgacttt gcttctgga 29

<210> SEQ ID NO 612
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (16)..(20)
<223> OTHER INFORMATION: At least one residue mutated or absent

<400> SEQUENCE: 612
gtactctttt actttgcttc tgga 24

<210> SEQ ID NO 613
<211> LENGTH: 19
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (11)..(15)
<223> OTHER INFORMATION: At least one residue mutated or absent

<400> SEQUENCE: 613
gtactctttt gcttctgga 19

<210> SEQ ID NO 614
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (26)..(30)
<223> OTHER INFORMATION: At least one residue mutated or absent

<400> SEQUENCE: 614
gtactctttt cattcgggtg actttgcttc tgga 34

<210> SEQ ID NO 615
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (21)..(25)
<223> OTHER INFORMATION: At least one residue mutated or absent

<400> SEQUENCE: 615
gtactctttt cattcacttt gcttctgga 29

<210> SEQ ID NO 616

<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (16)..(20)
<223> OTHER INFORMATION: At least one residue mutated or absent

<400> SEQUENCE: 616
gtactctttt cattcgcttc tgga 24

<210> SEQ ID NO 617
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (26)..(30)
<223> OTHER INFORMATION: At least one residue mutated or absent

<400> SEQUENCE: 617
gtactctttt cattccaatg actttgcttc tgga 34

<210> SEQ ID NO 618
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (21)..(25)
<223> OTHER INFORMATION: At least one residue mutated or absent

<400> SEQUENCE: 618
gtactctttt cattccaatg gcttctgga 29

<210> SEQ ID NO 619
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (26)..(30)
<223> OTHER INFORMATION: At least one residue mutated or absent

<400> SEQUENCE: 619
gtactctttt cattccaatg gggtggcttc tgga 34

<210> SEQ ID NO 620
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (26)..(30)
<223> OTHER INFORMATION: At least one residue mutated or absent

<400> SEQUENCE: 620
gtacttcata cattcgggtg actttgcttc tgga 34

```
<210> SEQ ID NO 621
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (21)..(25)
<223> OTHER INFORMATION: At least one residue mutated or absent

<400> SEQUENCE: 621

gtacttcata cattcacttt gcttctgga                                    29

<210> SEQ ID NO 622
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (16)..(20)
<223> OTHER INFORMATION: At least one residue mutated or absent

<400> SEQUENCE: 622

gtacttcata cattcgcttc tgga                                         24

<210> SEQ ID NO 623
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (26)..(30)
<223> OTHER INFORMATION: At least one residue mutated or absent

<400> SEQUENCE: 623

gtacttcata cattccaatg actttgcttc tgga                              34

<210> SEQ ID NO 624
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (21)..(25)
<223> OTHER INFORMATION: At least one residue mutated or absent

<400> SEQUENCE: 624

gtacttcata cattccaatg gcttctgga                                    29

<210> SEQ ID NO 625
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (26)..(30)
<223> OTHER INFORMATION: At least one residue mutated or absent

<400> SEQUENCE: 625

gtacttcata cattccaatg gggtggcttc tgga                              34
```

<210> SEQ ID NO 626
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (26)..(30)
<223> OTHER INFORMATION: At least one residue mutated or absent

<400> SEQUENCE: 626
gtacttcata cttttcaatg actttgcttc tgga 34

<210> SEQ ID NO 627
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (21)..(25)
<223> OTHER INFORMATION: At least one residue mutated or absent

<400> SEQUENCE: 627
gtacttcata cttttcaatg gcttctgga 29

<210> SEQ ID NO 628
<211> LENGTH: 34
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (26)..(30)
<223> OTHER INFORMATION: At least one residue mutated or absent

<400> SEQUENCE: 628
gtacttcata cttttcattc gggtggcttc tgga 34

<210> SEQ ID NO 629
<211> LENGTH: 24
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (16)..(20)
<223> OTHER INFORMATION: At least one residue mutated or absent

<400> SEQUENCE: 629
gtactctttt caatggcttc tgga 24

<210> SEQ ID NO 630
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (21)..(25)
<223> OTHER INFORMATION: At least one residue mutated or absent

<400> SEQUENCE: 630
gtactctttt caatggggtg gcttctgga 29

<210> SEQ ID NO 631
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (21)..(25)
<223> OTHER INFORMATION: At least one residue mutated or absent

<400> SEQUENCE: 631
gtactctttt cattcacttt gcttctgga 29

<210> SEQ ID NO 632
<211> LENGTH: 29
<212> TYPE: DNA
<213> ORGANISM: Artificial sequence
<220> FEATURE:
<223> OTHER INFORMATION: Exemplary element X variant
<220> FEATURE:
<221> NAME/KEY: misc_feature
<222> LOCATION: (21)..(25)
<223> OTHER INFORMATION: At least one residue mutated or absent

<400> SEQUENCE: 632
gtacttcata cattcgggtg gcttctgga 29

<210> SEQ ID NO 633
<211> LENGTH: 44
<212> TYPE: DNA
<213> ORGANISM: Artificial sequence
<220> FEATURE:
<223> OTHER INFORMATION: PPE-1-derived regulatory element scheme
<220> FEATURE:
<221> NAME/KEY: misc_feature
<222> LOCATION: (36)..(40)
<223> OTHER INFORMATION: At least one residue mutated or absent
<220> FEATURE:
<221> NAME/KEY: misc_feature
<222> LOCATION: (36)..(40)
<223> OTHER INFORMATION: Mutated fragment (or variation of) can apear
in multiple copies

<400> SEQUENCE: 633
gtacttcata cttttcattc caatggggtg actttgcttc tgga 44

<210> SEQ ID NO 634
<211> LENGTH: 35
<212> TYPE: DNA
<213> ORGANISM: Artificial sequence
<220> FEATURE:
<223> OTHER INFORMATION: PPE-1-derived regulatory element scheme

<400> SEQUENCE: 634
gtacttcata cttttcattc caatggggtg acttt 35

<210> SEQ ID NO 635
<211> LENGTH: 25
<212> TYPE: DNA
<213> ORGANISM: Artificial sequence
<220> FEATURE:
<223> OTHER INFORMATION: PPE-1-derived regulatory element scheme

<400> SEQUENCE: 635
cattccaatg gggtgacttt gcttc 25

<210> SEQ ID NO 636
<211> LENGTH: 29
<212> TYPE: DNA
<213> ORGANISM: Artificial sequence
<220> FEATURE:
<223> OTHER INFORMATION: PPE-1-derived regulatory element scheme

<400> SEQUENCE: 636
cattccaatg gggtgacttt gcttctgga 29

<210> SEQ ID NO 637
<211> LENGTH: 20
<212> TYPE: DNA
<213> ORGANISM: Artificial sequence
<220> FEATURE:
<223> OTHER INFORMATION: PPE-1-derived regulatory element scheme

<400> SEQUENCE: 637
cattccaatg gggtgacttt 20

<210> SEQ ID NO 638
<211> LENGTH: 14
<212> TYPE: DNA
<213> ORGANISM: Artificial sequence
<220> FEATURE:
<223> OTHER INFORMATION: PPE-1-derived regulatory element scheme

<400> SEQUENCE: 638
actttgcttc tgga 14

<210> SEQ ID NO 639
<211> LENGTH: 10
<212> TYPE: DNA
<213> ORGANISM: Artificial sequence
<220> FEATURE:
<223> OTHER INFORMATION: PPE-1-derived regulatory element scheme

<400> SEQUENCE: 639
actttgcttc 10

<210> SEQ ID NO 640
<211> LENGTH: 9
<212> TYPE: DNA
<213> ORGANISM: Artificial sequence
<220> FEATURE:
<223> OTHER INFORMATION: PPE-1-derived regulatory element scheme
<220> FEATURE:
<221> NAME/KEY: misc_feature
<222> LOCATION: (6)..(9)
<223> OTHER INFORMATION: One or more residues can be mutated or absent

<400> SEQUENCE: 640 gcttctgga 9

<210> SEQ ID NO 641
<211> LENGTH: 14
<212> TYPE: DNA
<213> ORGANISM: Artificial sequence
<220> FEATURE:
<223> OTHER INFORMATION: PPE-1-derived regulatory element scheme
<220> FEATURE:
<221> NAME/KEY: misc_feature
<222> LOCATION: (6)..(10)
<223> OTHER INFORMATION: At least one residue mutated or absent
<220> FEATURE:
<221> NAME/KEY: misc_feature
<222> LOCATION: (11)..(14)
<223> OTHER INFORMATION: One or more residues can be mutated or absent

```
<400> SEQUENCE: 641

actttgcttc tgga                                                       14


<210> SEQ ID NO 642
<211> LENGTH: 10
<212> TYPE: DNA
<213> ORGANISM: Artificial sequence
<220> FEATURE:
<223> OTHER INFORMATION: PPE-1-derived regulatory element scheme
<220> FEATURE:
<221> NAME/KEY: misc_feature
<222> LOCATION: (6)..(10)
<223> OTHER INFORMATION: At least one residue mutated or absent

<400> SEQUENCE: 642

actttgcttc                                                            10


<210> SEQ ID NO 643
<211> LENGTH: 9
<212> TYPE: DNA
<213> ORGANISM: Artificial sequence
<220> FEATURE:
<223> OTHER INFORMATION: PPE-1-derived regulatory element scheme
<220> FEATURE:
<221> NAME/KEY: misc_feature
<222> LOCATION: (1)..(5)
<223> OTHER INFORMATION: At least one residue mutated or absent
<220> FEATURE:
<221> NAME/KEY: misc_feature
<222> LOCATION: (6)..(9)
<223> OTHER INFORMATION: One or more residues can be mutated or absent

<400> SEQUENCE: 643

gcttctgga                                                              9


<210> SEQ ID NO 644
<211> LENGTH: 15
<212> TYPE: DNA
<213> ORGANISM: Artificial sequence
<220> FEATURE:
<223> OTHER INFORMATION: PPE-1-derived regulatory element scheme
<220> FEATURE:
<221> NAME/KEY: misc_feature
<222> LOCATION: (11)..(15)
<223> OTHER INFORMATION: At least one residue mutated or absent
<220> FEATURE:
<221> NAME/KEY: misc_feature
<222> LOCATION: (11)..(15)
<223> OTHER INFORMATION: Mutated fragment (or variation of) can apear
      in multiple copies

<400> SEQUENCE: 644

cattccaatg gcttc                                                      15
```